United States Patent
Wooddell et al.

(10) Patent No.: US 10,130,651 B2
(45) Date of Patent: Nov. 20, 2018

(54) RNAI THERAPY FOR HEPATITIS B VIRUS INFECTION

(71) Applicant: Arrowhead Pharmaceuticals, Inc., Pasadena, CA (US)

(72) Inventors: Christine I. Wooddell, Madison, WI (US); David B. Rozema, Cross Plains, WI (US); David L. Lewis, Madison, WI (US); Darren H. Wakefield, Fitchburg, WI (US); Lauren J. Almeida, Madison, WI (US)

(73) Assignee: Arrowhead Pharmaceuticals, Inc., Pasadena, CA (US)

(*) Notice: Subject to any disclaimer, the term of this patent is extended or adjusted under 35 U.S.C. 154(b) by 0 days.

(21) Appl. No.: 15/229,314

(22) Filed: Aug. 5, 2016

(65) Prior Publication Data

US 2017/0035796 A1    Feb. 9, 2017

Related U.S. Application Data

(60) Provisional application No. 62/370,754, filed on Aug. 4, 2016, provisional application No. 62/202,253, filed on Aug. 7, 2015.

(51) Int. Cl.
| | | |
|---|---|---|
| *A61K 31/713* | (2006.01) | |
| *A61K 38/16* | (2006.01) | |
| *A61K 47/54* | (2017.01) | |
| *A61K 47/59* | (2017.01) | |

(52) U.S. Cl.
CPC ............ *A61K 31/713* (2013.01); *A61K 38/16* (2013.01); *A61K 47/549* (2017.08); *A61K 47/554* (2017.08); *A61K 47/59* (2017.08)

(58) Field of Classification Search
None
See application file for complete search history.

(56) References Cited

U.S. PATENT DOCUMENTS

| | | | |
|---|---|---|---|
| 3,687,808 A | 8/1972 | Merigan, Jr. et al. |
| 4,469,863 A | 9/1984 | Ts'o et al. |
| 5,023,243 A | 6/1991 | Tullis |
| 5,034,506 A | 7/1991 | Summerton et al. |
| 5,134,066 A | 7/1992 | Rogers et al. |
| 5,212,295 A | 5/1993 | Cook |
| 5,214,134 A | 5/1993 | Weis et al. |
| 5,216,141 A | 6/1993 | Benner |
| 5,218,105 A | 6/1993 | Cook et al. |
| 5,264,562 A | 11/1993 | Matteucci |
| 5,266,423 A | 11/1993 | Cohen et al. |
| 5,321,131 A | 6/1994 | Agrawal et al. |
| 5,359,044 A | 10/1994 | Cook et al. |
| 5,399,676 A | 3/1995 | Froehler |
| 5,405,939 A | 4/1995 | Suhadolnik et al. |
| 5,453,496 A | 9/1995 | Caruthers et al. |
| 5,455,233 A | 10/1995 | Spielvogel et al. |
| 5,455,786 A | 10/1995 | Takeuchi et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,489,677 A | 2/1996 | Sanghvi et al. |
| 5,506,351 A | 4/1996 | McGee et al. |
| 5,519,134 A | 5/1996 | Acevedo et al. |
| 5,521,302 A | 5/1996 | Cook et al. |
| 5,539,082 A | 7/1996 | Nielsen et al. |
| 5,541,307 A | 7/1996 | Cook et al. |
| 5,552,540 A | 9/1996 | Haralambidis |
| 5,554,746 A | 9/1996 | Ravikumar et al. |
| 5,571,902 A | 11/1996 | Ravikumar et al. |
| 5,578,718 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |

(Continued)

FOREIGN PATENT DOCUMENTS

| | | |
|---|---|---|
| EP | 1752536 A1 | 2/2007 |
| WO | 1991006309 A1 | 5/1991 |

(Continued)

OTHER PUBLICATIONS

Lu et al., Inhibitory effect of oxymatrine on serum hepatitis B virus DNA in HBV transgenic mice, World J Gastroenterol, 2004, 1176-1179.*
Baenziger JU et al. "Galactose and N-Acetylgalactosamine-Specific Endocytosis of Glycopeptides by Isolated Rat Hepatocytes"; Cell; vol. 22, No. 2; p. 611-620; (1980).
Biessen et al. "Synthesis of Cluster Galactosides with High Affinity for the Hepatic Asialoglycoprotein Receptor" Journal of Medicinal Chemistry; 38(9): 1538-1546; (1995).
Chisari FV et al. "Expression of hepatitis B virus large envelope polypeptide inhibits hepatitis B surface antigen secretion in transgenic mice.", Journal of Virology; vol. 60, No. 3; p. 880-887; (1986).

(Continued)

*Primary Examiner* — J. E. Angell
(74) *Attorney, Agent, or Firm* — Robert Michael Teigen

(57) ABSTRACT

Described are compositions and methods for inhibition of Hepatitis B virus gene expression. RNA interference (RNAi) triggers and RNAi trigger conjugates for inhibiting the expression of Hepatitis B virus gene are described. Pharmaceutical compositions comprising one or more HBV RNAi triggers optionally with one or more additional therapeutics are also described. Delivery of the described HBV RNAi triggers to infected liver in vivo provides for inhibition of HBV gene expression and treatment.

18 Claims, 11 Drawing Sheets

Specification includes a Sequence Listing.

(56) References Cited

U.S. PATENT DOCUMENTS

| | | |
|---|---|---|
| 5,646,265 A | 7/1997 | McGee |
| 5,663,312 A | 9/1997 | Chaturvedula |
| 5,670,633 A | 9/1997 | Cook et al. |
| 5,700,920 A | 12/1997 | Altmann et al. |
| 5,885,968 A | 3/1999 | Biessen et al. |
| 6,127,533 A | 10/2000 | Cook et al. |
| 6,166,197 A | 12/2000 | Cook et al. |
| 6,172,209 B1 | 1/2001 | Manoharan et al. |
| 6,262,241 B1 | 7/2001 | Cook et al. |
| 6,271,358 B1 | 8/2001 | Manoharan et al. |
| 6,630,351 B1 | 10/2003 | Monahan et al. |
| 7,019,113 B2 | 3/2006 | Rozema et al. |
| 7,138,382 B2 | 11/2006 | Wolff et al. |
| 8,084,599 B2 | 12/2011 | Rossi et al. |
| 8,349,809 B2 | 1/2013 | Brown |
| 8,513,207 B2 | 8/2013 | Brown |
| 8,809,293 B2 | 8/2014 | Chin et al. |
| 2003/0124651 A1 | 7/2003 | Pasupuleti et al. |
| 2003/0130189 A1 | 7/2003 | Senter et al. |
| 2003/0206887 A1 | 11/2003 | Morrissey et al. |
| 2003/0220264 A1 | 11/2003 | Rozema et al. |
| 2004/0058446 A1 | 3/2004 | Wolff et al. |
| 2004/0162235 A1 | 8/2004 | Trubetskoy et al. |
| 2004/0162260 A1 | 8/2004 | Rozema et al. |
| 2005/0032733 A1 | 2/2005 | McSwiggen et al. |
| 2005/0250683 A9 | 11/2005 | Rozema et al. |
| 2006/0063731 A1 | 3/2006 | Lewis et al. |
| 2006/0292691 A1 | 12/2006 | McSwiggen et al. |
| 2007/0197460 A1* | 8/2007 | Fougerolles ....... C12N 15/1131 514/44 A |
| 2008/0113351 A1 | 5/2008 | Naito et al. |
| 2008/0145436 A1 | 6/2008 | Ng et al. |
| 2008/0152661 A1 | 6/2008 | Rozema et al. |
| 2009/0131360 A1 | 5/2009 | Woolf et al. |
| 2009/0169638 A1 | 7/2009 | Davis et al. |
| 2011/0123520 A1 | 5/2011 | Manoharan et al. |
| 2012/0100569 A1 | 4/2012 | Liu et al. |
| 2012/0172412 A1 | 7/2012 | Rozema et al. |
| 2013/0005793 A1* | 1/2013 | Chin ................... A61K 31/713 514/44 A |
| 2013/0281658 A1 | 10/2013 | Rozema et al. |

FOREIGN PATENT DOCUMENTS

| | | |
|---|---|---|
| WO | 1993007883 A1 | 4/1993 |
| WO | 2000022113 A1 | 4/2000 |
| WO | 2000031105 A1 | 6/2000 |
| WO | 2003020931 A2 | 3/2003 |
| WO | 2005065719 A1 | 7/2005 |
| WO | 2006017932 A1 | 2/2006 |
| WO | 2009126933 A2 | 10/2009 |
| WO | 2010129672 A1 | 11/2010 |
| WO | 2010135322 A1 | 11/2010 |
| WO | 2011003780 A2 | 1/2011 |
| WO | 2013003520 A1 | 1/2013 |
| WO | 2015050871 A2 | 5/2015 |
| WO | 2016077321 A1 | 5/2016 |

OTHER PUBLICATIONS

Connolly et al. "Binding and Endocytosis of Cluster Glycosides by Rabbit Hepatocytes. Evidence for a Short-Circuit Pathway That Does Not Lead to Degradation" Journal of Biological Chemistry; vol. 257, No. 2; p. 939-945; (1982).

Dempsey CE et al.; "Conribution of proline-14 to the structure and actions of melittin"; FEBS Letters; 281 (1-2_: p. 240-244; (1991).

Frier et al. "Improved free-energy parameters far predictions of RNA duplex stability"; Proceedings from the National Academy of Sciences USA; vol. 83; p. 9373-9377; (1986).

Guidotti LG et al. "Hepatitis B virus nucleocapsid particles do not cross the hepatocyte nuclear membrane in transgenic mice."; Journal of Virology; vol. 68, No. 9; p. 5469-5475; (1994).

Guidotti LG et al. "High-level hepatitis B virus replication in transgenic mice."; Journal of Virology; vol. 69, No. 10; p. 3158-6169;(1995).

Iobst ST et al. "Selective Sugar Binding to the Carbohydrate Recognition Domains of the Rat Hepatic and Macrophage Asialoglycoprotein Receptors." Journal of Biological Chemistry; 271(12); p. 6686-6693; (1996).

Livak and Schmittgen; "Analysis of Relative Gene Expression Data Using Real-Time Quantitative PCR and the 2(-Delta Delta C(T)) Method"; Methods 25; 402-408; (2001).

Pillai et al. "Repression of protein synthesis by miRNAs: how many mechanisms?" TRENDS in Cell Biology; vol. 17 (3); p. 118-126; (2007).

Rozema DB et al. "Endosomolysis by Masking of a Membrane Active Agent (EMMA) for Cytoplasmic Release of Macromolecules." Bioconjugate Chemistry; vol. 14, No. 51; p. 51-57; (2003).

Turner et al. "Free Energy Increments far Hydrogen Bonds in Nucleic Acid Base Pairs" Journal of the American Chemical Society; vol. 209; p. 3783-3785; (1987).

Weitzer S et al "The human RNA kinase hCLp1 is active on 3' transfer RNA exons and short interfering RNAs."; Nature; vol. 447; p. 222-227; (2007).

Werkmeister et al., "The Effect of Sequence Variations and Structure on the Cytolytic Activity of Melittin Peptides," Biochimica et Biophysica Acta; pp. 50-54; vol. 1157; (1993).

Werkmeister JA et al. "Sequence requirements for the activity of membrane-active peptides" Journal Peptide Research; 60(4): 232-238;(2002).

Wincott Fetal. "Synthesis, deprotection, analysis and purification of RNA and ribozymes" Nucleic Acids Research; 23(14): 2677-2684; (1995).

Wooddell CI, et al. "Long-term RNA interference from optimized siRNA expression constructs in adult mice."; Biochem Biophys Res Commun; 334; p. 117-127; (2005).

Yang PL et al. "Hydrodynamic injection of viral DNA: a mouse model of acute hepatitis B virus infection." PNAS; vol. 39: p. 13825-13830; (2002).

Zhang G et al. "High levels of foreign gene expression in hepatocytes after tail vein injection of naked plasmid DNA." Human Gene Therapy; vol. 10; p. 1735-1737; (1999).

GenBank Accession No. V01460; (1979).

Akhtar S et al., "Nonviral delivery of synthetic siRNAs in vivo," Journal of Clinical Investigation;117: 3623-3632; (2007).

Amarzguioui et al. "An algorithm far selection of functional siRNA sequences" Biochemical and Biophysical Research Communications; vol. 316, p. 1050-1058; (2004).

Asthana N. et al. "Dissection of antibacterial and toxic activity of melittin: a leucine zipper motif plays a crucial role in determining its hemolytic activity but not antibacterial activity" Journal of Biological Chemistry (2004) 279(53): 55042-55050.

Berkner KL et al., "Development of adenovirus vectors for the expression of heterologous genes," Bio Techniques (1988) 6: 616-629.

Blondelle SE et al. "Hemolytic and antimicrobial activities of the twenty-four individual omission analogues of melittin" Biochemistry (1991) 30(19): 4671-4678.

Blondelle SE et al. "influence of tryptophan residues on melittin's hemolytic activity" Biochimica et Biophysica Acta (1993) 1202(2): 331-336.

Boeckle S et al. "Melillin analogs with high lytic activity al endosomal pH enhance transfection with purified targeted PEI polyplexes" Journal Conlrolled Release (2006) 112(2): 240-248.

Boeckle Set al."C- versus N-terminally linked melillin-polyethylenimine conjugates: the site of linkage strongly influences activity of DNA polyplexes" Journal of Gene Medicine (2005) 7(10): 1335-1347.

Bucchini D et al., "Pancreatic expression of human insulin gene in transgenic mice," Proc. Natl. Acad. Sci. USA (1986) 83: 2511-2515.

Chalk et al. "Improved and automated prediction of effective siRNA" Biochemical and Biophysical Research Communications 2004 vol. 319, p. 264-274.

(56) References Cited

OTHER PUBLICATIONS

Chen S-H et al. "Gene therapy for brain tumors: Regression of experimental gliomas by adenovirus-mediated gene transfer in vivo," Proc. Natl. Acad. Sci. USA (1994) 91: 3054-3057.
Chen CP et al. "Gene transfer with poly-melittin peptides" Bioconjugate Chemistry (2006) 17(4): 1057-1062.
Chen et al., "Synthetic PEGylated Glycoproteins and Their Utility in Gene Delivery", Bioconjugate Chem.; vol. 18, 45; pp. 371-378; (2007).
Cone RD et al., "High-efficiency gene transfer into mammalian cells: Generation of helper-free recombinant retrovirus with broad mammalian host range," Proc. Natl. Acad. Sci. USA (1984) 81: 6349-6353.
Cook PD, "Medicinal Chemistry of Antisense Oligonucleotides-Future Opportunities." Anti-Cancer Drug Design (1991) 6: 585-607.
Cornetta K et al., "Safety issues related to retroviral-mediated gene transfer in humans," Human Gene Therapy (1991) 2: 5-14.
Brooke et al., "Pharmacokinetic Properties of Several Novel Oligonucleolide Analogs in Mice." J. Pharmacol. Exp. Ther. (1996), 277: 923-927.
Danos O et al., "Safe and efficient generation of recombinant retroviruses with amphotropic and ecotropic host ranges," Proc. Natl. Acad. Sci. USA (1988) 85: 6460-6464.
Delgado C et al., "The Uses and Properties of PEG-Linked Proteins," Critical Reviews in Therapeutic Drug Carrier Systems (1992) 9(3,4): 249-304.
Docherty K et al., "Nutrient regulation of insulin gene expression," FASEB J. (1994) 8:20-24.
Elbashir et al; "Functional anatomy of siRNAs for mediating efficient RNAi in *Drosophila melanogaster* embryo iysate" The EMBO Journal; vol. 20; No. 23; pp. 6877-6888; (2001).
Englisch U et al., "Chemically Modified Oligonucleotides as Probes and Inhibitors," Angewandte Chemie, International Edition (1991) 30(6): 613-629.
Findeis MA: "Stepwise Synthesis of a Galnac-Containing Cluster Glycoside Ligand of the Asialoglycoprotein Receptor", International Journal of Peptide and Protein Research, vol. 43, No. 5, Jan. 1, 1994, pp. 477-485.
Gassmann M et al., "Maintenance of an extrachromosomal plasmid vector in mouse embryonic stem cells," Proc. Natl. Acad. Sci. USA (1995) 92: 1292-1296.
Goncalves E et al. "Structural and thermodynamic aspects of the interaction between heparan sulfate and analogues of melittin" Biochemistry (2006) 45(9): 3086-3094.
Greene et al. Protective Groups in Organic Synthesis, Chapter 2, 2d ed., John Wiley & Sons, New York, 1991, and Oligonucleotides and Analogues a Practical Approach, Ekstein, F. Ed., IRL Press, NY, 1991.
Guzaev AP et al., "A Conformationally Preorganized Universal Solid Support for Efficient Oligonucleotide Synthesis," J. Am. Chem. Soc. (2003) 125: 2380-2381.
Hamm ML et al., "Incorporation of 2'-Deoxy-2'-mercaptocylidine into Oligonucleotides via Phosphoramidite Chemistry," J. Org. Chem. (1997) 62: 3415-3420.
Heale et al. "siRNA target site secondary structure predictions using local stable substructures" Nucleic Acids Research (2005) 33(3).
Holle L et al. "A matrix metalloproteinase 2 cleavable melittin/avidin conjugate specifically targets tumor cells in vitro and in vivo" International Journal of Oncology (2003) 22(1): 93-98.
Holle L et al. "In vitro- and in vivo-targeted tumor lysis by an MMP2 cleavable melittin-LAP fusion protein" International Journal of Oncology (2009) 35(4): 829-835.
Hsu K-HL et al., "Immunogenicity of Recombinant Adenovirus-Respiratory Syncytial Virus Vaccines with Adenovirus Types 4, 5, and 7 Vectors in Dogs and a Chimpanzee," J. Infectious Disease, (1992) 166: 769-775.
Ikeda et al., "Ligand-Targeting Delivery of Therapeutic siRNA," Pharmaceutical Research (2006) 23: 1631-1640.

Kabanov et al., "A new class of antivirals; antisense oligonucleotides combined with a hydrophobic substituent effectively inhibit influenza virus reproduction and synthesis of virus-specific proteins in MOCK cells," FEBS Lett. (1990) 259: 327-330.
Khvorova et al. "Functional siRNAs and miRNAs Exhibit Strand Bias" Cell 2003 vol. 115, p. 209-216.
King TP et al. "Structure-immunogenicity relationship of melittin, its transposed analogues, and D-melittin" Journal of Immunology (1994) 153(3): 1124-1131.
Kirby AJ "Effective Molarities far Intramolecular Reactions" Adv. Phys. Org. Chem.; (1980) p. 183-278.
Kroschwitz JL, "Monomers," Encyclopedia of Polymer Science and Engineering, John Wiley & Sons, New York, pp. 715-727. (1988).
Lebeau AM et al. "Targeting the cancer stroma with a fibroblast activation protein-activated promelittin protoxin" Molecular Cancer Therapeutics (2009) 8(5): 1378-1386.
Legendre JY et al: "Dioleoylmelittin As a Novel Serum-Insensitive Reagent Far Efficient Transfection of Mammalian Cells", Bioconjugate Chemistry, vol. 8, No. 1, Jan. 1, 1997, pp. 57-63.
Letsinger RL et al., "Cholesteryl-conjugated oligonucleotides: Synthesis, properties, and activity as inhibitors of replication of human immunodeficiency virus in cell culture," Proc. Natl Acad. Sci. USA (1989) 85: 5553-5556.
Li S et al., "Folate-Mediated Targeting of Antisense Oligodeoxynucleotides to Ovarian Cancer Cells," Pharmaceutical Research (1998) 15(10): 1540-1545.
Manoharan M et al., "Chemical Modifications to Improve Uptake and Bioavailability of Antisense Oligonucleotides," Ann. NY. Acad. Sci. (1992) 660: 306-309.
Manoharan M et al., "Introduction of a Lipophilic Thioether Tether in the Minor Groove of Nucleic Acids for Antisense Applications," Bioorg. & Med. Chem. Letters (1993) 3: 2765-2770.
Manoharan M et al., "Cholic Acid-Oligonucleotide Conjugates for Antisense Applications," Bioorg. Med. & Chem. Lett. (1994) 4: 1053-1060.
Manoharan M et al., "Oligonucleotide Conjugates: Alteration of the Pharmacokinetic Properties of Antisense Agents," Nucleosides & Nucleotides (1995) 14: 969-973.
Manoharan M et al., "Lipidic Nucleic Acids," Tetrahedron Letters (1995) 36: 3651-3654.
Manoharan M. "Oligonucleotide Conjugates as Potential Antisense Drugs with Improved Uptake. Biodistribution, Targeted Delivery, and Mechanism of Action," Antisense & Nucleic Acid Drug Devel. (2002) 12: 103-128.
Meyer M et al. "A dimethylmaleic acid-melittin-polylysine conjugate with reduced toxicity, pH-triggered endosomolytic activity and enhanced gene transfer potential" Journal of Gene Medicine (2007) 9(9): 797-805.
Mishra RK et al., "Improved leishmanicidal effect of phosphorothioate antisense oligonucleotides by LDL-mediated delivery," Biochim. et Biophysics Acta (1995) 1264: 229-237.
Ambardekar, V et al.; "The modification of siRNA with 3' cholesterol to increase nuclease protection and suppression of native mRNA by select siRNA polyplexes"; Biomaterials; vol. 32, Issue 5; pp. 1404-1411; Feb. 2011.
International Search Report and Written Opinion for corresponding International Application No. PCT/US16/45714.
Nawrot B et al., "Chemical and Structural Diversity of siRNA Molecules," Current Topics in Medicinal Chemistry (2006) 6: 913-925.
Nguyen T et al., "RNAi therapeutics: an update on delivery." Current Opinion in Molecular Therapeutics (2008) 10(2): 158-167.
Oberhaus ER et al., "Effective Incorporation of 2'-0-methyl-oligoribonucleotides Into Liposomes and Enhanced Cell Association Through Modification with Thiocholesterol," Nucl. Acids Research (1992) 20: 533-538.
Pei et al. "On the art of identifying effective and specific siRNAs" Nature Methods 2006 vol. 3(9), p. 670-676.
Perez-Paya E et al. "Determination of the secondary structure of selected melittin analogues with different haemolytic activities" Biochemical Journal (1994) 299(2): 587-591.

(56) References Cited

OTHER PUBLICATIONS

Polushin NN et al., "Synthesis of Oligonucleotides Containing 2'-Azido- and 2'-Amino-2'-deoxyuridine Using Phosphotriester Chemistry," Tetrahedron Letters (1996) 37(19): 3227-3230.
Raghuraman H et al. "Melittin: a membrane-active peptide with diverse functions" Bioscience Reports (2007) 27 (4-5): 189-223.
Reynolds et al. "Targeting the cancer stroma with a fibroblast activation protein-activated promelittin protoxin" Nature Biotechnology 2004.
Rivett DE et al. "Inhibition of membrane-active peptides by fatty acid-peptide hybrids" Journal of Protein Chemistry (1999) 18(3): 291-295.
Rosenfeld MA et al., "Adenovirus-mediated transfer of a recombinant alpha 1-antitrypsin gene to the lung epithelium in vivo," Science (1991) 252: 431-434.
Rosenfeld MA et al., "In viva transfer of the human cystic fibrosis transmembrane conductance regulator gene to the airway epithelium" Cell (1992) 68(1): 143-155.
Rozema DB et al. "Dynamic PolyConjugates far targeted in vivo delivery of siRNA to hepatocytes." PNAS USA; 104 (32): p. 12982-12987; (2007).
Saison-Behmoaras et al., "Short Modified Antisense Oligonucleotides Directed Against Ha-ras Point Mutation Induce Selective Cleavage of the mRNA and Inhibit T24 Cells Proliferation," The EMBO Journal (1991) 10: 1111-1118.
Samukov VV et al., "2-(4-Nitrophenyl)sulfonylethoxycarbonyl (NSC) Group as a Base-Labile a-Amino Protection for Solid Phase Peptide Synthesis," Tetrahedron Letters (1994) 35(42): 7821-7824.
Sanghvi, Antisense Research and Applications, (1993) Chapter 15, p. 289-302, Crooke ST and Lebleu Bed., CRC Press.
Schroeder E et al., "Hemolytic activity and action on the surface tension of aequeous solutions of synthetic melittins," Experientia (1971) 27(7):764-765 (XP001031342).
Schwarz et al. "Asymmetry in the Assembly of the RNAi Enzyme Complex" Cell 2003 vol. 115, p. 199-208.
Shea et al., "Synthesis, Hybridization Properties and Antiviral Activity of Lipid-oligodeoxynucleotide Conjugates," Nucl. Acids Research (1990) 18: 3777-3783.
Son DJ et al. "Therapeutic application of anti-arthritis, pain-releasing, and anti-cancer effects of bee venom and its constituent compounds" Pharmacology & Therapeutics (2007) 115(2): 246-270.
Svinarchuk et al, "Inhibition of HIV proliferation in MT-4 cells by antisense oligonucleotide conjugated to lipophilic groups," Biochimie (1993) 75: 49-54.
Takei J et al. "Self-association of disulfide-dimerized melittin analogues" Biochemistry (1998) 37(16): 5699-5708.
Thomson JB et al., "Synthesis and Properties of Diuridine Phosphate Analogues Containing Thio and Amino Modifications," J. Org. Chem. (1996) 61: 6273-6281.
Tosteson MT et al. "Primary structure of peptides and ion channels. Role of amino acid side chains in voltage gating of melittin channels" Biophysical Journal (1990) 58(6): 1367-1375.
Ui-Tei et al. "Guidelines for the selection of highly effective siRNA sequences far mammalian and chick RNA interference" Nucleic Acids Research 2004 vol. 32(3)936-948.
Wagner RW, "The state of the art in antisense research." Nature Medicine (1995) 1 (11): 1116-1118.
Williams DJ et al., "Thermodynamic Comparison of the Salt Dependence of Natural RNA Hairpins and RNA Hairpins with Non-Nucleotide Spacers," Biochemistry (1996) 35: 14665-14670.
Wolfrum C et al. "Mechanisms and optimization of in vivo delivery of lipophilic siRNAs", Nature Biotechnology, vol. 25, No. 10; pp. 1149-1157; Oct. 2007.
Wooddell, et al; "Hepatocyte—targeted RNAi Therapeutics for the Treatment of Chronic Hepatitis B Virus infection"; Molecular Therapy; vol. 21; No. 5; pp. 973-985; (2013).
Zamboni, "Liposomal, Nanoparticle, and Conjugated Formulations of Anticancer Agents," Clin. Cancer Res. (2005) 11: 8230-8234.
Zhang, Y-L et al "RNA Interference inhibits hepatitis B virus of different genotypes in vitro and in vivo." Bmc Microbial. 2010, vol. 10:214, p. 1-10.
GenBank Accession No. AP007263 (2004).
GenBank Accession No. AB 602818 (2010).
GenBank Accession No. AB644286 (2011).
GenBank Accession No. AB554024 (2010).

* cited by examiner (Alk-SS-C6)–RNA n=1-10, preferably n=4

(Alk-SS-C6)-RNA (Chol-ALNY)-RNA

A.

B.

A. AM02312-AS

B. AM02315-AS

C. AM02312-AS + AM02315-AS

A. AM02316-SS (TEG)

B. AM02319-SS (TEG)

C. AM02320-SS (C6)

A. AM02320-SS (C6) + AM02319 (TEG)

B. AM02323-SS (C6) + AM02316-SS (TEG)

C. AM02320-SS (C6) / AM02312-AS + AM02323-SS (C6) / AM02315-AS

M. AM2316-SS (TEG) / AM02312-AS + AM02319-SS (TEG) / AM02315-AS

N. AM02320-SS (C6) / AM02312-AS + AM02319-SS (TEG) / AM02315-AS

O. AM02316-SS (TEG) + AM02312-AS + AM02323-SS (C6) / AM02315-AS

RNAI THERAPY FOR HEPATITIS B VIRUS INFECTION

PRIORITY

The present application claims the benefit of U.S. Provisional Patent Application No. 62/370,754, filed Aug. 4, 2016, and U.S. Provisional Patent Application No. 62/202,253, filed Aug. 7, 2015, the contents of each of which are incorporated herein in their entirety.

SEQUENCE LISTING

The present application includes a Sequence Listing that has been submitted electronically in ASCII format and is hereby incorporated by reference in its entirety. The Sequence Listing, as amended, was submitted in ASCII format under the file name "30635-US1_SequenceListing.txt" and is 347 KB in size.

BACKGROUND

The Hepatitis B Virus is a strict hepatotrophic, double-stranded DNA containing virus. Although DNA is the genetic material, the replication cycle involves a reverse transcription step to copy a pregenomic RNA into DNA. Hepatitis B virus is classified as one member of the Hepadnaviruses and belongs to the family of Hepadnaviridae. The primary infection of adult humans with Hepatitis B Virus causes an acute hepatitis with symptoms of organ inflammation, fever, jaundice and increased liver transaminases in blood. Those patients that are not able to overcome the virus infection suffer a chronic disease progression over many years with increased risk of developing cirrhotic liver or liver cancer. Perinatal transmission from Hepatitis B virus-infected mothers to newborns also leads to chronic hepatitis.

Upon uptake by hepatocytes, the nucleocapsid is transferred to the nucleus and DNA is released. There, the DNA strand synthesis is completed and gaps repaired to give the covalently closed circular (ccc) supercoiled DNA of 3.2 kb. The cccDNA serves as a template for transcription of four major viral mRNAs, which are 3.5, 2.4, 2.1 and 0.7 kb long. All mRNAs are 5'-capped and polyadenylated at the 3'-end. There is sequence overlap at the 3'-end between all four mRNAs.

The 3.5 kb mRNA serves as template for core protein and polymerase production. In addition, the same transcript serves as a pre-genomic replication intermediate and allows the viral polymerase to initiate the reverse transcription into DNA. Core protein is needed for nucleocapsid formation. In addition, sequential processing activities transforms some core protein into the secretable e-antigen. The abundance of e-antigen in blood correlates with Hepatitis B Virus replication in liver and serves as an important diagnostic marker for monitoring the disease progression.

The 2.4 and 2.1 kb mRNAs carry the open reading frames pre-S1, pre-S2 and S for expression of viral large, medium and small surface antigen. The s-antigen is associated with infectious, complete particles. In addition, blood of infected patients also contain non-infectious particles derived from s-antigen alone, free of genomic DNA or polymerase. The function of these particles is not fully understood. The complete and lasting depletion of detectable s-antigen in blood is considered as a reliable indicator for Hepatitis B Virus clearance and thus, a successful cure.

The 0.7 kb mRNA encodes the X protein. This gene product is important for efficient transcription of viral genes and also acts as a transactivator on host gene expression. The latter activity seems to be important for hepatocyte transformation during development of liver cancer.

Patients with detectable s-antigen, e-antigen or viral DNA in the blood for more than 6 months are considered chronically infected. Nucleoside analogs as inhibitors of reverse transcriptase activity are typically the first treatment option for many patients. Lamivudine, Tenofovir, or Entecavir suppress Hepatitis B Virus replication, sometimes to undetectable levels. Improvement of liver function and reduction of liver inflammation are the most important benefits. However, only few patients achieve complete and lasting remission after the end of treatment. Furthermore, the Hepatitis B Virus develops drug resistance with increasing duration of treatment. This is especially difficult for patients co-infected with Hepatitis B and Human Immunodeficiency Virus. Both viruses are susceptible to nucleoside analogue drugs and may co-develop resistance.

A second treatment option is the administration of interferon-alpha. Here, patients receive high doses of interferon-alpha over a period of 6 months. The Asian genotype B gives very poor response rates. Co-infection with Hepatitis D or Human Immunodeficiency Virus has been shown to render interferon-alpha therapy completely ineffective. Patients with strong liver damage and heavy fibrotic conditions are not qualified for interferon-alpha therapy.

Despite significant advances in the field of Hepatitis B Virus treatment, there remains a need for agents that can selectively and efficiently silence the gene expression of the virus, block replication, and subsequently reduces viral burden in chronically infected patients.

SUMMARY

Described herein are Hepatitis B Virus (HBV)-specific RNA interference (RNAi) trigger molecules (also termed RNAi agent, RNAi trigger, or trigger) able to selectively and efficiently decrease expression of HBV, and their use in mediating RNA interference to inhibit the expression of Hepatitis B Virus genes, in particular the expression of the genes related to replication or pathogenesis of Hepatitis B Virus. Each RNAi trigger includes at least a sense strand and an antisense strand. The sense strand and the antisense strand can be partially, substantially, or fully complementary to each other. The length of the RNAi trigger sense and antisense strands described herein each can be 16 to 30 nucleotides in length. In some embodiments, the sense and antisense strands are independently 17 to 26 nucleotides in length. The sense and antisense strands can be either the same length or different lengths. The RNAi triggers described herein, upon delivery to a cell expressing HBV, inhibit the expression of one or more HBV genes in vivo. Examples of HBV RNAi trigger sense strands and antisense strands that can be used in a HBV RNAi trigger are provided in Tables 1A and 1B. Examples of HBV RNAi trigger duplexes are provided in Table 2.

An HBV RNAi trigger comprises a sense strand comprising a first sequence (passenger strand) and an antisense strand (guide strand) comprising a second sequence. In some embodiments, the sense strand comprises a core sequence which has an identity of at least 90% to at least a portion of an Hepatitis B Virus mRNA. The antisense strand comprises a nucleotide sequence which is substantially complementary to at least part of an mRNA encoding said Hepatitis B Virus gene. In some embodiments, the region of complementarity is less than 30 nucleotides in length. In some embodiments, the length of an RNAi trigger duplex length is in the range of about 16 to 30 nucleotides. In some embodiments, the length of a RNAi trigger duplex length is in the range of about 15 to 25 nucleotides. In some embodiments, an HBV RNAi trigger has a duplex length of about 18, 19, 20, 21, 22, 23 or 24 nucleotides. Exemplary sequences are provided in Tables 1A and 1B.

In some embodiments, an HBV RNAi trigger further comprises a targeting group. A targeting group can be linked to the 3' or 5' end of a sense strand or an antisense strand of an HBV RNAi trigger. In some embodiments, a targeting group is linked to the 3' or 5' end of the sense strand. In some embodiments, a targeting group is linked to the 5' end of the sense strand. In some embodiments, a targeting group comprises a hydrophobic group having 20 or more carbon atoms. In some embodiments, the hydrophobic group comprises a cholesterol or a cholesteryl group. In some embodiments, a targeting group comprises a galactose trimer.

In some embodiments, a targeting group is linked to the trigger via a linker. Suitable linkers include, but are not limited to: —$(CH_2)_n$— wherein n is 1-10 (in some embodiments n=6, i.e., C6 as used herein) and —$(O-CH_2-CH_2)_n$— or —$(CH_2-CH_2-O)_n$— wherein n=1-10 (in some embodiments n=3, i.e., triethylene gylcol (TEG)). A linker, with or without a targeting group, can be attached to the 5' or 3' end of any of the sense and/or antisense strands disclosed in Tables 1A and 1B.

In some embodiments, we describe combinations of at least two HBV RNAi triggers having different sequences. In some embodiments, the two or more different HBV RNAi triggers are each linked to targeting groups. In some embodiments, the two or more different HBV RNAi triggers are each linked to cholesterol targeting groups. In some embodiments, the two or more different HBV RNAi triggers are each linked to galactose trimer targeting groups. In some embodiments, when two different triggers are used, the first trigger is linked to a cholesterol and the second trigger is linked to a galactose trimer. In some embodiments, when two or more triggers are used, the two triggers are linked to their respective targeting groups using the same or similar linkers. In some embodiments, when two or more triggers are used, the two triggers are linked to their respective targeting groups using different linkers. In some embodiments, a first targeting group is linked to a first HBV RNAi trigger via a C6 linker and a second targeting group is linked to a second HBV RNAi trigger via a TEG linker. In some embodiments, the first and second targeting groups are both comprised of or consist of cholesterol or cholesteryl groups. In some embodiments, the first and second targeting groups are both comprised of or consist of galactose trimers or galactose tetramers. The use of different linkers can provide for improved differentiation and quantitative analysis of the triggers.

In some embodiments, compositions for delivering an HBV RNAi trigger to a liver cell in vivo are described, comprising: an HBV RNAi trigger conjugated to a targeting group. In some embodiments, the targeting group is a galactose trimer or a cholesterol.

In some embodiments, compositions for delivering an HBV RNAi trigger to a liver cell in vivo are described, comprising: a) an asialoglycoprotein receptor (ASGPr)-targeted reversibly masked melittin-like peptide (MLP), i.e. MLP delivery peptide (or simply delivery peptide), and b) an HBV RNAi trigger conjugated to a hydrophobic group containing at least 20 carbon atoms (RNA-conjugate), such as, but no limited to, a cholesterol or cholesteryl group. The MLP delivery peptide and the RNAi trigger-conjugate are synthesized separately, and may be supplied in separate containers or a single container. In some embodiments, the HBV RNAi trigger is not conjugated to the delivery peptide.

In some embodiments, we describe compositions for inhibiting expression of a Hepatitis B Virus gene, comprising: a) MLP-$(L-T)_x$ wherein, -L-T has the structure represented by —CO—C($CH_3$)=C(T)-COOH or —CO—C(T)=C($CH_3$)—COOH, wherein T comprises a targeting ligand having affinity for the an asialoglycoprotein receptor, and x is greater than 80% of the number of primary amines of a population of MLPs, b) a first HBV RNAi trigger comprising an antisense strand and a sense strand wherein the antisense strand comprises nucleotides 2-15, 2-19, 1-17, 1-21, or 1-26 of any of the antisense sequences provided in Table 1A, and the sense strand comprises any of the corresponding sense sequences provides in Table 1B covalently linked to a cholesteryl group via a TEG group, and c) a second HBV RNAi trigger comprising an antisense strand and a sense strand wherein the antisense strand comprises nucleotides 2-15, 2-19, 1-17, 1-21, or 1-26 of any of the antisense sequences provided in Table 1A, and the sense strand comprises any of the corresponding sense sequences provided in Table 1B covalently linked to a cholesteryl group via a C6 group. In some embodiments, any of the sense strand nucleotide sequences provided in Table 1B can have a Chol-TEG or Chol-C6 5' or 3' modification.

In some embodiments, one or more of the described HBV RNAi triggers and optionally an MLP delivery peptide are administered to a mammal in a pharmaceutically acceptable carrier or diluent. In some embodiments, the mammal is a human. In some embodiments, the RNAi trigger and delivery peptide are combined in a solution prior to administration to the mammal. In some embodiments, a delivery peptide and an RNAi trigger are co-administered to the mammal in separate solutions. In some embodiments, a delivery peptide and an RNAi trigger are administered to the mammal sequentially. For sequential administration, the delivery peptide may be administered prior to administration of the RNAi trigger. Alternatively, for sequential administration, the RNAi trigger may be administered prior to administration of the delivery peptide.

The use of Hepatitis B Virus RNAi triggers provide methods for therapeutic and/or prophylactic treatment of diseases/disorders which are associated with HBV infection. The described HBV RNAi triggers mediate RNA interference to inhibit the expression of one or more genes necessary for replication and/or pathogenesis of Hepatitis B Virus. In particular, HBV RNAi triggers inhibition viral polymerase, core protein, surface antigen, e-antigen and/or the X protein, in a cell, tissue or mammal. HBV RNAi triggers can be used to treat hepatitis B virus infection. HBV RNAi triggers can also be used to treat or prevent chronic liver diseases/disorders, inflammations, fibrotic conditions and proliferative disorders, like cancers, associated with hepatitis B virus infection. In some embodiments, the sequence is at least 13 contiguous nucleotides in length. Such methods comprise administration of HBV RNAi trigger to a human being or animal infected with HBV. Further, compositions for delivery of HBV RNAi triggers to liver cells in vive are described.

In some embodiments, the described HBV RNAi triggers are optionally combined with one or more additional (i.e., second, third, etc.) therapeutics. A second therapeutic can be another HBV RNAi trigger (e.g., a HBV RNAi trigger which targets a different sequence within the HBV genome). An additional therapeutic can also be a small molecule drug, antibody, antibody fragment, and/or vaccine. The HBV RNAi triggers, with or without the one or more additional therapeutics, can be combined with one or more excipients to form pharmaceutical compositions.

The pharmaceutical compositions comprising one or more HBV RNAi triggers can be administered in a number of ways depending upon whether local or systemic treatment is desired. Administration can be, but is not limited to, intravenous, intraarterial, subcutaneous, intraperitoneal, subdermal (e.g., via an implanted device), and intraparenchymal administration.

The described HBV RNAi triggers and/or compositions can be used in methods for therapeutic treatment of HBV infection or disease or conditions caused by HBV infection. Such methods comprise administration of an HBV RNAi trigger as described herein to a subject, e.g., a human or animal subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Further objects, features, and advantages will be apparent from the following detailed description when taken in conjunction with the accompanying drawings.

BRIEF DESCRIPTION OF THE FIGURES

FIG. 7. HPLC Chromatographs of (A) AM02312-AS, (B) AM02315-AS, and (C) AM02312-AS+AM02315-AS.

FIG. 10. HPLC Chromatographs of (A) AM02320-SS (C6)+AM02319 (TEG), (B) AM02323-SS (C6)+AM02316-SS (TEG), and (C) AM02320-SS (C6)/AM02312-AS+ AM02323-SS (C6)/AM02315-AS.

FIG. 11. HPLC Chromatographs of (A) AM2316-SS (TEG)/AM02312-AS+AM02319-SS (TEG)/AM02315-AS, (B) AM02320-SS (C6)/AM02312-AS+AM02319-SS (TEG)/AM02315-AS, and (C) AM02316-SS (TEG)+ AM02312-AS+AM02323-SS (C6)/AM02315-AS.

DETAILED DESCRIPTION

Figure 1:
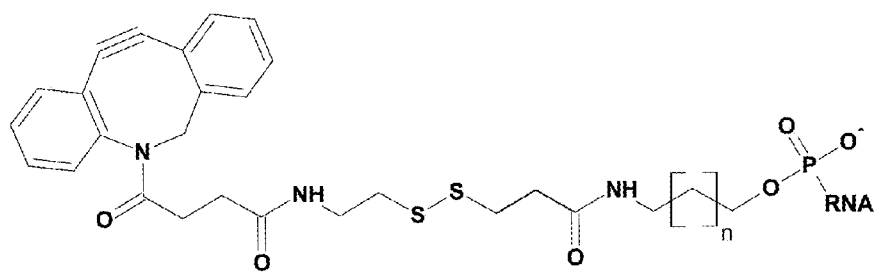
FIG. 1. Chemical structures representing HBV RNAi trigger targeting groups and linking groups.
Figure 1:
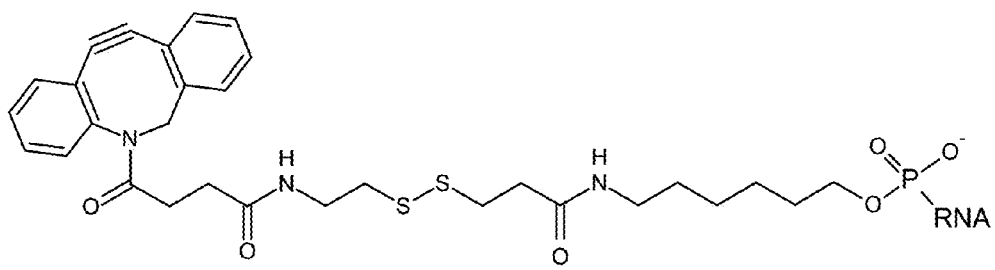
Figure 1:
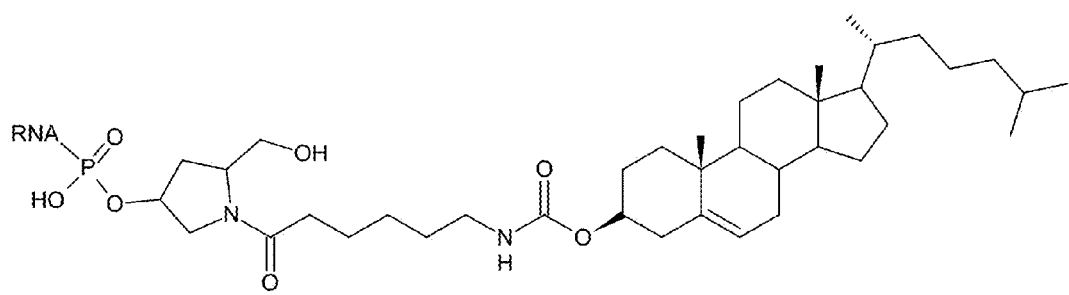

Described herein are RNAi triggers for inhibiting expression of the Hepatitis B Virus (referred to herein as HBV RNAi triggers). Each HBV RNAi trigger comprises a sense strand and an antisense strand. The sense strand and the antisense strand are partially, substantially, or fully complementary to each other. In some embodiments, the length of the herein described RNAi trigger sense and antisense strands are independently 16 to 30 nucleotides in length. In some embodiments, the length of the herein described RNAi trigger sense and antisense strands are independently 17 to 26 nucleotides in length. In some embodiments, the herein described RNAi trigger sense and antisense strands are independently 17, 18, 19, 20, 21, 22, 23, 24, 25, or 26 nucleotides in length. The sense and antisense strands can be either the same length or they can be different lengths. In some embodiments, the sense strand is about 19 nucleotides in length while the antisense strand is about 21 nucleotides in length. In some embodiments, the sense strand is about 21 nucleotides in length while the antisense strand is about 23 nucleotides in length. In other embodiments, the sense and antisense strands are independently 17-21 nucleotides in length. In some embodiments, both the sense and antisense strands are each 21-26 nucleotides in length. In some embodiments, both the sense and antisense strands are each 26 nucleotides in length. Examples of nucleotide sequences used in forming HBV RNAi trigger molecules are provided in Tables 1A and 1B.

An HBV RNAi trigger comprises a sense strand and an antisense strand each containing a core sequence of 16-23 nucleobases in length. An antisense strand core sequence is 100% (perfectly) complementary or at least 90% (substantially) complementary to a nucleotide sequence (sometimes referred to as a "target sequence") present in the HBV mRNA. A sense strand core sequence is 100% (perfectly) complementary or at least 90% (substantially) complementary to a sequence in the antisense strand, and thus the sense strand core sequence is perfectly identical or at least 90% identical to a nucleotide sequence (target sequence) present in the HBV mRNA. A sense strand core sequence can be the same length as a corresponding antisense core sequence or it can be a different length. In some embodiments, the antisense strand core sequence is 16, 17, 18, 19, 20, 21, 22, or 23 nucleotides in length. In some embodiments, the sense strand core sequence is 16, 17, 18, 19, 20, 21, 22, or 23 nucleotides in length.

The HBV RNAi trigger sense and antisense strands typically anneal to form a duplex. Within the complementary duplex region, the sense strand core sequence is at least 90% complementary or 100% complementary to the antisense core sequence. In some embodiments, the sense strand core sequence contains a sequence of at least 16, at least 17, at least 18, at least 19, at least 20, or at least 21 nucleotides that is at least 90% or 100% complementary to a corresponding 16, 17, 18, 19, 20, or 21 nucleotide sequence of the antisense strand core sequence (i.e., the sense strand and antisense core sequences of an HBV RNAi trigger have a region of at least 16, at least 17, at least 18, at least 19, at least 20, or at least 21 nucleotides that is at least 90% base paired or 100% base paired.)

RNAi triggers include, but are not limited to: short interfering RNAs (siRNAs), double-strand RNAs (dsRNA), micro RNAs (miRNAs), short hairpin RNAs (shRNA), and dicer substrates (e.g., U.S. Pat. Nos. 8,084,599, 8,349,809, and 8,513,207). The RNAi triggers described herein, upon delivery to a cell expressing an HBV gene, inhibit or knockdown expression of one or more HBV genes in vivo through the biological process of RNA interference (RNAi).

As used herein, the term "sequence" or "nucleotide sequence" refers to a succession or order of nucleobases, nucleotides, and/or nucleosides, described with a succession of letters using the standard nucleotide nomenclature and the key for modified nucleotides described herein.

The sense strand and/or the antisense strand may optionally and independently contain an additional 1, 2, 3, 4, 5, or 6 nucleotides (extension) at the 3' end, the 5' end, or both the 3' and 5' ends of the core sequences. The antisense strand additional nucleotides, if present, may or may not be complementary to the corresponding sequence in the HBV mRNA. The sense strand additional nucleotides, if present, may or may not be identical to the corresponding sequence in the HBV mRNA. The antisense strand additional nucleotides, if present, may or may not be complementary to the corresponding sense strand's additional nucleotides, if present.

As used herein, an extension comprises 1, 2, 3, 4, 5, or 6 nucleotides at the 5' and/or 3' end of the sense strand core sequence and/or antisense strand core sequence. The extension nucleotides on a sense strand may or may not be complementary to nucleotides, either core sequence nucleotides or extension nucleotides, in the corresponding antisense strand. Conversely, the extension nucleotides on an antisense strand may or may not be complementary to nucleotides, either core sequence nucleotides or extension nucleotides, in the corresponding sense strand. In some embodiments, both the sense strand and the antisense strand of an RNAi trigger contain 3' and 5' extensions. In some embodiments, one or more of the 3' extension nucleotides of one strand base pairs with one or more 5' extension nucleotides of the other strand. In other embodiments, one or more of 3' extension nucleotides of one strand do not base pair with one or more 5' extension nucleotides of the other strand. In some embodiments, an HBV RNAi trigger has an antisense strand having a 3' extension and a sense strand having a 5' extension.

The HBV RNAi triggers described herein are formed by annealing an antisense strand with a sense strand. In some embodiments, an HBV RNAi trigger antisense strand comprises a nucleotide sequence of any of the sequences in Table 1A. In some embodiments, an HBV RNAi trigger antisense strand comprises the sequence of nucleotides 1-17, 2-15, 2-17, 1-18, 2-18, 1-19, 2-19, 1-20, 2-20, 1-21, 2-21, 1-22, 2-22, 1-23, 2-23, 1-24, 2-24, 1-25, 2-25, 1-26, or 2-26 of any of the sequences in Table 1A. In some embodiments, an HBV RNAi trigger sense strand comprises the nucleotide sequence of any of the sequences in Table 1B. In some embodiments, an HBV RNAi trigger sense strand comprises the sequence of nucleotides 1-18, 1-19, 1-20, 1-21, 1-22, 1-23, 1-24, 1-25, 1-26, 2-19, 2-20, 2-21, 2-22, 2-23, 2-24, 2-25, 2-26, 3-20, 3-21, 3-22, 3-23, 3-24, 3-25, 3-26, 4-21, 4-22, 4-23, 4-24, 4-25, 4-26, 5-22, 5-23, 5-24, 5-25, 5-26, 6-23, 6-24, 6-25, 6-26, 7-24, 7-25, 7-25, 8-25, 8-26 of any of the sequences in Table 1B.

In some embodiments, the sense and antisense strands of the RNAi triggers described herein contain the same number of nucleotides. In some embodiments the sense and antisense strands of the RNAi triggers described herein contain different numbers of nucleotides. In some embodiments, the sense strand 5' end and the antisense strand 3' end of an RNAi trigger form a blunt end. In some embodiments, the sense strand 3' end and the antisense strand 5' end of an RNAi trigger form a blunt end. In some embodiments, both ends of an RNAi trigger form a blunt end. In some embodiments, neither end of an RNAi trigger is blunt-ended. As used herein a blunt end refers to an end of a double stranded trigger molecule in which the terminal nucleotides of the two annealed strands are complementary (form a complementary base-pair). In some embodiments, the sense strand 5' end and the antisense strand 3' end of an RNAi trigger form a frayed end. In some embodiments, the sense strand 3' end and the antisense strand 5' end of an RNAi trigger form a frayed end. In some embodiments, both ends of an RNAi trigger form a frayed end. In some embodiments, neither end of an RNAi trigger is a frayed end. As used herein a frayed end refers to an end of a double stranded trigger molecule in which the terminal nucleotides of the two annealed strands from a pair (i.e. do not form an overhang) but are not complementary (i.e. form a non-complementary pair). As used herein, an overhang is a stretch of one or more unpaired nucleotides at the end of one strand of a double stranded RNAi trigger molecule. The unpaired nucleotides may be on the sense strand or the antisense strand, creating either 3' or 5' overhangs. In some embodiments the RNAi trigger molecule contains: a blunt end and a frayed end, a blunt end and 5' overhang end, a blunt end and a 3' overhang end, a frayed end and a 5' overhand end, a frayed end and a 3' overhang end, two 5' overhang ends, two 3' overhang ends, a 5' overhang end and a 3' overhand end, two frayed ends, or two blunt ends.

A nucleotide base (or nucleobase) is a heterocyclic pyrimidine or purine compound which is a constituent of all nucleic acids and includes adenine (A), guanine (G), cytosine (C), thymine (T), and uracil (U). As used herein, "G", "g", "C", "c", "A", "a", "U", "u", and "T", each generally stand for a nucleobase, nucleoside, nucleotide or nucleotide mimic that contains guanine, cytosine, adenine, uracil and thymidine as a base. Also as used herein, the term "nucleotide" can include a modified nucleotide or nucleotide mimic, abasic site, or a surrogate replacement moiety.

As used herein, a "modified nucleotide" is a nucleotide other than a ribonucleotide (2'-hydroxyl nucleotide). In some embodiments, an HBV RNAi trigger contains one or more modified nucleotides. In some embodiments, at least 50%, at least 60%, at least 70%, at least 80%, at least 90%, at least 95%, or 100% of the nucleotides are modified. Modified nucleotides include, but are not limited to, deoxynucleotides, nucleotide mimics, abasic nucleotides (represented herein as X or Ab), 2'-modified nucleotides, 3' to 3' linkages (inverted) nucleotides (represented herein as invdN, invN, invn, invX), non-natural base-comprising nucleotides, bridged nucleotides, peptide nucleic acids, 2',3'-seco nucleotide mimics (unlocked nucleobase analogues, represented herein as $N_{UNA}$ or NUNA), locked nucleotides (represented herein as $N_{LNA}$ or NLNA), 3'-O-Methoxy (2' internucleotide linked) nucleotides (represented herein as 3'-OMen), 2'-F-Arabino nucleotides (represented herein as NfANA or $Nf_{ANA}$), morpholino nucleotides, vinyl phosphonate deoxyribonucleotides (represented herein as vpdN), and vinyl phosphonate nucleotides (represented herein as vpN). 2'-modified nucleotides (i.e. a nucleotide with a group other than a hydroxyl group at the 2' position of the five-membered sugar ring) include, but are not limited to, 2'-O-methyl nucleotides (represented herein as a lower case letter 'n' in a nucleotide sequence), 2'-deoxy-2'-fluoro nucleotides (represented herein as Nf, also represented herein as 2'-fluoro nucleotide), 2'-deoxy nucleotides (represented herein as dN), 2'-methoxyethyl (2'-O-2-methoxylethyl) nucleotides (represented herein as NM or 2'-MOE), 2'-amino nucleotides, and 2'-alkyl nucleotides. It is not necessary for all positions in a given compound to be uniformly modified. Conversely, more than one modification may be incorporated in a single HBV RNAi trigger or even in a single nucleotide thereof. The HBV RNAi trigger sense strands and antisense strands may be synthesized and/or modified by methods known in the art. Modification at one nucleotide is independent of modification of another nucleotide.

Modified nucleotides also include nucleotides having modified nucleobases. Modified nucleobases include, but are not limited to, synthetic and natural nucleobases, 5-substituted pyrimidines, 6-azapyrimidines and N-2, N-6 and O-6 substituted purines, including 2-aminopropyladenine, 5-propynyluracil and 5-propynylcytosine, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

In some embodiments, one or more nucleotides of an HBV RNAi trigger are linked by non-standard linkages or backbones (i.e. modified internucleoside linkages or modified backbones). In some embodiments, a modified internucleoside linkage is a non-phosphate-containing covalent internucleoside linkage. Modified internucleoside linkages or backbones include, but are not limited to, phosphorothioates, 5'-phosphorothioate group (represented herein as a lower case 's' before a nucleotide, as in sN, sn, sNf, or sdN), chiral phosphorothioates, thiophosphate, phosphorodithioates, phosphotriesters, aminoalkyl-phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, morpholino linkages, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. In other embodiments, a modified internucleoside linkage or backbone lacks a phosphorus atom. Modified internucleoside linkages lacking a phosphorus atom include, but are not limited to, short chain alkyl or cycloalkyl inter-sugar linkages, mixed heteroatom and alkyl or cycloalkyl inter-sugar linkages, or one or more short chain heteroatomic or heterocyclic inter-sugar linkages. In some embodiments, modified internucleoside backbones include, but are not limited to, siloxane backbones, sulfide, sulfoxide and sulfone backbones; formacetyl and thioformacetyl backbones, methylene formacetyl and thioformacetyl backbones, alkene containing backbones, sulfamate backbones, methyleneimino and methylenehydrazino backbones, sulfonate and sulfonamide backbones, amide backbones; and others having mixed N, O, S, and $CH_2$ component parts.

In some embodiments, an HBV RNAi trigger contains one or more modified nucleotides and one or more modified internucleoside linkages. In some embodiments, a 2'-modified nucleotide is combined with modified internucleoside linkage. For example, in some embodiments, a sense strand of an HBV RNAi trigger can contain 1, 2, 3, or 4 phosphorothioate linkages; an antisense strand of a HBV RNAi trigger can contain 1, 2, 3, or 4 phosphorothioate linkages; or both the sense strand and the antisense strand can independently contain 1, 2, 3, or 4 phosphorothioate linkages.

In some embodiments, a chemically-modified HBV RNAi trigger comprises a duplex having two strands, one or both of which can be chemically-modified, wherein each strand is about 17 to about 29 nucleotides. In some embodiments, an HBV RNAi trigger comprises one or more modified nucleotides while maintaining the ability to mediate RNAi inside a cell or reconstituted in vitro system. An HBV RNAi trigger can be modified wherein the chemical modification comprises one or more (e.g., about 1, 2, 3, 4, 5, 6, 7, 8, 9, 10, or more) of the nucleotides. In some embodiments, an HBV RNAi trigger comprises modified nucleotides as a percentage of the total number of nucleotides present in the HBV RNAi trigger. As such, an HBV RNAi trigger can generally comprise modified nucleotides from about 5% to about 100% of the nucleotide positions (e.g., about 5%, 10%, 15%, 20%, 25%, 30%, 35%, 40%, 45%, 50%, 55%, 60%, 65%, 70%, 75%, 80%, 85%, 90%, 95% or 100% of the nucleotide positions). The actual percentage of modified nucleotides present in a given HBV RNAi trigger depends on the total number of nucleotides present in the HBV RNAi trigger. The percent modification can be based upon the total number of nucleotides present in the sense strand, antisense strand, or both the sense and antisense strands. In addition, the actual percentage of modified nucleotides present in a given HBV RNAi trigger can also depend on the total number of purine and pyrimidine nucleotides present in the HBV RNAi trigger. For example, wherein all pyrimidine nucleotides and/or all purine nucleotides present in the HBV RNAi trigger are modified.

Representative HBV RNAi triggers are represented by the Duplex ID Nos. shown in Table 2. In some embodiments, an HBV RNAi trigger consists of any of the Duplex ID Nos. presented herein. In some embodiments an HBV RNAi trigger comprises of any of the Duplex ID Nos. presented herein. In some embodiments, an HBV RNAi trigger comprises the sense strand and antisense strand nucleotide sequences of any of the Duplex ID Nos. presented herein. In some embodiments, an HBV RNAi trigger comprises the sense strand and antisense strand nucleotide sequences of any of the Duplex ID Nos. presented herein and a targeting group and/or linking group wherein the targeting group and/or linking group is covalently linked to the sense strand or the antisense strand. In some embodiments, an HBV RNAi trigger comprises the sense strand and antisense strand modified nucleotide sequences of any of the Duplex ID Nos. presented herein. In some embodiments, an HBV RNAi trigger comprises the sense strand and antisense strand modified nucleotide sequences of any of the Duplex ID Nos. presented herein and a targeting group and/or linking group wherein the targeting group and/or linking group is covalently linked to the sense strand or the antisense strand.

In some embodiments, an HBV RNAi trigger contains or is conjugated to a targeting group, linking group, delivery polymer, delivery vehicle, and/or other non-nucleotide group. The targeting group, linking group, delivery polymer, delivery vehicle, and/or other non-nucleotide group can be covalently linked to the 3' and/or 5' end of either the sense strand and/or the antisense strand. In some embodiments, an HBV RNAi trigger comprises a targeting group, linking group, delivery polymer, delivery vehicle, or other non-nucleotide group linked to the 3' and/or 5' end of the sense strand. In some embodiments, a targeting group, linking group, delivery polymer, delivery vehicle, or other non-nucleotide group is linked to the 5' end of an HBV RNAi trigger sense strand. In some embodiments, a targeting group, linking group, delivery polymer, delivery vehicle, and/or other non-nucleotide group is linked directly or indirectly to the trigger via a linker/linking group. In some embodiments, a targeting group, linking group, delivery polymer, delivery vehicle, and/or other non-nucleotide group is linked to the RNAi trigger sense strand and/or antisense strand via a labile, cleavable, or reversible bond or linker.

A targeting group can enhance the pharmacokinetic or biodistribution properties of an RNAi trigger or conjugate to which it is attached to improve cell- or tissue-specific distribution and cell-specific uptake of the conjugate. In some instances, binding of a targeting group to a cell or cell receptor may initiate endocytosis. A targeting group can be monovalent, divalent, trivalent, tetravalent, or have higher valency. Representative targeting groups include, without limitation, compounds with affinity to cell surface molecule, cell receptor ligands, hapten, antibodies, monoclonal antibodies, antibody fragments, and antibody mimics with affinity to cell surface molecules.

Unmodified HBV RNAi trigger sense strand and antisense strand sequences are provided in Tables 1A and 1B. In forming HBV RNAi triggers, each of the nucleotides in each of the unmodified sequences listed in Tables 1A and 1B may be a modified nucleotide. Non-limiting examples of antisense and sense strands containing modified nucleotides are also provided in Tables 1A and 1B. In Tables 1A and 1B, the following notations are used to indicate modified nucleotides: N=2'-OH (unmodified) ribonucleotide (capital letter without for d indication); n=2'-O-methyl (2'-OMe) nucleotide; Nf=2'-deoxy-2'-fluoro nucleotide (also termed 2'-fluoro modified nucleotide); dN=2'-deoxy nucleotide (deoxynucleotide); $N_{UNA}$=2',3'-seco nucleotide mimics (unlocked nucleobase analogs); NM=2'-methoxyethyl nucleotide (also shown as 2'-MOE); (invdN)=3'-3' linked (inverted) deoxyribonucleotide (3'-3' linked nucleotide); (invAb)=3'-3' linked (inverted) abasic nucleotide (also shown as (invX)); x=abasic site; s=phosphorothioate linked nucleotide; p=phosphate; vp=vinyl phosphonate containing nucleotide.

TABLE 1A

HBV RNAi trigger antisense strand sequences.

| AS strand ID | Modified sequence (5'→3') | SEQ ID NO. | Unmodified sequence (5'→3') | SEQ ID NO. |
|---|---|---|---|---|
| AM00006-AS | dTAfcCfaAfuUfuAfuGfcCfuAfcAfgdTsdT | 210 | TACCAAUUUAUGCCUACAGTT | 1 |
| AM00008-AS | dTAfuGfaUfaAfaAfcGfcCfgCfaGfadTsdT | 211 | TAUGAUAAAACGCCGCAGATT | 2 |
| AM00010-AS | dTAfgAfuGfaUfuAfgGfcAfgAfgGfudTsdT | 212 | TAGAUGAUUAGGCAGAGGUTT | 3 |
| AM00139-AS | dTAfcAfaAfuGfgCfaCfuAfgUfaAfadTsdT | 213 | TACAAAUGGCACUAGUAAATT | 4 |
| AM00194-AS | dTAfcCfaAuNAuUfuAfuGfcCfuAfcAfgdTsdT | 214 | TACCAAUUUAUGCCUACAGTT | 1 |
| AM00195-AS | dTAfcCfaAfUuNAUfuAfuGfcCfuAfcAfgdTsdT | 215 | TACCAAUUUAUGCCUACAGTT | 1 |
| AM00438-AS | dTAfgAfuGUNAaUfuAfgGfcAfgAfgGfudTsdT | 216 | TAGAUGAUUAGGCAGAGGUTT | 3 |
| AM00439-AS | dTAfgAfuGfAUNAUfuAfgGfcAfgAfgGfudTsdT | 217 | TAGAUGAUUAGGCAGAGGUTT | 3 |
| AM01463-AS | pdTAfcCfaAfuUfuAfuGfcCfuAfcAfgdTsdT | 218 | TACCAAUUUAUGCCUACAGTT | 1 |
| AM01464-AS | pdTAfgAfuGfaUfuAfgGfcAfgAfgGfudTsdT | 219 | TAGAUGAUUAGGCAGAGGUTT | 3 |
| AM01933-AS | dTAfcCfaAUNAuUfuAfugcCfuAfcAfgdTsdT | 220 | TACCAAUUUAUGCCUACAGTT | 1 |
| AM01935-AS | dTsAfscCfaAUNAuUfuAfugcCfuAfcAfgsdTsdT | 221 | TACCAAUUUAUGCCUACAGTT | 1 |
| AM01937-AS | dTAfgAfuGfAUNAUfuAfggcAfgAfgGfudTsdT | 222 | TAGAUGAUUAGGCAGAGGUTT | 3 |
| AM01938-AS | dTsAfsgAfuGfAUNAUfuAfggcAfgAfgGfusdTsdT | 223 | TAGAUGAUUAGGCAGAGGUTT | 3 |
| AM01942-AS | dTAfcAfaAUNAuGfgCfaCfuAfgUfaAfadTsdT | 224 | TACAAAUGGCACUAGUAAATT | 4 |
| AM01943-AS | dTAfcAfaAfUUNAGfgCfaCfuAfgUfaAfadTsdT | 225 | TACAAAUGGCACUAGUAAATT | 4 |
| AM01944-AS | dTAfcAfaAUNAuGfgCfacuAfgUfaAfadTsdT | 226 | TACAAAUGGCACUAGUAAATT | 4 |
| AM01945-AS | dTsAfscAfaAUNAuGfgCfacuAfgUfaAfasdTsdT | 227 | TACAAAUGGCACUAGUAAATT | 4 |
| AM01946-AS | dTAfcAfaAfUUNAGfgCfacuAfgUfaAfadTsdT | 228 | TACAAAUGGCACUAGUAAATT | 4 |
| AM01947-AS | dTsAfscAfaAfUUNAGfgCfacuAfgUfaAfasdTsdT | 229 | TACAAAUGGCACUAGUAAATT | 4 |
| AM01985-AS | dTAfuGfaUUNAaAfaAfcGfcCfgCfaGfadTsdT | 230 | TAUGAUAAAACGCCGCAGATT | 2 |

TABLE 1A-continued

HBV RNAi trigger antisense strand sequences.

| AS strand ID | Modified sequence (5'→3') | SEQ ID NO. | Unmodified sequence (5'→3') | SEQ ID NO. |
|---|---|---|---|---|
| AM01986-AS | dTAfuGfaUfAUNAAfaAfcGfcCfgCfaGfadTsdT | 231 | TAUGAUAAACGCCGCAGAUU | 2 |
| AM01987-AS | dTAfuGfaUUNAaAfaAfcgcCfgCfaGfadTsdT | 232 | TAUGAUAAACGCCGCAGAUU | 2 |
| AM01988-AS | dTsAfsuGfaUUNAaAfaAfcgcCfgCfaGfasdTsdT | 233 | TAUGAUAAACGCCGCAGAUU | 2 |
| AM01989-AS | dTAfuGfaUfAUNAAfaAfcgcCfgCfaGfadTsdT | 234 | TAUGAUAAACGCCGCAGAUU | 2 |
| AM01990-AS | dTsAfsuGfaUfAUNAAfaAfcgcCfgCfaGfasdTsdT | 235 | TAUGAUAAACGCCGCAGAUU | 2 |
| AM02276-AS | dTsAfscCfaAfuUfuAfuGfcCfuAfcAfgsdTsdT | 236 | TACCAAUUUAUGCCUACAGUU | 1 |
| AM02277-AS | dTsAfscCfaAfuUfuAfugcCfuAfcAfgsdTsdT | 237 | TACCAAUUUAUGCCUACAGUU | 1 |
| AM02280-AS | dTsAfsgAfuGfaUfuAfgGfcAfgAfgGfusdTsdT | 238 | TAGAUGAUUAGGCAGAGGUUU | 3 |
| AM02281-AS | dTsAfsgAfuGfaUfuAfggcAfgAfgGfusdTsdT | 239 | TAGAUGAUUAGGCAGAGGUUU | 3 |
| AM02286-AS | dTsAfscAfaAfuGfgCfaCfuAfgUfaAfasdTsdT | 240 | TACAAAUGGCACUAGUAAAUU | 4 |
| AM02287-AS | dTsAfscAfaAfuGfgCfacuAfgUfaAfasdTsdT | 241 | TACAAAUGGCACUAGUAAAUU | 4 |
| AM02288-AS | dTsAfsuGfaUfaAfaAfcGfcCfgCfaGfasdTsdT | 242 | TAUGAUAAACGCCGCAGAUU | 2 |
| AM02289-AS | dTsAfsuGfaUfaAfaAfcgcCfgCfaGfasdTsdT | 243 | TAUGAUAAACGCCGCAGAUU | 2 |
| AM02312-AS | dTAfcCfaAfuUfuAfugcCfuAfcAfgdTsdT | 244 | TACCAAUUUAUGCCUACAGUU | 1 |
| AM02313-AS | dTAfgAfuGfaUfuAfggcAfgAfgGfudTsdT | 245 | TAGAUGAUUAGGCAGAGGUUU | 3 |
| AM02314-AS | dTAfcAfaAfuGfgCfacuAfgUfaAfadTsdT | 246 | TACAAAUGGCACUAGUAAAUU | 4 |
| AM02315-AS | dTAfuGfaUfaAfaAfcgcCfgCfaGfadTsdT | 247 | TAUGAUAAACGCCGCAGAUU | 2 |
| AM02366-AS | dTsAfscCfaAfuUfuAfugCfCfuAfcAfgGfccsUfsUfAu | 248 | TACCAAUUUAUGCCUACAGGCCUUAU | 5 |
| AM02367-AS | dTAfcCfaAfuUfuAfugCfCfuAfcAfgGfccUfsUfAu | 249 | TACCAAUUUAUGCCUACAGGCCUUAU | 5 |
| AM02368-AS | dTsAfscCfaAfuUfuAfugCfcuAfcAfgGfccsUfsUfAu | 250 | TACCAAUUUAUGCCUACAGGCCUUAU | 5 |
| AM02369-AS | dTsAfcCfaAfuUfuAfugCfcuAfcAfgGfccUfsUfAu | 251 | TACCAAUUUAUGCCUACAGGCCUUAU | 5 |
| AM02374-AS | dTsAfsuGfaUfaAfaAfcgCfCfgCfaGfaCfacsAfsUfAu | 252 | TAUGAUAAACGCCGCAGACACAUAU | 6 |
| AM02375-AS | dTAfuGfaUfaAfaAfcgCfCfgCfaGfaCfacAfsUfAu | 253 | TAUGAUAAACGCCGCAGACACAUAU | 6 |
| AM02376-AS | dTsAfsuGfaUfaAfaAfcgCfcgCfaGfaCfacsAfsUfAu | 254 | TAUGAUAAACGCCGCAGACACAUAU | 6 |
| AM02377-AS | dTAfuGfaUfaAfaAfcgCfcgCfaGfaCfacAfsUfAu | 255 | TAUGAUAAACGCCGCAGACACAUAU | 6 |
| AM02382-AS | dTsAfsgAfuGfaUfuAfgGfcAfgAfgGfuUfgasAfsUfAu | 256 | TAGAUGAUUAGGCAGAGGUUGAAUAU | 7 |
| AM02383-AS | dTsAfgAfuGfaUfuAfgGfcAfgAfgGfuUfgaAfsUfAu | 257 | TAGAUGAUUAGGCAGAGGUUGAAUAU | 7 |
| AM02384-AS | dTsAfsgAfuGfaUfuAfggCfagAfgGfuUfgasAfsUfAu | 258 | TAGAUGAUUAGGCAGAGGUUGAAUAU | 7 |
| AM02385-AS | dTsAfgAfuGfaUfuAfggCfagAfgGfuUfgaAfsUfAu | 259 | TAGAUGAUUAGGCAGAGGUUGAAUAU | 7 |
| AM02391-AS | dTsAfscCfaAfuUfuAfugcCfuAfcAfgdTsdT | 260 | TACCAAUUUAUGCCUACAGUU | 1 |
| AM02392-AS | dTsAfsuGfaUfaAfaAfcgcCfgCfaGfasdTsdT | 261 | TAUGAUAAACGCCGCAGAUU | 2 |
| AM02393-AS | dTsAfsgAfuGfaUfuAfggcAfgAfgGfudTsdT | 262 | TAGAUGAUUAGGCAGAGGUUU | 3 |
| AM02484-AS | pdTAfuGfaUfaAfaAfcgcCfgCfaGfadTsdT | 263 | TAUGAUAAACGCCGCAGAUU | 2 |
| AM02485-AS | pdTAfuGfaUfaAfaAfcGfcCfgCfaGfadTsdT | 264 | TAUGAUAAACGCCGCAGAUU | 2 |
| AM02575-AS | pdTAfcCfaAfuUfuAfugcCfuAfcAfgdTsdT | 265 | TACCAAUUUAUGCCUACAGUU | 1 |
| AM02577-AS | pdTAfgAfuGfaUfuAfggcAfgAfgGfudTsdT | 266 | TAGAUGAUUAGGCAGAGGUUU | 3 |
| AM02609-AS | aUfaAfaAfcgcCfgCfaGfadTsdT | 379 | AUAAACGCCGCAGAUU | 81 |
| AM02889-AS | usGfaUfaAfaAfcGfccGfcCfaGfaCfaCfaUfcuAu | 267 | UGAUAAACGCCGCAGACACAUCUAU | 8 |

TABLE 1A-continued

HBV RNAi trigger antisense strand sequences.

| AS strand ID | Modified sequence (5'→3') | SEQ ID NO. | Unmodified sequence (5'→3') | SEQ ID NO. |
|---|---|---|---|---|
| AM02892-AS | usGfaAfcAfaAfuGfgcAfCfuAfmgUfaAfaCfuuAu | 268 | UGAACAAAUGGCACUAGUAAACUUAU | 9 |
| AM02895-AS | usGfcGfuCfaGfcAfaaCfAfcUfuGfgCfaCfauAu | 269 | UGCGUCAGCAAACACUUGGCACAUAU | 10 |
| AM02898-AS | usGfaAfcCfaCfuGfaaCfAfaAfuGfgCfaCfuuAu | 270 | UGAACCACUGAACAAAUGGCACUUAU | 11 |
| AM02901-AS | usAfaCfgGfgCfaAfcaUfAfcCfuUfgAfuAfauAu | 271 | UAACGGGCAACAUACCUUGAUAAUAU | 12 |
| AM02904-AS | usAfcUfaGfuAfaAfcuGfAfgCfcAfgGfaGfauAu | 272 | UACUAGUAAACUGAGCCAGGAGAUAU | 13 |
| AM02907-AS | usGfgAfcAfaAfcGfggCfAfaCfaUfaCfcUfuuAu | 273 | UGGACAAACGGGCAACAUACCUUUAU | 14 |
| AM02910-AS | usAfcGfgGfcAfaCfauAfCfcUfuGfaUfaAfuuAu | 274 | UACGGGCAACAUACCUUGAUAAUUAU | 15 |
| AM02913-AS | usGfaAfgCfgAfaGfugCfAfcAfcGfgAfcCfguAu | 275 | UGAAGCGAAGUGCACACGGACCGUAU | 16 |
| AM02916-AS | usGfaUfaAfaAfcGfcCfgCfAfgaCfaCfaUfcuAu | 276 | UGAUAAACGCCGCAGACACAUCUAU | 8 |
| AM02919-AS | usGfaAfcAfaAfuGfgCfaCfUfagUfaAfaCfuuAu | 277 | UGAACAAAUGGCACUAGUAAACUUAU | 9 |
| AM02922-AS | usGfcGfuCfaGfcAfaAfcAfCfuuGfgCfaCfauAu | 278 | UGCGUCAGCAAACACUUGGCACAUAU | 10 |
| AM02925-AS | usGfaAfcCfaCfuGfaAfcAfAfauGfgCfaCfuuAu | 279 | UGAACCACUGAACAAAUGGCACUUAU | 11 |
| AM02928-AS | usAfcCfgGfgCfaAfcAfuUfCfcuUfgAfuAfauAu | 280 | UAACGGGCAACAUACCUUGAUAAUAU | 12 |
| AM02931-AS | usAfcUfaGfuAfaAfcUfgAfgFccAfgGfaGfauAu | 281 | UACUAGUAAACUGAGCCAGGAGAUAU | 13 |
| AM02934-AS | usGfgAfcAfaAfcGfgGfcAfAfcaUfaCfcUfuuAu | 282 | UGGACAAACGGGCAACAUACCUUUAU | 14 |
| AM02937-AS | usAfcGfgGfcAfaCfaUfaCfCfuuGfaUfaAfuuAu | 283 | UACGGGCAACAUACCUUGAUAAUUAU | 15 |
| AM02940-AS | usGfaAfgCfgAfaGfuGfcAfCfacGfgAfcCfguAu | 284 | UGAAGCGAAGUGCACACGGACCGUAU | 16 |
| AM02975-AS | usAfcCfaAfuUfuAfugCfCfuAfcAfgGfcCfuuAu | 285 | UACCAAUUUAUGCCUACAGGCCUUAU | 17 |
| AM02976-AS | usAfcCfaAfuUfuAfuGfcCfUfacAfgGfcCfuuAu | 286 | UACCAAUUUAUGCCUACAGGCCUUAU | 17 |
| AM02982-AS | usAfuGfaUfaAfaAfcgCfCfgCfaGfaCfaCfauAu | 287 | UAUGAUAAACGCCGCAGACACAUAU | 18 |
| AM02983-AS | usAfuGfaUfaAfaAfcGfcCfGfcaGfaCfaCfauAu | 288 | UAUGAUAAACGCCGCAGACACAUAU | 18 |
| AM02984-AS | usAfgAfuGfaUfuAfggCfAfgAfgGfuUfgAfauAu | 289 | UAGAUGAUUAGGCAGAGGUUGAAUAU | 19 |
| AM02985-AS | usAfgAfuGfaUfuAfgGfcAfGfagGfuUfgAfauAu | 290 | UAGAUGAUUAGGCAGAGGUUGAAUAU | 19 |
| AM03097-AS | dTGfaUfaAfaAfcGfcCfgCfaGfaCfadTsdT | 291 | TGAUAAACGCCGCAGACATT | 20 |
| AM03098-AS | dTGfaAfcAfaAfuGfgCfaCfuAfgUfadTsdT | 292 | TGAACAAAUGGCACUAGUATT | 21 |
| AM03099-AS | dTGfcGfuCfaGfcAfaAfcAfcUfuGfgdTsdT | 293 | TGCGUCAGCAAACACUUGGTT | 22 |
| AM03100-AS | dTGfaAfcCfaCfuGfaAfcAfaAfuGfgdTsdT | 294 | TGAACCACUGAACAAAUGGTT | 23 |
| AM03101-AS | dTAfaCfgGfgCfaAfcAfuAfcCfuUfgdTsdT | 295 | TAACGGGCAACAUACCUUGTT | 24 |
| AM03102-AS | dTAfcUfaGfuAfaAfcUfgAfgCfcAfgdTsdT | 296 | TACUAGUAAACUGAGCCAGTT | 25 |
| AM03103-AS | dTGfgAfcAfaAfcGfgGfcAfaCfaUfadTsdT | 297 | TGGACAAACGGGCAACAUATT | 26 |
| AM03104-AS | dTAfcGfgGfcAfaCfaUfaCfcUfuGfadTsdT | 298 | TACGGGCAACAUACCUUGATT | 27 |
| AM03105-AS | dTGfaAfgCfgAfaGfuGfcAfcAfcGfgdTsdT | 299 | TGAAGCGAAGUGCACACGGTT | 28 |
| AM03106-AS | dTUfcCfgCfgGfgAfuUfcAfgCfgCfcdTsdT | 300 | TUCCGCGGGAUUCAGCGCCTT | 29 |
| AM03495-AS | usGfsaAfcAfaAfuGfgCfaCfuAfgUfaAfacsusuAu | 301 | UGAACAAAUGGCACUAGUAAACUUAU | 9 |
| AM03500-AS | usGfgAfcAfaAfcGfgGfcAfaCfaUfaCfcususuAu | 302 | UGGACAAACGGGCAACAUACCUUUAU | 14 |
| AM03504-AS | usGfsaAfgCfgAfaGfuGfcAfcAfcGfgAfccsgsuAu | 303 | UGAAGCGAAGUGCACACGGACCGUAU | 16 |
| AM03508-AS | usAfscCfaAfuUfuAfuGfcCfuAfcAfgGfccsusuAu | 304 | UACCAAUUUAUGCCUACAGGCCUUAU | 17 |

TABLE 1A-continued

HBV RNAi trigger antisense strand sequences.

| AS strand ID | Modified sequence (5'→3') | SEQ ID NO. | Unmodified sequence (5'→3') | SEQ ID NO. |
|---|---|---|---|---|
| AM03512-AS | usAfsgAfuGfaUfuAfgGfcAfgAfgGfuUfgasasuAu | 305 | UAGAUGAUUAGGCAGAGGUUGAAUAU | 19 |
| AM03764-AS | usGfsaacaaAfuGfgcaCfuaguaaacsusuAu | 306 | UGAACAAAUGGCACUAGUAAACUUAU | 9 |
| AM03766-AS | usGfgacaaAfcGfggcAfacauaccusuAu | 307 | UGGACAAACGGGCAACAUACCUUUAU | 14 |
| AM03768-AS | usGfsaagcgAfaGfugcAfcacggaccsgsuAu | 308 | UGAAGCGAAGUGCACACGGACCGUAU | 16 |
| AM03770-AS | usAfsccaauUfuAfugcCfuacaggccsusuAu | 309 | UACCAAUUUAUGCCUACAGGCCUUAU | 17 |
| AM03772-AS | usAfsgaugaUfuAfggcAfgagguugasasuAu | 310 | UAGAUGAUUAGGCAGAGGUUGAAUAU | 19 |
| AM03864-AS | usGfsAfcAfaAfcGfgGfcAfaCfaUfaCfcususuAu | 311 | UGGACAAACGGGCAACAUACCUUUAU | 14 |
| AM03865-AS | usGfsgacaaAfcGfggcAfacauaccusuAu | 312 | UGGACAAACGGGCAACAUACCUUUAU | 14 |
| AM03912-AS | usAfsuGfaUfaAfaAfcGfcCfgCfaGfaCfascsauAu | 313 | UAUGAUAAACGCCGCAGACACAUAU | 18 |
| AM03913-AS | usAfsugauaAfaAfcgcCfgcagacascsauAu | 314 | UAUGAUAAACGCCGCAGACACAUAU | 18 |
| AM03916-AS | usGfsaUfaAfaAfcGfcCfgCfaGfaCfaCfasuscuAu | 315 | UGAUAAACGCCGCAGACACAUCUAU | 8 |
| AM03917-AS | usGfsauaaaAfcGfccgCfagacacasuscuAu | 316 | UGAUAAACGCCGCAGACACAUCUAU | 8 |
| AM04041-AS | vpusGfsgAfcAfaAfcGfgGfcAfaCfaUfaCfcususuAu | 317 | UGGACAAACGGGCAACAUACCUUUAU | 14 |
| AM04042-AS | vpusAfscCfaAfuUfuAfuGfcCfuAfcAfgGfccsusuAu | 318 | UACCAAUUUAUGCCUACAGGCCUUAU | 17 |
| AM04249-AS | dTAfcCfaAfuUfuAfuGfcCfuAfcAfgdTsdTp | 319 | TACCAAUUUAUGCCUACAGTT | 1 |
| AM04272-AS | asGfsuCfcGfcGfgGfaUfuCfaGfcGfcCfgAfscsuau | 320 | AGUCCGCGGGAUUCAGCGCCGACUAU | 30 |
| AM04273-AS | usUfsaAfaGfaGfaGfgUfgCfgCfcCfgGfuGfsgsuau | 321 | UUAAAGAGAGGUGCGCCCGGUGGUAU | 31 |
| AM04274-AS | usAfsaGfcGfaAfgUfgCfaCfaCfgGfuCfcGfsgsuau | 322 | UAAGCGAAGUGCACACGGUCCGGUAU | 32 |
| AM04275-AS | usUfsgAfaGfcGfaAfgUfgCfaCfaCfgGfaCfscsuau | 323 | UUGAAGCGAAGUGCACACGGACCUAU | 33 |
| AM04276-AS | asGfsuGfaAfgCfgAfaGfuGfcAfcAfcGfgAfscsuau | 324 | AGUGAAGCGAAGUGCACACGGACUAU | 34 |
| AM04277-AS | usAfsgAfgGfuGfaAfgCfgAfaGfuGfcAfcAfscsuau | 325 | UAGAGGUGAAGCGAAGUGCACACUAU | 35 |
| AM04278-AS | usCfsaGfaGfgUfgAfaGfcGfaAfgUfgCfaCfasasuau | 326 | UCAGAGGUGAAGCGAAGUGCACAUAU | 36 |
| AM04279-AS | usGfscAfgAfgGfuGfaAfgCfgAfaGfuGfcAfcscsuau | 327 | UGCAGAGGUGAAGCGAAGUGCACUAU | 37 |
| AM04280-AS | usCfsgGfuCfgUfuGfaCfaUfuGfcUfgGfgAfsgsuau | 328 | UCGGUCGUUGACAUUGCUGGGAGUAU | 38 |
| AM04281-AS | usCfsaAfgGfuCfgGfuCfgUfuGfaCfaUfuGfscsuau | 329 | UCAAGGUCGGUCGUUGACAUUGCUAU | 39 |
| AM04288-AS | usGfsaCffUfuUfaAfcCfuAfaUfcUfcCfuCfscsuau | 330 | UGACCUUUAACCUAAUCUCCUCCUAU | 40 |
| AM04289-AS | asUfsuUfaUfgCfcUfaCfaGfcCfuCfcUfaAfsusuau | 331 | AUUUAUGCCUACAGCCUCCUAAUUAU | 41 |
| AM04290-AS | asAfsuUfuAfuGfccCfuAfcAfgCfcUfcCfuAfsasuau | 332 | AAUUUAUGCCUACAGCCUCCUAAUAU | 42 |
| AM04291-AS | usAfsaUfuUfaUfgCfcUfaCfaGfcCfuCfcUfsasuau | 333 | UAAUUUAUGCCUACAGCCUCCUAUAU | 43 |
| AM04292-AS | usCfsaAfuUfuAfuGfccCfuAfcAfgCfcUfcCfsusuau | 334 | UCAAUUUAUGCCUACAGCCUCCUUAU | 44 |
| AM04293-AS | usCfscAfuUfuAfuGfcCfuAfcAfgCfcUfcCfscsuau | 335 | UCCAUUUAUGCCUACAGCCUCCUAU | 45 |
| AM04323-AS | usAfscGfcCfgCfaGfaCfaCfaUfcCfaGfcGfsasuau | 336 | UACGCCGCAGACACAUCCAGCGAUAU | 46 |
| AM04324-AS | usAfsaAfaCfgCfcGfcAfgAfcAfcAfuCfcAfsgsuau | 337 | UAAAACGCCGCAGACACAUCCAGUAU | 47 |
| AM04325-AS | usUfsaAfaAfcGfcCfgCfaGfaCfaCfaUfcCfsasuau | 338 | UUAAAACGCCGCAGACACAUCCAUAU | 48 |
| AM04326-AS | usUfsgAfuAfaAfaCfgCfcGfcAfgAfcAfcAfsusuau | 339 | UUGAUAAAACGCCGCAGACACAUUAU | 49 |
| AM04327-AS | usAfscGfgGfcAfaCfaUfaCfcUfuGfaUfaAfsusuau | 340 | UACGGGCAACAUACCUUGAUAAUUAU | 15 |
| AM04328-AS | usAfsaCfgGfgCfaAfcAfuAfcCfuUfgAfuAfsasuau | 341 | UAACGGGCAACAUACCUUGAUAAUAU | 12 |
| AM04329-AS | usAfsaAfcGfgGfcAfaCfaUfaCfcUfuGfaUfsasuau | 342 | UAAACGGGCAACAUACCUUGAUAUAU | 50 |

TABLE 1A-continued

HBV RNAi trigger antisense strand sequences.

| AS strand ID | Modified sequence (5'→3') | SEQ ID NO. | Unmodified sequence (5'→3') | SEQ ID NO. |
|---|---|---|---|---|
| AM04330-AS | usCfsaAfaCfgGfgCfaAfcAfuAfcCfuUfgAfsusuau | 343 | UCAAACGGGCAACAUACCUUGAUUAU | 51 |
| AM04331-AS | usAfscAfaAfcGfgGfcAfaCfaUfaCfcUfuGfsasuau | 344 | UACAAACGGGCAACAUACCUUGAUAU | 52 |
| AM04332-AS | usAfsgGfaCfaAfaCfgGfgCfaAfcAfuAfcCfsusuau | 345 | UAGGACAAACGGGCAACAUACCUUAU | 53 |
| AM04333-AS | usAfscUfaGfuAfaAfcUfgAfgCfcAfgGfaGfsasuau | 346 | UACUAGUAAACUGAGCCAGGAGAUAU | 13 |
| AM04334-AS | usGfsgCfaCfuAfgUfaAfaCfuGfaGfcCfaAfsgsuau | 347 | UGGCACUAGUAAACUGAGCCAAGUAU | 54 |
| AM04335-AS | usUfsgGfcAfcUfaGfuAfaAfcUfgAfgCfcAfsasuau | 348 | UUGGCACUAGUAAACUGAGCCAAUAU | 55 |
| AM04336-AS | usAfsaUfgGfcAfcUfaGfuAfaAfcUfgAfgCfscsuau | 349 | UAAUGGCACUAGUAAACUGAGCCUAU | 56 |
| AM04337-AS | usAfsaAfuGfgCfaCfuAfgUfaAfaCfuGfaGfscsuau | 350 | UAAAUGGCACUAGUAAACUGAGCUAU | 57 |
| AM04338-AS | usCfsaAfaUfgGfcAfcUfaGfuAfaAfcUfgAfsgsuau | 351 | UCAAAUGGCACUAGUAAACUGAGUAU | 58 |
| AM04339-AS | usAfscAfaAfuGfgCfaCfuAfgUfaAfaCfuGfsasuau | 352 | UACAAAUGGCACUAGUAAACUGAUAU | 59 |
| AM04340-AS | usUfsgAfaCfaAfaUfgGfcAfcUfaGfuAfaAfscsuau | 353 | UUGAACAAAUGGCACUAGUAAACUAU | 60 |
| AM04341-AS | asCfsuGfaAfcAfaAfuGfgCfaCfuAfgUfaAfsasuau | 354 | ACUGAACAAAUGGCACUAGUAAAUAU | 61 |
| AM04342-AS | usAfsaCfcAfcUfgAfaCfaAfaUfgGfcAfcUfsasuau | 355 | UAACCACUGAACAAAUGGCACUAUAU | 62 |
| AM04343-AS | usGfsaAfcCfaCfuGfaAfcAfaAfuGfgCfaCfsusuau | 356 | UGAACCACUGAACAAAUGGCACUUAU | 11 |
| AM04344-AS | usCfsgAfaCfcAfcUfgAfaCfaAfaUfgGfcAfscsuau | 357 | UCGAACCACUGAACAAAUGGCACUAU | 63 |
| AM04345-AS | usCfsaGfaGfgUfgAfaAfaAfgUfuGfcAfuGfsgsuau | 358 | UCAGAGGUGAAAAGUUGCAUGGUAU | 64 |
| AM04346-AS | usGfscAfgAfgGfuGfaAfaAfaGfuUfgCfaUfsgsuau | 359 | UGCAGAGGUGAAAAGUUGCAUGUAU | 65 |
| AM04347-AS | usGfsaUfgAfuUfaGfgCfaGfaGfgUfgAfaAfsasuau | 360 | UGAUGAUUAGGCAGAGGUGAAAAUAU | 66 |
| AM04348-AS | usGfsaGfaUfgAfuUfaGfgCfaGfaGfgUfgAfsasuau | 361 | UGAGAUGAUUAGGCAGAGGUGAAUAU | 67 |
| AM04357-AS | usCfsaCfgAfgUfcUfaGfaCfuCfuGfuGfgUfsasuau | 362 | UCACGAGUCUAGACUCUGUGGUAUAU | 68 |
| AM04358-AS | asUfsuGfaGfaGfaAfgUfcCfaCfcAfcGfaGfsusuau | 363 | AUUGAGAGAAGUCCACCACGAGUUAU | 69 |
| AM04359-AS | asAfsuUfgAfgAfgAfaGfuCfcAfcCfaCfgAfsgsuau | 364 | AAUUGAGAGAAGUCCACCACGAGUAU | 70 |
| AM04360-AS | usUfsaGfaAfaAfuUfgAfgAfgAfaGfuCfcAfscsuau | 365 | UUAGAAAAUUGAGAGAAGUCCACUAU | 71 |
| AM04361-AS | usGfscGfuCfaGfcAfaAfcAfcUfuGfgCfaCfsasuau | 366 | UGCGUCAGCAAACACUUGGCACAUAU | 10 |
| AM04362-AS | usUfsaUfgGfaUfcGfgCfaGfaGfgAfgCfcAfscsuau | 367 | UUAUGGAUCGGCAGAGGAGCCACUAU | 72 |
| AM04363-AS | usCfsaGfuAfuGfgAfuCfgGfcAfgAfgGfaGfscsuau | 368 | UCAGUAUGGAUCGGCAGAGGAGCUAU | 73 |
| AM04364-AS | usGfsgAfgUfuCfcGfcAfgUfaUfgGfaUfcGfsgsuau | 369 | UGGAGUUCCGCAGUAUGGAUCGGUAU | 74 |
| AM04441-AS | usAfscCfaAfuUfuAfuGfcCfuAfcAfgGfscscsu | 370 | UACCAAUUUAUGCCUACAGGCCU | 75 |
| AM04442-AS | usAfscsCfaAfuUfuAfuGfcCfuAfcAfgGfccsu | 371 | UACCAAUUUAUGCCUACAGGCCU | 75 |
| AM04443-AS | usAfscsCfaAfuUfuAfuGfcCfuAfcAfgGfsc | 372 | UACCAAUUUAUGCCUACAGGC | 76 |
| AM04446-AS | usGfsaAfgCfgAfaGfuGfcAfcAfcGfgAfcscsg | 373 | UGAAGCGAAGUGCACACGGACCG | 77 |
| AM04447-AS | usGfsasAfgCfgAfaGfuGfcAfcAfcGfgAfcscsg | 374 | UGAAGCGAAGUGCACACGGACCG | 77 |
| AM04448-AS | usGfsasAfgCfgAfaGfuGfcAfcAfcGfgAfsc | 375 | UGAAGCGAAGUGCACACGGAC | 78 |
| AM04459-AS | usGfsgAfcAfaAfcGfgGfcAfaCfaUfaCfcsusu | 376 | UGGACAAACGGGCAACAUACCUU | 79 |
| AM04460-AS | usGfsgsAfcAfaAfcGfgGfcAfaCfaUfaCfcusu | 377 | UGGACAAACGGGCAACAUACCUU | 79 |
| AM04461-AS | usGfsgsAfcAfaAfcGfgGfcAfaCfaUfaCfsc | 378 | UGGACAAACGGGCAACAUACC | 80 |
| AM04661-AS | usGfsugaAfgCfGfgfaagUfGfcAfcacsusu | 380 | UGUGAAGCGAAGUGCACACUU | 82 |

TABLE 1A-continued

HBV RNAi trigger antisense strand sequences.

| AS strand ID | Modified sequence (5'→3') | SEQ ID NO. | Unmodified sequence (5'→3') | SEQ ID NO. |
|---|---|---|---|---|
| AM04662-AS | usAfsaaaUfuGfAfgagaAfgUfccaccsasc | 381 | UAAAAUUGAGAGAAGUCCACCAC | 83 |
| AM04746-AS | usUfsgAfaGfcGfaAfgUfgCfaCfaCfgGfascscgcg | 382 | UUGAAGCGAAGUGCACACGGACCGCG | 84 |
| AM04747-AS | vpusUfsgAfaGfcGfaAfgUfgCfaCfaCfgGfascscgcg | 383 | UUGAAGCGAAGUGCACACGGACCGCG | 84 |
| AM04749-AS | usGfsuGfaAfgCfgAfaGfuGfcAfcAfcGfgsasccgc | 384 | UGUGAAGCGAAGUGCACACGGACCGC | 85 |
| AM04750-AS | vpusGfsuGfaAfgCfgAfaGfuGfcAfcAfcGfgsasccgc | 385 | UGUGAAGCGAAGUGCACACGGACCGC | 85 |
| AM04752-AS | usGfsaUfaAfaAfcGfcCfgCfaGfaCfaCfasusccgc | 386 | UGAUAAACGCCGCAGACACAUCCGC | 86 |
| AM04753-AS | vpusGfsaUfaAfaAfcGfcCfgCfaGfaCfaCfasusccgc | 387 | UGAUAAACGCCGCAGACACAUCCGC | 86 |
| AM04755-AS | usAfsuGfaUfaAfaAfcGfcCfgCfaGfaCfascsacgc | 388 | UAUGAUAAACGCCGCAGACACACGC | 87 |
| AM04756-AS | vpusAfsuGfaUfaAfaAfcGfcCfgCfaGfaCfascsacgc | 389 | UAUGAUAAACGCCGCAGACACACGC | 87 |
| AM04758-AS | asGfsuGfaAfgCfgAfaGfuGfcAfcAfcGfgsasccgc | 390 | AGUGAAGCGAAGUGCACACGGACCGC | 88 |
| AM04760-AS | asAfsuGfaUfaAfaAfcGfcCfgCfaGfaCfascsacgc | 391 | AAUGAUAAACGCCGCAGACACACGC | 89 |
| AM04762-AS | usGfsaAfgCfgAfaGfuGfcAfcAfcGfgAfcscsgcgc | 392 | UGAAGCGAAGUGCACACGGACCGCGC | 90 |
| AM04763-AS | vpusGfsaAfgCfgAfaGfuGfcAfcAfcGfgAfcscsgcgc | 393 | UGAAGCGAAGUGCACACGGACCGCGC | 90 |
| AM04765-AS | usGfsgAfcAfaAfcGfgGfcAfaCfaUfaCfcsusucgc | 394 | UGGACAAACGGGCAACAUACCUUCGC | 91 |
| AM04766-AS | vpusGfsgAfcAfaAfcGfgGfcAfaCfaUfaCfcsusucgc | 395 | UGGACAAACGGGCAACAUACCUUCGC | 91 |
| AM04768-AS | usAfscCfaAfuUfuAfuGfcCfuAfcAfgCfcsusccgc | 396 | UACCAAUUUAUGCCUACAGCCUCCGC | 92 |
| AM04769-AS | vpusAfscCfaAfuUfuAfuGfcCfuAfcAfgCfcsusccgc | 397 | UACCAAUUUAUGCCUACAGCCUCCGC | 92 |
| AM04782-AS | aAfuUfuAfuGfcCfuAfcAfgdTsdT | 398 | AAUUUAUGCCUACAGTT | 94 |
| AM04784-AS | uGfaUfuAfgGfcAfgAfgGfudTsdT | 399 | UGAUUAGGCAGAGGUTT | 93 |
| AM04789-AS | aAfuUfuAfugcCfuAfcAfgdTsdT | 400 | AAUUUAUGCCUACAGTT | 94 |
| AM05011-AS | usAfscsCfaAfuUfuAfuGfcCfuAfcAfgusu | 401 | UACCAAUUUAUGCCUACAGUU | 95 |
| AM05012-AS | usAfscsCfaAfuUfuAfuGfcCfuAfcAfggsc | 402 | UACCAAUUUAUGCCUACAGGC | 76 |
| AM05013-AS | vpusAfscsCfaAfuUfuAfuGfcCfuAfcAfgGfsc | 403 | UACCAAUUUAUGCCUACAGGC | 76 |
| AM05014-AS | vpusAfscsCfaAfuUfuAfuGfcCfuAfcAfgusu | 404 | UACCAAUUUAUGCCUACAGUU | 95 |
| AM05052-AS | asUfsusGfaGfaGfaAfgUfcCfaCfcAfcGfsa | 405 | AUUGAGAGAAGUCCACCACGA | 96 |
| AM05053-AS | asUfsusGfaGfaGfaAfgUfcCfaCfcCfaAfcgsa | 406 | AUUGAGAGAAGUCCACCACGA | 96 |
| AM05054-AS | asUfsusGfaGfaGfaAfgUfcCfaCfcAfcusu | 407 | AUUGAGAGAAGUCCACCACUU | 97 |
| AM05055-AS | vpusUfsusGfaGfaGfaAfgUfcCfaCfcAfcGfsa | 408 | UUUGAGAGAAGUCCACCACGA | 98 |
| AM05056-AS | asAfsusUfgAfgAfgAfaGfuCfcAfcCfaCfsg | 409 | AAUUGAGAGAAGUCCACCACG | 99 |
| AM05057-AS | asAfsusUfgAfgAfgAfaGfuCfcAfcCfacsg | 410 | AAUUGAGAGAAGUCCACCACG | 99 |
| AM05058-AS | asAfsusUfgAfgAfgAfaGfuCfcAfcCfausu | 411 | AAUUGAGAGAAGUCCACCAUU | 100 |
| AM05060-AS | vpusAfsusUfgAfgAfgAfaGfuCfcAfcCfaCfsg | 412 | UAUUGAGAGAAGUCCACCACG | 101 |
| AM05061-AS | usUfsasGfaAfaAfuUfgAfgAfgAfaGfuCfsc | 413 | UUAGAAAAUUGAGAGAAGUCC | 102 |
| AM05062-AS | vpusUfsasGfaAfaAfuUfgAfgAfgAfaGfuCfsc | 414 | UUAGAAAAUUGAGAGAAGUCC | 102 |

TABLE 1B

HBV RNAi trigger sense strand sequences.

| Strand ID | Modified sequence (5'→3') | SEQ ID NO. | Unmodified sequence (5'→3') | SEQ ID NO. |
|---|---|---|---|---|
| AM00005-SS | (Chol-ALNY)uAuCfuGfuAfgGfcAfuAfaAfuUfgGfuAf(invdT) | 415 | UAUCUGUAGGCAUAAAUUGGUAT | 103 |
| AM00007-SS | (Chol-ALNY)uAuUfcUfgCfgGfcGfuUfuUfaUfcAfuAf(invdT) | 416 | UAUUCUGCGGCGUUUUAUCAUAT | 104 |
| AM00009-SS | (Chol-ALNY)uAuAfcCfuCfuGfcCfuAfaUfcAfuCfuAf(invdT) | 417 | UAUACCUCUGCCUAAUCAUCUAT | 105 |
| AM00013-SS | (Toc)uAuAfcCfuCfuGfcCfuAfaUfcAfuCfuAf(invdT) | 418 | UAUACCUCUGCCUAAUCAUCUAT | 105 |
| AM00014-SS | (Chol-TEG)uAuAfcCfuCfuGfcCfuAfaUfcAfuCfuAf(invdT) | 419 | UAUACCUCUGCCUAAUCAUCUAT | 105 |
| AM00015-SS | (Chol-C6)uAuCfuGfuAfgGfcAfuAfaAfuUfgGfuAf(invdT) | 420 | UAUCUGUAGGCAUAAAUUGGUAT | 103 |
| AM00016-SS | (Chol-C6)uAuAfcCfuCfuGfcCfuAfaUfcAfuCfuAf(invdT) | 421 | UAUACCUCUGCCUAAUCAUCUAT | 105 |
| AM00029-SS | (NH2-C6)CfuGfuAfgGfcAfuAfaAfuUfgGfuAf(invdT) | 422 | CUGUAGGCAUAAAUUGGUAT | 106 |
| AM00039-SS | (NH2-C6)AfcCfuCfuGfcCfuAfaUfcAfuCfuAf(invdT) | 423 | ACCUCUGCCUAAUCAUCUAT | 107 |
| AM00138-SS | (NH2-C6)UfuUfaCfuAfgUfgCfcAfuUfuGfuAf(invdT) | 424 | UUUACUAGUGCCAUUUGUAT | 108 |
| AM00175-SS | (NH2-C6)uAuCfuGfuagGfcAfuAfaAfuUfgGfuAf(invdT) | 425 | UAUCUGUAGGCAUAAAUUGGUAT | 103 |
| AM00176-SS | (NH2-C6)uAuAfcCfucuGfcCfuAfaUfcAfuCfuAf(invdT) | 426 | UAUACCUCUGCCUAAUCAUCUAT | 105 |
| AM00177-SS | (NH2-C6)uAuCfuGfuAfgGfcAfuAfaAfuUfgGfuAf(invdT) | 427 | UAUCUGUAGGCAUAAAUUGGUAT | 103 |
| AM00178-SS | (NH2-C6)uAuAfcCfuCfuGfcCfuAfaUfcAfuCfuAf(invdT) | 428 | UAUACCUCUGCCUAAUCAUCUAT | 105 |
| AM00179-SS | (NH2-C6)CfuGfuagGfcAfuAfaAfuUfgGfuAf(invdT) | 429 | CUGUAGGCAUAAAUUGGUAT | 106 |
| AM00180-SS | (NH2-C6)AfcCfucuGfcCfuAfaUfcAfuCfuAf(invdT) | 430 | ACCUCUGCCUAAUCAUCUAT | 107 |
| AM00429-SS | (NH2-C6)AfcCfuCfugcCfuAfaUfcAfuCfuAf(invdT) | 431 | ACCUCUGCCUAAUCAUCUAT | 107 |
| AM00430-SS | (NH2-C6)AfcCfuCfuGfccuAfaUfcAfuCfuAf(invdT) | 432 | ACCUCUGCCUAAUCAUCUAT | 107 |
| AM00431-SS | (NH2-C6)AfcCfuCfuGfcCfuaaUfcAfuCfuAf(invdT) | 433 | ACCUCUGCCUAAUCAUCUAT | 107 |
| AM00432-SS | (NH2-C6)AfcCfuCfuGfcCfuAfaucAfuCfuAf(invdT) | 434 | ACCUCUGCCUAAUCAUCUAT | 107 |
| AM00433-SS | (NH2-C6)AfcCfuCfUfGfcCfuAfaUfcAfuCfuAf(invdT) | 435 | ACCUCUGCCUAAUCAUCUAT | 107 |
| AM00434-SS | (NH2-C6)AfcCfuCfuGfcCfCfuAfaUfcAfuCfuAf(invdT) | 436 | ACCUCUGCCUAAUCAUCUAT | 107 |
| AM00435-SS | (NH2-C6)AfcCfuCfuGfcCfUfAfaUfcAfuCfuAf(invdT) | 437 | ACCUCUGCCUAAUCAUCUAT | 107 |
| AM00436-SS | (NH2-C6)AfcCfuCfuGfcCfuAfAfUfcAfuCfuAf(invdT) | 438 | ACCUCUGCCUAAUCAUCUAT | 107 |
| AM00437-SS | (NH2-C6)AfcCfuCfuGfcCfuAfaUfCfAfuCfuAf(invdT) | 439 | ACCUCUGCCUAAUCAUCUAT | 107 |
| AM00440-SS | (NH2-C6)CUNAuGfuAfgGfcAfuAfaAfuUfgGfuAf(invdT) | 440 | CUGUAGGCAUAAAUUGGUAT | 106 |
| AM00441-SS | (NH2-C6)CfUUNAGfuAfgGfcAfuAfaAfuUfgGfuAf(invdT) | 441 | CUGUAGGCAUAAAUUGGUAT | 106 |
| AM00442-SS | (NH2-C6)AUNAcCfuCfuGfcCfuAfaUfcAfuCfuAf(invdT) | 442 | ACCUCUGCCUAAUCAUCUAT | 107 |
| AM00443-SS | (NH2-C6)AfCUNACfuCfuGfcCfuAfaUfcAfuCfuAf(invdT) | 443 | ACCUCUGCCUAAUCAUCUAT | 107 |
| AM00620-SS | CfuGfuAfgGfcAfuAfaAfuUfgGfuAf(invdT) | 444 | CUGUAGGCAUAAAUUGGUAT | 106 |
| AM00621-SS | AfcCfuCfuGfcCfuAfaUfcAfuCfuAf(invdT) | 445 | ACCUCUGCCUAAUCAUCUAT | 107 |
| AM01885-SS | (Chol-C6)uAuCfuGfuAfgGfcAfuAfaAfuUfgGfuAf(invdT)(TEG-Biotin) | 446 | UAUCUGUAGGCAUAAAUUGGUAT | 103 |
| AM01886-SS | (Chol-C6)uAuAfcCfuCfuGfcCfuAfaUfcAfuCfuAf(invdT)(TEG-Biotin) | 447 | UAUACCUCUGCCUAAUCAUCUAT | 105 |
| AM01934-SS | (NH2-C6)CfuGfuAfgGfCfAfuAfaAfuUfgGfuAf(invdT) | 448 | CUGUAGGCAUAAAUUGGUAT | 106 |
| AM01936-SS | (NH2-C6)CfuGfuAfgGfCfAfuAfaAfuUfgGfsusAf(invdT) | 449 | CUGUAGGCAUAAAUUGGUAT | 106 |
| AM01939-SS | (NH2-C6)AfcCfuCfuGfcCfCfuAfaUfcAfuCfsusAf(invdT) | 450 | ACCUCUGCCUAAUCAUCUAT | 107 |
| AM01940-SS | (NH2-C6)UfuUfaCfuAfgGfUfgCfcAfuUfuGfuAf(invdT) | 451 | UUUACUAGUGCCAUUUGUAT | 108 |

TABLE 1B-continued

HBV RNAi trigger sense strand sequences.

| Strand ID | Modified sequence (5'→3') | SEQ ID NO. | Unmodified sequence (5'→3') | SEQ ID NO. |
|---|---|---|---|---|
| AM01941-SS | (NH2-C6)UfuUfaCfuAfGfUfgCfcAfuUfuGfsusAf(invdT) | 452 | UUUACUAGUGCCAUUUGUAT | 108 |
| AM01963-SS | (Alk-SS-C6)CfuGfuAfgGfcAfuAfaAfuUfgGfuAf(invdT) | 453 | CUGUAGGCAUAAAUUGGUAT | 106 |
| AM01964-SS | (Alk-SS-C6)AfcCfuCfuGfcCfuAfaUfcAfuCfuAf(invdT) | 454 | ACCUCUGCCUAAUCAUCUAT | 107 |
| AM01965-SS | (Alk-SS-C6)UfuUfaCfuAfgUfgCfcAfuUfuGfuAf(invdT) | 455 | UUUACUAGUGCCAUUUGUAT | 108 |
| AM01979-SS | (NH2-C6)UfcUfgCfgGfcGfuUfuUfaUfcAfuAf(invdT) | 456 | UCUGCGGCGUUUUAUCAUAT | 109 |
| AM01984-SS | (Alk-SS-C6)UfcUfgCfgGfcGfuUfuUfaUfcAfuAf(invdT) | 457 | UCUGCGGCGUUUUAUCAUAT | 109 |
| AM01991-SS | (NH2-C6)UfcUfgCfgGfcCfGfuUfuUfaUfcAfuAf(invdT) | 458 | UCUGCGGCGUUUUAUCAUAT | 109 |
| AM01992-SS | (NH2-C6)UfcUfgCfgGfcCfGfuUfuUfaUfcAfsusAf(invdT) | 459 | UCUGCGGCGUUUUAUCAUAT | 109 |
| AM02080-SS | (Alk-SS-C6)AfcCfuCfuGfcCfCfuAfaUfcAfuCfuAf(invdT) | 460 | ACCUCUGCCUAAUCAUCUAT | 107 |
| AM02081-SS | (Alk-SS-C6)AfcCfuCfuGfcCfCfuAfaUfcAfuCfsusAf(invdT) | 461 | ACCUCUGCCUAAUCAUCUAT | 107 |
| AM02082-SS | (Alk-SS-C6)CfuGfuAfgGfcCfAfuAfaAfuUfgGfuAf(invdT) | 462 | CUGUAGGCAUAAAUUGGUAT | 106 |
| AM02083-SS | (Alk-SS-C6)CfuGfuAfgGfcCfAfuAfaAfuUfgGfsusAf(invdT) | 463 | CUGUAGGCAUAAAUUGGUAT | 106 |
| AM02187-SS | (Alk-SS-C6)UfuUfaCfuAfgGfUfgCfcAfuUfuGfsusAf(invdT) | 464 | UUUACUAGUGCCAUUUGUAT | 108 |
| AM02189-SS | (Alk-SS-C6)UfcUfgCfgGfcCfGfuUfuUfaUfcAfsusAf(invdT) | 465 | UCUGCGGCGUUUUAUCAUAT | 109 |
| AM02278-SS | (Alk-SS-C6)CfuGfuAfgGfcAfuAfaAfuUfgGfsusAf(invdT) | 466 | CUGUAGGCAUAAAUUGGUAT | 106 |
| AM02283-SS | (Alk-SS-C6)AfcCfuCfuGfcCfuAfaUfcAfuCfsusAf(invdT) | 467 | ACCUCUGCCUAAUCAUCUAT | 107 |
| AM02285-SS | (Alk-SS-C6)UfuUfaCfuAfgUfgCfcAfuUfuGfsusAf(invdT) | 468 | UUUACUAGUGCCAUUUGUAT | 108 |
| AM02291-SS | (Alk-SS-C6)UfcUfgCfgGfcGfuUfuUfaUfcAfsusAf(invdT) | 469 | UCUGCGGCGUUUUAUCAUAT | 109 |
| AM02316-SS | (Chol-TEG)uAuCfuGfuAfgGfcCfAfuAfaAfuUfgGfuAf(invdT) | 470 | UAUCUGUAGGCAUAAAUUGGUAT | 103 |
| AM02317-SS | (Chol-TEG)uAuAfcCfuCfuGfcCfCfuAfaUfcAfuCfuAf(invdT) | 471 | UAUACCUCUGCCUAAUCAUCUAT | 105 |
| AM02318-SS | (Chol-TEG)uAuUfuAfCfuAfgGfUfgCfcAfuUfuGfuAf(invdT) | 472 | UAUUUUACUAGUGCCAUUUGUAT | 110 |
| AM02319-SS | (Chol-TEG)uAuUfcUfgCfgGfcCfGfuUfuUfaUfcAfuAf(invdT) | 473 | UAUUCUGCGGCGUUUUAUCAUAT | 104 |
| AM02320-SS | (Chol-C6)uAuCfuGfuAfgGfcAfuAfaAfuUfgGfuAf(invdT) | 474 | UAUCUGUAGGCAUAAAUUGGUAT | 103 |
| AM02321-SS | (Chol-C6)uAuAfcCfuCfuGfcCfCfuAfaUfcAfuCfuAf(invdT) | 475 | UAUACCUCUGCCUAAUCAUCUAT | 105 |
| AM02322-SS | (Chol-C6)uAuUfuUfaCfuAfgUfgCfcAfuUfuGfuAf(invdT) | 476 | UAUUUUACUAGUGCCAUUUGUAT | 110 |
| AM02323-SS | (Chol-C6)uAuUfcUfgCfgGfcGfuUfuUfaUfcAfuAf(invdT) | 477 | UAUUCUGCGGCGUUUUAUCAUAT | 104 |
| AM02370-SS | (Chol-TEG)uAuAusGfscCfuGfuAfgGfCfAfuAfaAfuUfgGfsusAf | 478 | UAUAUGCCUGUAGGCAUAAAUUGGUA | 111 |
| AM02371-SS | (Chol-TEG)uAuAuGfcCfuGfuAfggCfAfuAfaAfuUfgGfu(invdA) | 479 | UAUAUGCCUGUAGGCAUAAAUUGGUA | 111 |
| AM02372-SS | (Chol-TEG)uAuAusGfscCfuGfuAfGfgCfAfuAfaAfuUfgGfsusAf | 480 | UAUAUGCCUGUAGGCAUAAAUUGGUA | 111 |
| AM02373-SS | (Chol-TEG)uAuAuGfcCfuGfuAfgGfgCfAfuAfaAfuUfgGfu(invdA) | 481 | UAUAUGCCUGUAGGCAUAAAUUGGUA | 111 |
| AM02378-SS | (Chol-TEG)uAuAusUfsgUfcUfgCfggCfGfuUfuUfaUfcAfsusAf | 482 | UAUAUUGUCUGCGGCGUUUUAUCAUA | 112 |
| AM02379-SS | (Chol-TEG)uAuAuUfgUfcUfgCfggCfGfuUfuUfaUfcAfu(invdA) | 483 | UAUAUUGUCUGCGGCGUUUUAUCAUA | 112 |
| AM02380-SS | (Chol-TEG)uAuAusUfsgUfcUfgCfGfgCfGfuUfuUfaUfcAfsusAf | 484 | UAUAUUGUCUGCGGCGUUUUAUCAUA | 112 |
| AM02381-SS | (Chol-TEG)uAuAuUfgUfcUfgCfGfgCfGfuUfuUfaUfcA | 485 | UAUAUUGUCUGCGGCGUUUUAUCAUA | 112 |

TABLE 1B-continued

HBV RNAi trigger sense strand sequences.

| Strand ID | Modified sequence (5'→3') | SEQ ID NO. | Unmodified sequence (5'→3') | SEQ ID NO. |
|---|---|---|---|---|
| | fu(invdA) | | | |
| AM02386-SS | (Chol-TEG)uAuAusCfsaAfcCfuCfugCfCfuAfaUfcAfuCfsusAf | 486 | UAUAUCAACCUCUGCCUAAUCAUCUA | 113 |
| AM02387-SS | (Chol-TEG)uAuAuCfaAfcCfuCfugCfCfuAfaUfcAfuCfu(invdA) | 487 | UAUAUCAACCUCUGCCUAAUCAUCUA | 113 |
| AM02388-SS | (Chol-TEG)uAuAusCfsaAfcCfuCfUfgCfCfuAfaUfcAfuCfsusAf | 488 | UAUAUCAACCUCUGCCUAAUCAUCUA | 113 |
| AM02389-SS | (Chol-TEG)uAuAuCfaAfcCfuCfUfgCfCfuAfaUfcAfuCfu(invdA) | 489 | UAUAUCAACCUCUGCCUAAUCAUCUA | 113 |
| AM02483-SS | UfcUfgCfgCfgCfGfuUfuUfaUfcAfuAf(invdT) | 490 | UCUGCGGCGUUUUAUCAUAT | 109 |
| AM02486-SS | UfcUfgCfgGfcGfuUfuUfaUfcAfuAf(invdT) | 491 | UCUGCGGCGUUUUAUCAUAT | 109 |
| AM02489-SS | (Chol-C6)uAuUfcUfgCfgGfcGfuUfuUfaUfcAfuAf(invdT) | 492 | UAUUCUGCGGCGUUUUAUCAUAT | 104 |
| AM02576-SS | CfuGfuAfgGfCfAfuAfaAfuUfgGfuAf(invdT) | 493 | CUGUAGGCAUAAAUUGGUAT | 106 |
| AM02578-SS | AfcCfuCfuGfcCfuAfaUfcAfuCfuAf(invdT) | 494 | ACCUCUGCCUAAUCAUCUAT | 107 |
| AM02888-SS | uAuAusUfgUfgUfcUfgcGfGfcGfuUfuUfaUfcAf(C6-SS-Alk-Me) | 495 | UAUAUUGUGUCUGCGGCGUUUUAUCA | 114 |
| AM02891-SS | uAuAusUfuUfaCfuAfguGfUfcAfuUfuGfuUfcAf(C6-SS-Alk-Me) | 496 | UAUAUUUUACUAGUGCCAUUUGUUCA | 115 |
| AM02894-SS | uAuAusUfgCfcAfaGfugUfUfuGfcUfgAfcGfcAf(C6-SS-Alk-Me) | 497 | UAUAUUGCCAAGUGUUUGCUGACGCA | 116 |
| AM02897-SS | uAuAusUfgCfcAfuUfugUfUfcAfgUfgGfuUfcAf(C6-SS-Alk-Me) | 498 | UAUAUUGCCAUUUGUUCAGUGGUUCA | 117 |
| AM02900-SS | uAuAusAfuCfaAfgGfuaUfGfuUfgCfcCfgUfuAf(C6-SS-Alk-Me) | 499 | UAUAUAUCAAGGUAUGUUGCCCGUUA | 118 |
| AM02903-SS | uAuAusUfcCfuGfgCfucAfGfuUfuAfcUfaGfuAf(C6-SS-Alk-Me) | 500 | UAUAUUCCUGGCUCAGUUUACUAGUA | 119 |
| AM02906-SS | uAuAusGfgUfaUfgUfugCfCfcGfuUfuGfuCfcAf(C6-SS-Alk-Me) | 501 | UAUAUGGUAUGUUGCCCGUUUGUCCA | 120 |
| AM02909-SS | uAuAusUfaUfcAfaGfguAfUfgUfuGfcCfcGfuAf(C6-SS-Alk-Me) | 502 | UAUAUUAUCAAGGUAUGUUGCCCGUA | 121 |
| AM02912-SS | uAuAusGfuCfcGfuGfugCfAfcUfuCfgCfuUfcAf(C6-SS-Alk-Me) | 503 | UAUAUGUCCGUGUGCACUUCGCUUCA | 122 |
| AM02915-SS | uAuAusUfgUfgUfCfugCfgGfcGfuUfuUfaUfcAf(C6-SS-Alk-Me) | 504 | UAUAUUGUGUCUGCGGCGUUUUAUCA | 114 |
| AM02918-SS | uAuAusUfuUfaCfUfagUfgCfcAfuUfuGfuUfcAf(C6-SS-Alk-Me) | 505 | UAUAUUUUACUAGUGCCAUUUGUUCA | 115 |
| AM02921-SS | uAuAusUfgCfcAfAfguGfuUfuGfcUfgAfcGfcAf(C6-SS-Alk-Me) | 506 | UAUAUUGCCAAGUGUUUGCUGACGCA | 116 |
| AM02924-SS | uAuAusUfgCfcAfUfuuGfuUfcAfgUfgGfuUfcAf(C6-SS-Alk-Me) | 507 | UAUAUUGCCAUUUGUUCAGUGGUUCA | 117 |
| AM02927-SS | uAuAusAfuCfaAfGfguAfuGfuUfgCfcCfgUfuAf(C6-SS-Alk-Me) | 508 | UAUAUAUCAAGGUAUGUUGCCCGUUA | 118 |
| AM02930-SS | uAuAusUfcCfuGfgCfucCfaGfuUfuAfcUfaGfuAf(C6-SS-Alk-Me) | 509 | UAUAUUCCUGGCUCAGUUUACUAGUA | 119 |
| AM02933-SS | uAuAusGfgUfaUfGfuuGfcCfcGfuUfuGfuCfcAf(C6-SS-Alk-Me) | 510 | UAUAUGGUAUGUUGCCCGUUUGUCCA | 120 |
| AM02936-SS | uAuAusUfaUfcAfAfggUfaUfgUfuGfcCfcGfuAf(C6-SS-Alk-Me) | 511 | UAUAUUAUCAAGGUAUGUUGCCCGUA | 121 |
| AM02939-SS | uAuAusGfuCfcGfUfguGfcAfcUfuCfgCfuUfcAf | 512 | UAUAUGUCCGUGUGCACUUCGCUUCA | 122 |

TABLE 1B-continued

HBV RNAi trigger sense strand sequences.

| Strand ID | Modified sequence (5'→3') | SEQ ID NO. | Unmodified sequence (5'→3') | SEQ ID NO. |
|---|---|---|---|---|
| | (C6-SS-Alk-Me) | | | |
| AM02978-SS | uAuAusGfcCfuGfuAfggCfAfuAfaAfuUfgGfuAf (C6-SS-Alk-Me) | 513 | UAUAUGCCUGUAGGCAUAAAUUGGUA | 111 |
| AM02979-SS | uAuAusGfcCfuGfuAfggCfAfuAfaAfuUfgGfuAf (C11-PEG3-NAG3) | 514 | UAUAUGCCUGUAGGCAUAAAUUGGUA | 111 |
| AM02981-SS | uAuAusGfcCfuGfUfagGfcAfuAfaAfuUfgGfuAf (C6-SS-Alk-Me) | 515 | UAUAUGCCUGUAGGCAUAAAUUGGUA | 111 |
| AM02987-SS | uAuAusUfgUfcUfgCfggCfGfuUfuUfaUfcAfuAf (C6-SS-Alk-Me) | 516 | UAUAUUGUCUGCGGCGUUUUAUCAUA | 112 |
| AM02988-SS | uAuAusUfgUfcUfgCfggCfGfuUfuUfaUfcAfuAf (C11-PEG3-NAG3) | 517 | UAUAUUGUCUGCGGCGUUUUAUCAUA | 112 |
| AM02990-SS | uAuAusUfgUfcUfGfcgGfcUfuUfuUfaUfcAfuAf (C6-SS-Alk-Me) | 518 | UAUAUUGUCUGCGGCGUUUUAUCAUA | 112 |
| AM02992-SS | uAuAusCfaAfcCfuCfugCfCfuAfaUfcAfuCfuAf (C6-SS-Alk-Me) | 519 | UAUAUCAACCUCUGCCUAAUCAUCUA | 113 |
| AM02993-SS | uAuAusCfaAfcCfuCfugCfCfuAfaUfcAfuCfuAf (C11-PEG3-NAG3) | 520 | UAUAUCAACCUCUGCCUAAUCAUCUA | 113 |
| AM02995-SS | uAuAusCfaAfcCfUfcuGfcCfuAfaUfcAfuCfuAf (C6-SS-Alk-Me) | 521 | UAUAUCAACCUCUGCCUAAUCAUCUA | 113 |
| AM03087-SS | (Chol-TEG)uAuUfgUfcUfgCfgGfcGfuUfuUfaUfcAf(invdT) | 522 | UAUUGUCUGCGGCGUUUUAUCAT | 123 |
| AM03088-SS | (Chol-TEG)uAuUfaCfuAfgUfgCfcAfuUfgUfuUfcAf(invdT) | 523 | UAUUACUAGUGCCAUUGUUCAT | 124 |
| AM03089-SS | (Chol-TEG)uAuCfcAfaGfuGfuUfuGfcUfgAfcGfcAf(invdT) | 524 | UAUCCAAGUGUUUGCUGACGCAT | 125 |
| AM03090-SS | (Chol-TEG)uAuCfcAfuUfuGfuUfcAfgUfgGfuUfcAf(invdT) | 525 | UAUCCAUUUGUUCAGUGGUUCAT | 126 |
| AM03091-SS | (Chol-TEG)uAuCfaAfgGfuAfuGfuUfgCfcCfgUfuAf(invdT) | 526 | UAUCAAGGUAUGUUGCCCGUUAT | 127 |
| AM03092-SS | (Chol-TEG)uAuCfuGfgCfuCfaGfuUfuAfcUfaGfuAf(invdT) | 527 | UAUCUGGCUCAGUUUACUAGUAT | 128 |
| AM03093-SS | (Chol-TEG)uAuUfaUfgUfuGfcCfcGfuUfuGfuCfcAf(invdT) | 528 | UAUUAUGUUGCCCGUUUGUCCAT | 129 |
| AM03094-SS | (Chol-TEG)uAuUfcAfaGfgUfaUfgUfuGfcCfcGfuAf(invdT) | 529 | UAUUCAAGGUAUGUUGCCCGUAT | 130 |
| AM03095-SS | (Chol-TEG)uAuCfcGfuGfuGfcAfcUfuCfgCfuUfcAf(invdT) | 530 | UAUCCGUGUGCACUUCGCUUCAT | 131 |
| AM03096-SS | (Chol-TEG)uAuGfgCfgCfuGfaAfuCfcCfgCfgGfaAf(invdT) | 531 | UAUGGCGCUGAAUCCCGCGGAAT | 132 |
| AM03493-SS | uAuAusUfsuUfaCfuAfgUfgCfcAfuUfuGfuUfca(NAG13) | 532 | UAUAUUUUACUAGUGCCAUUUGUUCA | 115 |
| AM03494-SS | uAuAususuuacuagUfgCfcauuuguuca(NAG13) | 533 | UAUAUUUUACUAGUGCCAUUUGUUCA | 115 |
| AM03496-SS | uAuAususuuaCfuagUfgCfcauuuguuca(NAG13) | 534 | UAUAUUUUACUAGUGCCAUUUGUUCA | 115 |
| AM03497-SS | uAuAusGfsgUfaUfgUfuGfcCfcGfuUfuGfuCfca(NAG13) | 535 | UAUAUGGUAUGUUGCCCGUUUGUCCA | 120 |
| AM03498-SS | uAuAusgsguauguuGfcCfcguuuguCfca(NAG13) | 536 | UAUAUGGUAUGUUGCCCGUUUGUCCA | 120 |
| AM03499-SS | uAuAusgsguauguuGfcCfcguuugucca(NAG13) | 537 | UAUAUGGUAUGUUGCCCGUUUGUCCA | 120 |
| AM03501-SS | uAuAusGfsuCfcGfuGfuGfcAfcUfcCfgCfuUfca(NAG13) | 538 | UAUAUGUCCGUGUGCACUUCGCUUCA | 122 |
| AM03502-SS | uAuAusgsuCfcGfuguGfcAfcuuCfgCfuuca(NAG13) | 539 | UAUAUGUCCGUGUGCACUUCGCUUCA | 122 |
| AM03503-SS | uAuAusgsuccguguGfcAfcuucgcuuca(NAG13) | 540 | UAUAUGUCCGUGUGCACUUCGCUUCA | 122 |
| AM03505-SS | uAuAusGfscCfuGfuAfgGfcAfuAfaAfuUfgGfua(NAG13) | 541 | UAUAUGCCUGUAGGCAUAAAUUGGUA | 111 |
| AM03506-SS | uAuAusgscCfuguagGfcAfuaaauuggua(NAG13) | 542 | UAUAUGCCUGUAGGCAUAAAUUGGUA | 111 |
| AM03507-SS | uAuAusgsccguagGfcAfuaaauuggua(NAG13) | 543 | UAUAUGCCUGUAGGCAUAAAUUGGUA | 111 |
| AM03509-SS | uAuAusCfsaAfcCfuCfuGfcCfuAfaUfcAfuCfua(NAG13) | 544 | UAUAUCAACCUCUGCCUAAUCAUCUA | 113 |

TABLE 1B-continued

HBV RNAi trigger sense strand sequences.

| Strand ID | Modified sequence (5'→3') | SEQ ID NO. | Unmodified sequence (5'→3') | SEQ ID NO. |
|---|---|---|---|---|
| AM03510-SS | uAuAusCfsaacCfuCfuGfcCfuaaucauCfua(NAG13) | 545 | UAUAUCAACCUCUGCCUAAUCAUCUA | 113 |
| AM03511-SS | uAuAuscsaaccucuGfcCfuaaucaucua(NAG13) | 546 | UAUAUCAACCUCUGCCUAAUCAUCUA | 113 |
| AM03763-SS | uAuAusuuacuagUfGfCfcauuuguuca(NAG13) | 547 | UAUAUUUACUAGUGCCAUUUGUUCA | 115 |
| AM03765-SS | uAuAusgsguauguuGfCfCfcguuugucca(NAG13) | 548 | UAUAUGGUAUGUUGCCCGUUUGUCCA | 120 |
| AM03767-SS | uAuAusguccgugugGfCfAfcuucgcuuca(NAG13) | 549 | UAUAUGUCCGUGUGCACUUCGCUUCA | 122 |
| AM03769-SS | uAuAusgsccguagGfCfAfuaaauuggua(NAG13) | 550 | UAUAUGCCUGUAGGCAUAAAUUGGUA | 111 |
| AM03771-SS | uAuAuscsaaccucuGfCfCfuaaucaucua(NAG13) | 551 | UAUAUCAACCUCUGCCUAAUCAUCUA | 113 |
| AM03914-SS | uAuAuusgsucugcgGfCfGfuuuuaucaua(NAG13) | 552 | UAUAUUGUCUGCGGCGUUUUAUCAUA | 112 |
| AM03915-SS | uAuAusgsucugcgGfcGfuuuuaucaua(NAG13) | 553 | UAUAUUGUCUGCGGCGUUUUAUCAUA | 112 |
| AM03918-SS | uAuAusgsgugucugCfGfGfcguuuuauca(NAG13) | 554 | UAUAUUGUGUCUGCGGCGUUUUAUCA | 114 |
| AM03919-SS | uAuAuusgsugucugCfgGfcguuuuauca(NAG13) | 555 | UAUAUUGUGUCUGCGGCGUUUUAUCA | 114 |
| AM03963-SS | (Chol-TEG)uAuUfcUfgCfgGfCfGfuUfuUfaUfcAfuAf(invdT)(TEG-Biotin) | 556 | UAUUCUGCGGCGUUUUAUCAUAT | 104 |
| AM03964-SS | (Chol-C6)uAuCfuGfuAfgGfCfAfuAfaAfuUfgGfuAf(invdT)(TEG-Biotin) | 557 | UAUCUGUAGGCAUAAAUUGGUAT | 103 |
| AM04262-SS | uauauscsggcgcugAfAfUfcccgcggac(invdT)(NAG13) | 558 | UAUAUCGGCGCUGAAUCCCGCGGACT | 133 |
| AM04263-SS | uauausasccgggcgCfAfCfcucucuuua(invdA)(NAG13) | 559 | UAUAUACCGGGCGCACCUCUCUUUAA | 134 |
| AM04264-SS | uauausgsgaccgugUfGfCfacuucgcuu(invdA)(NAG13) | 560 | UAUAUGGACCGUGUGCACUUCGCUUA | 135 |
| AM04265-SS | uauaususccgugugCfAfCfuuucgcuuca(invdA)(NAG13) | 561 | UAUAUUCCGUGUGCACUUCGCUUCAA | 136 |
| AM04266-SS | uauauscscgugugcAfCfUfucgcuucac(invdT)(NAG13) | 562 | UAUAUCCGUGUGCACUUCGCUUCACT | 137 |
| AM04267-SS | uauausgsugcacuuCfGfCfuucaccucu(invdA)(NAG13) | 563 | UAUAUGUGCACUUCGCUUCACCUCUA | 138 |
| AM04268-SS | uauaususgcacuucGfCfUfucaccucug(invdA)(NAG13) | 564 | UAUAUUGCACUUCGCUUCACCUCUGA | 139 |
| AM04269-SS | uauausgscacuucgCfUfUfcaccucugc(invdA)(NAG13) | 565 | UAUAUGCACUUCGCUUCACCUCUGCA | 140 |
| AM04270-SS | uauauscsccagcaaUfGfUfcaacgaccg(invdA)(NAG13) | 566 | UAUAUCCCAGCAAUGUCAACGACCGA | 141 |
| AM04271-SS | uauausasaugucaaCfGfAfccgaccuug(invdA)(NAG13) | 567 | UAUAUAAUGUCAACGACCGACCUUGA | 142 |
| AM04282-SS | uauausasggagauuAfGfGfuuaaagguc(invdA)(NAG13) | 568 | UAUAUAGGAGAUUAGGUUAAAGGUCA | 143 |
| AM04283-SS | uauaususaggaggcUfGfUfaggcauaaa(invdT)(NAG13) | 569 | UAUAUUAGGAGGCUGUAGGCAUAAAT | 144 |
| AM04284-SS | uauausasggaggcuGfUfAfggcauaaau(invdT)(NAG13) | 570 | UAUAUAGGAGGCUGUAGGCAUAAAUT | 145 |
| AM04285-SS | uauausgsgaggcugUfAfGfgcauaaauu(invdA)(NAG13) | 571 | UAUAUGGAGGCUGUAGGCAUAAAUUA | 146 |
| AM04286-SS | uauausgsaggcuguAfGfGfcauaaauug(invdA)(NAG13) | 572 | UAUAUGAGGCUGUAGGCAUAAAUUGA | 147 |
| AM04287-SS | uauausasggcuguaGfGfCfauaaauugg(invdA)(NAG13) | 573 | UAUAUAGGCUGUAGGCAUAAAUUGGA | 148 |
| AM04297-SS | uauausgscuggaugUfGfUfcugcggcgu(invdA)(NAG13) | 574 | UAUAUGCUGGAUGUGUCUGCGGCGUA | 149 |
| AM04298-SS | uauausgsgaugugucUfGfUfcggcguuuu(invdA)(NAG13) | 575 | UAUAUGGAUGUGUCUGCGGCGUUUA | 150 |
| AM04299-SS | uauausgsaugugucUfGfCfggcguuuua(invdA)(NAG13) | 576 | UAUAUGAUGUGUCUGCGGCGUUUAA | 151 |
| AM04300-SS | uauausgsugucugcGfGfCfguuuuauca(invdA)(NAG13) | 577 | UAUAUGUGUCUGCGGCGUUUUAUCAA | 152 |
| AM04301-SS | uauaususaucaagGfUfAfUfguugcccgu(invdA)(NAG13) | 578 | UAUAUUAUCAAGGUAUGUUGCCCGUA | 121 |
| AM04302-SS | uauausasucaagguAfUfGfuugcccguu(invdA)(NAG13) | 579 | UAUAUAUCAAGGUAUGUUGCCCGUUA | 118 |
| AM04303-SS | uauaususcaagguaUfGfUfugcccguuu(invdA)(NAG13) | 580 | UAUAUUCAAGGUAUGUUGCCCGUUUA | 153 |
| AM04304-SS | uauauscsaagguauGfUfUfgcccguuug(invdA)(NAG13) | 581 | UAUAUCAAGGUAUGUUGCCCGUUUGA | 154 |

TABLE 1B-continued

HBV RNAi trigger sense strand sequences.

| Strand ID | Modified sequence (5'→3') | SEQ ID NO. | Unmodified sequence (5'→3') | SEQ ID NO. |
|---|---|---|---|---|
| AM04305-SS | uauausasagguaugUfUfGfcccguuugu(invdA)(NAG13) | 582 | UAUAUAAGGUAUGUUGCCCGUUUGUA | 155 |
| AM04306-SS | uauausgsuauguugCfCfCfguuugalccu(invdA)(NAG13) | 583 | UAUAUGUAUGUUGCCCGUUUGUCCUA | 156 |
| AM04307-SS | uauaususccuggcuCfAfGfuuuacuagu(invdA)(NAG13) | 584 | UAUAUUCCUGGCUCAGUUUACUAGUA | 119 |
| AM04308-SS | uauaususggcucagUfUfUfacuagugcc(invdA)(NAG13) | 585 | UAUAUUGGCUCAGUUUACUAGUGCCA | 157 |
| AM04309-SS | uauausgsgcucaguUfUfAfcuagugcca(invdA)(NAG13) | 586 | UAUAUGGCUCAGUUUACUAGUGCCAA | 158 |
| AM04310-SS | uauauscsucaguuuAfCfUfagugccauu(invdA)(NAG13) | 587 | UAUAUCUCAGUUUACUAGUGCCAUUA | 159 |
| AM04311-SS | uauaususcaguuuaCfUfAfgugccauuu(invdA)(NAG13) | 588 | UAUAUUCAGUUUACUAGUGCCAUUUA | 160 |
| AM04312-SS | uauauscsaguuuacUfAfGfugccauuug(invdA)(NAG13) | 589 | UAUAUCAGUUUACUAGUGCCAUUUGA | 161 |
| AM04313-SS | uauausasguuuacuAfGfUfgccauuugu(invdA)(NAG13) | 590 | UAUAUAGUUUACUAGUGCCAUUUGUA | 162 |
| AM04314-SS | uauausususuacuaguGfCfCfauuuguuca(invdA)(NAG13) | 591 | UAUAUUACUAGUGCCAUUUGUUCAA | 163 |
| AM04315-SS | uauaususacuagugCfCfAfuuuguucag(invdT)(NAG13) | 592 | UAUAUUACUAGUGCCAUUUGUUCAGT | 164 |
| AM04316-SS | uauausgsugccauuUfGfUfucaguggbuu(invdA)(NAG13) | 593 | UAUAUGUGCCAUUUGUUCAGUGGUUA | 165 |
| AM04317-SS | uauaususgccauuuGfUfUfcaguggbuuc(invdA)(NAG13) | 594 | UAUAUUGCCAUUUGUUCAGUGGUUCA | 117 |
| AM04318-SS | uauausgsccauuugUfUfCfaguggbuucg(invdA)(NAG13) | 595 | UAUAUGCCAUUUGUUCAGUGGUUCGA | 167 |
| AM04319-SS | uauausasugcaacuUfUfUfucaccucug(invdA)(NAG13) | 596 | UAUAUAUGCAACUUUUUCACCUCUGA | 168 |
| AM04320-SS | uauaususgcaacuuUfUfUfcaccucugc(invdA)(NAG13) | 597 | UAUAUUGCAACUUUUUCACCUCUGCA | 169 |
| AM04321-SS | uauaususucaccucUfGfCfcuaaucauc(invdA)(NAG13) | 598 | UAUAUUCACCUCUGCCUAAUCAUCA | 170 |
| AM04322-SS | uauauscsaccucugCfCfUfaaucaucuc(invdA)(NAG13) | 599 | UAUAUCACCUCUGCCUAAUCAUCUCA | 171 |
| AM04349-SS | uauauscscacagagUfCfUfagacucgug(invdA)(NAG13) | 600 | UAUAUCCACAGAGUCUAGACUCGUGA | 172 |
| AM04350-SS | uauaususcguggbugGfAfCfuucucucaa(invdT)(NAG13) | 601 | UAUAUUCGUGGUGGACUUCUCUCAAT | 173 |
| AM04351-SS | uauauscsguggbuggAfCfUfucucucaau(invdT)(NAG13) | 602 | UAUAUCGUGGUGGACUUCUCUCAAUT | 174 |
| AM04352-SS | uauausgsgacuucuCfUfCfaauuuucua(invdA)(NAG13) | 603 | UAUAUGGACUUCUCUCAAUUUUCUAA | 175 |
| AM04353-SS | uauaususgccaaguGfUfUfugcugacgc(invdA)(NAG13) | 604 | UAUAUUGCCAAGUGUUUGCUGACGCA | 116 |
| AM04354-SS | uauausgsgcuccucUfGfCfcgauccaua(invdA)(NAG13) | 605 | UAUAUGGCUCCUCUGCCGAUCCAUAA | 176 |
| AM04355-SS | uauaususccucugcCfGfAfuccauacug(invdA)(NAG13) | 606 | UAUAUUCCUCUGCCGAUCCAUACUGA | 177 |
| AM04356-SS | uauausgsauccauaCfUfGfcggaacucc(invdA)(NAG13) | 607 | UAUAUGAUCCAUACUGCGGAACUCCA | 178 |
| AM04444-SS | (NAG25)uusgsccuguagGfCfAfuaaaauugguaus(invdT) | 608 | UUGCCUGUAGGCAUAAAUUGGUAUT | 179 |
| AM04445-SS | (NAG25)uauausgsccuguagGfCfAfuaaaauuggu(invdA) | 609 | UAUAUGCCUGUAGGCAUAAAUUGGUA | 111 |
| AM04449-SS | (NAG25)uusgsuccgugugCfAfCfcuucgcuucaus(invdT) | 610 | UUGUCCGUGUGCACUUCGCUUCAUT | 180 |
| AM04458-SS | (NAG25)uusgsguauguugCfCfCfguuugucaus(invdT) | 611 | UUGGUAUGUUGCCCGUUUGUCCAUT | 181 |
| AM04659-SS | gsusguGfcAfCfUfucgcuucaca(NAG13) | 612 | GUGUGCACUUCGCUUCACA | 182 |
| AM04660-SS | gsgsuggaCfuUfCfUfcucaAfUfuuua(NAG13) | 613 | GGUGGACUUCUCUCAAUUUA | 166 |
| AM04682-SS | (NAG25)gsusguGfcAfCfUfucgcuucaCM(invdA) | 614 | GUGUGCACUUCGCUUCACA | 182 |
| AM04683-SS | (NAG25)gsgsuggaCfuUfCfUfcucaAfUfuuTM(invdA) | 615 | GGUGGACUUCUCUCAAUUUA | 183 |
| AM04745-SS | (NAG25)cgcggusccgugugCfAfCffuucgcuucAM(invdA) | 616 | CGCGGUCCGUGUGCACUUCGCUUCAA | 184 |
| AM04748-SS | (NAG25)gcggucscgugugcAfCfUfucgcuucaCM(invdA) | 617 | GCGGUCCGUGUGCACUUCGCUUCACA | 185 |
| AM04751-SS | (NAG25)gcggausgugucugCfGfGfcguuuuauCM(invdA) | 618 | GCGGAUGUGUCUGCGGCGUUUUAUCA | 186 |

TABLE 1B-continued

HBV RNAi trigger sense strand sequences.

| Strand ID | Modified sequence (5'→3') | SEQ ID NO. | Unmodified sequence (5'→3') | SEQ ID NO. |
|---|---|---|---|---|
| AM04754-SS | (NAG25)gcgugusgucugcgGfCfGfuuuuaucaTM(invdA) | 619 | GCGUGUGUCUGCGGCGUUUUAUCATA | 187 |
| AM04757-SS | (NAG25)gcggucscgugugcAfCfUfucgcuucaCM(invdT) | 620 | GCGGUCCGUGUGCACUUCGCUUCACT | 188 |
| AM04759-SS | (NAG25)gcgugusgucugcgGfCfGfuuuuaucaTM(invdT) | 621 | GCGUGUGUCUGCGGCGUUUUAUCATT | 189 |
| AM04761-SS | (NAG25)gcgcggsuccgugu GfCfAfcuucgcuuCM(invdA) | 622 | GCGCGGUCCGUGUGCACUUCGCUUCA | 190 |
| AM04764-SS | (NAG25)gcgaagsguauguuCfCfCfcguuugucCM(invdA) | 623 | GCGAAGGUAUGUUGCCCGUUUGUCCA | 191 |
| AM04767-SS | (NAG25)gcggagsgcuguagGfCfAfuaaauuggTM(invdA) | 624 | GCGGAGGCUGUAGGCAUAAAUUGGTA | 192 |
| AM04781-SS | uGfuAfgGfcAfuAfaAfuUfgGfuAf(invdT) | 625 | UGUAGGCAUAAAUUGGUAU | 193 |
| AM04783-SS | cCfuCfuGfcCfuAfaUfcAfuCfuAf(invdT) | 626 | CCUCUGCCUAAUCAUCUAU | 194 |
| AM04787-SS | cUfgCfgGfCfGfuUfuUfaUfcAfuAf(invdT) | 627 | CUGCGGCGUUUUAUCAUAU | 195 |
| AM04788-SS | uGfuAfgGfCfAfuAfaAfuUfgGfuAf(invdT) | 628 | UGUAGGCAUAAAUUGGUAU | 193 |
| AM05010-SS | (NAG25)scsuguagGfCfAfuaaauugguauus(invAb) | 629 | CUGUAGGCAUAAAUUGGUAUUx | 196 |
| AM05015-SS | (NAG25)sgsccuguagGfCfAfuaaauuggaus(invAb) | 630 | GCCUGUAGGCAUAAAUUGGUAx | 197 |
| AM05016-SS | (NAG25)sgsccuguagGfCfAfuaaauuggus(invdA) | 631 | GCCUGUAGGCAUAAAUUGGUA | 198 |
| AM05017-SS | (NAG25)sgsccuguagGfCfAfuaaauugguAMs(invAb) | 632 | GCCUGUAGGCAUAAAUUGGUAx | 197 |
| AM05018-SS | (NAG25)sgsccuguagGfCfAfuaaauuggTMAMs(invAb) | 633 | GCCUGUAGGCAUAAAUUGGTAx | 199 |
| AM05019-SS | (NAG25)sasacuguagGfCfAfuaaauuggaus(invAb) | 634 | AACUGUAGGCAUAAAUUGGUAx | 200 |
| AM05034-SS | (NAG25)suscguggugGfAfCfuucucucaaus(invAb) | 635 | UCGUGGUGGACUUCUCUCAAUx | 201 |
| AM05046-SS | (NAG25)sasaguggugGfAfCfuucucucaaus(invAb) | 636 | AAGUGGUGGACUUCUCUCAAUx | 202 |
| AM05047-SS | (NAG25)suscguggugGfAfCfuucucucaAMTMs(invAb) | 637 | UCGUGGUGGACUUCUCUCAATx | 203 |
| AM05048-SS | (NAG25)scsguggugGfAfCfUfucucucaauus(invAb) | 638 | CGUGGUGGACUUCUCUCAAUUx | 204 |
| AM05049-SS | (NAG25)sasauggugGfAfCfUfucucucaauus(invAb) | 639 | AAUGGUGGACUUCUCUCAAUUx | 205 |
| AM05050-SS | (NAG25)scsguggugGfAfCfUfucucucaaTMTMs(invAb) | 640 | CGUGGUGGACUUCUCUCAATTx | 206 |
| AM05051-SS | (NAG25)sgsgacuucuCfUfCfaauuuucuaas(invAb) | 641 | GGACUUCUCUCAAUUUUCUAAx | 207 |
| AM05063-SS | (NAG25)scsguggugGfCfUfucucucaauas(invAb) | 642 | CGUGGUGGACUUCUCUCAAUAx | 208 |
| AM05064-SS | (NAG25)suscguggugGfAfCfuucucucaaas(invAb) | 643 | UCGUGGUGGACUUCUCUCAAAx | 209 |

TABLE 2

Examples of HBV RNAi trigger duplexes.

| Duplex ID | Antisense Strand ID | Sense Strand ID |
|---|---|---|
| AD00003 | AM00006-AS | AM00005-SS |
| AD00004 | AM00008-AS | AM00007-SS |
| AD00005 | AM00010-AS | AM00009-SS |
| AD00007 | AM00010-AS | AM00013-SS |
| AD00008 | AM00010-AS | AM00014-SS |
| AD00009 | AM00006-AS | AM00015-SS |
| AD00010 | AM00010-AS | AM00016-SS |
| AD00022 | AM00010-AS | AM00039-SS |
| AD00073 | AM00139-AS | AM00138-SS |
| AD00076 | AM00006-AS | AM00029-SS |
| AD00077 | AM00006-AS | AM00179-SS |
| AD00078 | AM00006-AS | AM00177-SS |
| AD00079 | AM00006-AS | AM00175-SS |
| AD00081 | AM00010-AS | AM00180-SS |
| AD00082 | AM00010-AS | AM00178-SS |
| AD00083 | AM00010-AS | AM00176-SS |
| AD00131 | AM00194-AS | AM00029-SS |
| AD00132 | AM00195-AS | AM00029-SS |
| AD00239 | AM00010-AS | AM00429-SS |
| AD00240 | AM00010-AS | AM00430-SS |
| AD00241 | AM00010-AS | AM00431-SS |
| AD00242 | AM00010-AS | AM00432-SS |
| AD00243 | AM00010-AS | AM00433-SS |
| AD00244 | AM00010-AS | AM00434-SS |
| AD00245 | AM00010-AS | AM00435-SS |
| AD00246 | AM00010-AS | AM00436-SS |
| AD00247 | AM00010-AS | AM00437-SS |
| AD00248 | AM00438-AS | AM00039-SS |
| AD00249 | AM00439-AS | AM00039-SS |
| AD00250 | AM00010-AS | AM00442-SS |

TABLE 2-continued

Examples of HBV RNAi trigger duplexes.

| Duplex ID | Antisense Strand ID | Sense Strand ID |
|---|---|---|
| AD00251 | AM00006-AS | AM00440-SS |
| AD00252 | AM00006-AS | AM00441-SS |
| AD00253 | AM00010-AS | AM00443-SS |
| AD00341 | AM00006-AS | AM00620-SS |
| AD00342 | AM00010-AS | AM00621-SS |
| AD00709 | AM01463-AS | AM00620-SS |
| AD00710 | AM01464-AS | AM00621-SS |
| AD01099 | AM01933-AS | AM01934-SS |
| AD01100 | AM01935-AS | AM01936-SS |
| AD01101 | AM01937-AS | AM00434-SS |
| AD01102 | AM01938-AS | AM01939-SS |
| AD01103 | AM01942-AS | AM00138-SS |
| AD01104 | AM01943-AS | AM00138-SS |
| AD01105 | AM01944-AS | AM01940-SS |
| AD01106 | AM01945-AS | AM01940-SS |
| AD01107 | AM01946-AS | AM01941-SS |
| AD01108 | AM01947-AS | AM01941-SS |
| AD01129 | AM00006-AS | AM01885-SS |
| AD01130 | AM00010-AS | AM01886-SS |
| AD01137 | AM00139-AS | AM01965-SS |
| AD01138 | AM00006-AS | AM01963-SS |
| AD01139 | AM00010-AS | AM01964-SS |
| AD01140 | AM00008-AS | AM01979-SS |
| AD01141 | AM01985-AS | AM01979-SS |
| AD01142 | AM01986-AS | AM01979-SS |
| AD01143 | AM01987-AS | AM01991-SS |
| AD01144 | AM01988-AS | AM01992-SS |
| AD01145 | AM01989-AS | AM01991-SS |
| AD01146 | AM01990-AS | AM01992-SS |
| AD01167 | AM00008-AS | AM01984-SS |
| AD01245 | AM00439-AS | AM01964-SS |
| AD01246 | AM01937-AS | AM02080-SS |
| AD01247 | AM01938-AS | AM02081-SS |
| AD01248 | AM00194-AS | AM01963-SS |
| AD01249 | AM01933-AS | AM02082-SS |
| AD01250 | AM01935-AS | AM02083-SS |
| AD01310 | AM01986-AS | AM01984-SS |
| AD01319 | AM01988-AS | AM02189-SS |
| AD01320 | AM01990-AS | AM02189-SS |
| AD01358 | AM02276-AS | AM02278-SS |
| AD01359 | AM02277-AS | AM02083-SS |
| AD01360 | AM02280-AS | AM02283-SS |
| AD01361 | AM02281-AS | AM02081-SS |
| AD01362 | AM02286-AS | AM02285-SS |
| AD01363 | AM02287-AS | AM02187-SS |
| AD01364 | AM02288-AS | AM02291-SS |
| AD01365 | AM02289-AS | AM02189-SS |
| AD01382 | AM02312-AS | AM02316-SS |
| AD01383 | AM02313-AS | AM02317-SS |
| AD01384 | AM02314-AS | AM02318-SS |
| AD01385 | AM02315-AS | AM02319-SS |
| AD01386 | AM02312-AS | AM02320-SS |
| AD01387 | AM02313-AS | AM02321-SS |
| AD01388 | AM02314-AS | AM02322-SS |
| AD01389 | AM02315-AS | AM02323-SS |
| AD01425 | AM02366-AS | AM02370-SS |
| AD01426 | AM02367-AS | AM02371-SS |
| AD01427 | AM02368-AS | AM02372-SS |
| AD01428 | AM02369-AS | AM02373-SS |
| AD01429 | AM02374-AS | AM02378-SS |
| AD01430 | AM02375-AS | AM02379-SS |
| AD01431 | AM02376-AS | AM02380-SS |
| AD01432 | AM02377-AS | AM02381-SS |
| AD01433 | AM02382-AS | AM02386-SS |
| AD01434 | AM02383-AS | AM02387-SS |
| AD01435 | AM02384-AS | AM02388-SS |
| AD01436 | AM02385-AS | AM02389-SS |
| AD01438 | AM02391-AS | AM02320-SS |
| AD01439 | AM02392-AS | AM02317-SS |
| AD01440 | AM02393-AS | AM02321-SS |
| AD01461 | AM02392-AS | AM02319-SS |
| AD01493 | AM02315-AS | AM02483-SS |
| AD01494 | AM02484-AS | AM02483-SS |
| AD01495 | AM02485-AS | AM02486-SS |
| AD01496 | AM00008-AS | AM02486-SS |
| AD01497 | AM00008-AS | AM02489-SS |
| AD01562 | AM02575-AS | AM02576-SS |
| AD01563 | AM02577-AS | AM02578-SS |
| AD01785 | AM02889-AS | AM02888-SS |
| AD01786 | AM02892-AS | AM02891-SS |
| AD01787 | AM02895-AS | AM02894-SS |
| AD01788 | AM02898-AS | AM02897-SS |
| AD01789 | AM02901-AS | AM02900-SS |
| AD01790 | AM02904-AS | AM02903-SS |
| AD01791 | AM02907-AS | AM02906-SS |
| AD01792 | AM02910-AS | AM02909-SS |
| AD01793 | AM02913-AS | AM02912-SS |
| AD01794 | AM02916-AS | AM02915-SS |
| AD01795 | AM02919-AS | AM02918-SS |
| AD01796 | AM02922-AS | AM02921-SS |
| AD01797 | AM02925-AS | AM02924-SS |
| AD01798 | AM02928-AS | AM02927-SS |
| AD01799 | AM02931-AS | AM02930-SS |
| AD01800 | AM02934-AS | AM02933-SS |
| AD01801 | AM02937-AS | AM02936-SS |
| AD01802 | AM02940-AS | AM02939-SS |
| AD01875 | AM02975-AS | AM02978-SS |
| AD01876 | AM02975-AS | AM02979-SS |
| AD01877 | AM02976-AS | AM02981-SS |
| AD01878 | AM02982-AS | AM02987-SS |
| AD01879 | AM02982-AS | AM02988-SS |
| AD01880 | AM02983-AS | AM02990-SS |
| AD01881 | AM02984-AS | AM02992-SS |
| AD01882 | AM02984-AS | AM02993-SS |
| AD01883 | AM02985-AS | AM02995-SS |
| AD01956 | AM03097-AS | AM03087-SS |
| AD01957 | AM03098-AS | AM03088-SS |
| AD01958 | AM03099-AS | AM03089-SS |
| AD01959 | AM03100-AS | AM03090-SS |
| AD01960 | AM03101-AS | AM03091-SS |
| AD01961 | AM03102-AS | AM03092-SS |
| AD01962 | AM03103-AS | AM03093-SS |
| AD01963 | AM03104-AS | AM03094-SS |
| AD01964 | AM03105-AS | AM03095-SS |
| AD01965 | AM03106-AS | AM03096-SS |
| AD02718 | AM03495-AS | AM03493-SS |
| AD02719 | AM03495-AS | AM03496-SS |
| AD02720 | AM03495-AS | AM03494-SS |
| AD02721 | AM03500-AS | AM03497-SS |
| AD02722 | AM03500-AS | AM03498-SS |
| AD02723 | AM03500-AS | AM03499-SS |
| AD02724 | AM03504-AS | AM03501-SS |
| AD02725 | AM03504-AS | AM03502-SS |
| AD02726 | AM03504-AS | AM03503-SS |
| AD02727 | AM03508-AS | AM03505-SS |
| AD02728 | AM03508-AS | AM03506-SS |
| AD02729 | AM03508-AS | AM03507-SS |
| AD02730 | AM03512-AS | AM03509-SS |
| AD02731 | AM03512-AS | AM03510-SS |
| AD02732 | AM03512-AS | AM03511-SS |
| AD02933 | AM03495-AS | AM03763-SS |
| AD02934 | AM03764-AS | AM03494-SS |
| AD02935 | AM03764-AS | AM03763-SS |
| AD02936 | AM03764-AS | AM03496-SS |
| AD02937 | AM03500-AS | AM03765-SS |
| AD02938 | AM03766-AS | AM03499-SS |
| AD02939 | AM03766-AS | AM03765-SS |
| AD02940 | AM03504-AS | AM03767-SS |
| AD02941 | AM03768-AS | AM03503-SS |
| AD02942 | AM03768-AS | AM03767-SS |
| AD02943 | AM03508-AS | AM03769-SS |
| AD02944 | AM03770-AS | AM03507-SS |
| AD02945 | AM03770-AS | AM03769-SS |
| AD02946 | AM03512-AS | AM03771-SS |
| AD02947 | AM03772-AS | AM03511-SS |
| AD02948 | AM03772-AS | AM03771-SS |
| AD03055 | AM03864-AS | AM03765-SS |
| AD03056 | AM03865-AS | AM03499-SS |
| AD03057 | AM03865-AS | AM03765-SS |
| AD03096 | AM03912-AS | AM03914-SS |

TABLE 2-continued

Examples of HBV RNAi trigger duplexes.

| Duplex ID | Antisense Strand ID | Sense Strand ID |
|---|---|---|
| AD03097 | AM03913-AS | AM03914-SS |
| AD03098 | AM03912-AS | AM03915-SS |
| AD03099 | AM03913-AS | AM03915-SS |
| AD03100 | AM03916-AS | AM03918-SS |
| AD03101 | AM03917-AS | AM03918-SS |
| AD03102 | AM03916-AS | AM03919-SS |
| AD03103 | AM03917-AS | AM03919-SS |
| AD03153 | AM02315-AS | AM03963-SS |
| AD03154 | AM02312-AS | AM03964-SS |
| AD03217 | AM04041-AS | AM03765-SS |
| AD03218 | AM04042-AS | AM03507-SS |
| AD03350 | AM04249-AS | AM00620-SS |
| AD03363 | AM04272-AS | AM04262-SS |
| AD03364 | AM04273-AS | AM04263-SS |
| AD03365 | AM04274-AS | AM04264-SS |
| AD03366 | AM04275-AS | AM04265-SS |
| AD03367 | AM04276-AS | AM04266-SS |
| AD03368 | AM04277-AS | AM04267-SS |
| AD03369 | AM04278-AS | AM04268-SS |
| AD03370 | AM04279-AS | AM04269-SS |
| AD03371 | AM04280-AS | AM04270-SS |
| AD03372 | AM04281-AS | AM04271-SS |
| AD03373 | AM04288-AS | AM04282-SS |
| AD03374 | AM04289-AS | AM04283-SS |
| AD03375 | AM04290-AS | AM04284-SS |
| AD03376 | AM04291-AS | AM04285-SS |
| AD03377 | AM04292-AS | AM04286-SS |
| AD03378 | AM04293-AS | AM04287-SS |
| AD03381 | AM04323-AS | AM04297-SS |
| AD03382 | AM04324-AS | AM04298-SS |
| AD03383 | AM04325-AS | AM04299-SS |
| AD03384 | AM04326-AS | AM04300-SS |
| AD03385 | AM04327-AS | AM04301-SS |
| AD03386 | AM04328-AS | AM04302-SS |
| AD03387 | AM04329-AS | AM04303-SS |
| AD03388 | AM04330-AS | AM04304-SS |
| AD03389 | AM04331-AS | AM04305-SS |
| AD03390 | AM04332-AS | AM04306-SS |
| AD03391 | AM04333-AS | AM04307-SS |
| AD03392 | AM04334-AS | AM04308-SS |
| AD03393 | AM04335-AS | AM04309-SS |
| AD03394 | AM04336-AS | AM04310-SS |
| AD03395 | AM04337-AS | AM04311-SS |
| AD03396 | AM04338-AS | AM04312-SS |
| AD03397 | AM04339-AS | AM04313-SS |
| AD03398 | AM04340-AS | AM04314-SS |
| AD03399 | AM04341-AS | AM04315-SS |
| AD03400 | AM04342-AS | AM04316-SS |
| AD03401 | AM04343-AS | AM04317-SS |
| AD03402 | AM04344-AS | AM04318-SS |
| AD03403 | AM04345-AS | AM04319-SS |
| AD03404 | AM04346-AS | AM04320-SS |
| AD03405 | AM04347-AS | AM04321-SS |
| AD03406 | AM04348-AS | AM04322-SS |
| AD03407 | AM04357-AS | AM04349-SS |
| AD03408 | AM04358-AS | AM04350-SS |
| AD03409 | AM04359-AS | AM04351-SS |
| AD03410 | AM04360-AS | AM04352-SS |
| AD03411 | AM04361-AS | AM04353-SS |
| AD03412 | AM04362-AS | AM04354-SS |
| AD03413 | AM04363-AS | AM04355-SS |
| AD03414 | AM04364-AS | AM04356-SS |
| AD03498 | AM03508-AS | AM04445-SS |
| AD03499 | AM04441-AS | AM04444-SS |
| AD03500 | AM04442-AS | AM04444-SS |
| AD03501 | AM04443-AS | AM04444-SS |
| AD03502 | AM04446-AS | AM04449-SS |
| AD03503 | AM04447-AS | AM04449-SS |
| AD03504 | AM04448-AS | AM04449-SS |
| AD03509 | AM04459-AS | AM04458-SS |
| AD03510 | AM04460-AS | AM04458-SS |
| AD03511 | AM04461-AS | AM04458-SS |
| AD03669 | AM04661-AS | AM04659-SS |
| AD03670 | AM04662-AS | AM04660-SS |
| AD03679 | AM04661-AS | AM04682-SS |
| AD03680 | AM04662-AS | AM04683-SS |
| AD03724 | AM04746-AS | AM04745-SS |
| AD03725 | AM04747-AS | AM04745-SS |
| AD03726 | AM04749-AS | AM04748-SS |
| AD03727 | AM04750-AS | AM04748-SS |
| AD03728 | AM04752-AS | AM04751-SS |
| AD03729 | AM04753-AS | AM04751-SS |
| AD03730 | AM04755-AS | AM04754-SS |
| AD03731 | AM04756-AS | AM04754-SS |
| AD03732 | AM04758-AS | AM04757-SS |
| AD03733 | AM04760-AS | AM04759-SS |
| AD03734 | AM04762-AS | AM04761-SS |
| AD03735 | AM04763-AS | AM04761-SS |
| AD03736 | AM04765-AS | AM04764-SS |
| AD03737 | AM04766-AS | AM04764-SS |
| AD03738 | AM04768-AS | AM04767-SS |
| AD03739 | AM04769-AS | AM04767-SS |
| AD03750 | AM04782-AS | AM04781-SS |
| AD03751 | AM04784-AS | AM04783-SS |
| AD03753 | AM02609-AS | AM04787-SS |
| AD03754 | AM04789-AS | AM04788-SS |
| AD03967 | AM04443-AS | AM05010-SS |
| AD03968 | AM05011-AS | AM05010-SS |
| AD03969 | AM04443-AS | AM05015-SS |
| AD03970 | AM05011-AS | AM05019-SS |
| AD03971 | AM05012-AS | AM05015-SS |
| AD03972 | AM04443-AS | AM05016-SS |
| AD03973 | AM04443-AS | AM05017-SS |
| AD03974 | AM04443-AS | AM05018-SS |
| AD03975 | AM05013-AS | AM05015-SS |
| AD03976 | AM05014-AS | AM05019-SS |
| AD03977 | AM05013-AS | AM05017-SS |
| AD03978 | AM05013-AS | AM04444-SS |
| AD04001 | AM05052-AS | AM05034-SS |
| AD04002 | AM05053-AS | AM05034-SS |
| AD04003 | AM05054-AS | AM05046-SS |
| AD04004 | AM05052-AS | AM05047-SS |
| AD04005 | AM05055-AS | AM05064-SS |
| AD04006 | AM05056-AS | AM05048-SS |
| AD04007 | AM05057-AS | AM05048-SS |
| AD04008 | AM05058-AS | AM05049-SS |
| AD04009 | AM05056-AS | AM05050-SS |
| AD04010 | AM05060-AS | AM05063-SS |
| AD04011 | AM05061-AS | AM05051-SS |
| AD04012 | AM05062-AS | AM05051-SS |

In some embodiments, an HBV RNAi trigger is prepared or provided as a salt, mixed salt, or a free-acid.

Targeting groups and linking groups, as indicated in Tables 1A and 1B, include, but are not limited to, (Chol-TEG), (Chol-C6), (Chol-ALNY), (NH2-C6), (C6-SS-Alk-Me), (Alk-SS-C6), (C11-PEG3-NAG3), (NAG13), (NAG25), (Toc), and (TEG-Biotin). In some embodiments, any of the HBV RNAi trigger sense strands listed in Table 1B which contains a 3' or 5' targeting group or linking group, may alternatively contain no 3' or 5' targeting group or linking group, or may contain a different 3' or 5' targeting group or linking group.

Figure 2:
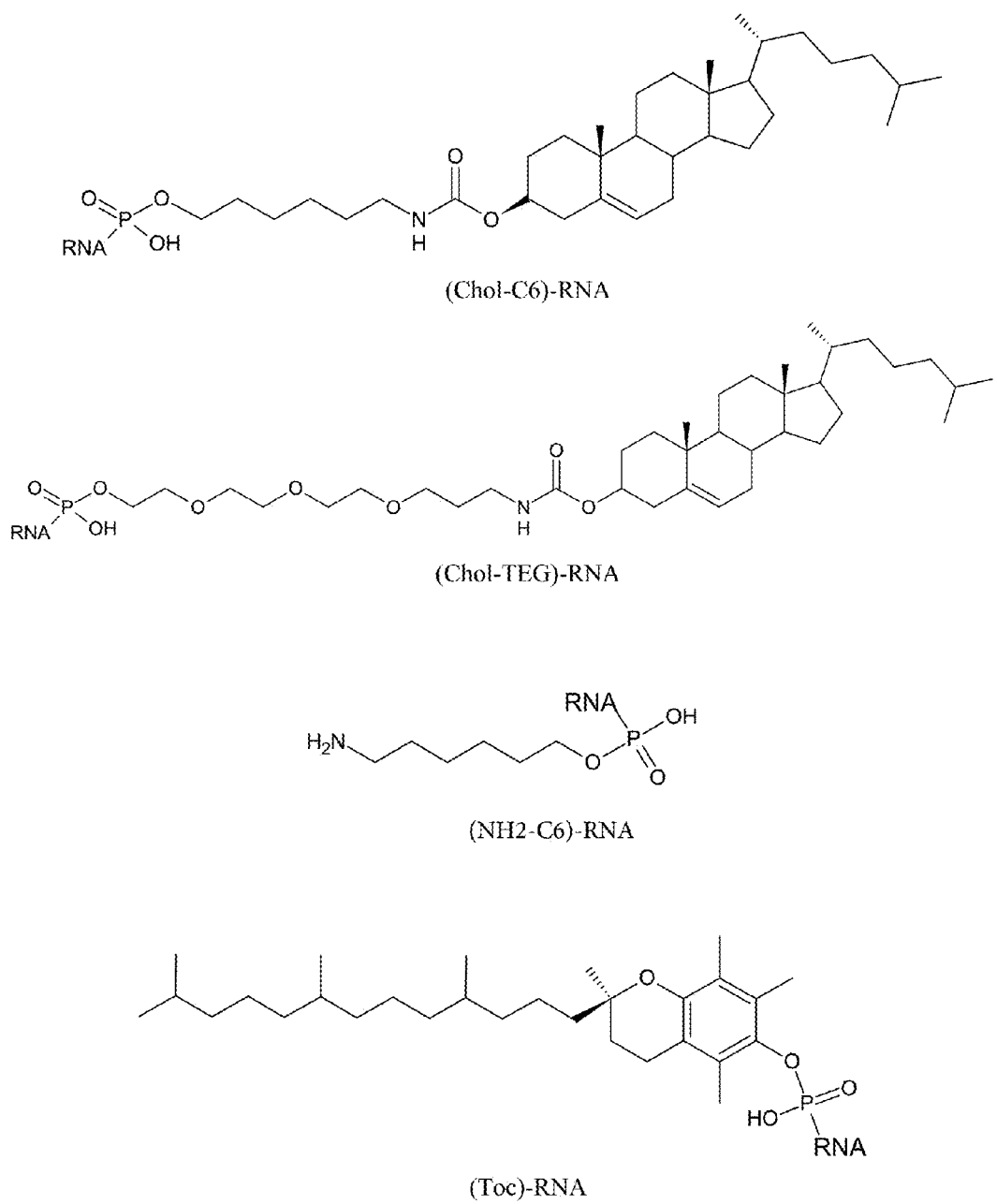
FIG. 2. Chemical structures representing HBV RNAi trigger targeting groups and linking groups.

Structures for targeting groups and linking groups linked the RNAi trigger indicated in Table 1B are shown below and in FIG. 1 and FIG. 2. (RNAi trigger is indicated by RNA or trigger).

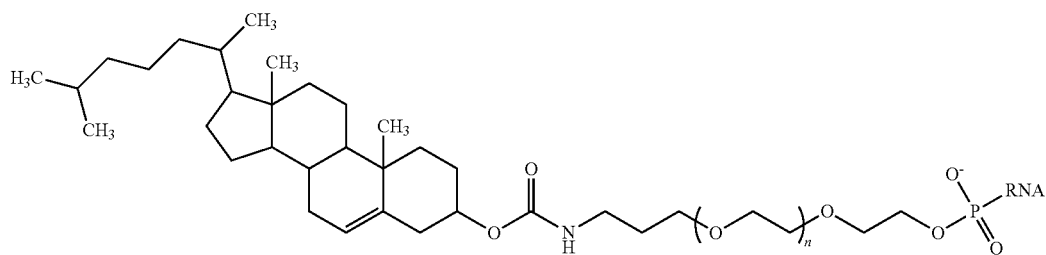
(Chol-TEG)—RNA, n = 1-10, In some embodiments, n = 2.
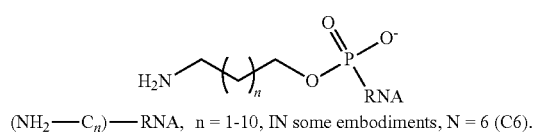
(NH$_2$—C$_n$)—RNA, n = 1-10, IN some embodiments, N = 6 (C6).
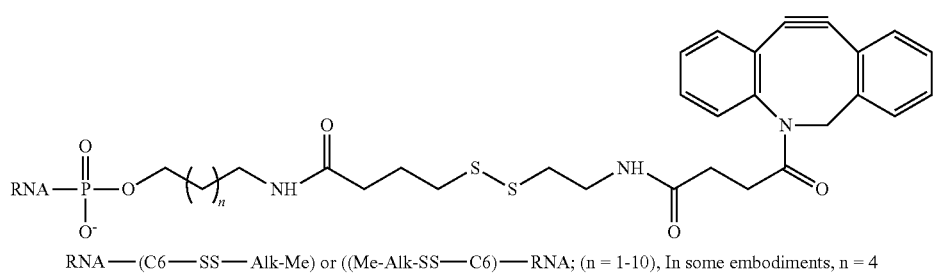
RNA—(C6—SS—Alk-Me) or ((Me-Alk-SS—C6)—RNA; (n = 1-10), In some embodiments, n = 4
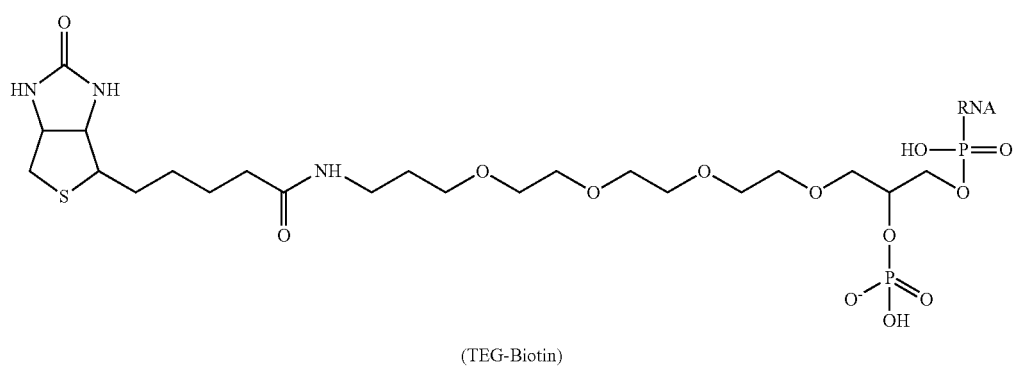
(TEG-Biotin)
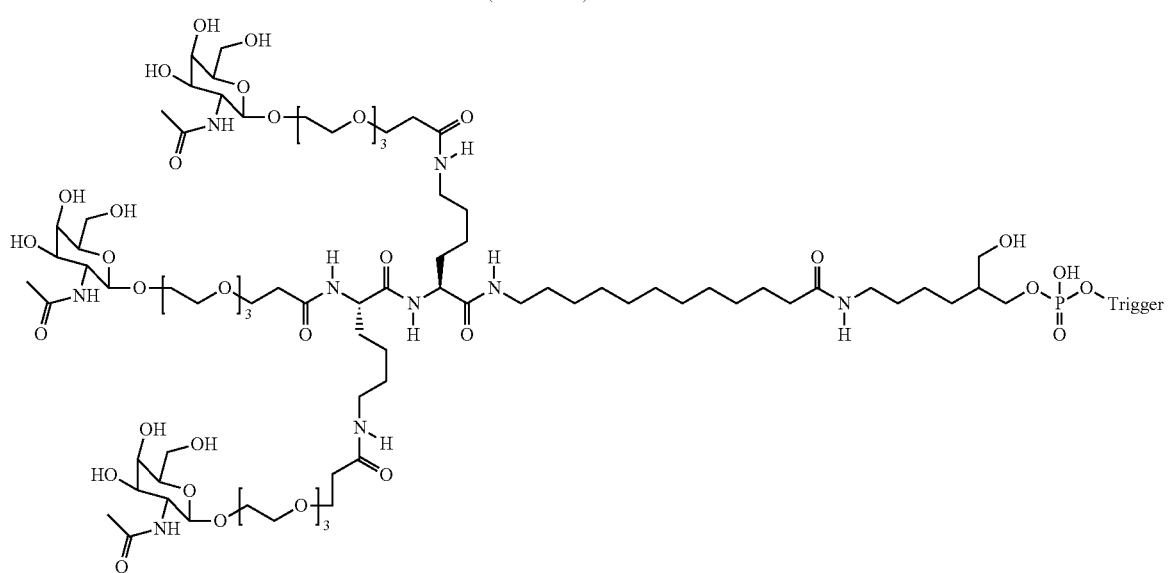
(C11-PEG3-NAG3)-Trigger -continued

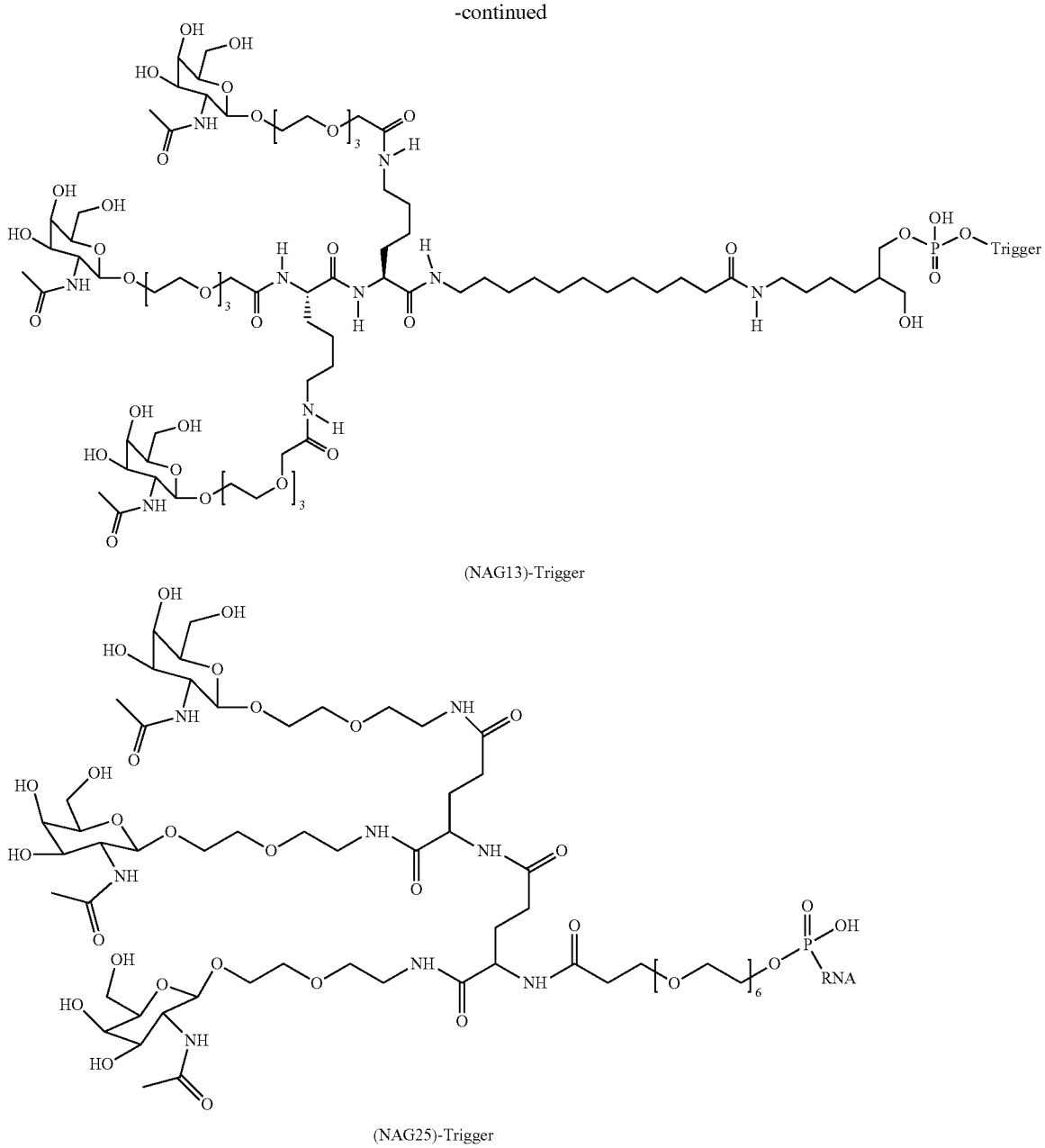

(NAG13)-Trigger (NAG25)-Trigger

In Vivo Delivery

Described herein are methods for delivering HBV RNAi triggers to liver cells in a mammal in vivo. In some embodiments, a delivery vehicle may be used. A delivery vehicle is a compound which improves delivery of the RNAi agent to the cell. A delivery vehicle can be, but is not limited to: a polymer, such as an amphipathic polymer, membrane active polymer, a peptide, such as a melittin or melittin-like peptide, a reversibly modified polymer or peptide, or a lipid. In some embodiments, an HBV RNAi trigger is linked to a targeting ligand that comprises a galactose derivative. In some embodiments, an HBV RNAi trigger is linked to a targeting ligand that comprises or consists of a galactose trimer. In some embodiments, HBV RNAi trigger delivery systems are described comprising a small delivery peptide, MLP, derived from bee venom peptide and one or more independently targeted HBV RNAi triggers.

In some embodiments, an RNAi trigger as described herein is linked to a galactose trimer. As used herein, a galactose trimer comprises a molecule having three or four terminal galactose derivatives. As used herein, the term galactose derivative includes both galactose and derivatives of galactose having affinity for the asialoglycoprotein receptor equal to or greater than that of galactose. A galactose trimer contains three or four galactose derivatives each linked to a central branch point through its C-1 carbon. In some embodiments, a galactose derivative is linked to the branch point via a linker or spacer. In some embodiments, the linker or spacer is a flexible hydrophilic spacer (U.S. Pat. No. 5,885,968; Biessen et al. J. Med. Chem. 1995 Vol. 39 p. 1538-1546), such as, but not limited to: a PEG spacer. In some embodiments, the PEG spacer is a PEG3 spacer. The branch point can be any small molecule which permits attachment of three to four galactose derivatives and further permits attachment of the branch point to the RNAi agent. Attachment of the branch point to the RNAi agent may occur through a linker or spacer. In some embodiments, the linker or spacer comprises a flexible hydrophilic spacer, such as, but not limited to: a PEG spacer. In some embodiments, a PEG spacer is a PEG3 spacer (three ethylene units). In other embodiments, the PEG spacer has 1 to 20 ethylene units ($PEG_1$ to $PEG_{20}$). In some embodiments, a galactose derivative comprises an N-acetylgalactosamine (GalNAc or NAG). Other saccharides having affinity for the asialoglycoprotein receptor may be selected from the list comprising: galactose, galactosamine, N-formyl-galactosamine, N-acetyl-galactosamine, N-propionyl-galactosamine, N-n-butanoylgalactosamine, and N-iso-butanoylgalactosamine. The affinities of numerous galactose derivatives for the asialoglycoprotein receptor have been studied (see for example: Iobst, S. T. and Drickamer, K. *J.B.C.* 1996, 271, 6686) or are readily determined using methods well known and commonly used in the art. Other terms common in the art for galactose trimer having three terminal galactose derivatives include tri-antennary galactose, tri-valent galactose. Other terms common in the art for galactose trimer include galactose cluster. It is known that tri-antennary galactose derivative clusters are bound to the ASGPr with greater affinity than bi-antennary or mono-antennary galactose derivative structures (Baenziger and Fiete, 1980, Cell, 22, 611-620; Connolly et al., 1982, J. Biol. Chem., 257, 939-945).

In some embodiments compositions are described comprising:

MLP-(L-M)$_x$ plus N-T, wherein N is a HBV RNAi trigger, T is a targeting group (comprising a hydrophobic group having 20 or more carbon atoms, such as a cholesterol), MLP is a melitiin-like peptide as describe herein, and masking agent M contains an ASGPr ligand as described herein covalently linked to MLP via a physiologically labile reversible linkage L. As used herein, MLP-(L-M)$_x$ is an MLP delivery peptide or delivery peptide. Cleavage of L restores an unmodified amine on MLP. In some embodiments, optional group Y is linked to the amino terminal end, carboxyl terminal end, or cysteine of an MLP. If present, Y can comprise: an ASGPr ligand, a polyethyleneglycol (PEG), or an ASGPr ligand-PEG. x is an integer greater than 1. In its unmodified state, MLP is membrane active. However, delivery peptide MLP-(L-M)$_x$ is not membrane active. Reversible modification of MLP primary amines, by attachment of M, reversibly inhibits or inactivates membrane activity of MLP. A sufficient percentage of MLP primary amines are modified to inhibit membrane activity of the polymer and provide for hepatocyte targeting. In some embodiments, x has a value greater than 80%, greater than 90%, or greater than 95% of the number of primary amines on MLP, as determined by the quantity of primary amines on MLP in the absence of any masking agents. More specifically, x has a value greater than 80% and up to 100% of the primary amines on MLP. It is noted that MLP typically contains 3-5 primary amines (including the amino terminus (if unmodified) and typically 2-4 Lysine residues). Therefore, modification of a percentage of amines is meant to reflect the modification of a percentage of MLP amines in a population of MLPs. A population of MLPs means the population of MLPs in a defined sample size that would be relevant to a person of ordinary skill in the art, such as the population in a container, dose, or manufactured batch. In some embodiments, the population of MLPs is the pool of MLP in a manufactured batch. Upon cleavage of reversible linkages L, unmodified amines are restored thereby reverting MLP to its unmodified, membrane active state. In some embodiments, a reversible linkage is a pH labile linkage, such as a disubstituted maleamate linkage. MLP-(L-M)$_x$, an ASGPr-targeted reversibly masked membrane active polymer (delivery peptide), and T-N, a polynucleotide-conjugate, are synthesized or manufactured separately. Neither T nor N are covalently linked directly or indirectly to MLP, L, or M. Electrostatic or hydrophobic association of the polynucleotide or the polynucleotide-conjugate with the masked or unmasked polymer is not required for in vivo liver delivery of the polynucleotide. The masked polymer and the polynucleotide conjugate can be supplied in the same container or in separate containers. They may be combined prior to administration, co-administered, or administered sequentially.

In some embodiments, an ASGPr-targeted reversibly masked MLP comprises an MLP reversibly modified by reaction of primary amines on the peptide with ASGPr ligand-containing masking agents. An amine is reversibly modified if cleavage of the modifying group restores the amine. Reversible modification of the MLP with the masking agents disclosed herein reversibly inhibits membrane activity of the MLP. In the masked state, the reversibly masked MLP does not exhibit membrane disruptive activity. In some embodiments, more than 80%, or more than 90%, of the amines on the MLP are reversibly modified.

MLP, as used herein, is a small amphipathic membrane active peptide, comprising about 23 to about 32 amino acids, derived from the naturally occurring in bee venom peptide melittin. The naturally occurring melittin contains 26 amino acids and is predominantly hydrophobic on the amino terminal end and predominantly hydrophilic (cationic) on the carboxy terminal end. In some embodiments, an MLP is isolated from a biological source or synthetic. A synthetic polymer is formulated or manufactured by a chemical process "by man" and is not created by a naturally occurring biological process. As used herein, MLP encompasses the naturally occurring bee venom peptides of the MLP family that can be found in, for example, venom of the species: *Apis florea*, *Apis mellifera*, *Apis cerana*, *Apis dorsata*, *Vespula maculifrons*, *Vespa magnifica*, *Vespa velutina*, *Polistes* sp. HQL-2001, and *Polistes hebraeus*. As used herein, MLP also encompasses synthetic peptides having amino acid sequence identical to or similar to naturally occurring MLPs. Specifically, MLP amino acid sequence encompass those shown in Table 3. In addition to the amino acids which retain melittin's inherent high membrane activity, 1-8 amino acids can be added to the amino or carboxy terminal ends of the peptide. Specifically, cysteine residues can be added to the amino or carboxy termini. The list in Table 3 is not meant to be exhaustive, as other conservative amino acid substitutions are readily envisioned. Synthetic MLPs can contain naturally occurring L form amino acids or the enantiomeric D form amino acids (inverso). The MLP amino acid sequence can also be reversed (retro). Retro MLP can have L form amino acids or D form amino acids (retroinverso). Two MLPs can also be covalently linked to form an MLP dimer. An MLP can have modifying groups, other than masking agents, that enhance tissue targeting or facilitate in vivo circulation attached to either the amino terminal or carboxy terminal ends of the peptide. However, as used herein, MLP does not include chains or polymers containing more than two MLPs covalently linked to one another or to another polymer or scaffold.

In some embodiments, a melittin-like peptide (MLP) comprises an *Apis florea* (little or dwarf honey bee) melittin, *Apis mellifera* (western or European or big honey bee) melittin, *Apis dorsata* (giant honey bee) melittin, *Apis cerana* (oriental honey bee) melittin or derivatives thereof (including amino acid substitutions). In some embodiments, MLP comprises the sequence: $Xaa_1$-$Xaa_2$-$Xaa_3$-Ala-$Xaa_5$-Leu-$Xaa_7$-Val-Leu-$Xaa_{10}$-$Xaa_{11}$-$Xaa_{12}$-Leu-Pro-$Xaa_{15}$-Leu-$Xaa_{17}$-$Xaa_{18}$-Trp-$Xaa_{20}$-$Xaa_{21}$-$Xaa_{22}$-$Xaa_{23}$-$Xaa_{24}$-$Xaa_{25}$-$Xaa_{26}$ wherein:
- $Xaa_1$ is leucine, D-leucine, isoleucine, norleucine, tyrosine, tryptophan, valine, alanine, dimethylglycine, glycine, histidine, phenylalanine, or cysteine,
- $Xaa_2$ is isoleucine, leucine, norleucine, or valine,
- $Xaa_3$ is glycine, leucine, or valine,
- $Xaa_5$ is isoleucine, leucine, norleucine, or valine,
- $Xaa_7$ is lysine, serine, asparagine, alanine, arginine, or histidine,
- $Xaa_{10}$ is alanine, threonine, or leucine,
- $Xaa_{11}$ is threonine or cysteine,
- $Xaa_{12}$ is glycine, leucine, or tryptophan,
- $Xaa_{15}$ is threonine or alanine,
- $Xaa_{17}$ is isoleucine, leucine, norleucine, or valine,
- $Xaa_{18}$ is serine or cysteine,
- $Xaa_{20}$ is isoleucine, leucine, norleucine, or valine,
- $Xaa_{21}$ is lysine or alanine,
- $Xaa_{22}$ is asparagine or arginine,
- $Xaa_{23}$ is lysine or alanine,
- $Xaa_{24}$ is arginine or lysine,
- $Xaa_{25}$ is lysine, alanine, or glutamine,
- $Xaa_{26}$ is optional and if present is glutamine, cysteine, glutamine-$NH_2$, or cysteine-$NH_2$; and,
- and at least two of $Xaa_{21}$, $Xaa_{23}$, and $Xaa_{25}$ are lysine.

In some embodiments, MLP comprises the sequence: $Xaa_1$-$Xaa_2$-$Xaa_3$-Ala-$Xaa_5$-Leu-$Xaa_7$-Val-Leu-$Xaa_{10}$-$Xaa_{11}$-$Xaa_{12}$-Leu-Pro-$Xaa_{15}$-Leu-$Xaa_{71}$-Ser-Trp-$Xaa_{20}$-Lys-$Xaa_{22}$-Lys-Arg-Lys-$Xaa_{26}$ wherein:
- $Xaa_1$ is leucine, D-leucine, norleucine, or tyrosine,
- $Xaa_2$ is isoleucine, leucine, norleucine, or valine,
- $Xaa_3$ is glycine, leucine, or valine,
- $Xaa_5$ is isoleucine, valine, leucine, or norleucine,
- $Xaa_7$ is lysine, serine, asparagine, alanine, arginine, or histidine,
- $Xaa_{10}$ is alanine, threonine, or leucine,
- $Xaa_{11}$ is threonine, or cysteine,
- $Xaa_{12}$ is glycine, leucine, or tryptophan,
- $Xaa_{15}$ is threonine, or alanine,
- $Xaa_{17}$ is isoleucine, leucine, or norleucine,
- $Xaa_{20}$ is isoleucine, leucine, or norleucine,
- $Xaa_{22}$ is asparagine or arginine, and
- $Xaa_{26}$ is glutamine or cysteine.

In some embodiments, MLP comprises the sequence: $Xaa_1$-$Xaa_2$-Gly-Ala-$Xaa_5$-Leu-Lys-Val-Leu-Ala-$Xaa_{11}$-Gly-Leu-Pro-Thr-Leu-$Xaa_{17}$-Ser-Trp-$Xaa_{20}$-Lys-$Xaa_{22}$-Lys-Arg-Lys-$Xaa_{26}$ wherein:
- $Xaa_1$, $Xaa_2$, $Xaa_5$, $Xaa_{17}$ and $Xaa_{20}$ are independently isoleucine, leucine, or norleucine,
- $Xaa_{11}$ is threonine or cysteine,
- $Xaa_{22}$ is Asparagine or arginine, and
- $Xaa_{26}$ is glutamine or cysteine.

TABLE 3

MLP amino acid sequences.

| SEQ ID NO | MLP Sequence | Name |
|---|---|---|
| 644 | GIGAILKVLATGLPTLISWIKNKRKQ | *Apis florea* |
| 645 | AIGAILKVLATGLPTLISWIKNKRKQ | G1A |
| 646 | CIGAILKVLATGLPTLISWIKNKRKQ | G1C |
| 647 | FIGAILKVLATGLPTLISWIKNKRKQ | G1F |
| 648 | HIGAILKVLATGLPTLISWIKNKRKQ | G1H |
| 649 | IIGAILKVLATGLPTLISWIKNKRKQ | G1I |
| 650 | LIGAILKVLATGLPTLISWIKNKRKQ | G1L |
| 651 | NleIGAILKVLATGLPTLISWIKNKRKQ | G1Nle |
| 652 | VIGAILKVLATGLPTLISWIKNKRKQ | G1V |
| 653 | WIGAILKVLATGLPTLISWIKNKRKQ | G1W |
| 654 | YIGAILKVLATGLPTLISWIKNKRKQ | G1Y |
| 655 | GIGAILKVLACGLPTLISWIKNKRKQ | T11C dMel |
| 656 | GIGAILKVLATLLPTLISWIKNKRKQ | G12L |
| 657 | GIGAILKVLATWLPTLISWIKNKRKQ | G12W |
| 658 | GIGAILKVLATGLPTLISWIKTKRKQ | N22T |
| 659 | YIGAILNVLATGLPTLISWIKNKRKQ | G1Y, K7N |
| 660 | YIGAILAVLATGLPTLISWIKNKRKQ | G1Y, K7A |

TABLE 3-continued

MLP amino acid sequences.

| SEQ ID NO | MLP Sequence | Name |
|---|---|---|
| 661 | LIGAILSVLATGLPTLISWIKNKRKQ | G1L, K7S |
| 662 | LIGAILRVLATGLPTLISWIKNKRKQ | G1L, K7R |
| 663 | LIGAILHVLATGLPTLISWIKNKRKQ | G1L, K7H |
| 664 | LIGAILKVLACGLPTLISWIKNKRKQ | G1L, T11C |
| 665 | LIGAILKVLATLLPTLISWIKNKRKQ | G1L, G12L |
| 666 | YIGAILKVLATGLLTLISWIKNKRKQ | G1Y, P14L |
| 667 | LIGAILKVLATGLPCLISWIKNKRKQ | G1L, T15C |
| 668 | LIGAILKVLATGLPTLICWIKNKRKQ | G1L, S18C |
| 669 | YIGAILKVLATGLPTLISAIKNKRKQ | G1Y, W19A |
| 670 | GIGAILKVLACGLPTLISWLKNKRKQ | T11C, I20L |
| 671 | YIGAILKVLATGLPTLISWIANKRKQ | G1Y, K21A |
| 672 | YIGAILKVLATGLPTLISWIKNARKQ | G1Y, K23A |
| 673 | LIGAILKVLATGLPTLISWIKNKAKQ | G1L, R24A |
| 674 | YIGAILKVLATGLPTLISWIKNKRAQ | G1Y, K25A |
| 675 | YIGAILKVLATGLPTLISWIKNKRKC | G1Y, Q26C |
| 676 | LLGAILKVLACGLPTLISWIKNKRKQ | G1L, I2L, T11C |
| 677 | LIGALLKVLACGLPTLISWIKNKRKQ | G1L, I5L, T11C |
| 678 | YIGAILAVLATGLPTLISWIANKRKQ | G1Y, K7A, K21A |
| 679 | YIGAILAVLATGLPTLISWIKNARKQ | G1Y, K7A, K23A |
| 680 | LIGAILKVLACGLPTLLSWIKNKRKQ | G1L, T11C, I17L |
| 681 | LIGAILKVLACGlPTLICWIKNKRKQ | G1L, T11C, S18C |
| 682 | GIGAILKVLACGLPGLIGWIKNKRKQ | T11G, T15G, S18G |
| 683 | GIGAILKVLACGLPALIAWIKNKRKQ | T11A, T15A, S18A |
| 684 | YIGAILAVLATGLPTLISWIANARKQ | G1Y, K7A, K21A, K23A |
| 685 | YIAAILKVLAAALATLISWIKNKRKQ | G1Y, G3A, T11A, G12A, P14A |
| 686 | LLGALLKVLATGLPTLLSWLKNKRKQ | G1L, I2L, I5L, I17L, I20L |
| 687 | LNleGANleLKVLATGLPTLNleSWNleKNKRKQ | G1L, I2Nle, I5Nle, I17Nle, I20Nle |
| 688 | LVGAVLKVLATGLPTLVSWVKNKRKQ | G1L, I2V, I5V, I17V, I20V |
| 689 | GLGALLKVLACGLPTLLSWLKNKRKQ | I2L, I5L, T11C, I17L, I20L |
| 690 | GNleGANleLKVLACGLPTLNleSWNleKNKRKQ | I2Nle, I5Nle, T11C, I17Nle, I20Nle |
| 691 | CEDDLLLGAILKVLATGLPTLISWIKNKRKQ | CEDDL-Mel G1L, I2L |
| 692 | CLVVLIVVAILKVLATGLPTLISWIKNKRKQ | CLVVL-Mel G1I, I2V, G3V |
| 693 | GIGAVLKVLTTGLPALISWIKRKRQQ | *Apis mellifera* |
| 694 | CLIGAILKVLATGLPTLISWIKNKRKQ | C-Mel G1L |
| 695 | CNIelGAILKVLATGLPTLISWIKNKRKQ | C-Mel G1Nle |
| 696 | GLIGAILKVLATGLPTLISWIKNKRKQ | G-Mel G1L |
| 697 | LLIGAILKVLATGLPTLISWIKNKRKQ | L-Mel G1L |
| 698 | KLKLIGAILKVLATGLPTLISWIKNKRKQ | KLK-Mel G1L |

TABLE 3-continued

MLP amino acid sequences.

| SEQ ID NO | MLP Sequence | Name |
|---|---|---|
| 699 | KLKYIGAILKVLATGLPTLISWIKNKRKQ | KLK-Mel G1Y |
| 700 | CKLKLIGAILKVLATGLPTLISWIKNKRKQ | CKLK-Mel G1L |
| 701 | CKLKNIelGAILKVLATGLPTLISWIKNKRKQ | CKLK-Mel G1Nle |
| 702 | GKLKLIGAILKVLATGLPTLISWIKNKRKQ | GKLK-Mel G1L |
| 703 | CPANLIGAILKVLATGLPTLISWIKNKRKQ | CPAN-dMel G1L |
| 704 | DEPLRAIGAILKVLATGLPTLISWIKNKRKQ | DEPLR-Mel G1A |
| 705 | GIGAILKVLATGLPTLISWIKNKRKQC | Mel-Cys |
| 706 | LIGAILKVLATGLPTLISWIKNKRKQC | G1L Mel-Cys |
| 707 | NleIGAILKVLATGLPTLISWIKNKRKQC | G1Nle Mel-C |
| 708 | LIGAILKVLATGLPTLISWIKNKRKQKLKC | G1L Mel-KLKC |
| 709 | YIGAILKVLATGLPTLISWIKNKRKQPLGIAGQC | G1Y Mel-PLGIAGQC |
| 710 | LIGAILKVLATGLPTLISWIKNKRKQKKKKK | G1L Mel-KKKKK |
| 711 | YIGAILKVLATGLPTLISWIKNKRKQGFKGC | G1Y Mel-GFKGC |
| 712 | CFKLIGAILKVLATGLPTLISWIKNKRKQC | CFK-G1L Mel-C |
| 713 | FGAILKVLATGLPTLISWIKNKRKQ | G1F, I2Δ |
| 714 | LIGAILKVLATGLPTLISWIKNK | G1L Mel (1-23) |
| 715 | LIGAVLKVLTTGLPALISWIK | G1L, L5V, A10T, T15A Mel (1-21) |
| 716 | LIGAVLKVLTTGLPALISWIKGE | G1L, L5V, A10T, T15A, N22G, K23E Mel (1-23) |
| 717 | QKRKNKIWSILTPLGTALVKLIAGIL | G1L retroMel |
| 718 | KLKQKRKNKIWSILTPLGTALVKLIAGIL | G1L retroMel-KLK |
| 719 | GIGAVLKVLTTGLPALISWISRKKRQQ | I5V, A10T, T15A, N22R, R24K, K25R Mel-Q |
| 720 | GIGARLKVLTTGLPRISWIKRKRQQ | I5R, A10T, T15R, L16Δ, N22R, K25Q |
| 721 | GIGAILKVLSTGLPALISWIKRKRQE | A10S, T15A, N22R, K25Q, Q26E |
| 722 | GIGAVLKVLTTGLPALIGWIKRKRQQ | I5V, A10T, T15A, S18G, N22R, K25Q |
| 723 | GIGAVLKVLATGLPALISWIKRKRQQ | I5V, T15A, N22R, K25Q |
| 724 | GIGAVLKVLSTGLPALISWIKRKRQQ | I5V, A10S, T15A, N22R, K25Q |
| 725 | GIGAILRVLATGLPTLISWIKNKRKQ | K7R |
| 726 | GIGAILKVLATGLPTLISWIKRKRKQ | N22R |
| 727 | GIGAILKVLATGLPTLISWIKKKKQQ | N22K, R24K, K25Q |
| 728 | GIGAILKVLATGLPTLISWIKNKRKQGSKKKK | Mel-GSKKKK |
| 729 | KKGIGAILKVLATGLPTLISWIKNKRKQ | KK-Mel |
| 730 | GIGAILEVLATGLPTLISWIKNKRKQ | K7E Mel |
| 731 | GIGAVLKVLTTGLPALISWIKRKR | I5V, T15A, N22R, 25-26Δ |
| 732 | GIGAVLKVLTTGLPALISWIKR | I5V, T15A, N22R, 23-26Δ |
| 733 | CIGAVLKVLTTGLPALISWIKRKRQQ | G1C, I5V, A10T, T15A, N22R, K25Q |
| 734 | QQRKRKIWSILAPLGTTLVKLVAGIG | I5V, A10T, T15A, N22R retroMel |
| 735 | QQRKRKIWSILAPLGTTLVKLVAGIC | G1C, I5V, A10T, T15A, N22R retroMel |

TABLE 3-continued

MLP amino acid sequences.

| SEQ ID NO | MLP Sequence | Name |
|---|---|---|
| 736 | QQKKKKIWSILAPLGTTLVKLVAGIC | G1C, I5V, A10T, T15A, N22R, R24K retroMel |
| 737 | QKRKNKIWSILTPLGTALVKLIAGIG | Q25K retro Mel |
| 738 | QQRKRKIWSILAALGTTLVKLVAGIC | G1C, I5V, A10T, P14A, T15A, N22R retroMel |
| 739 | QKRKNKIWSILTPLGTALVKLIAGIG-NH$_2$ | Retroinverso (dMel) | dMel = Melittin peptide having D-form amino acids

In some embodiments, the ASGPr ligand-containing masking agent has a neutral charge and comprises an ASGPr ligand linked to a disubstituted maleic anhydride amine-reactive group. In some embodiments, the ASGPr ligand has affinity for the ASGPr greater than or equal to galactose (a galactose derivative). Galactose derivative include, but are not limited to: galactosamine, N-acetylgalactosamine, lactose, N-formylgalactosamine, N-acetyl-galactosamine, N-propionylgalactosamine, N-n-butanoylgalactosamine, and N-iso-butanoyl-galactosamine.

In some embodiments, a masking agent comprises a neutral hydrophilic disubstituted alkylmaleic anhydride having the structure represented by:

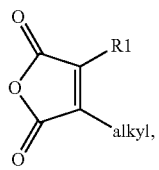

wherein in which R1 comprises an asialoglycoprotein receptor (ASGPr) ligand and alkyl can be, but is not limited to, methyl (—CH$_3$), ethyl (—CH$_2$CH$_3$), or propyl (—CH$_2$CH$_2$CH$_3$). An example of a substituted alkylmaleic anhydride consists of a 2-propionic-3-alkylmaleic anhydride derivative. A neutral hydrophilic 2-propionic-3-alkylmaleic anhydride derivative is formed by attachment of a neutral hydrophilic group to a 2-propionic-3-alkylmaleic anhydride through the 2-propionic-3-alkylmaleic anhydride γ-carboxyl group:

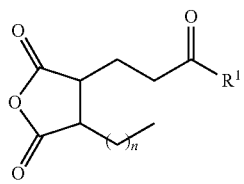

wherein R1 comprises a neutral ASGPr ligand and n=0 or 1. In some embodiments, the ASGPr ligand is linked to the anhydride via a short PEG linker.

In some embodiments, the galactose ligand is linked to the anhydride through a PEG linker as illustrated by the structure:

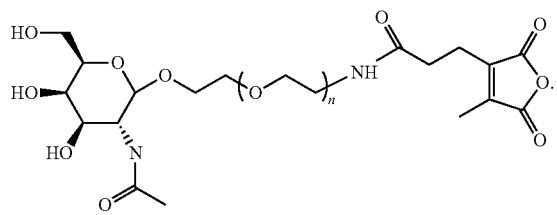

wherein n is an integer between 1 and 19.

Reaction of an amine with a cyclic anhydride to form an amide acid.

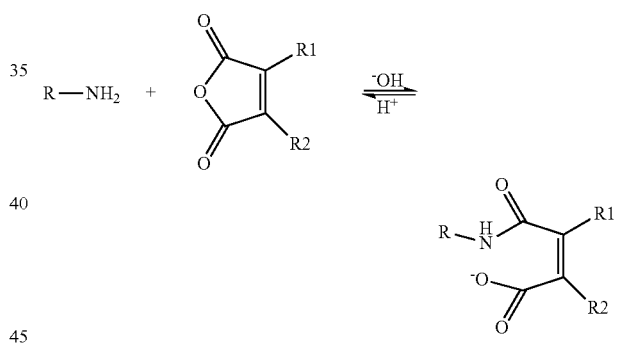

Cleavage of the amide acid to form an amine and an anhydride is pH-dependent and is greatly accelerated at acidic pH.

The membrane active polyamine can be conjugated to masking agents in the presence of an excess of masking agents. The excess masking agent may be removed from the conjugated delivery peptide prior to administration of the delivery peptide.

ASGPr Ligand

Targeting moieties or groups enhance the pharmacokinetic or biodistribution properties of a conjugate to which they are attached to improve cell-specific distribution and cell-specific uptake of the conjugate. Galactose derivatives have been used to target molecules to hepatocytes in vivo through their binding to the asialoglycoprotein receptor (ASGPr) expressed on the surface of hepatocytes. As used herein, an ASGPr ligand comprises a galactose derivative having affinity for the ASGPr equal to or greater than that of galactose. Binding of ASGPr ligands to the ASGPr(s) facilitates cell-specific targeting to hepatocytes and endocytosis of the molecule into hepatocytes. ASGPr ligands may be selected from the group comprising: lactose, galactose, N-acetylgalactosamine (GalNAc), galactosamine, N-formylgalactosamine, N-acetyl-galactosamine, N-propionylgalactosamine, N-n-butanoylgalactosamine, and N-iso-butanoyl-galactosamine (Iobst, S. T. and Drickamer, K. *J.B.C.* 1996, 271, 6686). ASGPr ligands can be monomeric (e.g., having a single galactosamine) or multimeric (e.g., having multiple galactosamines). In some embodiments, the MLP is reversibly masked by attachment of ASGPr ligand masking agents to 280% or ≥90% of primary amines on the peptide.

RNAi Trigger-Hydrophobic Group Conjugate

We have found that conjugation of an HBV RNAi trigger to a hydrophobic group, such as a cholesterol or cholesteryl group, and co-administration of the RNAi trigger conjugate with an MLP delivery peptide provides for efficient, functional delivery of the HBV RNAi trigger to liver cells, particularly hepatocytes, in vivo. In some embodiments, an HBV RNAi trigger is covalently conjugated to a hydrophobic group. A trigger can be synthesized or modified such that it contains a reactive group A. The targeting group can also be synthesized or modified such that it contains a reactive group B. Reactive groups A and B are chosen such that they can be linked via a covalent linkage using methods known in the art. The hydrophobic group may be linked to the 3' or the 5' end of an HBV RNAi trigger. In some embodiments, a hydrophobic group is linked to either the sense strand or the antisense strand of the RNAi trigger. In some embodiments, a hydrophobic group is linked to the sense strand of the RNAi trigger.

In some embodiments, hydrophobic groups useful as polynucleotide targeting moieties may be selected from the group consisting of: alkyl group, alkenyl group, alkynyl group, aryl group, aralkyl group, aralkenyl group, and aralkynyl group, each of which may be linear, branched, or cyclic, cholesterol, cholesterol derivative, sterol, steroid, and steroid derivative. Hydrophobic targeting moieties are typically hydrocarbons, containing only carbon and hydrogen atoms. In some embodiments, the hydrophobic group can be, but is not limited to, cholesterol, dicholesterol, tocopherol, ditocopherol, didecyl, didodecyl, dioctadecyl, didodecyl, dioctadecyl, isoprenoid, and choleamide. Attachment of a hydrophobic targeting group to an HBV RNAi trigger does not provide efficient functional in vivo delivery of the HBV RNAi trigger in the absence of co-administration of the delivery peptide. While siRNA-cholesterol conjugates have been reported by others to deliver siRNA (siRNA-cholesterol) to liver cells in vivo, in the absence of any additional delivery vehicle, high concentrations of siRNA are required and delivery efficacy is poor. When combined with the delivery peptides described herein, delivery of the RNAi trigger is greatly improved. By providing the HBV RNAi trigger-cholesterol and a delivery peptide, efficacy of HBV RNAi trigger is increased about 100 fold. In some embodiments, a targeting group is linked to either the sense strand or the antisense strand of the RNAi trigger. Substitutions or heteroatoms which maintain hydrophobicity, for example fluorine, may be permitted. The hydrophobic targeting group may be attached to the 3' or 5' end of the HBV RNAi trigger using methods known in the art. For HBV RNAi triggers having 2 strands, the hydrophobic group may be attached to either strand.

Hydrophobic group indicates in qualitative terms that the chemical moiety is water-avoiding. Typically, such chemical group is not water soluble, and tends not to form hydrogen bonds. Hydrophobic groups dissolve in fats, oils, lipids, and non-polar solvents and have little to no capacity to form hydrogen bonds. Hydrocarbons containing two (2) or more carbon atoms, certain substituted hydrocarbons, cholesterol, and cholesterol derivatives are examples of hydrophobic groups and compounds. Hydrophobic groups are typically hydrocarbons, containing only carbon and hydrogen atoms. In some embodiments, non-polar substitutions or non-polar heteroatoms which maintain hydrophobicity, and include, for example fluorine, are permitted. The term includes aliphatic groups, aromatic groups, acyl groups, alkyl groups, alkenyl groups, alkynyl groups, aryl groups, aralkyl groups, aralkenyl groups, and aralkynyl groups, each of which may be linear, branched, or cyclic. The term hydrophobic group also includes: sterols, steroids, cholesterol, and steroid and cholesterol derivatives. As used herein, cholesteryl group means a compound comprising cholesterol or cholesterol derivative(s).

As used herein, membrane active peptides are surface active, amphipathic peptides that are able to induce one or more of the following effects upon a biological membrane: an alteration or disruption of the membrane that allows non-membrane permeable molecules to enter a cell or cross the membrane, pore formation in the membrane, fission of membranes, or disruption or dissolving of the membrane. As used herein, a membrane, or cell membrane, comprises a lipid bilayer. The alteration or disruption of the membrane can be functionally defined by the peptide's activity in at least one the following assays: red blood cell lysis (hemolysis), liposome leakage, liposome fusion, cell fusion, cell lysis, and endosomal release. Membrane active peptides that can cause lysis of cell membranes are also termed membrane lytic peptides. Peptides that preferentially cause disruption of endosomes or lysosomes over plasma membranes are considered endosomolytic. The effect of membrane active peptides on a cell membrane may be transient. Membrane active peptides possess affinity for the membrane and cause a denaturation or deformation of bilayer structures.

The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. A non-natural or synthetic polynucleotide is a polynucleotide that is polymerized in vitro or in a cell free system and contains the same or similar bases but may contain a backbone of a type other than the natural ribose or deoxyribose-phosphate backbone. Polynucleotides can be synthesized using any known technique in the art. Polynucleotide backbones known in the art include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups on the nucleotide such as, but not limited to, amines, alcohols, thiols, carboxylates, and alkylhalides. The term base encompasses any of the known base analogs of DNA and RNA. A polynucleotide may contain ribonucleotides, deoxyribonucleotides, synthetic nucleotides, or any suitable combination. Polynucleotides may be polymerized in vitro, they may be recombinant, contain chimeric sequences, or derivatives of these groups. A polynucleotide may include a terminal cap group at the 5'-end, the 3'-end, or both the 5' and 3' ends. The cap group can be, but is not limited to, an inverted deoxy abasic group, an inverted deoxy thymidine, a thymidine, or 3' glyceryl modification.

An RNA interference (RNAi) trigger is a molecule capable of inducing RNA interference through interaction with the RNA interference pathway machinery of mammalian cells to degrade or inhibit translation of messenger RNA (mRNA) transcripts of a transgene in a sequence specific manner. Two primary HBV RNAi triggers are small (or short) interfering RNAs (siRNAs) and micro RNAs (miRNAs). HBV RNAi triggers may be selected from the group comprising: siRNA, microRNA, double-strand RNA (dsRNA), short hairpin RNA (shRNA), and expression cassettes encoding RNA capable of inducing RNA interference. RNAi triggers comprise a double stranded structure typically containing 15-50 base pairs. In some embodiments, RNAi triggers comprise a double strand structure having 17-26 base pairs and having a nucleotide sequence identical (perfectly complementary) or nearly identical (partially complementary) to a coding sequence in an expressed target gene or RNA within the cell. An RNAi trigger may have dinucleotide 3' overhangs. An RNAi trigger may be composed of two annealed polynucleotides or a single polynucleotide that forms a hairpin structure. An RNAi trigger comprises a sense region and an antisense region. In some embodiments, an RNAi trigger is assembled from two oligonucleotide fragments wherein one fragment comprises the nucleotide sequence of the antisense strand of the RNAi trigger and a second fragment comprises nucleotide sequence of the sense region of the RNAi trigger. In some embodiments, the sense strand is connected to the antisense strand via a linker molecule, such as a polynucleotide linker or a non-nucleotide linker. MicroRNAs (miRNAs) are small noncoding RNA gene products about 22 nucleotides long that direct destruction or translational repression of their mRNA targets. If the complementarity between the miRNA and the target mRNA is partial, translation of the target mRNA is repressed. If complementarity is extensive, the target mRNA is cleaved. For miRNAs, the complex binds to target sites usually located in the 3' UTR of mRNAs that typically share only partial homology with the miRNA. A "seed region"—a stretch of about seven (7) consecutive nucleotides on the 5' end of the miRNA that forms perfect base pairing with its target—plays a key role in miRNA specificity. Binding of the RISC/miRNA complex to the mRNA can lead to either the repression of protein translation or cleavage and degradation of the mRNA. Recent data indicate that mRNA cleavage happens preferentially if there is perfect homology along the whole length of the miRNA and its target instead of showing perfect base-pairing only in the seed region (Pillai et al. 2007).

An HBV RNAi trigger can be chemically modified. Non-limiting examples of such chemical modifications include: phosphorothioate internucleotide linkages, 2'-O-methyl ribonucleotides, 2'-deoxy-2'-fluoro ribonucleotides, 2'-deoxy ribonucleotides, "universal base" nucleotides, 5-C-methyl nucleotides, and inverted deoxyabasic residue incorporation. These chemical modifications, when used in various polynucleotide constructs, are shown to preserve polynucleotide activity in cells while at the same time increasing the serum stability of these compounds. Chemically modified RNAi trigger can also minimize the possibility of activating interferon activity in humans.

The term complementarity refers to the ability of a polynucleotide to form hydrogen bond(s) with another polynucleotide sequence by either traditional Watson-Crick or other non-traditional types. In reference to the polynucleotide molecules, the binding free energy for a polynucleotide molecule with its target (effector binding site) or complementary sequence is sufficient to allow the relevant function of the polynucleotide to proceed, e.g., enzymatic mRNA cleavage or translation inhibition. Determination of binding free energies for nucleic acid molecules is well known in the art (Frier et al. 1986, Turner et al. 1987). A percent complementarity indicates the percentage of bases, in a contiguous strand, in a first polynucleotide molecule which can form hydrogen bonds (e.g., Watson-Crick base pairing) with a second polynucleotide sequence (e.g., 5, 6, 7, 8, 9, 10 out of 10 being 50%, 60%, 70%, 80%, 90%, and 100% complementary). Perfectly complementary means that all the bases in a contiguous strand of a polynucleotide sequence will hydrogen bond with the same number of contiguous bases in a second polynucleotide sequence.

By inhibit, down-regulate, or knockdown gene expression, it is meant that the expression of the gene, as measured by the level of RNA transcribed from the gene or the level of polypeptide, protein or protein subunit translated from the RNA, is reduced below that observed in the absence of the blocking polynucleotide-conjugates. In some embodiments, inhibition, down-regulation, or knockdown of gene expression, with a polynucleotide delivered by the described compositions, is below the level observed in the presence of a control inactive nucleic acid, a nucleic acid with scrambled sequence or with inactivating mismatches, or in absence of conjugation of the polynucleotide to the masked polymer.

In Vivo Administration

In pharmacology and toxicology, a route of administration is the path by which a drug, fluid, poison, or other substance is brought into contact with the body. In general, methods of administering drugs and nucleic acids for treatment of a mammal are well known in the art and can be applied to administration of the described compositions. In some embodiments, the described compositions can be administered via any suitable route, such as, but not limited to, parenterally, in a preparation appropriately tailored to that route. Thus, in some embodiments, the described compositions can be administered by injection, for example, intravenously, intramuscularly, intracutaneously, subcutaneously, or intraperitoneally. In some embodiments, pharmaceutical compositions comprising a pharmaceutically acceptable carrier or excipient are described.

Parenteral routes of administration include intravascular (intravenous, intraarterial), intramuscular, intraparenchymal, intradermal, subdermal, subcutaneous, intratumor, intraperitoneal, intrathecal, subdural, epidural, and intralymphatic injections that use a syringe and a needle or catheter. Intravascular herein means within a tubular structure called a vessel that is connected to a tissue or organ within the body. Within the cavity of the tubular structure, a bodily fluid flows to or from the body part. Examples of bodily fluid include blood, cerebrospinal fluid (CSF), lymphatic fluid, or bile. Examples of vessels include arteries, arterioles, capillaries, venules, sinusoids, veins, lymphatics, bile ducts, and ducts of the salivary or other exocrine glands. The intravascular route includes delivery through the blood vessels such as an artery or a vein. The blood circulatory system provides systemic spread of the pharmaceutical.

In some embodiments, an HBV RNAi trigger-targeting group conjugate is co-administered with a delivery peptide. By co-administered it is meant that the HBV RNAi trigger and the delivery peptide are administered to the mammal such that both are present in the mammal at the same time. The HBV RNAi trigger-targeting group conjugate and the delivery peptide may be administered simultaneously or they may be delivered sequentially. For simultaneous administration, they may be mixed prior to administration. For sequential administration, either the HBV RNAi trigger-targeting group conjugate or the delivery peptide may be administered first.

Pharmaceutical Compositions

In some embodiments, at least one of the described HBV RNAi triggers is used in the preparation of a pharmaceutical composition (i.e., medicament) for treatment of a subject that would benefit from reduction or inhibition in HBV expression. These pharmaceutical compositions are useful in the inhibition of the expression of the HBV gene in a cell, a tissue, or an organism. In some embodiments, the described pharmaceutical compositions are used to treat a subject having a disease or disorder that would benefit from reduction or inhibition in HBV expression.

As used herein, a pharmaceutical composition or medicament comprises a pharmacologically effective amount of at least one of the described HBV RNAi triggers and one or more pharmaceutically acceptable excipients. Pharmaceutically acceptable excipients (excipients) are substances other than the Active Pharmaceutical ingredient (API, therapeutic product, e.g., RNAi trigger) that have been appropriately evaluated for safety and are intentionally included in the drug delivery system. Excipients do not exert or are not intended to exert a therapeutic effect at the intended dosage. Excipients may act to a) aid in processing of the drug delivery system during manufacture, b) protect, support or enhance stability, bioavailability or patient acceptability of the API, c) assist in product identification, and/or d) enhance any other attribute of the overall safety, effectiveness, of delivery of the API during storage or use. A pharmaceutically acceptable excipient may or may not be an inert substance.

Excipients include, but are not limited to: absorption enhancers, anti-adherents, anti-foaming agents, anti-oxidants, binders, binders, buffering agents, carriers, coating agents, colors, delivery enhancers, dextran, dextrose, diluents, disintegrants, emulsifiers, extenders, fillers, flavors, glidants, humectants, lubricants, oils, polymers, preservatives, saline, salts, solvents, sugars, suspending agents, sustained release matrices, sweeteners, thickening agents, tonicity agents, vehicles, water-repelling agents, and wetting agents.

A pharmaceutical composition can contain other additional components commonly found in pharmaceutical compositions. Such additional components include, but are not limited to: anti-pruritics, astringents, local anesthetics, or anti-inflammatory agents (e.g., antihistamine, diphenhydramine, etc.). It is also envisioned that cells, tissues or isolated organs that express or comprise the herein defined RNAi triggers may be used as "pharmaceutical compositions". As used herein, "pharmacologically effective amount," "therapeutically effective amount," or simply "effective amount" refers to that amount of an RNAi trigger to produce the intended pharmacological, therapeutic or preventive result.

In some embodiments, a described HBV RNAi trigger is combined one or more additional therapeutics or treatments including, but not limited to: a second HBV RNAi trigger or other RNAi agent, a small molecule drug, an antibody, an antibody fragment, and/or a vaccine.

The described HBV RNAi triggers and pharmaceutical compositions comprising HBV RNAi triggers disclosed herein may be packaged or included in a kit, container, pack, or dispenser. The HBV RNAi triggers and pharmaceutical compositions comprising said HBV RNAi triggers may be packaged in pre-filled syringes or vials.

Method of Treatment

In some embodiments, the HBV RNAi triggers described herein are used to treat a subject infected with HBV. In some embodiments, the described HBV RNAi triggers are used to treat at least one symptom in a subject having a HBV infection. The subject is administered a therapeutically effective amount of any one or more of the described RNAi triggers.

In some embodiments, the HBV RNAi triggers are used to treat or manage a clinical presentation wherein a subject infected with HBV. The subject is administered a therapeutically or effective amount of one or more of the HBV RNAi triggers or HBV RNAi trigger-containing compositions described herein. In some embodiments, the method comprises administering a composition comprising an HBV RNAi trigger molecule described herein to a subject to be treated.

As used herein, the terms "silence," "reduce," "inhibit," "down-regulate," or "knockdown gene expression," when referring to an HBV gene, mean that the expression of the gene, as measured by the level of RNA transcribed from the gene or the level of polypeptide, protein, or protein subunit translated from the mRNA in a cell, group of cells, or tissue, in which the HBV gene is transcribed, is reduced when the cell, group of cells, or tissue, is treated with the described HBV RNAi triggers as compared to a second cell, group of cells, or tissue that has or has not been so treated or compared to the same cell, group of cells, or tissue, prior to administration of the HBV RNAi trigger.

In some embodiments, the gene expression level and/or mRNA level of an HBV gene in a subject to whom a described HBV RNAi trigger is administered is reduced by at least about 5%, 10%, 15%, 20%, 25%, 30%, 35%, 40%, 45%, 50%, 55%, 60%, 65%, 70%, 75%, 80%, 85%, 90%, 95%, or 98% relative to the subject prior to being administered the HBV RNAi trigger or to a subject not receiving the HBV RNAi trigger. The gene expression level and/or mRNA level in the subject may be reduced in a cell, group of cells, and/or tissue of the subject.

In some embodiments, the protein level of HBV in a subject to whom a described HBV RNAi trigger has been administered is reduced by at least about 5%, 10%, 15%, 20%, 25%, 30%, 35%, 40%, 45%, 50%, 55%, 60%, 65%, 70%, 75%, 80%, 85%, 90%, 95%, or 98% relative to the subject prior to being administered the HBV RNAi trigger or to a subject not receiving the HBV RNAi trigger. The protein level in the subject may be reduced in a cell, group of cells, tissue, blood, and/or other fluid of the subject. A reduction in gene expression, mRNA, or protein levels can be assessed by any methods known in the art. Reduction or decrease in HBV mRNA level and/or protein level are collectively referred to herein as a reduction or decrease in HBV or inhibiting or reducing the expression of HBV.

"Introducing into a cell", when referring to an RNAi trigger, means functionally delivering the RNAi trigger into a cell. By functional delivery, it is meant that the RNAi trigger is delivered to the cell and has the expected biological activity, (e.g., sequence-specific inhibition of gene expression).

The route of administration is the path by which an RNAi trigger is brought into contact with the body. In general, methods of administering drugs and nucleic acids for treatment of a subject are well known in the art and can be applied to administration of the compositions described herein. The compounds described herein can be administered via any suitable route in a preparation appropriately tailored to the particular route. Thus, the compounds described herein can be administered by injection, for example, intravenously, intramuscularly, intracutaneously, subcutaneously, or intraperitoneally.

EXAMPLES

Example 1. MLP Synthesis

All MLPs were made using peptide synthesis techniques standard in the art. Suitable MLPs can be all L-form amino acids, all D-form amino acids (inverso). Independently of L or D form, the MLP sequence can be reversed (retro).

Example 2. Amino Terminal Modification of MLPs

Solutions of CKLK-MLP (20 mg/ml), TCEP-HCl (28.7 mg/ml, 100 mM), and MES-Na (21.7 mg/ml, 100 mM) were prepared in dH$_2$O. In a 20 ml scintillation vial, CKLK-MLP (0.030 mmol, 5 ml) was reacted with 1.7 molar equivalents TCEP-HCl (0.051 mmol, 0.51 ml) and left to stir at room temperature for 30 min. MES-Na (2 ml) and Water (1.88 ml) were then added in amounts to yield final concentrations of 10 mg/ml MLP and 20 mM MES-Na. The pH was checked and adjusted to pH 6.5-7. A solution of NAG-PEG2-Br (100 mg/ml) was prepared in dH$_2$O. NAG-PEG2-Br (4.75 eq, 0.142 mmol, 0.61 ml) was added, and the solution was left to stir at room temperature for 48 h.

Alternatively, in a 20 ml scintillation vial, Cys-MLP (0.006 mmol, 1 ml) was reacted with 1.7 molar equivalents TCEP-HCl (0.010 mmol, 100 µl) and left to stir at room temperature for 30 min. MES-Na (400 µl) and water (390 µl) were added in amounts to yield final concentrations of 10 mg/ml MLP and 20 mM MES-Na. The pH was checked and adjusted to pH 6.5-7. A solution of NAG-PEGs-Maleimide (100 mg/ml) was prepared in dH$_2$O. NAG-PEGs-Maleimide (2 eq, 0.012 mmol, 110 µl) was added, and the solution was left to stir at room temperature for 48 h.

Samples were purified on a Luna 10µ C18 100 Å 21.2× 250 mm column. Buffer A: H$_2$O 0.1% TFA and Buffer B: MeCN, 10% Isopropyl Alcohol, 0.1% TFA. Flow rate of 15 ml/min, 35% A to 62.5% B in 20 min.

Other amino terminal modifications were made using similar means. Carboxyl terminal modifications were made substituting MLPs having carboxyl terminal cysteines for MLPs having amino terminal cysteines.

Compounds Used to Modified Cys-MLP or MLP-Cys:

formula II

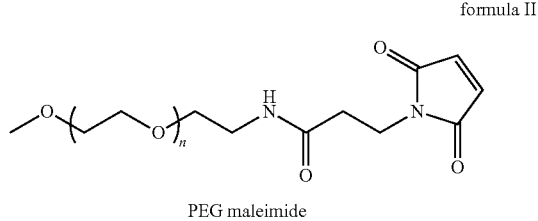

PEG maleimide n is an integer from 1 to 120 (PEG molecular weight up to about 5 kDa)

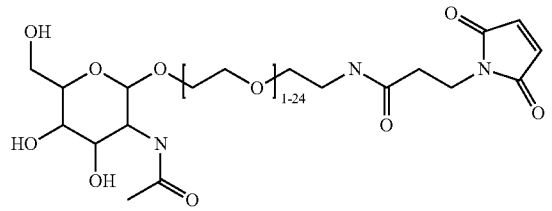

NAG-PEG maleimide - formula I

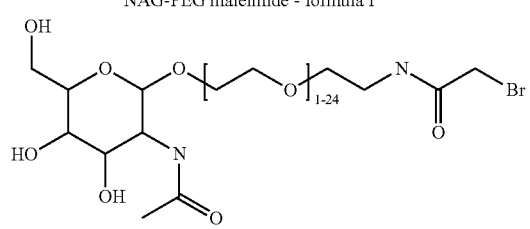

N-NAG-PEG bromo acetimide

Peptides having acetyl, dimethyl, stearoyl, myristoyl, and PEG amino or carboxyl terminal modifications, but not terminal cysteine residues, were generated on resin during peptide synthesis using methods typical in the art.

Example 3. Masking Agents Synthesis

A. pH Labile Masking Agents: Steric Stabilizer CDM-PEG and Targeting Group CDM-NAG (N-Acetyl Galactosamine) Syntheses.

To a solution of CDM (300 mg, 0.16 mmol) in 50 mL methylene chloride was added oxalyl chloride (2 g, 10 wt. eq.) and dimethylformamide (5 µl). The reaction was allowed to proceed overnight, after which the excess oxalyl chloride and methylene chloride were removed by rotary evaporation to yield the CDM acid chloride. The acid chloride was dissolved in 1 mL of methylene chloride. To this solution was added 1.1 molar equivalents polyethylene glycol monomethyl ether (MW average 550) for CDM-PEG or (aminoethoxy)ethoxy-2-(acetylamino)-2-deoxy-β-D-galactopyranoside (i.e. amino bisethoxyl-ethyl NAG) for CDM-NAG, and pyridine (200 µl, 1.5 eq) in 10 mL of methylene chloride. The solution was then stirred 1.5 h. The solvent was then removed and the resulting solid was dissolved into 5 mL of water and purified using reverse-phase HPLC using a 0.1% TFA water/acetonitrile gradient.

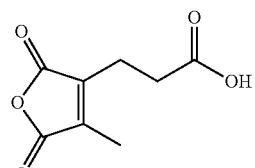

CDM

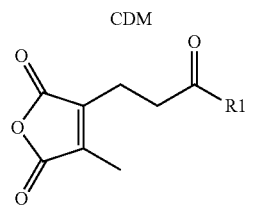

Generic Disubstituted Maleic Anhydride Masking Agent

R1 comprises a neutral ASGPr ligand. In some embodiments, the Masking Agent in uncharged.

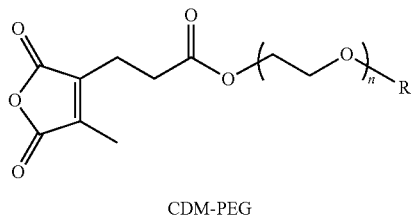

CDM-PEG

R is a methyl or ethyl, and n is an integer from 2 to 100. In some embodiments, the PEG contains from 5 to 20 ethylene units (n is an integer from 5 to 20). In some embodiments, the PEG contains 10-14 ethylene units (n is an integer from 10 to 14). The PEG may be of variable length and have a mean length of 5-20 or 10-14 ethylene units. Alternatively, the PEG may be monodisperse, uniform or discrete; having, for example, exactly 11 or 13 ethylene units.

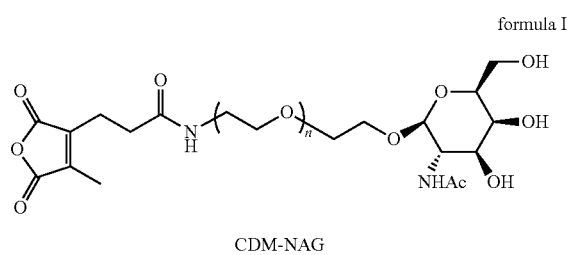

formula I

CDM-NAG n is an integer from 1 to 10. As shown above, a PEG spacer may be positioned between the anhydride group and the ASGPr ligand. In some embodiments, a PEG spacer contains 1-10 ethylene units.

Alternatively an alkyl spacer may be used between the anhydride and the N-acetylgalactosamine.

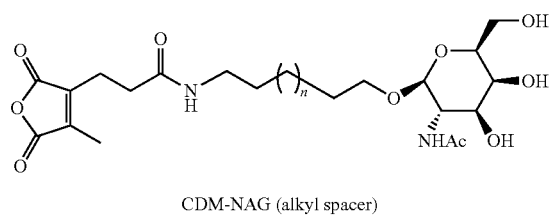

CDM-NAG (alkyl spacer)

n is a integer from 0 to 6.

Other spacers or linkers may be used bet between the anhydride and the N-acetyl-galactosamine. In some embodiments, a hydrophilic spacer or linker is used. In some embodiments, a neutral spacer or linker is used.

Example 4. Reversible Modification/Masking of MLP

A. Modification with Maleic Anhydride-Based Masking Agents.

Prior to modification, 5×mg of disubstituted maleic anhydride masking agent (e.g. CDM-NAG) was lyophilized from a 0.1% aqueous solution of glacial acetic acid. To the dried disubstituted maleic anhydride masking agent was added a solution of x mg MLP in 0.2×mL of isotonic glucose and 10×mg of HEPES free base. Following complete dissolution of anhydride, the solution was incubated for at least 30 min at RT prior to animal administration. Reaction of disubstituted maleic anhydride masking agent with the peptide yielded:

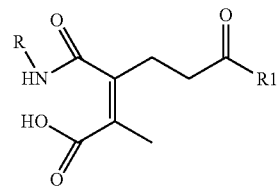

wherein R is MLP and R1 comprises a ASGPr ligand (e.g. NAG). The anhydride carboxyl produced in the reaction between the anhydride and the polymer amine exhibits $\sim\!\!1\!/\!20^{th}$ of the expected charge (Rozema et al. Bioconjugate Chemistry 2003). Therefore, the membrane active polymer is effectively neutralized rather than being converted to a highly negatively charged polyanion.

In some embodiments, the masked MLP (MLP-(CDM-NAG)) was in a solution containing 125 mg MLP, 500 mg dextran 1K, 3.18 mg sodium carbonate, 588 mg sodium bicarbonate in 5 ml water. In some embodiments, the MLP-(CDM-NAG) was lyophilized.

B. Modification with Protease Cleavable Masking Agents.

1×mg of peptide and 10×mg HEPES base at 1-10 mg/mL peptide was masked by addition of 2-6×mg of amine-reactive p-nitrophenyl carbonate or N-hydroxysuccinimide carbonate derivatives of the NAG-containing protease cleavable substrate. The solution was then incubated at least 1 h at room temperature (RT) before injection into animals.

Example 5. HBV RNAi Trigger-Targeting Molecule Conjugates (1) RNAi Trigger Conjugation to Alkyl Groups.

A 5'-C10-NHS ester modified sense strand of RNAi trigger (NHSC10-RNAi trigger, or COC9-RNAi trigger) was prepared employing 5'-Carboxy-Modifier C10 amidite from Glen Research (Virginia, USA). The activated RNA, still attached to the solid support was used for conjugation with lipophilic amines listed in Table 1 below. 100 mg of the sense strand CPG (loading 60 µmol/g, 0.6 µmol RNA) were mixed with 0.25 mmol of the corresponding amine obtained from, Sigma Aldrich Chemie GmbH (Taufkirchen, Germany) or Fluka (Sigma-Aldrich, Buchs, Switzerland).

TABLE 4

Lipophilic amines used in forming hydrophobic group-RNAi trigger conjugates

| Nr | Lipophilic Amine | mg | mmol | solvent |
|---|---|---|---|---|
| 2 | N-Hexylamine | 25 | 0.25 | 1 mL $CH_2Cl_2$ |
| 3 | Dodecylamine | 50 | 0.25 | 0.55 mL $CH_3CN$, 0.45 mL $CH_2Cl_2$ |
| 4 | Octadecylamine | 67 | 0.25 | 1 mL $CH_2Cl_2$ |
| 5 | Didecylamine | 74 | 0.25 | 1 mL $CH_2Cl_2$ |
| 6 | Didodecylamine | 88 | 0.25 | 1 mL $CH_2Cl_2$ |
| 7 | Dioctadecylamine | 67 | 0.12 | 0.45 mL $CH_2Cl_2$, 0.45 mL Cyclohexan |

The mixture was shaken for 18 h at 40° C. The RNA was cleaved from the solid support and deprotected with an aqueous ammonium hydroxide solution ($NH_3$, 33%) at 45° C. overnight. The 2'-protecting group was removed with TEA×3HF at 65° C. for 3.5 h. The crude oligoribonucleotides were purified by RP-HPLC (Resource RPC 3 ml, buffer: A: 100 mM TEAA in water, B: 100 mM TEAA in 95% $CH_3CN$, gradient: 3% B to 70% B in 15 CV, except for Nr 7: gradient from 3% B to 100% B in 15 CV).

To generate RNAi trigger from RNA single strands, equimolar amounts of complementary sense and antisense strands were mixed in annealing buffer (20 mM sodium phosphate, pH 6.8; 100 mM sodium chloride), heated at 80° C. for 3 min, and cooled to RT over a period of 3-4 h. The RNAi triggers, which are directed against factor VII mRNA were characterized by gel electrophoresis.

(2) HBV RNAi Trigger Conjugation to Cholesterol—

HBV RNAi trigger-cholesterol conjugates were synthesized using methods standard in the art. Cholesterol can be attached to the 5' or 3' termini of the sense or antisense strand of the trigger. In some embodiments, attachment is to the 5' end of the sense strand of the trigger. Trigger-Cholesterol can also be made post trigger synthesis using RNA strands containing a reactive group (e.g. thiol, amine, or carboxyl) using methods standard in the art.

Example 6. Administration of HBV RNAi Triggers In Vivo, and Delivery to Hepatocytes RNAi triggers and masked MLPs were synthesized as described above. Six to eight week old mice (strain C57BL/6 or ICR, ~18-20 g each) were obtained from Harlan Sprague Dawley (Indianapolis Ind.). Mice were housed at least 2 days prior to injection. Feeding was performed ad libitum with Harlan Teklad Rodent Diet (Harlan, Madison Wis.). Mice were injected with 0.2 mL solution of delivery peptide and 0.2 mL RNAi trigger conjugates into the tail vein. For simultaneous injection of delivery peptide and RNAi trigger, the RNAi trigger-conjugate was added to modified peptide prior to injection and the entire amount was injected. The composition was soluble and nonaggregating in physiological conditions. Solutions were injected by infusion into the tail vein. Injection into other vessels, e.g. retro-orbital injection, are predicted to be equally effective.

MLPs having the indicated sequence were reversibly modified with CDM-NAG (5×) as described above. The indicated amount of MLP was then co-injected with the indicated amount of ApoB RNAi trigger-cholesterol conjugate. Effect on ApoB levels were determined as described above.

TABLE 5

Inhibition of ApoB activity in normal liver cells in mice treated with ApoB-RNAi trigger cholesterol conjugate and the indicated CDM-NAG reversibly inhibited MLP.

| MLP SEQ ID NO | μg peptide | μg ApoB RNAi Trigger | percent ApoB knockdown |
|---|---|---|---|
| 645 | 100 | 100 | 88 |
| 646 | 100 | 100 | 37 |
| 647 | 100 | 50 | 94 |
| 648 | 400 | 100 | 78 |
| 649 | 50 | 100 | 34 |
| 650 (D-form) | 50 | 100 | 93 |
| 651 | 100 | 100 | 96 |
| 652 | 100 | 100 | 91 |
| 653 | 200 | 200 | 96 |
| 654 | 100 | 50 | 95 |
| 654 (C-term $NH_2$) | 200 | 200 | 94 |
| 656 | 80 | 100 | 58 |
| 657 | 80 | 100 | 51 |
| 658 | 50 | 100 | 34 |
| 659 | 80 | 100 | 32 |
| 660 | 400 | 100 | 83 |
| 661 | 100 | 100 | 89 |
| 662 | 100 | 100 | 92 |
| 663 | 100 | 100 | 97 |
| 664 | 100 | 50 | 81 |
| 665 | 400 | 100 | 93 |
| 667 | 100 | 100 | 95 |
| 668 | 100 | 100 | 93 |
| 671 | 100 | 100 | 95 |
| 672 | 100 | 100 | 42 |
| 673 | 100 | 100 | 87 |
| 674 | 100 | 100 | 77 |
| 675 | 100 | 100 | 93 |
| 678 | 100 | 100 | 14 |
| 681 | 100 | 100 | 88 |
| 682 | 50 | 100 | 32 |
| 683 | 50 | 100 | 38 |
| 686 | 400 | 100 | 96 |
| 687 | 100 | 100 | 99 |
| 688 | 100 | 100 | 24 |
| 689 | 100 | 100 | 87 |
| 690 | 100 | 100 | 78 |
| 693 | 400 | 100 | 72 |
| 694 | 100 | 100 | 89 |
| 695 | 100 | 100 | 84 |
| 696 | 100 | 100 | 91 |
| 699 | 300 | 100 | 72 |
| 700 | 150 | 100 | 91 |
| 701 | 100 | 200 | 90 |
| 702 | 50 | 100 | 85 |
| 705 | 400 | 100 | 83 |
| 706 | 400 | 100 | 82 |
| 707 | 400 | 50 | 89 |
| 708 | 100 | 100 | 97 |
| 709 | 100 | 100 | 79 |
| 710 | 400 | 100 | 96 |
| 711 | 400 | 100 | 96 |
| 712 | 100 | 100 | 79 |
| 714 | 400 | 100 | 69 |
| 715 | 400 | 100 | 69 |
| 716 | 400 | 100 | 92 |
| 717 | 400 | 100 | 56 |
| 718 | 400 | 100 | 50 |
| 733 | 400 | 200 | 85 |
| 735 | 400 | 200 | 55 |

Example 7. Reduction in Hepatitis B Virus (HBV) In Vivo Following Delivery of HBV RNAi Triggers with MLP Delivery Peptide A) pHBV Model Mice:

At day −42, 6 to 8 week old female NOD.CB17-Prkdscid/ NcrCrl (NOD-SCID) mice were transiently transfected in vivo with MC-HBV1.3 by hydrodynamic tail vein injection (Yang P L et al. "Hydrodynamic injection of viral DNA: a mouse model of acute hepatitis B virus infection." *PNAS USA* 2002 Vol. 99: p. 13825-13830). MC-HBV1.3 is a plasmid-derived minicircle that contains the same terminally redundant human hepatitis B virus sequence HBV1.3 as in the HBV1.3.32 transgenic mice (GenBank accession #V01460) (Guidotti L G et al. "High-level hepatitis B virus replication in transgenic mice. J Virol 1995 Vol. 69, p 6158-6169.). 10 µg MC-HBV1.3 in Ringer's Solution in a total volume of 10% of the animal's body weight was injected into mice via tail vein to create pHBV model of chronic HBV infection. The solution was injected through a 27-gauge needle in 5-7 seconds as previously described (Zhang G et al. "High levels of foreign gene expression in hepatocytes after tail vein injection of naked plasmid DNA." Human Gene Therapy 1999 Vol. 10, p 1735-1737.). At day −21, three weeks post transfection, Hepatitis B surface antigen (HBsAg) HBsAg expression levels in serum were measured by ELISA and the mice were grouped according to average HBsAg expression levels.

B) HBV RNAi Triggers:
Structure of the Cholesterol-C6-RNAi Trigger:

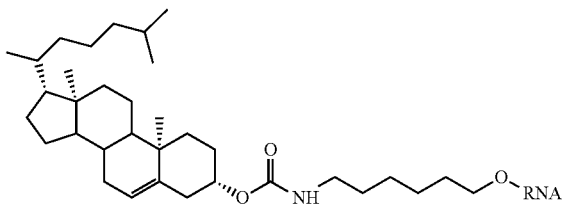

AD00009 and AD00010 were synthesized, purified, hydridized (sense and anti-sense strands), and combined at a 1:1 molar ratio. The combined RNAi triggers were used for all subsequent procedures.

Hepatitis B Virus RNAi triggers are described in U.S. Patent Publication US 2013-0005793 (U.S. Pat. No. 8,809, 293), which is incorporated herein by reference.

C) MLP Delivery Peptide:
CDM-NAG was added to MLP, SEQ ID NO: 650 (GIL MLP, L-form), in a 250 mM HEPES-buffered aqueous solution at a 5:1 (w/w) ratio at room temperature and incubated for 30 min to yield MLP delivery peptide. The reaction mixture was adjusted to pH 9.0 with 4 M NaOH. The extent of the reaction was assayed using 2,4,6-trinitrobenzene-sulfonic acid and determined to be >95%. MLP delivery peptide was purified by tangential flow in 10 mM bicarbonate buffer, pH 9.0, to which 10% dextran (w/w) was added. The final purified material was lyophilized.

D) Formation of HBV RNAi Trigger Delivery Composition:
5 mg lyophilized MLP delivery peptide was resuspended with 1 mL water. MLP delivery peptide was then combined with HBV RNAi triggers at a 1:1 ratio (w/w) (~5.49:1 molar ratio). Isotonic glucose was added as necessary to bring the volume of each injection to 200 µl.

In some embodiments, the HBV RNAi triggers were at a concentration of 26 g/L in a solution that also contained 0.069 g/L sodium phosphate monobasic monohydrate and 0.071 g/L sodium phosphate dibasic heptahydrate.

In some embodiments, a 4.8 ml injected solution contained 25.0 g/L HBV RNAi triggers, 25.0 g/LMLP-(CDM-NAG), 0.066 g/L sodium phosphate monobasic monohydrate, 0.068 g/L sodium phosphate dibasic heptahydrate, 0.1 g/L dextran 1K, 0.318 g/L sodium carbonate and 0.588 g/L sodium bicarbonate.

E) RNAi Trigger Delivery:
At day 1, each mouse was then given a single IV administration via tail vein of 200 µl containing 2, 4, or 8 mg/kg MLP delivery peptide+HBV RNAi triggers, isotonic glucose, or 8 mg/kg MLP delivery peptide.

F) Analyses:
At various times, before and after administration of MLP delivery peptide+HBV RNAi triggers, isotonic glucose, or MLP delivery peptide alone, serum HBsAg, serum HBV DNA, or liver HBV RNA were measured. HBV expression levels were normalized to control mice injected with isotonic glucose.

i) Serum Collection:
Mice were anesthetized with 2-3% isoflurane and blood samples were collected from the submandibular area into serum separation tubes (Sarstedt AG & Co., Nühmbrecht, Germany). Blood was allowed to coagulate at ambient temperature for 20 min. The tubes were centrifuged at 8,000×g for 3 min to separate the serum and stored at 4° C.

ii) Serum Hepatitis B Surface Antigen (HBsAg) Levels:
Serum was collected and diluted 10 to 2000-fold in PBS containing 5% nonfat dry milk. Secondary HBsAg standards diluted in the nonfat milk solution were prepared from serum of ICR mice (Harlan Sprague Dawley) that had been transfected with 10 µg HBsAg-expressing plasmid pRc/CMV-HBs (Aldevron, Fargo, N. Dak.). HBsAg levels were determined with a GS HBsAg EIA 3.0 kit (Bio-Rad Laboratories, Inc., Redmond, Wash.) as described by the manufacturer. Recombinant HBsAg protein, ayw subtype, also diluted in nonfat milk in PBS, was used as a primary standard (Aldevron).

HBsAg expression for each animal was normalized to the control group of mice injected with isotonic glucose in order to account for the non-treatment related decline in expression of MC-HBV1.3. First, the HBsAg level for each animal at a time point was divided by the pre-treatment level of expression in that animal (Day −1) in order to determine the ratio of expression "normalized to pre-treatment". Expression at a specific time point was then normalized to the control group by dividing the "normalized to pre-treatment" ratio for an individual animal by the average "normalized to pre-treatment" ratio of all mice in the isotonic glucose control group.

iii) Serum HBV DNA Levels:
Equal volumes of serum from mice in a group were pooled to a final volume of 100 µL. DNA was isolated from serum samples using the QIAamp MinElute Virus Spin Kit (Qiagen, Valencia, Calif.) following the manufacturer's instructions. Sterile 0.9% saline was added to each sample to a final volume of 200 µL. Serum samples were added to tubes containing buffer and protease. Carrier RNA was added to aid in the isolation of small amounts of DNA. 1 ng of pHCR/UbC-SEAP plasmid DNA (Wooddell C I, et al. "Long-term RNA interference from optimized siRNA expression constructs in adult mice." *Biochem Biophys Res Commun* (2005) 334, 117-127) was added as a recovery control. After incubating 15 min at 56° C., nucleic acids were precipitated from the lysates with ethanol and the entire solution applied to a column. After washing, the samples were eluted into a volume of 50 µL Buffer AVE.

The number of copies of HBV genomes in DNA isolated from the pHBV mouse model serum was determined by qPCR. Plasmid pSEAP-HBV353-777, encoding a short segment of the HBV genome within the S gene (bases 353-777 of GenBank accession #V01460), was used to create a six log standard curve. Samples with recovery of DNA below 2 standard deviations from the average, based on detection of pHCR/UbC-SEAP were omitted. TaqMan chemistry-based primers and probes with fluor/ZEN/IBFQ were utilized.

HBV Primers:

```
                                        (SEQ IF NO: 740)
5'-GCCGGACCTGCATGACTA-3'
and (SEQ IF NO: 741)
5'-GGTACAGCAACAGGAGGGATACATA-3'
```

HBV Probe: 6-Carboxyfluorescein (FAM)-Labeled Reporter:

```
                                        (SEQ IF NO: 742)
5'-FAM/CTGCTCAAGGAACCTC-3'
``` hHCR (HCR/UbC-SEAP) Primers:

```
                                        (SEQ IF NO: 743)
5'-CATGCCACCTCCAACATCCACTC-3'

(SEQ IF NO: 744)
5-GGCATAGCCACTTACTGACGACTC-3'
``` hHCR Probe

```
                                        (SEQ IF NO: 745)
5'-FAM/TTGTCCTGGC/ZEN/GTGGTTTAGGTAGTGTGA/IBFQ-3'
``` qPCR assays were performed on a 7500 Fast or StepOne Plus Real-Time PCR system (Life Technologies). For evaluation of HBV DNA in serum, DNA was isolated from duplicate purification steps from pooled group serum samples. Quantitations of HBV DNA and recovery control plasmid were determined by qPCR reactions performed in triplicate. The probes to quantitate HBV and pHCR/UbC-SEAP were included in each reaction.

iv) HBV RNA Analysis:

At various times, mice were euthanized and the liver was excised and placed into a 50-mL conical tube containing 12 ml of TRI Reagent RT (Molecular Research Center, Inc., Cincinnati, Ohio). Total RNA was isolated following the manufacturer's recommendation. Briefly, livers in TRI Reagent were homogenized using a Bio-Gen PRO200 tissue homogenizer (Pro Scientific, Inc., Oxford, Conn.) for approximately 30 seconds. 1 ml homogenate was added to 0.2 ml chloroform, mixed, and phases were separated by centrifugation. 0.1 ml of aqueous phase was removed, precipitated with isopropyl alcohol, and centrifuged. The resultant pellet was washed with 75% ethanol and resuspended in 0.4-0.6 ml nuclease-free water. Total RNA (50-500 ng) was reverse transcribed using the High Capacity cDNA Reverse Transcription Kit (Life Technologies, Grand Island, N.Y.). The cDNA was then diluted 1:50 and multiplex RT-qPCR was performed using 5' exonuclease chemistry with forward primer 5'-GCCGGACCTGCATGACTA-3' (SEQ IF NO: 746), reverse primer 5'-GGTACAGCAACAGGAGGGATACATA-3' (SEQ IF NO: 747), and 6-carboxyfluorescein (FAM)-labeled reporter 5'-CTGCTCAAGGAACCTC-3' (SEQ IF NO: 748) for detection of HBV.

The RT-qPCR probe binds to all HBV RNA except the gene X transcript, which is expressed at nearly undetectable levels. Thus, the probe measured total HBV RNA. Gene expression assays for HBV, mouse β-actin, and Gene Expression Master Mix (Life Technologies, Grand Island, N.Y.) were utilized. Gene expression data were analyzed using the comparative $C_T$ method of relative quantification (Livak K J et al. "Analysis of relative gene expression data using real-time quantitative PCR and the 2(−Delta Delta C(T))" Method. Methods 2001 Vol. 25, p 402-408).

Total RNA from each animal was reverse transcribed to generate cDNA. The cDNA was assayed by duplicate qPCR reactions that measured the HBV total RNA and the endogenous control, mouse β-actin mRNA, in the same reaction.

$$\Delta\Delta C_T = (C_{T_{target}} - C_{T_{control}})_{sample} - (C_{T_{target}} - C_{T_{control}})_{reference}$$

Relative Expression = $2^{-\Delta\Delta C_T}$

Relative Expression of an individual = GEOMEAN of replicates

Low Range and High Range refer to $2^{-Avg.\Delta\Delta C_T + S.D.\Delta C_T}$ and $2^{-Avg.\Delta\Delta C_T - S.D.\Delta C_T}$.

v) Quantitation of RNAi Trigger in Tissues:

The levels of total guide strand, total full-length guide strand, and 5'-phosphorylated full length guide strand for HBV RNAi triggers AD00009 and AD00010 in the liver were measured at various times by fluorescent PNA probe hybridization and HPLC anion exchange chromatography. The guide strand becomes 5'-phosphorylated by endogenous cytoplasmic CLP 1 kinase (Weitzer S et al "The human RNA kinase hCLp1 is active on 3' transfer RNA exons and short interfering RNAs." Nature 2007 Vol. 447, p 222-227.). A fluorescently-labeled, sequence-specific peptide-nucleic acid (PNA) probe that hybridized to the guide strand was added to homogenized liver tissue. The probe-guide strand hybrid was analyzed by HPLC anion exchange chromatography that separated the guide strand based on charge.

Tissues were collected and immediately frozen in liquid nitrogen. Tissue samples were pulverized while frozen. Up to 25 mg frozen powder was solubilized in 1 mL of diluted Affymetrix Lysis Solution (one part Affymetrix Lysis Solution, two parts nuclease-free water) containing 50 µg/ml proteinase K. Samples were sonicated with a micro stick sonicator and incubated at 65° C. for 30 min. If samples needed further dilution, this was performed before the hybridization step, using the Affymetrix Lysis Solution diluted as described above. Serial dilutions of RNAi trigger standards were also prepared in diluted Lysis Solution.

RNAi Trigger Standard: RD74

```
sense
                                        (SEQ IF NO: 749)
(NH2C6)CfuGfuAfgGfcAfuAfaAfuUfgGfuAf(invdT)

anti-sense
                                        (SEQ IF NO: 750)
pdTAfcCfaAfuUfuAfuGfcCfuAfcAfgdTsdT
```

RNAi Trigger Standard: RD77

```
sense
                                        (SEQ IF NO: 751)
(NH2C6)AfcCfuCfuGfcCfuAfaUfcAfuCfuAf(invdT)

anti-sense
                                        (SEQ IF NO: 752)
pdTAfgAfuGfaUfuAfgGfcAfgAfgGfudTsdT
``` n=2'-O-methyl, Nf=2'-Fluoro, dN=deoxyribose, inv=inverted, s=phosphorothioate bond.

SDS was precipitated from the standards and samples by adding 10 µl of 3M KCl to 100 µl of the tissue sample solution. After incubating 10 min on ice, samples were centrifuged for 15 min at 2,700×g. Quantitation of RNAi trigger was performed with the supernatant.

Sequence-specific peptide-nucleic acid (PNA) probes containing a fluorescent Atto 425 label at the N-terminus attached to the PNA chain via two ethylene glycol linkers (OO=PEG2; PNA Bio, Thousand Oaks, Calif.) were designed to bind to the antisense strand of each HBV RNAi trigger.

Peptide-Nucleic Acid (PNA) Probes

```
for AD00009
                              (SEQ IF NO: 753)
Atto425-OO-CTGTAGGCATAAATT for AD00010
                              (SEQ IF NO: 754)
Atto425-OO-ACCTCTGCCTAATCA
```

To 55 µl diluted serum sample was added 143 µL nuclease-free water, 11 µl 200 mM Tris-HCl (pH 8), and 11 µl 1 µM AD9 or AD10 PNA-probe solution in 96-well conical-bottom plates. The plate was sealed and incubated at 95° C. for 15 min in a thermal cycler. The temperature of the thermal cycler was reduced to 54° C. and samples were incubated for another 15 min. After incubation, samples were stored at 4° C. until they were loaded onto an autosampler for HPLC analysis.

HPLC analysis was carried out using a Shimadzu HPLC system equipped with an LC-20AT pump, SIL-20AC autosampler, RF-10Axl fluorescence detector, and a CTO-20Ac column oven (Shimadzu Scientific Instruments, Columbia, Md.). The 96-well plate from the hybridization step was loaded onto the autosampler. Injection volumes of 100 µl were made onto a DNAPac PA-100 4×250 mm analytical column (#DX043010; Fisher Scientific, Pittsburgh, Pa.) with an attached 4×50 mm guard column (#DXSP4016; Fisher Scientific, Pittsburgh, Pa.). Analysis was carried out at a flow rate of 1 ml/min with a column oven temperature of 50° C. A gradient elution using mobile phase A (10 mM Tris-HCl (pH 7), 100 mM NaCl, 30% (v/v) Acetonitrile) and mobile phase B (10 mM Tris-HCl (pH 7), 900 mM NaCl, 30% (v/v) Acetonitrile).

Fluorescence detection was set to an excitation of 436 nm and an emission of 484 nm with a medium gain setting of 4. Concentrations of analytes eluted in the 7-10 min range were calculated using a 12-point external standard calibration curve. Calibration curves were generated with PNA-hybridized full length phosphorylated RNAi trigger RD74 and RD77.

TABLE 6

Gradient and elution times for PNA probe hybridization and HPLC anion exchange chromatography analysis of RNAi trigger in liver.

| Time (min) | % Eluent A | % Eluent B | Curve |
|---|---|---|---|
| 0 | 80 | 20 | |
| 1.00 | 80 | 20 | Linear |
| 11.00 | 40 | 60 | Linear |
| 11.50 | 0 | 100 | Linear |
| 13.00 | 0 | 100 | Linear |
| 14.50 | 80 | 20 | Linear |
| 23.00 | 80 | 20 | Linear | iv) Clinical Chemistry:

Clinical chemistry markers in mouse serum were measured using a COBAS Integra 400 (Roche Diagnostics, Indianapolis, Ind.) chemical analyzer according to the manufacturer's instructions.

G) Hepatitis B Virus (HBV) Knockdown In Vivo:

HBV DNA:

Maximum HBV DNA knockdown occurred at days 8 and 15 in mice treated with 8 mg/kg MLP delivery peptide+HBV RNAi triggers. Total HBV DNA in serum was reduced by 294-fold and 345-fold, respectively. On day 29, HBV DNA in serum of mice remained 13.5-fold lower than untreated control mice. Total HBV DNA was reduced 91.8-fold and 6.5-fold on day 8 in mice treated with 4 mg/kg and 2 mg/kg MLP delivery peptide+HBV RNAi triggers, respectively.

HBsAg in Serum:

Maximum knockdown occurred at days 8 and 15 in mice treated with 8 mg/kg MLP delivery peptide+HBV RNAi triggers. HBsAg in serum was reduced by 270-fold and 139-fold, respectively. On day 29, HBsAg in serum was 7.3-fold lower than untreated control mice. HBsAg in serum was reduced 71.4-fold and 5.4-fold and on day 8 in mice treated with 4 mg/kg and 2 mg/kg MLP delivery peptide+HBV RNAi triggers, respectively.

The duration of effect from a single 8 mg/kg dose was at least 28 days. HBsAg and HBV DNA were reduced by more than 95% through Day 22. HBV DNA and HBsAg levels in serum from mice that were injected with MLP delivery peptide (without HBV RNAi triggers) remained comparable to levels in mice that received a single injection of isotonic glucose (Table 7).

HBV RNA in Liver:

Maximum knockdown occurred at day 8 in mice treated with 8 mg/kg MLP delivery peptide+HBV RNAi triggers. Total HBV RNA in liver was reduced by an average of 12.5-fold. On day 29, total HBV RNA in the liver was 3.4-fold lower than the average of the untreated control group. Total HBV RNA was reduced 5.8-fold and 1.6-fold on day 8 in mice treated with 4 mg/kg and 2 mg/kg MLP delivery peptide+HBV RNAi triggers, respectively (Table 7).

Quantitation of RNAi Trigger in Tissues:

Injection of 8 mg/kg MLP delivery peptide+HBV RNAi triggers into pHBV model mice resulted in approximately 80 ng/g HBV RNAi triggers in the cytoplasm of hepatocytes on day 8, as evidenced by 5' phosphorylation of about 40 ng/g each full-length AD00009 and AD00010 guide strands. The resulting pharmacodynamic effects on day 8 were 93% knockdown of total HBV RNA and greater than 99% reduction in HBsAg and HBV DNA in the serum. On day 22, almost all of the guide strand in the liver was 5' phosphorylated and full-length (Table 7).

Clinical Chemistry:

Liver and renal functions were evaluated on day −1 (pre-injection) and day 2 (24 hours post-injection). There were no MLP delivery peptide+HBV RNAi trigger-related changes in clinical chemistry nor was there any evidence of toxicity from either MLP delivery peptide+HBV RNAi triggers or MLP delivery peptide alone administration.

TABLE 7

Knockdown of HBsAg and HBV RNA and presence of 5' phosphorylated RNAi trigger in liver following intravascular administration of MLP delivery peptide + HBV RNAi triggers in HBV mouse model.

| day | MLP delivery peptide + HBV RNAi triggers (mg/kg) | HBsAg relative knockdown | HBV RNA relative knockdown | 5' phosphorylated RNAi trigger guide strand (ng/g liver tissue) |
|---|---|---|---|---|
| 8  | 8 | 99.6 ± 0.4% | 93% | 76 |
| 15 | 8 | 99.3 ± 1.4% | 80% | 27 |
| 22 | 8 | 97 ± 5%     | 76% | 12 |
| 29 | 8 | 86 ± 15%    | 71% | 2-15 |
| 8  | 4 | 99%         | 83% | 28 |
| 8  | 2 | 82%         | 36% | 7 |

Example 8. Antiviral Efficacy of RNAi in Chronic HBV Infection in Chimpanzee

A single chimpanzee chronically infected with HBV genotype B (chimpanzee 4x0139; genotype B; viral load ~7×10$^9$ GE/ml, 51.3-51.5 kg) was given the MLP delivery peptide+HBV RNAi triggers (AD00009 and AD00010) by IV infusion. The viral HBV DNA titer of this animal for 2 years preceding this trial ranged from 4×10$^9$ to 1.3×10$^{10}$ Genome Equivalents/ml (baseline value for this study). Blood samples was taken at health check (day −7) and again immediately before dosing to serve as the baseline samples (day 1). The health check included physical exam, CBC, and whole blood chemistries. 2 mg/kg MLP delivery peptide+HBV RNAi triggers (20.6 ml of 5 mg/ml MLP delivery peptide) was administered at day 1 by IV push over 3 minutes. 3 mg/kg MLP delivery peptide+HBV RNAi triggers (30.9 ml of 5 mg/ml MLP delivery peptide) was administered at day 15 by IV push over 3 minutes. Blood samples were obtained on days 4, 8, 11, 15, 22, 29, 36, 43, 57, 64, 71, 78, and 85. Liver biopsies were obtained three times, at health check, day 29 and day 57. Animals were sedated for all procedures. Sedations for bleeds and dosing were accomplished with Telazol™ (2 mg/kg) and xylazine (100 mg) administered intramuscularly as immobilizing agents. Yohimbine is used as a reversal agent for Xylazine at the end of the procedure.

Assays for Serum and Liver HBV DNA.

HBV DNA levels were determined for serum and liver biopsy samples (baseline and days 29 and 57) using a TaqMan assay targeting the core and X regions. Both assays should detect all genomes. DNA was purified from 100 µl of serum or homogenized liver tissue using the Qiagen QiaAmp DNA Mini Kit (cat#51304), according to the manufacturer's protocol. DNA samples were analyzed by real time PCR using TaqMan technology with primers and probe designed against the HBV core gene.

forward primer, HBV core F 5' CGAGGCAGGTC-CCCTAGAAG 3' (SEQ ID NO: 755);
reverse primer, HBV core R 5' TGCGACGCGGY-GATTG 3' (SEQ ID NO: 756);
probe, HBV core probe 5' 6-FAM/AGAACTCCCTCGC-CTCGCAGACG-6-TAM 3' (SEQ ID NO: 757).

Liver DNA and RNA was also analyzed with primers and probe designed against the HBV X gene forward primer, HBV X F-CCGTCTGTGCCTTCTCATCTG (SEQ ID NO: 758)
reverse primer, HBV X R-AGTCCAAGAGTYCTCT-TATGYAAGACCTT (SEQ ID NO: 759)
probe, HBV X 5' 6-FAM/CCGTGTGCACTrCGC-TrCACCTCTGC-6-TAM 3' (SEQ ID NO: 760)

A plasmid containing an HBV DNA insert was used to generate a standard curve for each TaqMan assay ranging from 10 GE to 1 million GE. Samples were analyzed in TaqMan assays using an ABI 7500 sequence detector using the following cycle parameters: 2 min at 50° C./10 min at 95° C./45 cycles of 15 sec at 95° C./1 min at 60° C.

Liver HBV DNA levels were decreased 2.4-fold (core region PCR assay) and 2.7-fold (X region PCR assay) below baseline levels on day 29.

Serum HBV DNA levels dropped rapidly after the first dose with a 17-fold decline by day 4. The levels increased between days 8-15 from 18.8 to 6.7-fold below baseline. Following the second dose on day 15, a drop in viral DNA was observed, reaching 35.9-fold decline from baseline on day 22.

Serum HBsAg and HBeAg Analyses.

HBsAg levels were determined using an ELISA kit from BioRad (GS HBsAg EIA 3.0). Quantification of surface antigen was determined by comparing OD to known surface antigen standards. HBeAg quantification was determined for all bleeds using an ELISA kit from DiaSorin (ETI-EBK Plus).

HBsAg levels were markedly reduced, declining from a baseline level of 824 µg/ml to 151 µg/ml on day 29. Values had declined significantly by day 4 following the first dose of ARC 520 (18% decrease compared to baseline values). The values continued to drop through day 15 to 53% of baseline (2.1-fold), and reached the maximum decline of 81% (5.2-fold) on day 29.

Serum levels of HBeAg were 136 ng/ml at baseline and dropped to 12.5 ng/ml (10.9-fold) by day 4 following the first injection of ARC 520. Levels increased to 46 ng/ml (2.9-fold below baseline) on day 15. Following the second injection, the levels declined again to 28 ng/ml on day 22.

RT-PCR Analysis of Cytokine and Chemokines.

The transcript levels for ISG15, CXCL 11 (I-TAC), CXCL10 (IP-10), CXCL9 (Mig), Interferon gamma (IFNγ) and GAPDH were determined by quantitative RT-PCR. Briefly, 200 ng of total cell RNA from liver was analyzed by qRT-PCR assay using primers and probe from ABI Assays-on-Demand™ and an ABI 7500 TaqMan sequence analyzer (Applied Biosystems/Ambion, Austin, Tex.). The qRT-PCR was performed using reagents from the RNA UltraSense™ One-Step Quantitative RT-PCR System (Invitrogen Corporation, Carlsbad, Calif.), and the following cycle settings: 48° C., 30 min; 95° C., 10 min; and 95° C., 15 sec; and 60° C., 1 min, the latter two for 45 cycles. Liver biopsies were immediately placed in RNAlater® Stabilization Reagent and processed as described by the manufacturer and RNA was extracted using RNA-Bee (Tel-Test, Inc Friendswood, Tex.) for total cell RNA. No substantial induction of these genes was noted.

Luminex Analysis of Cytokines and Chemokines.

Monitoring of cytokines and chemokines was performed using a Luminex 100 with the xMAP (multi-analyte platform) system using a 39-plex human cytokine/chemokine kit (Millipore; Billerica, Mass.). Dilutions of standards for each cytokine were evaluated in each assay. Dilutions of standards for each cytokine were evaluated in each run to provide quantification. The following cytokines/chemokines were evaluated in serum samples using a luminex method: EGF, Eotaxin, FGF-2, Flt-3 Ligand, Fractalkine (CX3CL1), G-CSF, GM-CSF, GRO, IFNα2, IFNγ, IL-10, IL-12p40, IL-12p70, IL-13, IL-15, IL-17, IL-1α, IL-β, IL-1 Receptor antagonist, IL-2, IL-3, IL-4, IL-5, IL-6, IL-7, IL-8, IL-9, IL-10, MCP-1 (CCL2), MCP-3 (CCL7), MDC (CCL22), MIP-1α (CCL3), MIP-1β (CCL4), sCD40L, sIL-2 Receptor antagonist, TGFα, TNFα, TNFβ, VEGF. Similar to the hepatic transcripts, no substantial changes in chemokines and cytokines were observed during the therapy.

Clinical Pathology.

Blood chemistries were determined with a Unicel DxC 600 Analyzer (Beckman Coulter, Inc., and Diagnostic Chemicals Ltd, Oxford, Conn., USA). Whole blood chemistries had the following measurements: Na, K, Cl, Ca, $CO_2$, Phos., ALT, AST, GGT, LDH, Direct Bilirubin, Total Bilirubin, Alk Phos, BUN, Creatine, Creatine Kinase, Glucose, Total protein, Albumin, Cholesterol, Triglycerides. Values from uninfected animals from the same colony were used to establish normal ranges. Liver biopsies were taken from the anesthetized animal by a standard procedure. Biopsy material was divided immediately into a fraction for histopathology, and DNA and RNA analysis. Sections for histopathology were processed for fixation in 10% formalin in PBS, paraffin embedded and stained with hematoxylin and eosin. Fractions for DNA analysis were snap frozen. Fractions for RNA analysis were placed in RNAlater® Stabilization Reagent.

Immunohistochemical Staining of Liver.

Liver biopsies were fixed in buffered-formalin, paraffin embedded, and sectioned at 4 microns. Slides were de-paraffinized in EZ-DeWax (BioGenex; HK 585-5K) 2× for 5 min and rinsed with water. Antigen retrieval was performed in a microwave pressure cooker for 15 min at 1000 Watts and 15 min at 300 Watts in citrate buffer (antigen retrieval solution; BioGenex; HK 086-9K). Cooled slides were rinsed with water and PBS and treated sequentially with peroxidase suppressor, universal block, and avidin (all reagents from Pierce 36000 Immunohisto Peroxidase Detection Kit). Slides were incubated sequentially for 1 h at room temperature with primary antibody diluted in universal block containing a biotin block, for 0.5 h with biotinylated goat anti-mouse IgG, and for 0.5 h with avidin-biotin complex (ABC). Slides were developed with Immpact Nova Red peroxidase substrate (Vector, SK-4805; Burlingame Calif.), counter stained Mayers (Lillie's) hematoxylin (DAKO, S3309), dehydrated and mounted in non-aqueous mounting media (Vector, VectaMount; H-5000). Rabbit anti-HBV core was prepared from purified core particles expressed in baculovirus.

Most hepatocytes were positive for HBV core antigen with intense staining of the cytoplasm and some staining of the nucleus. A decline in staining occurred at day 29 that was considered significant.

Example 9. Reduction in Hepatitis B Virus (HBV) In Vivo Transgenic Mouse Model Following Delivery of HBV RNAi Triggers Using MLP Delivery Peptide A) Transgenic HBV Model Mice:

Transgenic HBV1.3.32 mice contain a single copy of the terminally redundant, 1.3-genome length human HBV genome of the ayw strain (GenBank accession number V01460) integrated into the mouse chromosomal DNA. High levels of HBV replication occur in the livers of these mice (Guidotti L G et al. "High-level hepatitis B virus replication in transgenic mice." J Virol 1995 Vol. 69, p 6158-6169).

Mice were selected for the study on the basis of the HBeAg level in their serum upon weaning. Mice were grouped such that the average HBeAg levels was similar in each group. Student's T-test was used to assure there were no significant differences between any of the groups relative to the control siLuc group.

MLP delivery peptide HBV RNAi trigger delivery composition (MLP delivery peptide+HBV RNAi triggers were prepared as described. AD00009, AD00010, RNAi trigger standard RD74, and RNAi trigger standard RD77 were prepared as described.

siLuc (Firefly Luciferase RNAi Trigger)

```
sense strand
                                        (SEQ ID NO: 761)
Chol-uAuCfuUfaCfgCfuGfaGfuAfcUfuCfgAf(invdT)

anti-sense
                                        (SEQ ID NO: 762)
UfsCfgAfaGfuAfcUfcAfgCfgUfaAfgdTsdT
```

B) HBV RNAi Trigger Delivery:

Female HBV1.3.32 mice, 1.8-7.7 months old, were given a single IV injection into the retro-orbital sinus of 200 μl per 20 g body weight of 3 mg/kg or 6 mg/kg MLP delivery peptide+HBV RNAi triggers on day 1. Control mice injected with isotonic glucose or 6 mg/kg MLP delivery peptide+siLuc.

Serum Collection:

Mice were briefly anesthetized with 50% $CO_2$ and blood samples were collected from the retro-orbital sinus using heparinized Natelson micro blood collecting tubes (#02-668-10, Fisher Scientific, Pittsburgh, Pa.). Blood was transferred to microcentrifuge tubes, remaining at ambient temperature for 60-120 min during collection. Samples were then centrifuged at 14,000 rpm for 10 min to separate the serum, which was then stored at −20° C.

C) HBcAg Knockdown:

A qualitative assessment of HBV core antigen (HBcAg) distribution in the cytoplasm of hepatocytes following MLP delivery peptide mediated delivery of HBV RNAi triggers was performed by immunohistochemical staining of liver sections. The presence of cytoplasmic HBcAg indicates that the protein is being actively expressed. Tissue samples were fixed in 10% zinc-buffered formalin, embedded in paraffin, sectioned (3 μm), and stained with hematoxylin (Chisari F V et al. "Expression of hepatitis B virus large envelope polypeptide inhibits hepatitis B surface antigen secretion in transgenic mice." J Virol 1986 Vol. 60, p 880-887). The intracellular distribution of HBcAg was assessed by the labeled-avidin-biotin detection procedure (Guidotti L G et al. "Hepatitis B virus nucleocapsid particles do not cross the hepatocyte nuclear membrane in transgenic mice." J Virol 1994 Vol. 68, 5469-5475). Paraffin-embedded sections in PBS, pH 7.4, were treated for 10 min at 37° C. with 3% hydrogen peroxide and washed with PBS. After the sections were blocked with normal goat serum for 30 min at room temperature, rabbit anti-HBcAg (Dako North America, Inc., Carpinteria, Calif.) primary antiserum was applied at a 1:100 dilution for 60 min at 37° C. After a wash with PBS, a secondary antiserum consisting of biotin-conjugated goat anti-rabbit immunoglobulin G F(ab9)2 (Sigma-Aldrich Co. LLC., St. Louis, Mo.) was applied at a 1:100 dilution for 30 min at 37° C. The antibody coated slides were washed with PBS, treated with the streptavidin-horseradish peroxidase conjugate (ExtrAvidin; Sigma-Aldrich Co. LLC., St. Louis, Mo.) at a 1:600 dilution for 30 min at 37° C., stained with 3-amino-9-ethyl carbazole (AEC; Shandon-Lipshaw, Pittsburgh, Pa.), and counterstained with Mayer's hematoxylin before being mounted. HBcAg levels and distribution within the hepatocytes were visually assessed. Cytoplasmic HBcAg was greatly reduced relative to nuclear HBcAg at days 15 and 29 following injection of 6 mg/kg MLP delivery peptide+HBV RNAi triggers, indicating knockdown of HBcAg expression.

TABLE 8

Qualitative assessment of HBcAg staining in the nucleus (n) compared to HBcAg staining in the cytoplasm (c).

| Treatment | day | nuclear (n) vs. cytoplasmic (c) distribution |
|---|---|---|
| Isotonic glucose | 8 | n = c |
|  | 8 | n = c |
| 6 mg/kg MLP delivery peptide + siLuc | 8 | n = c |
| 6 mg/kg MLP delivery peptide + HBV RNAi triggers | 8 | n = c |
|  | 8 | n = c |
|  | 15 | n >> c | treated with 6 mg/kg melittein delivery peptide+HBV RNAi triggers. These transgenic mice are known to produce HBeAg in their kidneys. The level of circulating HBeAg originating from the kidneys is not known.

TABLE 9

Relative HBeAg expression normalized to day −1 and mean of combined control groups on day 3 or day 8

| | day | |
|---|---|---|
| treatment | 3 | 8 |
| Isotonic glucose | 1.09 ± 0.35 | 0.86 ± 0.09 |
| 6 mg/kg MLP delivery peptide + siLuc | 0.91 ± 0.04 | 1.14 ± 0.21 |
| 3 mg/kg MLP delivery peptide + HBV RNAi triggers | 0.15 ± 0.05 | 0.29 ± 0.12 |
| 6 mg/kg MLP delivery peptide + HBV RNAi triggers | 0.12 ± 0.07 | 0.27 ± 0.17 |

TABLE 10

Relative HBeAg expression normalized to day −1 of each group

| | day | | | | | | |
|---|---|---|---|---|---|---|---|
| treatment | −1 | 0.25 | 3 | 8 | 15 | 22 | 29 |
| Isotonic glucose | 1.00 | 1.37 ± 0.26 | 1.75 ± 0.65 | 1.08 ± 0.14 | — | — | — |
| 6 mg/kg MLP delivery peptide + siLuc | 1.00 | 1.43 ± 0.09 | 1.46 ± 0.07 | 1.43 ± 0.30 | — | — | — |
| 3 mg/kg MLP delivery peptide + HBV RNAi triggers | 1.00 | 1.01 ± 0.26 | 0.24 ± 0.08 | 0.37 ± 0.16 | 0.51 ± 0.15 | — | — |
| 6 mg/kg MLP delivery peptide + HBV RNAi triggers | 1.00 | 0.96 ± 0.25 | 0.20 ± 0.11 | 0.34 ± 0.22 | 0.32 ± 0.14 | 0.25 ± 0.13 | 0.34 ± 0.18 |

TABLE 8-continued

Qualitative assessment of HBcAg staining in the nucleus (n) compared to HBcAg staining in the cytoplasm (c).

| Treatment | day | nuclear (n) vs. cytoplasmic (c) distribution |
|---|---|---|
|  | 15 | n >> c |
|  | 29 | n >> c |
|  | 29 | n >> c |

D) HBeAg Knockdown:

The effect of MLP delivery peptide mediated delivery of HBV RNAi trigger delivery on HBV e antigen (HBeAg) was determined by ELISA. Serum was collected from the mice at pre-injection day −1, 6 hours post-injection, and on days 3, 8, 15, 22, and 29. HBeAg analysis was performed with the HBe enzyme linked immunosorbent assay (ELISA) as described by the manufacturer (Epitope Diagnostics, San Diego, Calif.) using 2 μl of mouse serum. The level of antigen was determined in the linear range of the assay. The HBeAg levels for each animal and at each time point were normalized to the day −1 pre-dose level. The MLP delivery peptide+HBV RNAi triggers treatment groups were separately compared to the isotonic glucose group or the siLuc group. Paired T-tests were used to evaluate changes in HBeAg expression from day 3 to day 8.

The levels of HBeAg was reduced by 85-88% (7-8 fold) and day 3 and approximately 71-73% at day 8 for both dose levels. HBeAg remained reduced ~66% at day 29 in animals E) HBV RNA Knockdown:

HBV produces at least 6 mRNA species that are in length: 3.5 kilobases (kb) (2 types), 2.4 kb, 2.1 kb (2 types) and 0.7 kb. One 3.5 kb mRNA that encodes HBeAg. HBeAg is a secreted protein. The other 3.5 kb mRNA is the pre-genomic RNA (pgRNA), which is translated to produce the core protein (HBcAg) and the polymerase. The pgRNA is reverse transcribed to generate the virion DNA. HBcAg protein monomers assemble to form the capsid that encloses the virion DNA. The 2.4 kb and 2.1 kb mRNAs encode the envelope (S) protein that are also called S antigen (HBsAg). The HBsAg proteins form the envelope around the viral capsid (Because transgenic HBV1.3.32 mice produce antibodies to this protein, HBsAg was not measured.). The 0.7 kb mRNA encodes X protein and is usually undetectable in transgenic mice.

After mice were sacrificed, liver tissue was frozen in liquid nitrogen and stored at −70° C. prior to total RNA extraction. RNA was isolated and levels of the HBV transcripts were evaluated and quantitated relative to the housekeeping gene glyceraldehyde 3-phosphate dehydrogenase (GAPDH) by Northern blotting and by quantitative real-time PCR (RT-qPCR).

Northern Analysis.

RNA (Northern) filter hybridization analyses were performed using 10 μg of total cellular RNA. Filters were probed with $^{32}$P-labeled HBV (strain ayw) genomic DNA to detect HBV sequences and mouse glyceraldehyde-3-phosphate dehydrogenase (GAPDH) cDNA to detect the GAPDH transcript used as an internal control. The radioactive hybridization signals corresponding to the 3.5 kb HBV RNA and the 2.1 kb RNA bands in the Northern blot were normalized to the signal corresponding to the GAPDH mRNA band from the same animal. The 2.1 kb HBV RNA:GAPDH ratio from each animal was divided by the average of this ratio in the combined controls groups, consisting of 4 mice injected with isotonic glucose and 4 mice treated with MLP delivery peptide+siLuc, to determine treatment-specific changes in the 2.1 kb HBV RNA. The 3.5 kb HBV RNA was analyzed by the same method. In both cases error is shown as the standard deviation of the ratio. Statistical significance was determined by a Student's two-tailed t-test. Results from RNA filter hybridization (Northern blot) analyses of total cellular RNA from liver tissue are shown in Table 11. MLP delivery peptide+HBV RNAi triggers treatment reduced viral RNA content in liver. No effects on viral RNA levels in liver were observed in animals receiving isotonic glucose or MLP delivery peptide+siLuc treatments.

(Life Technologies, Grand Island, N.Y.) followed by qPCR quantification using SYBR Green and an Applied Biosystems 7300 Real-Time PCR System. Thermal cycling consisted of an initial denaturation step for 10 min at 95° C. followed by 40 cycles of denaturation (15 sec at 95° C.) and annealing/extension (1 min at 60° C.). The relative HBV 3.5 kb RNA expression levels were estimated using the comparative CT (ΔCT) method with normalization to mouse GAPDH RNA. The PCR primers used were 5'-GC-CCCTATCCTATCAACACTCCGG-3' (SEQ ID NO: 763) (HBV 3.5 kb RNA sense primer, coordinates 2,311 to 2,335), 5'-TCGTCTGCGAGGCGAGGGA-3' (SEQ ID NO: 764) (HBV 3.5 kb RNA antisense primer, coordinates 2401 to 2382), 5'-TCTGGAAAGCTGTGGCGTG-3' (SEQ ID NO: 765) (mouse GAPDH sense primer), and 5'-CCAGT-GAGCTCCCGTTCAG-3' (SEQ ID NO: 766) (mouse GAPDH antisense primer), respectively.

TABLE 11

Northern blot analysis of knockdown of 2.1 kb HBV RNA encoding HBsAg following single does MLP delivery peptide + HBV RNAi triggers treatment in transgenic mice.

| treatment | day | HBV RNA/ GAPDH | fold reduction | P-value[a] | % RNA knockdown[b] |
|---|---|---|---|---|---|
| Isotonic glucose | 8 | 2.79 ± 0.70 | | | |
| 6 mg/kg MLP delivery peptide + siLuc | 8 | 2.91 ± 0.20 | | | |
| 3 mg/kg MLP delivery peptide + HBV RNAi triggers | 8 | 0.527 ± 0.111 | 5.4 | <0.0001 | 81.5 ± 3.4 |
| | 15 | 1.23 ± 0.84 | 2.3 | 0.002 | 56.7 ± 2.6 |
| 6 mg/kg MLP delivery peptide + HBV RNAi triggers | 8 | 0.0487 ± 0.0419 | 58.4 | <0.0001 | 98.3 ± 1.3 |
| | 15 | 0.0301 ± 0.0159 | 94.3 | <0.0001 | 98.9 ± 0.05 |
| | 29 | 0.324 ± 0.220 | 8.8 | <0.0001 | 88.6 ± 6.7 |

[a]Comparison of the mean of the treatment group against the combined mean of the control groups using a two-tailed unpaired t test.
[b]HBV RNA levels normalized to combined average of control groups.

TABLE 12

Northern blot analysis of knockdown of 3.5 kb HBV RNA following single does MLP delivery peptide + HBV RNAi triggers treatment in transgenic mice.

| treatment | day | HBV RNA/ GAPDH | P-value[a] | fold reduction[b] |
|---|---|---|---|---|
| Isotonic glucose | 8 | 1.72 ± 0.47 | | |
| 6 mg/kg MLP delivery peptide + siLuc | 8 | 1.72 ± 0.11 | | |
| 3 mg/kg MLP delivery peptide + HBV RNAi triggers | 8 | 0.949 ± 0.458 | 0.006 | 1.8 |
| | 15 | 1.11 ± 0.64 | 0.045 | 1.6 |
| 6 mg/kg MLP delivery peptide + HBV RNAi triggers | 8 | 0.335 ± 0.226 | <0.0001 | 5.1 |
| | 15 | 0.795 ± 0.340 | 0.0009 | 2.2 |
| | 29 | 0.969 ± 0.483 | 0.008 | 1.8 |

[a]Comparison of the mean of the treatment group against the combined mean of the control groups using a two-tailed unpaired t test.
[b]HBV RNA levels normalized to combined average of control groups.

RT-qPCR Analysis.

Quantitative PCR following a reverse transcription step (RT-qPCR) was used to measure the level of GAPDH and HBV 3.5 kb transcripts in HBV1.3.32 mouse liver RNA. After DNase I treatment, 1 µg of RNA was used for cDNA synthesis using the TaqMan reverse transcription reagents

TABLE 13

RT-qPCT analysis of knockdown of 3.5 kb HBV RNA following single does MLP delivery peptide + HBV RNAi triggers treatment in transgenic mice.

| treatment | day | HBV RNA/ GAPDH | P-value[a] | fold reduction[b] |
|---|---|---|---|---|
| Isotonic glucose | 8 | 2.88 ± 2.60 | | |
| 6 mg/kg MLP delivery peptide + siLuc | 8 | 2.36 ± 0.69 | | |
| 6 mg/kg MLP delivery peptide + HBV RNAi triggers | 8 | 0.292 ± 0.280 | 0.45 | 8.8 |
| | 15 | 0.452 ± 0.285 | 0.03 | 5.7 |
| | 29 | 1.98 ± 1.45 | 0.55 | 1.3 |

[a]Comparison of the mean of the treatment group against the combined mean of the control groups using a two-tailed unpaired t test.
[b]HBV RNA levels normalized to combined average of control groups.

F) HBV DNA Replication Intermediate Knockdown:

After mice were sacrificed, liver tissue was frozen in liquid nitrogen and stored at −70° C. prior to DNA extraction. DNA was isolated from the liver and the HBV replicative intermediates were evaluated and quantitated relative to the transgene by Southern blotting. Southern blot analysis of 20 µg HindIII-digested total cellular DNA was performed using a $^{32}$P-labelled HBV (strain ayw) genomic DNA. Relative levels of HBV replicative intermediates, the relaxed circular DNA (HBV RC DNA) and single-stranded DNA (HBV SS DNA), were normalized to levels of the HBV transgene (HBV transgene DNA) in the same animal following phosphorimager quantitation. The signal from the combined HBV RC and SS DNA: HBV Tg DNA from each animal was divided by the average of this ratio in the combined controls groups, consisting of 4 mice injected with isotonic glucose and 4 mice co-injected with MLP delivery peptide and siLuc, to determine treatment-specific changes in the replicative intermediates. Southern blot analysis indicated that all groups treated with MLP delivery peptide+HBV RNAi triggers had reduced levels of HBV replicative intermediates (Tables 14-16). HBV DNA replication intermediates remained greatly suppressed for four weeks after a single injection of 6 mg/kg MLP delivery peptide+HBV RNAi triggers. Replicative intermediates were reduced 98-99% (64-74 fold) at one and two weeks and 97% (29-fold) at four weeks.

TABLE 14

HBV replication intermediate levels normalized to a combined average of control groups

| treatment | day | | fold reduction |
|---|---|---|---|
| Isotonic glucose | 8 | 0.959 ± 0.495 | |
| 6 mg/kg MLP delivery peptide + siLuc | 8 | 1.042 ± 0.236 | |
| 3 mg/kg MLP delivery peptide + HBV RNAi triggers | 8 | 0.145 ± 0.029 | 6.9 |
|  | 15 | 0.240 ± 0.079 | 4.2 |
| 6 mg/kg MLP delivery peptide + HBV RNAi triggers | 8 | 0.016 ± 0.027 | 63.5 |
|  | 15 | 0.013 ± 0.004 | 74.1 |
|  | 29 | 0.034 ± 0.033 | 29.1 |

TABLE 15

Ratio of HBV Replication Intermediates/HBV Tg DNA as evaluated by Southern blot analysis.

| treatment | day | Ratio HBV Replication Intermediates/HBV Transgene DNA | P-value |
|---|---|---|---|
| Isotonic glucose | 8 | 37.3 ± 22.3 | |
| 6 mg/kg MLP delivery peptide + siLuc | 8 | 40.5 ± 10.6 | |
| combined average | | 38.9 | |
| 3 mg/kg MLP delivery peptide + HBV RNAi triggers | 8 | 5.63 ± 1.29 | 0.0006 |
|  | 15 | 9.33 ± 3.54 | 0.001 |
| 6 mg/kg MLP delivery peptide + HBV RNAi triggers | 8 | 0.61 ± 1.23 | 0.0003 |
|  | 15 | 0.52 ± 0.17 | 0.0003 |
|  | 29 | 1.34 ± 1.47 | 0.0003 |

G) Quantitation of HBV RNAi Trigger in Liver:

The amounts of HBV RNAi trigger guide strands in the livers of MLP delivery peptide+HBV RNAi triggers treated mice were quantitated by hybridization with a fluorescent peptide nucleic acid (PNA) probe as described. The PNA-hybridization method allowed quantitation of the total amount of guide strand, including metabolites of AD00009 and AD00010 (total, total full-length, 5' phosphorylated full-length, and non-phosphorylated full-length) per weight of tissue. The presence of full length 5' phosphorylated guide strand indicated efficient delivery of the RNAi trigger to the target cell cytoplasm.

TABLE 16

HBV RNAi trigger guide strand measured in liver homogenates.

| day | MLP delivery peptide + HBV RNAi triggers (mg/kg) | AD00009 guide strand (ng/g tissue) | | | HBVRNAi trigger 10 guide strand (ng/g tissue) | | |
|---|---|---|---|---|---|---|---|
| | | 5' phosph. full length | total full length | total | 5' phosph full length | total full length | total |
| 8 | 3 | 3.8 ± 1.4 | 3.8 ± 1.4 | 14.8 ± 3.8 | 0.8 ± 1.3 | 0.8 ± 1.3 | 0.8 ± 1.3 |
| 8 | 6 | 17.9 ± 8.2 | 21.3 ± 10.2 | 76.8 ± 34.1 | 11.5 ± 6.7 | 12.6 ± 7.6 | 18.8 ± 11.4 |
| 15 | 3 | 0.0 ± 0.0 | 0.0 ± 0.0 | 4.6 ± 1.6 | 0.0 ± 0.0 | 0.0 ± 0.0 | 3.4 ± 2.0 |
| 15 | 6 | 9.5 ± 2.2 | 9.5 ± 2.2 | 35.0 ± 15.7 | 4.8 ± .09 | 4.8 ± .09 | 5.9 ± 1.5 |
| 29 | 6 | 0.5 ± 0.8 | 0.5 ± 0.8 | 2.3 ± 2.4 | 0.0 ± 0.0 | 0.0 ± 0.0 | 2.1 ± 2.2 |

Figure 3:
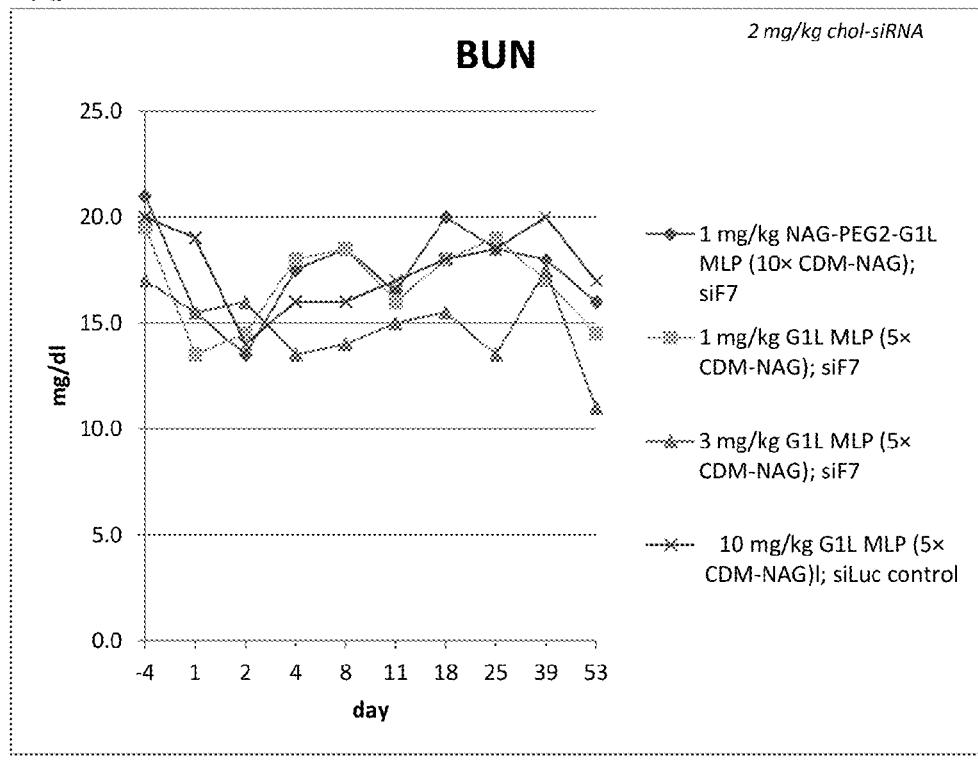
FIG. 3 Graph illustrating (A) blood urea nitrogen (BUN) levels and (B) creatinine levels in primates treated with reversibly modified MLP delivery peptides and RNAi trigger-cholesterol conjugates.
Figure 3:
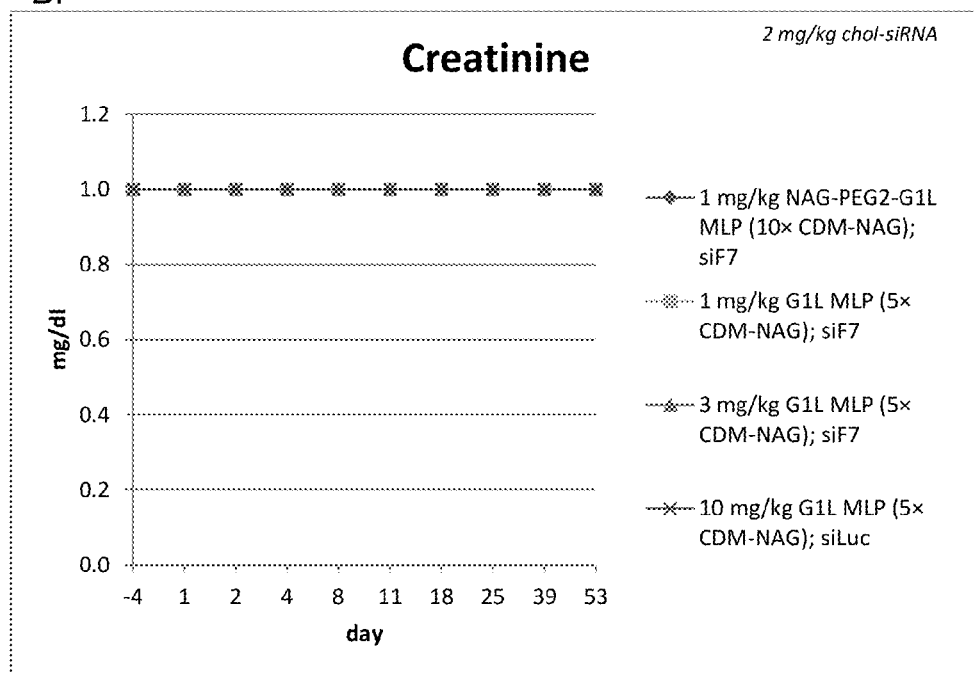
Figure 4:
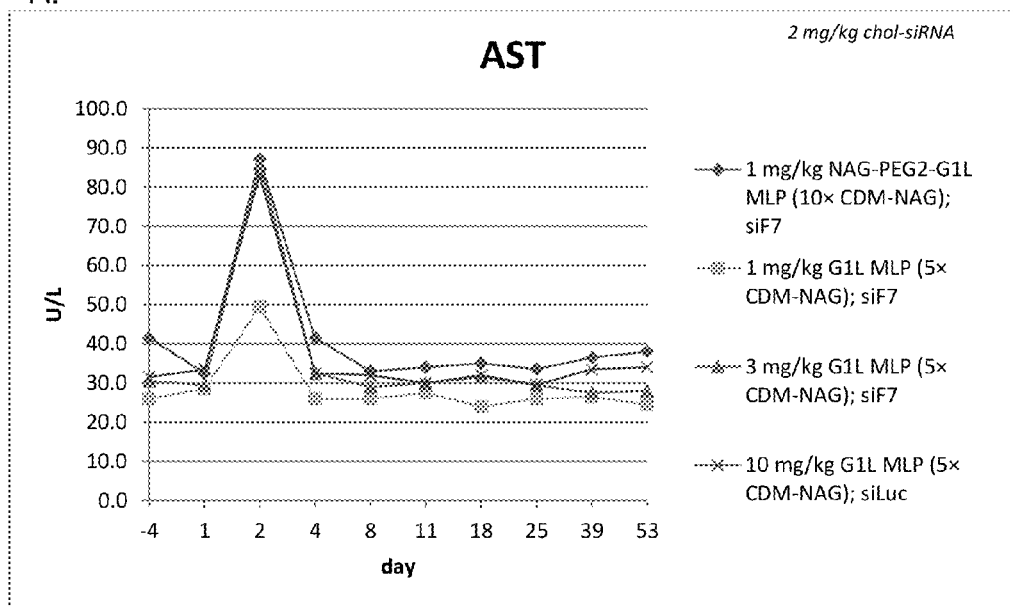
FIG. 4. Graph illustrating (A) aspartate aminotransferase (AST) levels and (B) alanine transaminase (ALT) levels in primates treated with reversibly modified MLP delivery peptides and RNAi trigger-cholesterol conjugates.
Figure 4:
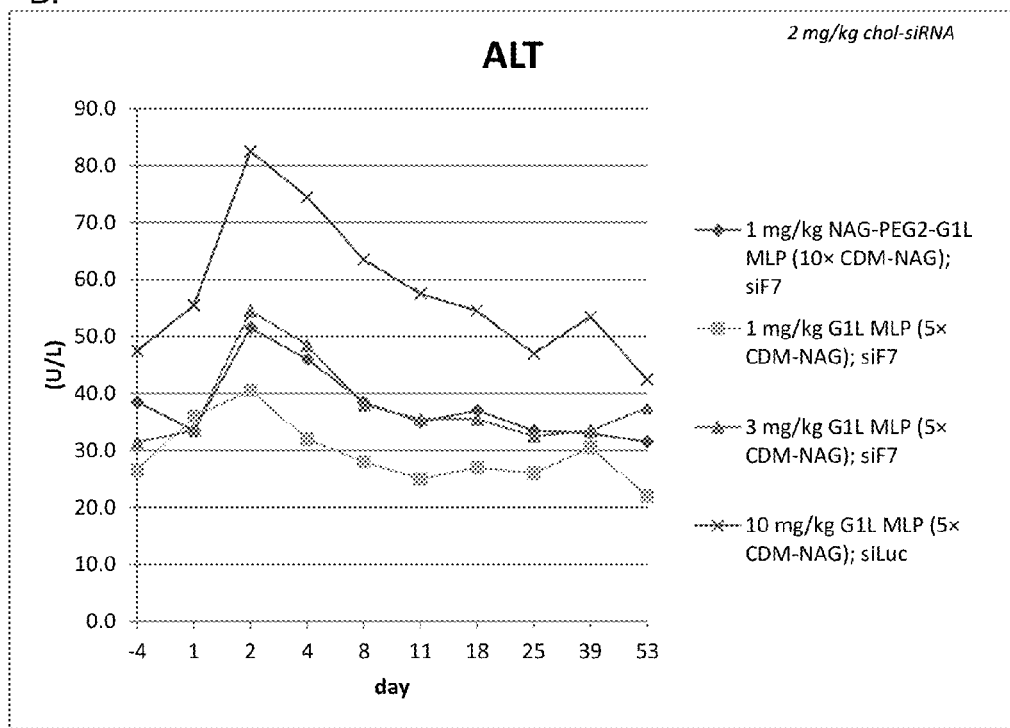

H) Clinical Chemistry:

Serum for clinical chemistry and cytokine evaluation was collected from each mouse at day −1 prior to injection and at 6 hr and 48 hr post-injection. Clinical chemistry analysis of alanine aminotransferase (ALT), Aspartate aminotransferase (AST), blood urea nitrogen (BUN), and creatinine was measured using a COBAS Integra 400 (Roche Diagnostics, Indianapolis, Ind.) chemical analyzer according to the manufacturer's instructions. Each assay required 2-23 µL serum, depending on the test. Clinical chemistries from all groups of animals were compared before and after injection by one-way ANOVA. Bonferroni's Multiple Comparison Test was used to compare individual group values before and after injection. There were no increases in ALT, AST, BUN, or creatinine 48 hr post-injection (FIGS. 3-4). A panel of 25 mouse cytokines were evaluated using a MILLIPLEX MAP Mouse Cytokine/Chemokine Magnetic Bead Panel—Premixed 25 Plex—Immunology Multiplex Assay (Catalog #MCYTOMAG-70K-PMX, EMD Millipore Corporation, Billerica, Mass.): granulocyte colony-stimulating factor (G-CSF), granulocyte macrophage colony-stimulating factor (GM-CSF), interferon gamma (IFN-γ), interleukin-1 alpha (IL-1α), interleukin-1 beta (IL-1β), interleukin-2 (IL-2), interleukin-4 (IL-4), interleukin-5 (IL-5), interleukin-6 (IL-6), interleukin-7 (IL-7), interleukin-9 (IL-9), interleukin-10 (IL-10), interleukin-12 subunit p40 (IL-12p40), interleukin-12 subunit p70 (IL-12p70), interleukin-13 (IL-13), interleukin-15 (IL-15), interleukin-17 (IL-17), interferon gamma-induced protein-10 (IP-10), keratinocyte-derived cytokine (KC), monocyte chemoattractant protein-1 (MCP-1), macrophage inflammatory protein-1 alpha (MIP-1α), macrophage inflammatory protein-1 beta (MIP-1β), macrophage inflammatory protein-2 (MIP2), regulated on activation, normal T cell expressed and secreted (RANTES) and tumor necrosis factor alpha (TNF-α). A few cytokines were elevated by the handling procedures, but appeared unrelated to MLP delivery peptide+HBV RNAi triggers treatment.

IL-6 levels were elevated in all groups at 6 h post-injection. Elevation was higher in mice receiving 3 mg/kg MLP delivery peptide+HBV RNAi triggers and highest—8-fold above the upper limit of normal (up to 170 pg/ml)—in mice receiving 6 mg/kg MLP delivery peptide+HBV RNAi triggers. IL-6 levels returned to normal by day 3, 48 hr after injection.

KC levels were elevated at 6 h, up to 40-fold above the upper limit of normal (103 pg/ml), but this elevation was similar in all treatment groups.

IP-10 levels were elevated less than 2-fold at 6 h and in some samples at 48 h. However, elevations were also in the isotonic glucose control group.

MIP2 is normally undetectable in mouse serum, but levels were elevated after injection in all groups, primarily at 6 hr.

G-CSF levels, while slightly elevated, 3-4 fold average at 6 hr post-injection, the group averages remained within normal range.

TNF-α and MCP-1 were elevated in all groups at 6 h, but remained well below the upper limit of normal.

One out of 12 mice injected with 6 mg/kg MLP delivery peptide+HBV RNAi triggers had an IL-7 level approximately 3-fold higher than the upper limit of normal at 6 h: 80 pg/ml.

Evaluation of liver or kidney toxicity showed minimal adverse effects. There were no increases relative to pre-injection in clinical chemistry markers for liver or kidney. Elevation of some cytokines was observed pre-dosing and a few cytokines were elevated by handling procedures that appeared to be unrelated to MLP delivery peptide+HBV RNAi triggers treatment.

Example 10. Reduction in Hepatitis B Virus (HBV) In Vivo Following Delivery of HBV RNAi Triggers with MLP Delivery Peptide pHBV Model Mice:

At day −28, 6 to 8 week old female NOD.CB17-Prkdscid/NcrCrl (NOD-SCID) mice were transiently transfected in vivo with MC-HBV 1.3 by hydrodynamic tail vein injection as described.

MLP Delivery Peptide:

CDM-NAG was added to MLP, SEQ ID NO: 650 (GIL MLP, L-form), in a 250 mM HEPES-buffered aqueous solution at a 5:1 (w/w) ratio at room temperature and incubated for 30 min to yield MLP delivery peptide. The reaction mixture was adjusted to pH 9.0 with 4 M NaOH. The extent of the reaction was assayed using 2,4,6-trinitrobenzene-sulfonic acid and determined to be >95%. MLP delivery peptide was purified by tangential flow in 10 mM bicarbonate buffer, pH 9.0, to which 10% dextran (w/w) was added. The final purified material was lyophilized.

Formulation of HBV RNAi Trigger Delivery Composition:

5 mg lyophilized MLP delivery peptide was resuspended with 1 mL water. MLP delivery peptide was then combined with HBV RNAi triggers (AD01385 or AD01386) at the various dose levels.

RNAi Trigger Delivery:

At Day 1, each mouse was given a single IV administration via tail vein of 200 µl per 20 gram body weight of saline containing MLP delivery peptide+HBV RNAi triggers.

Analyses:

At various time points, before and after administration of MLP delivery peptide+HBV RNAi triggers, serum HBsAg and serum HBV DNA were measured. The HBsAg level in serum for each animal at a time point was divided by the pre-treatment level in that animal in order to determine the ratio of HBsAg in serum "normalized to pre-treatment". The HBV DNA level in serum for each group at a time point was also divided by the pre-treatment level in that group in order to determine the ratio of HBV DNA in serum "normalized to pre-treatment". In order to account for non-treatment related decline in expression of MC-HBV 1.3 or pHBV 1.3.—the "normalized to pre-treatment" ratio for an individual animal at a time point was then divided by the average "normalized to pre-treatment" ratio of all mice in the saline control group at the same time point to obtain the ratio of HBsAg, or HBV DNA, in serum "normalized to pre-treatment and control".

Serum Collection:

Mice were anesthetized with 2-3% isoflurane and blood samples were collected from the submandibular area into serum separation tubes (Sarstedt AG & Co., Nümbrecht, Germany). Blood was allowed to coagulate at ambient temperature for 20 min. The tubes were centrifuged at 8,000×g for 3 min to separate the serum and stored at 4° C.

Serum Hepatitis B surface antigen (HBsAg) and Serum HBV DNA levels were measured as described.

TABLE 17

Summary of serum HBsAg in pHBV mice following co-administration of 3 mg/kg MLP delivery peptide plus 1.5 mg/kg AD01385, or 1.5 mg/kg AD01386, or 1.5 mg/kg AD01385 + 1.5 mg/kg AD01386.

| Treatment | Mean HBsAg in serum (ng/mL) | | | | | | |
| --- | --- | --- | --- | --- | --- | --- | --- |
| | day −2 | day 5 | day 8 | day 15 | day 22 | day 29 | day 36 |
| Saline | 6291 ± 2304 | 6740 ± 3538 | 5825 ± 2789 | 3052 ± 1428 | 3186 ± 1506 | 3124 ± 1569 | 3140 ± 1198 |
| 1.5 mg/kg AD01385 | 7218 ± 4071 | 878 ± 697 | 1905 ± 1232 | 2309 ± 1315 | 2163 ± 1255 | 2418 ± 1470 | 2067 ± 870 |
| 1.5 mg/kg AD01386 | 6219 ± 5606 | 125 ± 98 | 109 ± 120 | 273 ± 321 | 738 ± 670 | 1627 ± 1487 | 2252 ± 1565 |
| 1.5 mg/kg AD01385 + 1.5 mg/kg AD01386 | 7864 ± 7833 | 139 ± 119 | 138 ± 103 | 331 ± 253 | 1131 ± 1037 | 2066 ± 2259 | 2553 ± 2154 |

TABLE 18

Summary of serum HBsAg levels normalized to pre-dose and the saline control group in pHBV mice following co-administration of 3 mg/kg MLP delivery peptide plus 1.5 mg/kg AD01385, or 1.5 mg/kg AD01386, or 1.5 mg/kg AD01385 + 1.5 mg/kg AD01386.

| treatment | HBsAg in serum (mean ± SD) (normalized to pre-dose and saline control group) | | | |
|---|---|---|---|---|
| | day −2 | day 5 | day 8 | day 15 |
| Saline | 1.000 ± 0.000 | 1.000 ± 0.163 | 1.000 ± 0.295 | 1.000 ± 0.179 |
| 1.5 mg/kg AD01385 | 1.000 ± 0.000 | 0.108 ± 0.026 | 0.282 ± 0.030 | 0.665 ± 0.135 |
| 1.5 mg/kg AD01386 | 1.000 ± 0.000 | 0.021 ± 0.007 | 0.016 ± 0.008 | 0.078 ± 0.027 |
| 1.5 mg/kg AD01385 + 1.5 mg/kg AD01386 | 1.000 ± 0.000 | 0.019 ± 0.006 | 0.023 ± 0.007 | 0.102 ± 0.018 |

| | day 22 | day 29 | day 36 |
|---|---|---|---|
| Saline | 1.000 ± 0.127 | 1.000 ± 0.204 | 1.000 ± 0.095 |
| 1.5 mg/kg AD01385 | 0.589 ± 0.109 | 0.660 ± 0.175 | 0.592 ± 0.140 |
| 1.5 mg/kg AD01386 | 0.237 ± 0.041 | 0.526 ± 0.045 | 0.808 ± 0.151 |
| 1.5 mg/kg AD01385 + 1.5 mg/kg AD01386 | 0.308 ± 0.051 | 0.515 ± 0.077 | 0.679 ± 0.103 |

TABLE 19

Serum HBV DNA in pHBV mice following co-administration of 3 mg/kg MLP delivery peptide plus 1.5 mg/kg AD01385, or 1.5 mg/kg AD01386, or 1.5 mg/kg AD01385 + 1.5 mg/kg AD01386

| Treatment | Mean HBV DNA in serum (copies/mL) | | | | | | |
|---|---|---|---|---|---|---|---|
| | day −2 | day 5 | day 8 | day 15 | day 22 | day 29 | day 36 |
| Saline | $2.04 \times 10^8 \pm 2.06 \times 10^7$ | $1.99 \times 10^8 \pm 3.41 \times 10^7$ | $1.87 \times 10^8 \pm 2.81 \times 10^7$ | $1.32 \times 10^8 \pm 1.32 \times 10^8$ | $1.49 \times 10^8 \pm 5.26 \times 10^6$ | $1.32 \times 10^8 \pm 2.34 \times 10^7$ | $1.19 \times 10^8 \pm 1.27 \times 10^7$ |
| 1.5 mg/kg AD01385 | $2.04 \times 10^8 \pm 1.12 \times 10^7$ | $9.84 \times 10^6 \pm 5.55 \times 10^5$ | $1.64 \times 10^7 \pm 2.80 \times 10^6$ | $7.69 \times 10^7 \pm 7.69 \times 10^7$ | $7.60 \times 10^7 \pm 6.87 \times 10^6$ | $7.69 \times 10^7 \pm 8.74 \times 106$ | $6.91 \times 10^7 \pm 9.55 \times 10^5$ |
| 1.5 mg/kg AD01386 | $2.24 \times 10^8 \pm 1.97 \times 10^7$ | $4.42 \times 10^6 \pm 1.37 \times 10^5$ | $2.37 \times 10^6 \pm 1.65 \times 10^5$ | $1.04 \times 10^8 \pm 1.04 \times 10^8$ | $4.94 \times 10^7 \pm 3.57 \times 10^6$ | $1.04 \times 10^8 \pm 2.69 \times 10^6$ | $9.53 \times 10^7 \pm 1.13 \times 10^7$ |
| 1.5 mg/kg AD01385 + 1.5 mg/kg AD01386 | $2.30 \times 10^8 \pm 8.91 \times 10^6$ | $4.71 \times 10^6 \pm 6.96 \times 10^4$ | $2.41 \times 10^6 \pm 1.03 \times 10^6$ | $1.07 \times 10^8 \pm 1.07 \times 10^8$ | $6.71 \times 10^7 \pm 1.37 \times 10^6$ | $1.07 \times 10^8 \pm 8.16 \times 106$ | $1.26 \times 10^8 \pm 3.24 \times 10^6$ |

TABLE 20

Serum HBV DNA in pHBV mice following co-administration of 3 mg/kg MLP delivery peptide plus 1.5 mg/kg AD01385, or 1.5 mg/kg AD01386, or 1.5 mg/kg AD01385 + 1.5 mg/kg AD01386.

| Treatment | Mean HBV DNA in serum (normalized to pre-dose and saline control group) | | | | | | |
|---|---|---|---|---|---|---|---|
| | day −2 | day 5 | day 8 | day 15 | day 22 | day 29 | day 36 |
| Saline | 1.000 ± 0.000 | 1.000 ± 0.071 | 1.000 ± 0.249 | 1.000 ± 0.017 | 1.000 ± 0.066 | 1.000 ± 0.275 | 1.000 ± 0.006 |
| 1.5 mg/kg AD01385 | 1.000 ± 0.000 | 0.050 ± 0.000 | 0.087 ± 0.020 | 0.474 ± 0.029 | 0.510 ± 0.074 | 0.571 ± 0.034 | 0.582 ± 0.040 |
| 1.5 mg/kg AD01386 | 1.000 ± 0.000 | 0.020 ± 0.002 | 0.011 ± 0.002 | 0.153 ± 0.004 | 0.303 ± 0.048 | 0.710 ± 0.080 | 0.728 ± 0.022 |
| 1.5 mg/kg AD01385 + 1.5 mg/kg AD01386 | 1.000 ± 0.000 | 0.021 ± 0.001 | 0.011 ± 0.005 | 0.105 ± 0.055 | 0.399 ± 0.007 | 0.707 ± 0.026 | 0.939 ± 0.061 |

Figure 5:
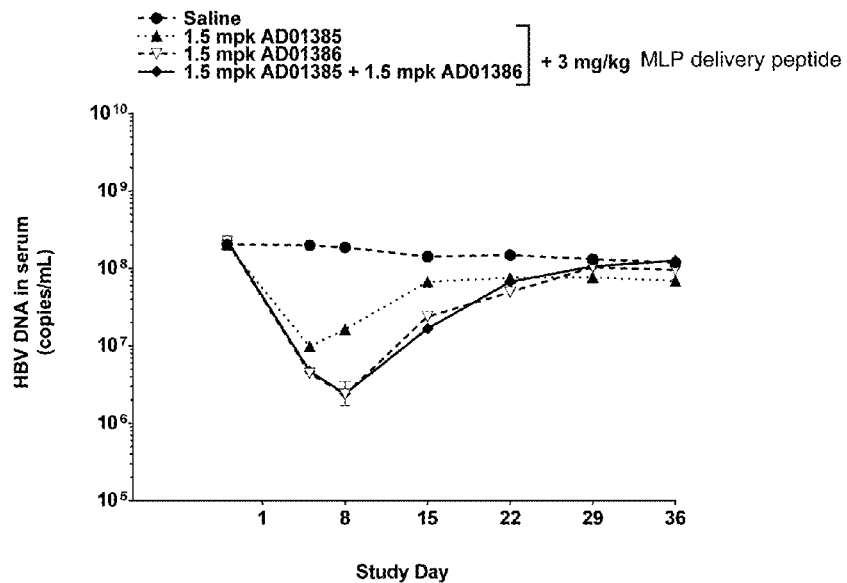
FIG. 5. Graphs showing serum HBV DNA in pHBV mice following co-administration of 3 mg/kg MLP delivery peptide plus (A) 1.5 mg/kg AD01385 or 1.5 mg/kg AD01386 or (B) 1.5 mg/kg AD01385+1.5 mg/kg AD01386.
Figure 5:
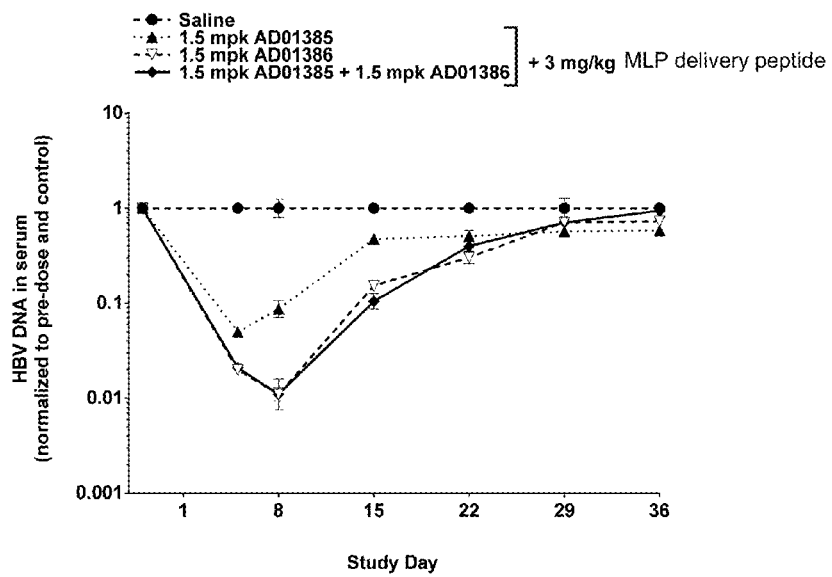

Results are also shown in FIG. 5, showing nearly 2 log knockdown at day 8.

Example 11. Reduction in the Hepatitis B Virus (HBV) Viral Protein HBsAg in Chronically HBV Infected Chimpanzee Following Delivery of HBV RNAi Triggers with MLP Delivery Peptide Chimpanzee:

Animal 95A010 is a 19 year old female chimpanzee (date of birth Aug. 7, 1995) weighing 66 kg that was exposed to HBV at birth. At the start of the study she was HBeAg-negative and anti-HBe positive, and had a HBV DNA titer of $3.7 \times 10^3$ copies/mL serum.

Formulation of HBV RNAi Trigger Delivery Composition:

MLP delivery peptide, Vial 1 contained MLP-(CDM-NAG) lyophilized in a sterile 10 mL glass vial at a strength of 125 mg. Active Pharmaceutical Ingredient (API), Vial 2, contained an equimolar mixture of AD0009 and AD0010 as a liquid at a strength of 26 mg/mL total RNAi trigger in 5.3 mL phosphate buffer in a sterile 10 mL glass vial. The 4.8 mL liquid from Vial 2 was added to Vial 1 and swirled to dissolve. The resulting solution contained 125 mg/vial at a nominal concentration of 25 mg/mL with respect to the active pharmaceutical ingredient in 5 mL. A sufficient number of paired vials were prepared for the indicated dose. To dose with 2 mg/kg MLP delivery peptide+1 mg/kg AD01385+1 mg/kg AD01386, a 26 mg/mL solution containing an equimolar amount of AD01385 and ADO 1386 in a phosphate buffer was used to solubilize MLP delivery peptide Vial 1.

RNAi Trigger Delivery.

Chimp 95A010 was infused with 2 mg/kg MLP delivery peptide (formulated as MLP delivery peptide)+1 mg/kg AD0009+1 mg/mL AD0010 at an infusion rate of 10 mg/minute with respect to MLP delivery peptide. After HBsAg levels had returned to baseline following ARC-520 treatment, the chimp was infused with 2 mg/kg MLP delivery peptide+1 mg/kg AD01385+1 mg/kg AD01386.

Serum Hepatitis B Surface Antigen (HBsAg) Levels:

Serum was collected and diluted $10^4$ to $10^5$-fold in PBS containing 5% nonfat dry milk. In all other ways the assay was performed as described above.

Figure 6:
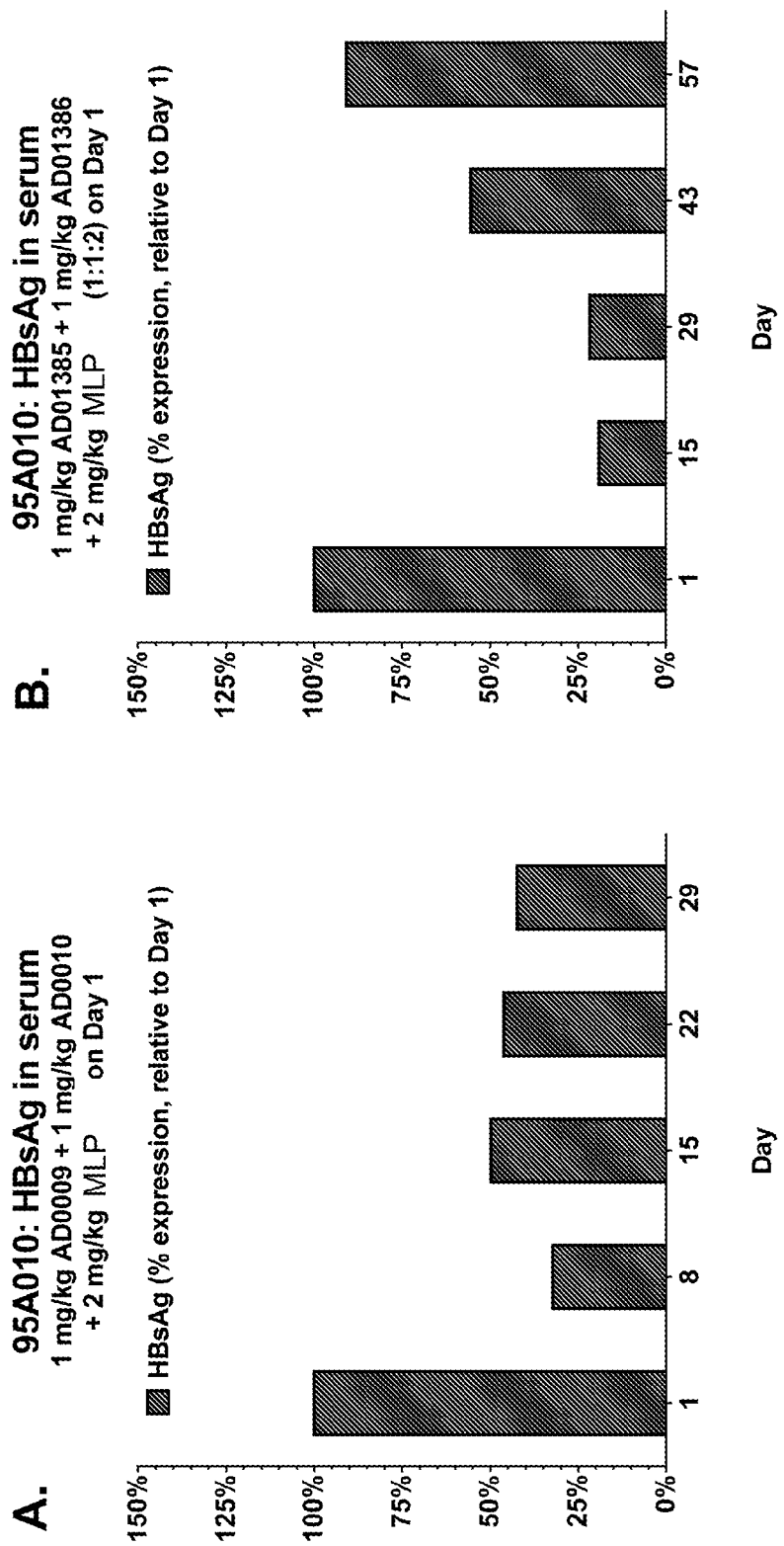
FIG. 6. Graphs showing Serum HBsAg in chimpanzee 95A010 following co-administration of (A) 2 mg/kg MLP delivery peptide, 1 mg/kg AD0009 and 1 mg/kg AD0010; or (B) 2 mg/kg MLP delivery peptide, 1 mg/kg AD01386 and 1 mg/kg AD01385.
Figure 7:
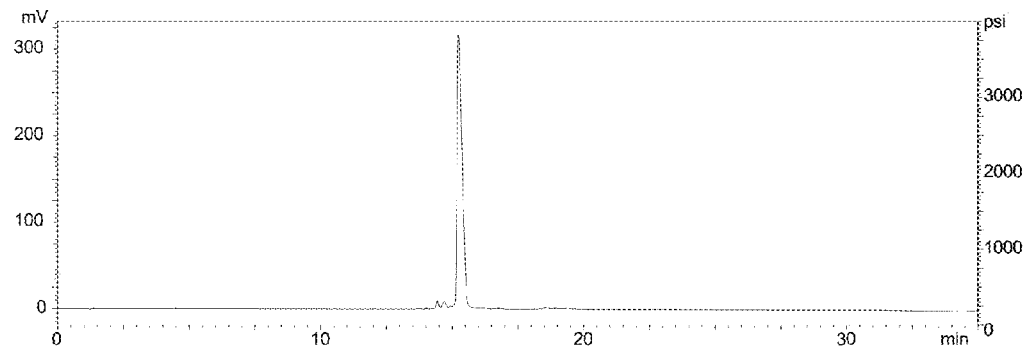
Figure 7:
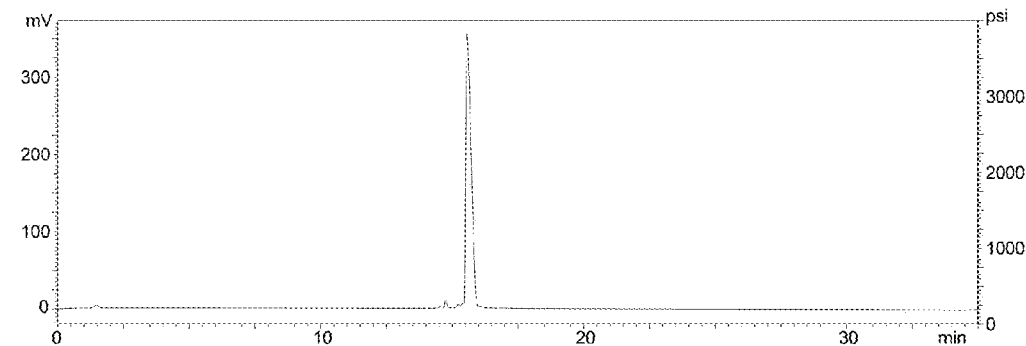
Figure 7:
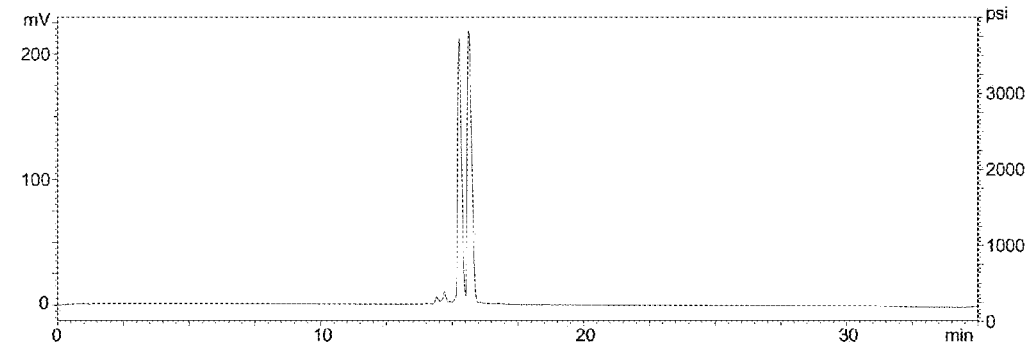
Figure 8:
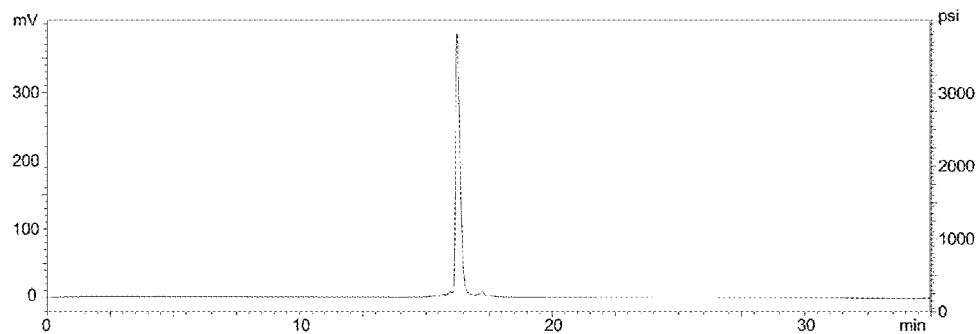
FIG. 8. HPLC Chromatographs of (A) AM02316-SS (TEG), (B) AM02319-SS (TEG), and (C) AM02320-SS (C6).
Figure 8:
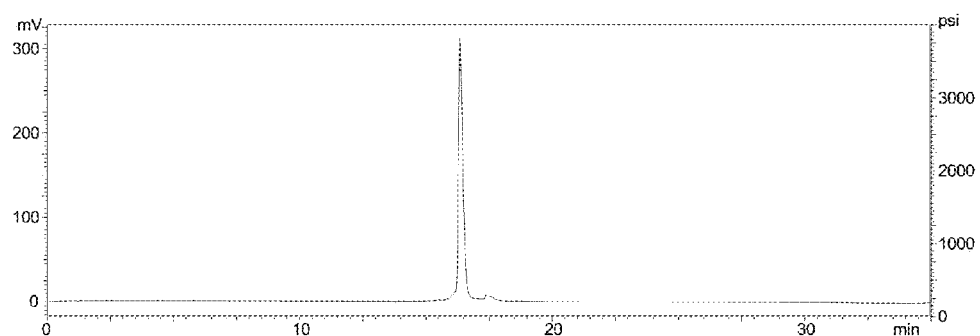
Figure 8:
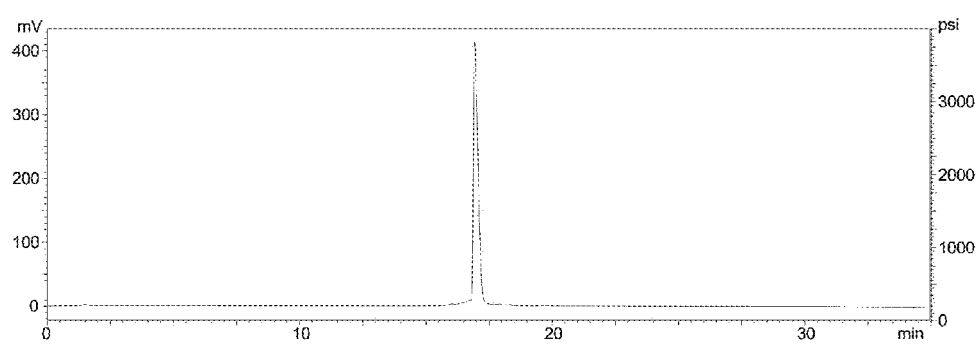
Figure 9:
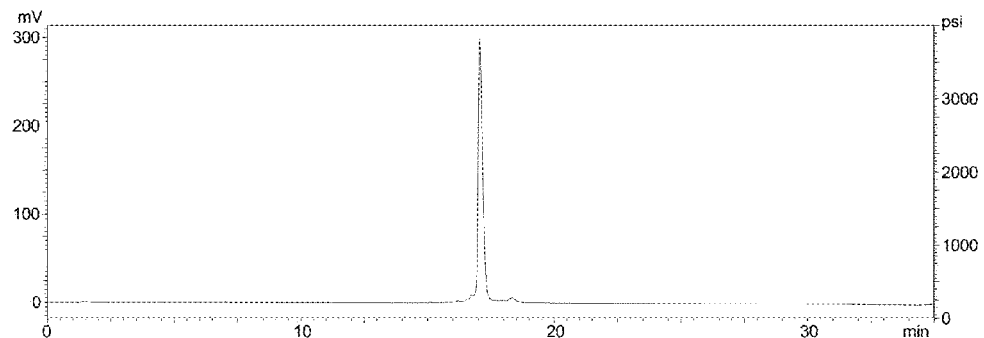
FIG. 9. HPLC Chromatographs of (A) AM02323-SS (C6), (B) AM02320-SS (C6)+AM02323-SS (C6), and (C) AM02319-SS (TEG)+AM02316-SS (TEG).
Figure 9:
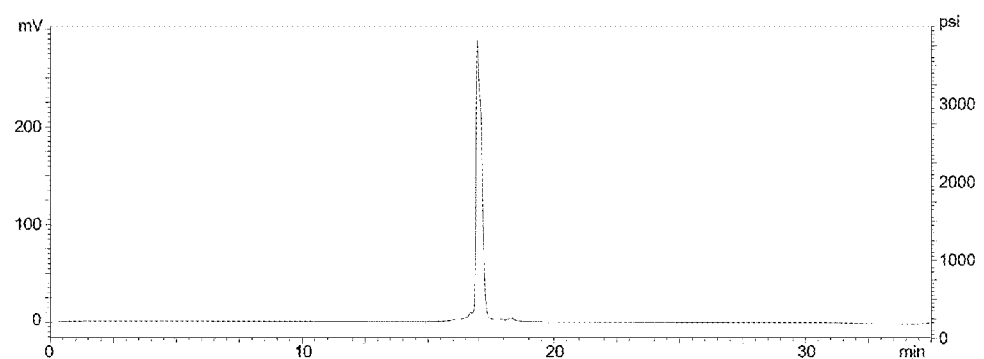
Figure 9:
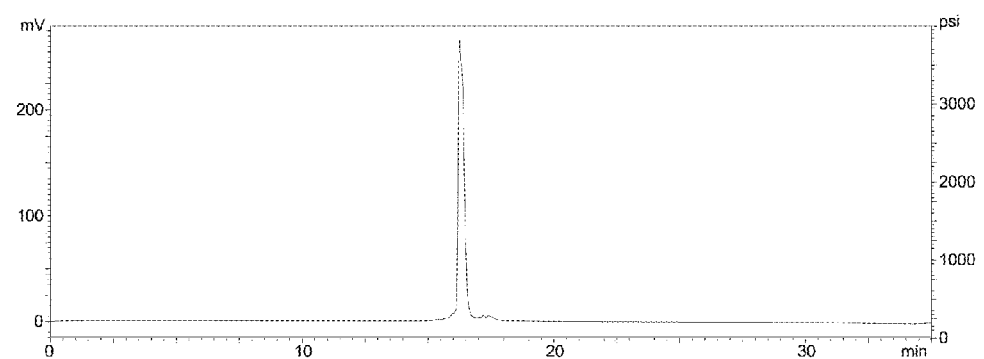
Figure 10:
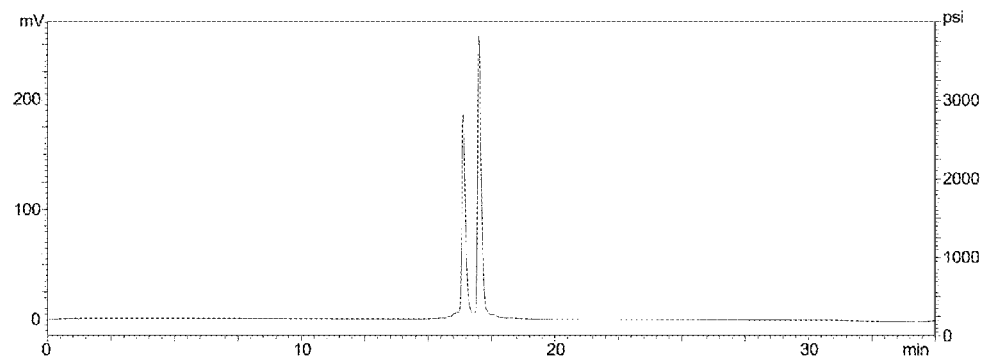
Figure 10:
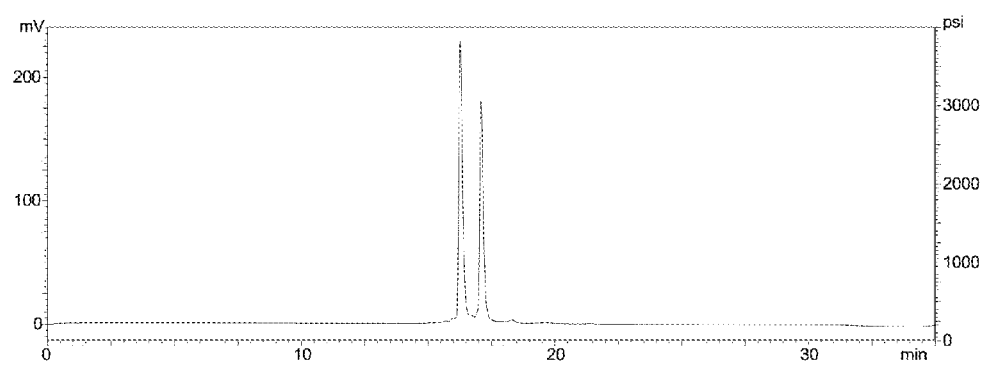
Figure 10:
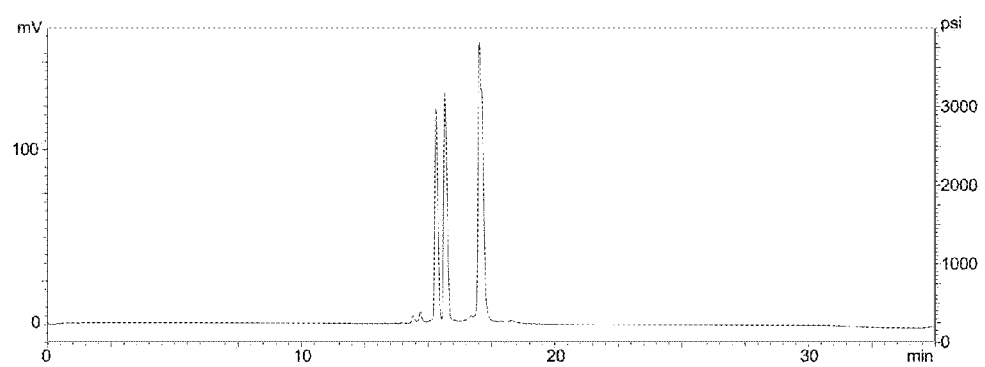
Figure 11:
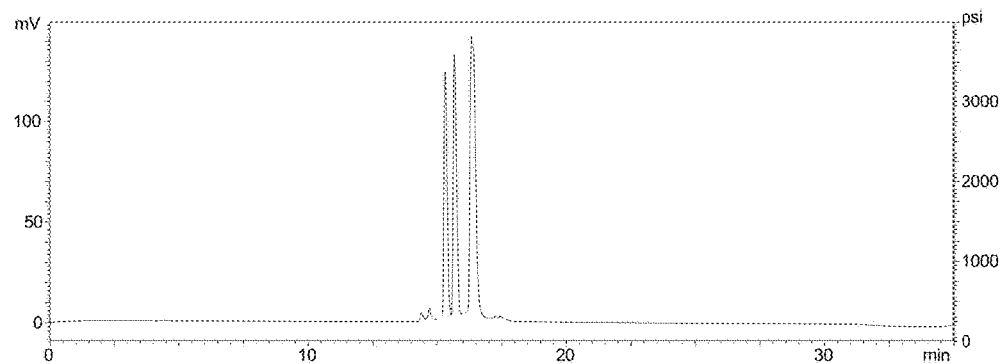
Figure 11:
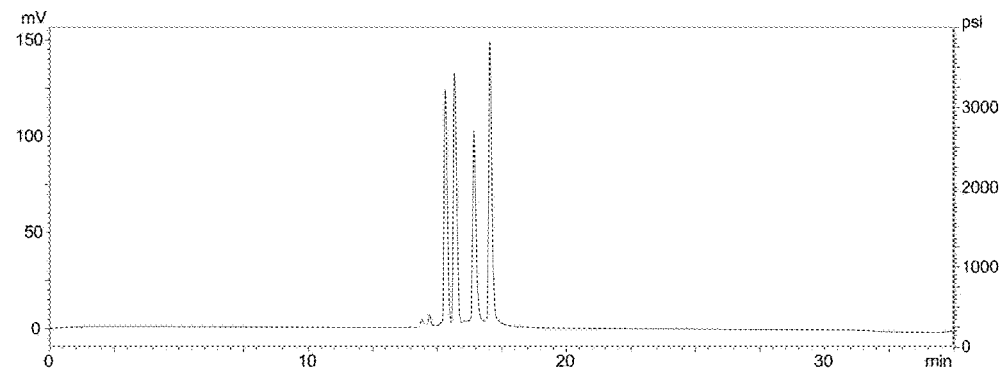
Figure 11:
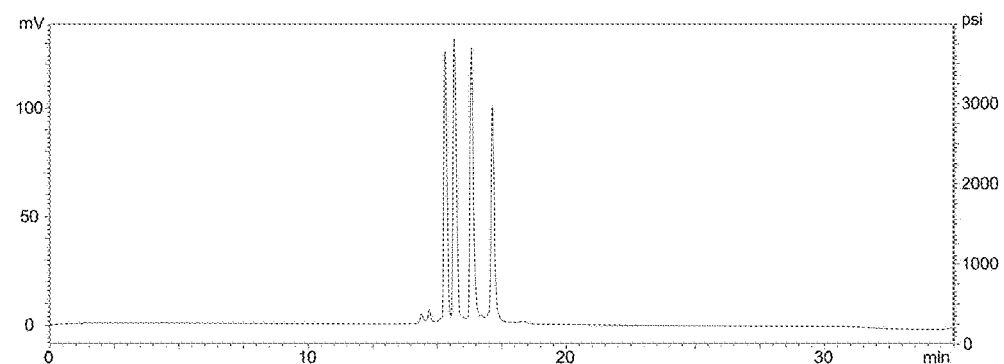

Data:

At Day 15 HBsAg levels were reduced 50% following injection of 1 mg/kg AD0009+AD0010 and 81% following injection of 1 mg/kg AD01385+AD01386, in both cases with 2 mg/kg MLP delivery peptide (FIG. 6).

TABLE 21

Summary of serum HBsAg in chimpanzee 95A010 following co-administration of 2 mg/kg MLP delivery peptide, 1 mg/kg AD0009 and 1 mg/kg AD0010.

| Day of Treatment | HBsAg (µg/mL) Mean of replicates: | % Expression, relative to "Day 1" of treatment Mean of replicates: |
|---|---|---|
| 1 | 72.47 | 100.0% |
| 8 | 23.41 | 32.3% |
| 15 | 36.19 | 49.9% |
| 22 | 33.41 | 46.1% |
| 29 | 30.74 | 42.4% |

TABLE 22

Summary of serum HBsAg in chimpanzee 95A010 following co-administration of 2 mg/kg MLP delivery peptide, 1 mg/kg AD01386 and 1 mg/kg AD01385.

| Day of Treatment | HBsAg (µg/mL) Mean of replicates: | % Expression, relative to day of injection Mean of replicates: |
|---|---|---|
| 1 | 47.55 | 100.00% |
| 15 | 9.04 | 19.01% |
| 29 | 10.33 | 21.73% |
| 43 | 26.40 | 55.52% |
| 57 | 43.20 | 90.85% |

Example 12. Reduction in Hepatitis B Virus (HBV) In Vivo pHBV Model Mice:

At day −35, 6 to 8 week old female NOD.CB17-Prkdscid/NcrCrl (NOD-SCID) mice were transiently transfected in vivo with MC-HBV1.3 by hydrodynamic tail vein injection (Yang P L et al. "Hydrodynamic injection of viral DNA: a mouse model of acute hepatitis B virus infection." *Proc Natl Acad Sci USA* 2002 Vol. 99: p. 13825-13830). MC-HBV1.3 is a plasmid-derived minicircle that contains the same terminally redundant human hepatitis B virus sequence HBV 1.3 as in the HBV1.3.32 transgenic mice (GenBank accession #V01460) (Guidotti L G et al. "High-level hepatitis B virus replication in transgenic mice. J Virol 1995 Vol. 69, p 6158-6169.). 5 µg MC-HBV 1.3 in Ringer's Solution in a total volume of 10% of the animal's body weight was injected into mice via tail vein to create pHBV model of chronic HBV infection. The solution was injected through a 27-gauge needle in 5-7 seconds as previously described (Zhang G et al. "High levels of foreign gene expression in hepatocytes after tail vein injection of naked plasmid DNA." Human Gene Therapy 1999 Vol. 10, p 1735-1737.). At day −7, four weeks after transfection, Hepatitis B surface antigen (HBsAg) HBsAg expression levels in serum were measured by ELISA and the mice were grouped according to average HBsAg expression levels.

RNAi Trigger Delivery:

At day 1, each mouse was then given a single subcutaneous administration of 200 µl containing HBV RNAi trigger and normal saline. A typical site for performing injections between the skin and muscle (i.e. subcutaneous injections) was into the loose skin over the neck and shoulder area, but other sites with loose folds of skin can also be used.

Analyses:

At various times, before and after administration of HBV RNAi triggers or normal saline, serum HBsAg, serum HBV DNA, or liver HBV RNA were measured. HBV expression levels were normalized to control mice injected with normal saline.

i) Serum Collection:

Mice were anesthetized with 2-3% isoflurane and blood samples were collected from the submandibular area into serum separation tubes (Sarstedt AG & Co., Nümbrecht, Germany). Blood was allowed to coagulate at ambient temperature for 20 min. The tubes were centrifuged at 8,000×g for 3 min to separate the serum and stored at 4° C.

ii) Serum Hepatitis B Surface Antigen (HBsAg) Levels:

Serum was collected and diluted 10 to 2000-fold in PBS containing 5% nonfat dry milk. Secondary HBsAg standards diluted in the nonfat milk solution were prepared from serum of ICR mice (Harlan Sprague Dawley) that had been transfected with 10 µg HBsAg-expressing plasmid pRc/CMV-HBs (Aldevron, Fargo, N. Dak.). HBsAg levels were determined with a GS HBsAg EIA 3.0 kit (Bio-Rad Laboratories, Inc., Redmond, Wash.) as described by the manufacturer. Recombinant HBsAg protein, ayw subtype, also diluted in nonfat milk in PBS, was used as a primary standard (Aldevron).

HBsAg expression for each animal was normalized to the control group of mice injected with normal saline in order to account for the non-treatment related decline in expression of MC-HBV1.3. First, the HBsAg level for each animal at a time point was divided by the pre-treatment level of expression in that animal (Day −1) in order to determine the ratio of expression "normalized to pre-treatment". Expression at a specific time point was then normalized to the control group by dividing the "normalized to pre-treatment" ratio for an individual animal by the average "normalized to pre-treatment" ratio of all mice in the normal saline control group.

TABLE 23

Hepatitis B virus (HBV) knockdown in vivo as determined by HBsAg in serum.

| RNAi trigger | HBsAg in serum at nadir (norm. fraction) | % KD at nadir | Day of nadir |
|---|---|---|---|
| AD03364 | 0.37 | 62.9% | 8 |
| AD03365 | 0.58 | 42.2% | 8 |
| AD03366 | 0.64 | 93.5% | 8 |
| AD03367 | 0.027 | 97.3% | 8 |
| AD03368 | 0.35 | 65.4% | 15 |
| AD03369 | 0.55 | 45.0% | 15 |
| AD03370 | 0.70 | 29.6% | 8 |
| AD03373 | 0.083 | 91.7% | 8 |
| AD03374 | 0.072 | 92.8% | 8 |
| AD03375 | 0.37 | 63.0% | 8 |
| AD03376 | 0.32 | 68.3% | 8 |
| AD03377 | 0.23 | 76.6% | 8 |
| AD03378 | 0.17 | 82.9% | 8 |
| AD03381 | 0.54 | 46.3% | 8 |
| AD03382 | 0.63 | 37.0% | 8 |
| AD03383 | 0.80 | 20.2% | 8 |
| AD03384 | 0.64 | 35.5% | 15 |
| AD03385 | 0.46 | 53.9% | 15 |
| AD03386 | 0.67 | 32.8% | 8 |
| AD03387 | 0.50 | 50.4% | 8 |
| AD03388 | 0.47 | 53.1% | 15 |
| AD03389 | 0.44 | 55.8% | 8 |
| AD03390 | 0.45 | 55.0% | 8 |
| AD03396 | 0.46 | 54.4% | 8 |
| AD03397 | 0.50 | 50.3% | 8 |
| AD03398 | 0.46 | 54.0% | 8 |
| AD03399 | 0.22 | 77.9% | 8 |
| AD03401 | 0.39 | 61.2% | 8 |
| AD03402 | 0.40 | 60.2% | 8 |
| AD03403 | 0.11 | 88.5% | 8 |
| AD03404 | 0.37 | 62.5% | 8 |
| AD03405 | 0.13 | 87.3% | 8 |
| AD03406 | 0.088 | 91.2% | 8 |
| AD03408 | 0.016 | 98.4% | 22 |
| AD03409 | 0.008 | 99.2% | 15 |
| AD03410 | 0.057 | 94.3% | 15 |
| AD03411 | 0.28 | 72.4% | 8 |
| AD03412 | 0.75 | 24.6% | 15 |
| AD03413 | 0.51 | 49.0% | 8 |
| AD03414 | 0.40 | 60.0% | 8 |
| AD03217 | 0.065 | 92.9% | 15 |
| AD03055 | 0.11 | 89.1% | 8 |
| AD03218 | 0.047 | 95.0% | 15 |
| AD02729 | 0.095 | 90.5% | 8 |
| AD03498 | 0.087 | 91.3% | 8 |
| AD03499 | 0.069 | 93.1% | 15 |
| AD03500 | 0.095 | 90.5% | 8 |

TABLE 23-continued

Hepatitis B virus (HBV) knockdown in vivo as determined by HBsAg in serum.

| RNAi trigger | HBsAg in serum at nadir (norm. fraction) | % KD at nadir | Day of nadir |
|---|---|---|---|
| AD03501 | 0.046 | 95.4% | 15 |
| AD03502 | 0.17 | 83.0% | 8 |
| AD03503 | 0.20 | 79.8% | 8 |
| AD03504 | 0.19 | 81.1% | 8 |
| AD03509 | 0.14 | 86.5% | 15 |
| AD03510 | 0.32 | 68.2% | 15 |
| AD03511 | 0.11 | 88.9% | 15 |

Example 13. Chromatography Analysis of HBV RNAi Triggers

Clinical development requires that the active pharmaceutical ingredient (API) be quantified in a drug product. When the drug product is a mixture of two APIs, such as with the combination of AD01385 and AD01386, quantitation requires clean analytical separation. For oligonucleotides APIs, clean analytical separation is difficult due to compositional similarities of oligonucleotides of the same length. To facilitate the chromatographic separation of the sense strands of AD01385 and AD01386 mixture, a linker containing six carbons (C6) between cholesterol and the oligonucleotide was incorporated in one strand and a triethylene oxide (TEG) linker was used in the other strand. These linkers have different hydrophobicities which allow for chromatographic resolution. The RNAi trigger sense strands are separated by anion exchange chromatography using a Thermo Scientific DNAPac PA-200 column using a gradient from 70:30 mixture of (10 mM NaHCO3 (pH 11.3)/50 mM NaBr/45% ACN):(10 mM NaHCO3 (pH 11.3)/650 mM NaBr/45% ACN) to 100% of the 650 mM NaBr solution (See FIGS. 24-28). The peaks for the sense strands were analyzed for the resolution ($R_s$), which is calculated as:

$$R_s = (t_{R2} - t_{R1})/((0.5*(w_1 + w_2)) \tag{1}$$

where $t_{R1}$ and $t_{R2}$ are the retention times for the two strands, and $w_1$ and $w_2$ are the peak widths at the baseline. If $R_s > 2$, the peaks are considered resolved. We calculate that the mixtures of sense strands with different permutations of C6 and TEG linkers have the following resolutions:

TEG:TEG resolution $R_s = 0.44$ (Not resolved)

C6:C6 resolution $R_s = 0.15$ (Not resolved)

C6:TEG resolution $R_s = 2.7$ (Resolved)

The RNAi trigger sense strands with the same Cholesterol targeting group linkage (both C6 or both TEG) were not resolved. In contrast, we were able to determine the concentrations of sense strands with TEG and C6 linkers from mixtures of the two due to their well-resolved chromatographic separations. The results, shown in Table 23 and in FIGS. 7-11 show that two HBV RNAi triggers are better resolved when linked by two different linkers.

In some embodiments, HBV RNAi triggers AD1385 and AD1386 are combined to form a therapeutic RNAi treatment for HBV infection.

TABLE 24

Chromatographic analyses of HBV RNAi trigger strands.

| Sample Mixture | Linker(s) | AM02312-AS | AM02315-AS | AM02316-SS | AM02319-SS | AM02320-SS | AM02323-SS | resolved |
|---|---|---|---|---|---|---|---|---|
| Antisense strands | | | | | | | | |
| Separate runs | | 15.2 | 15.6 | | | | | |
| Antisense strand combination | | | | | | | | |
| AM02312-AS + AM02315-AS | | 15.3 | 15.6 | | | | | partial |
| Sense Strands | | | | | | | | |
| Separate runs | TEG | | | 16.2 | 16.3 | | | |
| Separate runs | C6 | | | | | 16.9 | 17.1 | |
| Sense strand combinations | | | | | | | | |
| AM02320-SS + AM02323-SS | C6/C6 | | | | | 17.0 | 17.0 | no |
| AM02319-SS + AM02316-SS | TEG/TEG | | | 16.3 | 16.3 | | | no |
| AM02320-SS + AM02319-SS | C6/TEG | | | | 16.4 | 17.0 | | YES |
| AM02323-SS + AM02316-SS | C6/TEG | | | 16.3 | | | 17.1 | YES |
| Duplexes | | | | | | | | |
| AM02320-SS/AM02312-AS | C6 | 15.3 | | | | 17.0 | | YES |
| AM02319-SS/AM02315-AS | TEG | | 15.6 | | 16.4 | | | YES |
| AM02316-SS/AM02312-AS | TEG | 15.3 | | 16.3 | | | | YES |
| RNAi trigger combinations | | | | | | | | |
| AM02320-SS/AM02312-AS + AM02323-SS/AM02315-AS | C6 C6 | 15.3 | 15.7 | | | 17.0 | 17.0 | no |
| AM02316-SS/AM02312-AS + AM02319-SS/AM02315-SS | TEG TEG | 15.3 | 15.7 | 16.3 | 16.3 | | | no |
| AM02320-SS/AM02312-AS + AM02319-SS/AM02315-AS | C6 TEG | 15.3 | 15.7 | | 16.4 | 17.0 | | YES |
| AM02316-SS/AM02312-AS + AM02323-SS/AM02315-AS | TEG C6 | 15.3 | 15.7 | 16.3 | | | 17.1 | YES |

The invention claimed is:

1. A composition for inhibiting expression of a hepatitis B virus (HBV) gene comprising:
   a) a first HBV RNAi trigger comprising an antisense strand and a sense strand, wherein the antisense strand comprises the nucleotide sequence of SEQ ID NO: 2, and the sense strand comprises the nucleotide sequence of SEQ ID NO: 104; and
   b) a second HBV RNAi trigger comprising an antisense strand and a sense strand, wherein the antisense strand comprises the nucleotide sequence of SEQ ID NO: 1, and the sense strand comprises the nucleotide sequence of SEQ ID NO: 103.

2. The composition of claim 1, wherein the first HBV RNAi trigger comprises a sense strand covalently linked to a cholesteryl group via a TEG group, and the second HBV RNAi trigger comprises a sense strand covalently linked to a cholesteryl group via a C6 group.

3. The composition of claim 1, wherein the antisense strand and/or the sense strand of the first HBV RNAi trigger comprises at least one modified nucleotide or modified internucleoside linkage.

4. The composition of claim 1, wherein the antisense strand and/or the sense strand of the second HBV RNAi trigger comprises at least one modified nucleotide or modified internucleoside linkage.

5. The composition of claim 1, wherein at least 50% of the nucleotides of the first HBV RNAi trigger and at least 50% of the nucleotides of the second HBV RNAi trigger are modified nucleotides.

6. The composition of claim 1, wherein the first HBV RNAi trigger comprises the duplex AD01385 (SEQ ID NOs: 247 and 473).

7. The composition of claim 1, wherein the second HBV RNAi trigger comprises the duplex AD01386 (SEQ ID NOs: 244 and 474).

8. The composition of claim 7, wherein the first HBV RNAi trigger comprises the duplex AD01385 (SEQ ID NOs: 247 and 473) and the second HBV RNAi trigger comprises the duplex AD01386 (SEQ ID NOs: 244 and 474).

9. The composition of claim 1, wherein the composition further comprises:

$$MLP\text{-}(L\text{-}T)_x,$$

wherein MLP is a melittin-like peptide,
-L-T has the structure represented by —CO—C(CH$_3$)=C(T)-COOH or —CO—C(T)=C(CH$_3$)—COOH,
T comprises a targeting ligand having affinity for an asialoglycoprotein receptor, and
x is greater than 80% of the number of primary amines of a population of MLPs.

10. The composition of claim 8, wherein the composition further comprises:

$$MLP\text{-}(L\text{-}T)_x,$$

wherein MLP is a melittin-like peptide,
-L-T has the structure represented by —CO—C(CH$_3$)=C(T)-COOH or —CO—C(T)=C(CH$_3$)—COOH,
T comprises a targeting ligand having affinity for an asialoglycoprotein receptor, and
x is greater than 80% of the number of primary amines of a population of MLPs.

11. The composition of claim 1, wherein the sense strand of the first and/or second HBV RNAi trigger is conjugated to a targeting ligand having affinity for an asialoglycoprotein receptor.

12. The composition of claim 11, wherein the targeting ligand having affinity for an asialoglycoprotein receptor is a galactose trimer comprised of three terminal galactose derivatives.

13. The composition of claim 1, further comprising one or more additional therapeutics.

14. The composition of claim 1, wherein the composition further comprises a pharmaceutically acceptable excipient.

15. The composition of claim 14, wherein the pharmaceutically acceptable excipient comprises dextran.

16. A method of inhibiting expression of an HBV gene in a subject having an HBV infection, the method comprising administering to the subject an effective amount of the composition of claim 1.

17. A method of treating a subject having an HBV infection, the method comprising administering to the subject an effective amount of the composition of claim 1.

18. The composition of claim 12, wherein the galactose derivatives are N-acetylgalactosamine.

* * * * *

SEQUENCE LISTING

<160> NUMBER OF SEQ ID NOS: 766

<210> SEQ ID NO 1
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 1
taccaauuua ugccuacagt t                                           21

<210> SEQ ID NO 2
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 2
taugauaaaa cgccgcagat t                                           21

```
<210> SEQ ID NO 3
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 3
tagaugauua ggcagaggut t                                              21

<210> SEQ ID NO 4
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 4
tacaaauggc acuaguaaat t                                              21

<210> SEQ ID NO 5
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-25
<223> OTHER INFORMATION: /mod_base = "2'-hydroxy nucleoside"

<400> SEQUENCE: 5
taccaauuua ugccuacagg ccuuau                                         26

<210> SEQ ID NO 6
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-25
<223> OTHER INFORMATION: /mod_base = "2'-hydroxy nucleoside"

<400> SEQUENCE: 6
taugauaaaa cgccgcagac acauau                                         26

<210> SEQ ID NO 7
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-25
<223> OTHER INFORMATION: /mod_base = "2'-hydroxy nucleoside"

<400> SEQUENCE: 7
tagaugauua ggcagagguu gaauau                                         26
```

<210> SEQ ID NO 8
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 8
ugauaaaacg ccgcagacac aucuau                                    26

<210> SEQ ID NO 9
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 9
ugaacaaaug gcacuaguaa acuuau                                    26

<210> SEQ ID NO 10
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 10
ugcgucagca aacacuuggc acauau                                    26

<210> SEQ ID NO 11
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 11
ugaaccacug aacaaauggc acuuau                                    26

<210> SEQ ID NO 12
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 12
uaacgggcaa cauaccuuga uaauau                                    26

<210> SEQ ID NO 13
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 13
uacuaguaaa cugagccagg agauau                                    26

<210> SEQ ID NO 14
<211> LENGTH: 26
<212> TYPE: RNA
<213> ORGANISM: artificial sequence
<220> FEATURE:
<223> OTHER INFORMATION: HBV RNAi trigger antisense strand

```
-continued

<400> SEQUENCE: 14
uggacaaacg ggcaacauac cuuuau                                              26

<210> SEQ ID NO 15
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 15
uacgggcaac auaccuugau aauuau                                              26

<210> SEQ ID NO 16
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 16
ugaagcgaag ugcacacgga ccguau                                              26

<210> SEQ ID NO 17
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 17
uaccaauuua ugccuacagg ccuuau                                              26

<210> SEQ ID NO 18
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 18
uaugauaaaa cgccgcagac acauau                                              26

<210> SEQ ID NO 19
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 19
uagaugauua ggcagagguu gaauau                                              26

<210> SEQ ID NO 20
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 20
```
tgauaaaacg ccgcagacat t          21

<210> SEQ ID NO 21
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 21
tgaacaaaug gcacuaguat t          21

<210> SEQ ID NO 22
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 22
tgcgucagca aacacuuggt t          21

<210> SEQ ID NO 23
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 23
tgaaccacug aacaaauggt t          21

<210> SEQ ID NO 24
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 24
taacgggcaa cauaccuugt t          21

<210> SEQ ID NO 25
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 25
tacuaguaaa cugagccagt t                                              21

<210> SEQ ID NO 26
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 26
tggacaaacg ggcaacauat t                                              21

<210> SEQ ID NO 27
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 27
tacgggcaac auaccuugat t                                              21

<210> SEQ ID NO 28
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 28
tgaagcgaag ugcacacggt t                                              21

<210> SEQ ID NO 29
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2-19
<223> OTHER INFORMATION: /mod_base = "2'-hydroxy nucleoside"

<400> SEQUENCE: 29
tuccgcggga uucagcgcct t                                              21

<210> SEQ ID NO 30
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 30
aguccgcggg auucagcgcc gacuau                                         26

<210> SEQ ID NO 31
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 31
uuaaagagag gugcgcccgg ugguau                                        26

<210> SEQ ID NO 32
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 32
uaagcgaagu gcacacgguc cgguau                                        26

<210> SEQ ID NO 33
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 33
uugaagcgaa gugcacacgg accuau                                        26

<210> SEQ ID NO 34
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 34
agugaagcga agugcacacg gacuau                                        26

<210> SEQ ID NO 35
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 35
uagaggugaa gcgaagugca cacuau                                        26

<210> SEQ ID NO 36
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 36
ucagagguga agcgaagugc acauau                                        26

<210> SEQ ID NO 37
<211> LENGTH: 26
<212> TYPE: RNA
<213> ORGANISM: artificial sequence
<220> FEATURE:
<223> OTHER INFORMATION: HBV RNAi trigger antisense strand

```
<400> SEQUENCE: 37
ugcagaggug aagcgaagug cacuau                                        26

<210> SEQ ID NO 38
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 38
ucggucguug acauugcugg gaguau                                        26

<210> SEQ ID NO 39
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 39
ucaaggucgg ucguugacau ugcuau                                        26

<210> SEQ ID NO 40
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 40
ugaccuuuaa ccuaaucucc uccuau                                        26

<210> SEQ ID NO 41
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 41
auuuaugccu acagccuccu aauuau                                        26

<210> SEQ ID NO 42
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 42
aauuuaugcc uacagccucc uaauau                                        26

<210> SEQ ID NO 43
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 43
uaauuuaugc cuacagccuc cuauau                                        26

<210> SEQ ID NO 44
```

```
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 44
ucaauuuaug ccuacagccu ccuuau                                    26

<210> SEQ ID NO 45
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 45
uccaauuuau gccuacagcc uccuau                                    26

<210> SEQ ID NO 46
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 46
uacgccgcag acacauccag cgauau                                    26

<210> SEQ ID NO 47
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 47
uaaaacgccg cagacacauc caguau                                    26

<210> SEQ ID NO 48
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 48
uuaaaacgcc gcagacacau ccauau                                    26

<210> SEQ ID NO 49
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 49
uugauaaaac gccgcagaca cauuau                                    26

<210> SEQ ID NO 50
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 50
```
uaaacgggca acauaccuug auauau                                          26

<210> SEQ ID NO 51
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 51
ucaaacgggc aacauaccuu gauuau                                          26

<210> SEQ ID NO 52
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 52
uacaaacggg caacauaccu ugauau                                          26

<210> SEQ ID NO 53
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 53
uaggacaaac gggcaacaua ccuuau                                          26

<210> SEQ ID NO 54
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 54
uggcacuagu aaacugagcc aaguau                                          26

<210> SEQ ID NO 55
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 55
uuggcacuag uaaacugagc caauau                                          26

<210> SEQ ID NO 56
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 56
uaauggcacu aguaaacuga gccuau                                          26

<210> SEQ ID NO 57
<211> LENGTH: 26
<212> TYPE: RNA

<213> ORGANISM: artificial sequence
<220> FEATURE:
<223> OTHER INFORMATION: HBV RNAi trigger antisense strand

<400> SEQUENCE: 57
uaaauggcac uaguaaacug agcuau 26

<210> SEQ ID NO 58
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 58
ucaaauggca cuaguaaacu gaguau 26

<210> SEQ ID NO 59
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 59
uacaaauggc acuaguaaac ugauau 26

<210> SEQ ID NO 60
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 60
uugaacaaau ggcacuagua aacuau 26

<210> SEQ ID NO 61
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 61
acugaacaaa uggcacuagu aaauau 26

<210> SEQ ID NO 62
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 62
uaaccacuga acaaauggca cuauau 26

<210> SEQ ID NO 63
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 63
ucgaaccacu gaacaaaugg cacuau 26

```
<210> SEQ ID NO 64
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 64
ucagagguga aaaguugca ugguau                                              26

<210> SEQ ID NO 65
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 65
ugcagaggug aaaaguugc auguau                                              26

<210> SEQ ID NO 66
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 66
ugaugauuag gcagagguga aaauau                                             26

<210> SEQ ID NO 67
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 67
ugagaugauu aggcagaggu gaauau                                             26

<210> SEQ ID NO 68
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 68
ucacgagucu agacucugug guauau                                             26

<210> SEQ ID NO 69
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 69
auugagagaa guccaccacg aguuau                                             26

<210> SEQ ID NO 70
<211> LENGTH: 26
<212> TYPE: RNA
<213> ORGANISM: artificial sequence
<220> FEATURE:
```

```
<223> OTHER INFORMATION: HBV RNAi trigger antisense strand

<400> SEQUENCE: 70
aauugagaga aguccaccac gaguau                                          26

<210> SEQ ID NO 71
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 71
uuagaaaauu gagagaaguc cacuau                                          26

<210> SEQ ID NO 72
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 72
uuauggaucg gcagaggagc cacuau                                          26

<210> SEQ ID NO 73
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 73
ucaguaugga ucggcagagg agcuau                                          26

<210> SEQ ID NO 74
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 74
uggaguuccg caguauggau cgguau                                          26

<210> SEQ ID NO 75
<211> LENGTH: 23
<212> TYPE: RNA
<213> ORGANISM: artificial sequence
<220> FEATURE:
<223> OTHER INFORMATION: HBV RNAi trigger antisense strand

<400> SEQUENCE: 75
uaccaauuua ugccuacagg ccu                                             23

<210> SEQ ID NO 76
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 76
uaccaauuua ugccuacagg c                                               21
```

```
<210> SEQ ID NO 77
<211> LENGTH: 23
<212> TYPE: RNA
<213> ORGANISM: artificial sequence
<220> FEATURE:
<223> OTHER INFORMATION: HBV RNAi trigger antisense strand

<400> SEQUENCE: 77
ugaagcgaag ugcacacgga ccg                                         23

<210> SEQ ID NO 78
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 78
ugaagcgaag ugcacacgga c                                           21

<210> SEQ ID NO 79
<211> LENGTH: 23
<212> TYPE: RNA
<213> ORGANISM: artificial sequence
<220> FEATURE:
<223> OTHER INFORMATION: HBV RNAi trigger antisense strand

<400> SEQUENCE: 79
uggacaaacg ggcaacauac cuu                                         23

<210> SEQ ID NO 80
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 80
uggacaaacg ggcaacauac c                                           21

<210> SEQ ID NO 81
<211> LENGTH: 17
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 1-15
<223> OTHER INFORMATION: /mod_base = "2'-hydroxy nucleoside"

<400> SEQUENCE: 81
auaaaacgcc gcagatt                                                17

<210> SEQ ID NO 82
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 82
ugugaagcga agugcacacu u                                           21

<210> SEQ ID NO 83
<211> LENGTH: 23
<212> TYPE: RNA
```

<213> ORGANISM: artificial sequence
<220> FEATURE:
<223> OTHER INFORMATION: HBV RNAi trigger antisense strand

<400> SEQUENCE: 83
uaaaauugag agaaguccac cac                                              23

<210> SEQ ID NO 84
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 84
uugaagcgaa gugcacacgg accgcg                                           26

<210> SEQ ID NO 85
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 85
ugugaagcga agugcacacg gaccgc                                           26

<210> SEQ ID NO 86
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 86
ugauaaaacg ccgcagacac auccgc                                           26

<210> SEQ ID NO 87
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 87
uaugauaaaa cgccgcagac acacgc                                           26

<210> SEQ ID NO 88
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 88
agugaagcga agugcacacg gaccgc                                           26

<210> SEQ ID NO 89
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 89
aaugauaaaa cgccgcagac acacgc                                           26

```
<210> SEQ ID NO 90
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 90
ugaagcgaag ugcacacgga ccgcgc                                              26

<210> SEQ ID NO 91
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 91
uggacaaacg ggcaacauac cuucgc                                              26

<210> SEQ ID NO 92
<211> LENGTH: 26
<212> TYPE: RNA
<213> ORGANISM: artificial sequence
<220> FEATURE:
<223> OTHER INFORMATION: HBV RNAi trigger antisense strand

<400> SEQUENCE: 92
uaccaauuua ugccuacagc cuccgc                                              26

<210> SEQ ID NO 93
<211> LENGTH: 17
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 1-15
<223> OTHER INFORMATION: /mod_base = "2'-hydroxy nucleoside"

<400> SEQUENCE: 93
ugauuaggca gaggutt                                                        17

<210> SEQ ID NO 94
<211> LENGTH: 17
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 1-15
<223> OTHER INFORMATION: /mod_base = "2'-hydroxy nucleoside"

<400> SEQUENCE: 94
aauuuaugcc uacagtt                                                        17

<210> SEQ ID NO 95
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 95
```
uaccaauuua ugccuacagu u                           21

<210> SEQ ID NO 96
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 96
auugagagaa guccaccacg a                           21

<210> SEQ ID NO 97
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 97
auugagagaa guccaccacu u                           21

<210> SEQ ID NO 98
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 98
uuugagagaa guccaccacg a                           21

<210> SEQ ID NO 99
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 99
aauugagaga aguccaccac g                           21

<210> SEQ ID NO 100
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 100
aauugagaga aguccaccau u                           21

<210> SEQ ID NO 101
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 101
uauugagaga aguccaccac g                           21

<210> SEQ ID NO 102
<211> LENGTH: 21
<212> TYPE: RNA
<213> ORGANISM: artificial sequence
<220> FEATURE:
<223> OTHER INFORMATION: HBV RNAi trigger antisense strand

<400> SEQUENCE: 102
uuagaaaauu gagagaaguc c                                              21

<210> SEQ ID NO 103
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-22
<223> OTHER INFORMATION: /mod_base = "2'-hydroxy nucleoside"

<400> SEQUENCE: 103
uaucuguagg cauaaauugg uat                                            23

<210> SEQ ID NO 104
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-22
<223> OTHER INFORMATION: /mod_base = "2'-hydroxy nucleoside"

<400> SEQUENCE: 104
uauucugcgg cguuuuauca uat                                            23

<210> SEQ ID NO 105
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-22
<223> OTHER INFORMATION: /mod_base = "2'-hydroxy nucleoside"

<400> SEQUENCE: 105
uauaccucug ccuaaucauc uat                                            23

<210> SEQ ID NO 106
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-19
<223> OTHER INFORMATION: /mod_base = "2'-hydroxy nucleoside"

<400> SEQUENCE: 106
cuguaggcau aaauugguat                                                20

<210> SEQ ID NO 107
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:

```
<221> NAME/KEY: modified base
<222> LOCATION: 1-19
<223> OTHER INFORMATION: /mod_base = "2'-hydroxy nucleoside"

<400> SEQUENCE: 107
accucugccu aaucaucuat                                           20

<210> SEQ ID NO 108
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-19
<223> OTHER INFORMATION: /mod_base = "2'-hydroxy nucleoside"

<400> SEQUENCE: 108
uuuacuagug ccauuuguat                                           20

<210> SEQ ID NO 109
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-19
<223> OTHER INFORMATION: /mod_base = "2'-hydroxy nucleoside"

<400> SEQUENCE: 109
ucugcggcgu uuuaucauat                                           20

<210> SEQ ID NO 110
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-25
<223> OTHER INFORMATION: /mod_base = "2'-hydroxy nucleoside"

<400> SEQUENCE: 110
uauuuuacua gugccauuug uat                                       23

<210> SEQ ID NO 111
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 111
uauaugccug uaggcauaaa uuggua                                    26

<210> SEQ ID NO 112
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 112
uauauugucu gcggcguuuu aucaua                                    26
```

<210> SEQ ID NO 113
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 113
uauaucaacc ucugccuaau caucua                                              26

<210> SEQ ID NO 114
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 114
uauauugugu cugcggcguu uuauca                                              26

<210> SEQ ID NO 115
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 115
uauauuuuac uagugccauu uguuca                                              26

<210> SEQ ID NO 116
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 116
uauauugcca aguguuugcu gacgca                                              26

<210> SEQ ID NO 117
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 117
uauauugcca uuguucagu gguuca                                               26

<210> SEQ ID NO 118
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 118
uauauaucaa gguauguugc ccguua                                              26

<210> SEQ ID NO 119
<211> LENGTH: 26
<212> TYPE: RNA
<213> ORGANISM: artificial sequence
<220> FEATURE:

<223> OTHER INFORMATION: HBV RNAi trigger sense strand

<400> SEQUENCE: 119
uauauuccug gcucaguuua cuagua 26

<210> SEQ ID NO 120
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 120
uauaugguau guugcccguu ugucca 26

<210> SEQ ID NO 121
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 121
uauauuauca agguauguug cccgua 26

<210> SEQ ID NO 122
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 122
uauauguccg ugugcacuuc gcuuca 26

<210> SEQ ID NO 123
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-22
<223> OTHER INFORMATION: /mod_base = “2'-hydroxy nucleoside”

<400> SEQUENCE: 123
uauugucugc ggcguuuuau cat 23

<210> SEQ ID NO 124
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-22
<223> OTHER INFORMATION: /mod_base = “2'-hydroxy nucleoside”

<400> SEQUENCE: 124
uauuacuagu gccauuuguu cat 23

<210> SEQ ID NO 125
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: mod

```
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-22
<223> OTHER INFORMATION: /mod_base = "2'-hydroxy nucleoside"

<400> SEQUENCE: 130
uauucaaggu auguugcccg uat                                          23

<210> SEQ ID NO 131
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-22
<223> OTHER INFORMATION: /mod_base = "2'-hydroxy nucleoside"

<400> SEQUENCE: 131
uauccgugug cacuucgcuu cat                                          23

<210> SEQ ID NO 132
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-22
<223> OTHER INFORMATION: /mod_base = "2'-hydroxy nucleoside"

<400> SEQUENCE: 132
uauggcgcug aaucccgcgg aat                                          23

<210> SEQ ID NO 133
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-25
<223> OTHER INFORMATION: /mod_base = "2'-hydroxy nucleoside"

<400> SEQUENCE: 133
uauaucggcg cugaaucccg cggact                                       26

<210> SEQ ID NO 134
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 134
uauauaccgg gcgcaccucu cuuuaa                                       26

<210> SEQ ID NO 135
<211> LENGTH: 26
<212> TYPE: RNA
<213> ORGANISM: artificial sequence
<220> FEATURE:
<223> OTHER INFORMATION: HBV RNAi trigger sense strand
```

<400> SEQUENCE: 135
uauauggacc gugugcacuu cgcuua                                              26

<210> SEQ ID NO 136
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 136
uauauuccgu gugcacuucg cuucaa                                              26

<210> SEQ ID NO 137
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-25
<223> OTHER INFORMATION: /mod_base = "2'-hydroxy nucleoside"

<400> SEQUENCE: 137
uauauccgug ugcacuucgc uucact                                              26

<210> SEQ ID NO 138
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 138
uauaugugca cuucgcuuca ccucua                                              26

<210> SEQ ID NO 139
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 139
uauauugcac uucgcuucac cucuga                                              26

<210> SEQ ID NO 140
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 140
uauaugcacu ucgcuucacc ucugca                                              26

<210> SEQ ID NO 141
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 141
uauaucccag caaugucaac gaccga                                         26

<210> SEQ ID NO 142
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 142
uauauaaugu caacgaccga ccuuga                                         26

<210> SEQ ID NO 143
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 143
uauauaggag auuagguuaa agguca                                         26

<210> SEQ ID NO 144
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-25
<223> OTHER INFORMATION: /mod_base = "2'-hydroxy nucleoside"

<400> SEQUENCE: 144
uauauuagga ggcuguaggc auaaat                                         26

<210> SEQ ID NO 145
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-25
<223> OTHER INFORMATION: /mod_base = "2'-hydroxy nucleoside"

<400> SEQUENCE: 145
uauauaggag gcuguaggca uaaaut                                         26

<210> SEQ ID NO 146
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 146
uauauggagg cguaggcau aaauua                                          26

<210> SEQ ID NO 147
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 147
uauaugaggc uguaggcaua aauuga					26

<210> SEQ ID NO 148
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 148
uauauaggcu guaggcauaa auugga					26

<210> SEQ ID NO 149
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 149
uauaugcugg augugucugc ggcgua					26

<210> SEQ ID NO 150
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 150
uauauggaug ugucugcggc guuuua					26

<210> SEQ ID NO 151
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 151
uauaugaugu gucugcggcg uuuuaa					26

<210> SEQ ID NO 152
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 152
uauauguguc ugcggcguuu uaucaa					26

<210> SEQ ID NO 153
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 153
uauauucaag guauguugcc cguuua					26

<210> SEQ ID NO 154
<211> LENGTH: 26
<212> TYPE: RNA

```
<213> ORGANISM: artificial sequence
<220> FEATURE:
<223> OTHER INFORMATION: HBV RNAi trigger sense strand

<400> SEQUENCE: 154
uauaucaagg uauguugccc guuuga                                              26

<210> SEQ ID NO 155
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 155
uauauaaggu auguugcccg uuugua                                              26

<210> SEQ ID NO 156
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 156
uauauguaug uugcccguuu guccua                                              26

<210> SEQ ID NO 157
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 157
uauauuggcu caguuuacua gugcca                                              26

<210> SEQ ID NO 158
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 158
uauauggcuc aguuuacuag ugccaa                                              26

<210> SEQ ID NO 159
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 159
uauaucucag uuuacuagug ccauua                                              26

<210> SEQ ID NO 160
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 160
uauauucagu uuacuagugc cauuua                                              26
```

<210> SEQ ID NO 161
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 161
uauaucaguu uacuagugcc auuuga                                              26

<210> SEQ ID NO 162
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 162
uauauaguuu acuagugcca uuugua                                              26

<210> SEQ ID NO 163
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 163
uauauuuacu agugccauuu guucaa                                              26

<210> SEQ ID NO 164
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-25
<223> OTHER INFORMATION: /mod_base = "2'-hydroxy nucleoside"

<400> SEQUENCE: 164
uauauuacua gugccauuug uucagt                                              26

<210> SEQ ID NO 165
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 165
uauaugugcc auuuguucag ugguua                                              26

<210> SEQ ID NO 166
<211> LENGTH: 21
<212> TYPE: RNA
<213> ORGANISM: artificial sequence
<220> FEATURE:
<223> OTHER INFORMATION: HBV RNAi trigger sense strand

<400> SEQUENCE: 166
gguggacuuc ucucaauuuu a                                                   21

<210> SEQ ID NO 167

```
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 167
uauaugccau uguucagug guucga                                             26

<210> SEQ ID NO 168
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 168
uauauaugca acuuuucac cucuga                                             26

<210> SEQ ID NO 169
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 169
uauauugcaa cuuuucacc ucugca                                             26

<210> SEQ ID NO 170
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 170
uauauuucac cucugccuaa ucauca                                            26

<210> SEQ ID NO 171
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 171
uauaucaccu cugccuaauc aucuca                                            26

<210> SEQ ID NO 172
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 172
uauauccaca gagcuagac ucguga                                             26

<210> SEQ ID NO 173
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
```

```
<222> LOCATION: 1-25
<223> OTHER INFORMATION: /mod_base = "2'-hydroxy nucleoside"

<400> SEQUENCE: 173
uauauucgug guggacuucu cucaat                                     26

<210> SEQ ID NO 174
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-25
<223> OTHER INFORMATION: /mod_base = "2'-hydroxy nucleoside"

<400> SEQUENCE: 174
uauaucgugg uggacuucuc ucaaut                                     26

<210> SEQ ID NO 175
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 175
uauauggacu cucucaauu uucuaa                                      26

<210> SEQ ID NO 176
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 176
uauauggcuc cucugccgau ccauaa                                     26

<210> SEQ ID NO 177
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 177
uauauuccuc ugccgaucca uacuga                                     26

<210> SEQ ID NO 178
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 178
uauaugaucc auacugcgga acucca                                     26

<210> SEQ ID NO 179
<211> LENGTH: 25
<212> TYPE: DNA
<213> ORGANISM: artificial sequence
<220> FEATURE:
<223> OTHER INFORMATION: HBV RNAi trigger sense strand
<220> FEATURE:
```

<221> NAME/KEY: modified base
<222> LOCATION: 1-25
<223> OTHER INFORMATION: /mod_base = "2'-hydroxy nucleoside"

<400> SEQUENCE: 179
uugccuguag gcauaaauug guaut                              25

<210> SEQ ID NO 180
<211> LENGTH: 25
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-25
<223> OTHER INFORMATION: /mod_base = "2'-hydroxy nucleoside"

<400> SEQUENCE: 180
uuguccgugu gcacuucgcu ucaut                              25

<210> SEQ ID NO 181
<211> LENGTH: 25
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-25
<223> OTHER INFORMATION: /mod_base = "2'-hydroxy nucleoside"

<400> SEQUENCE: 181
uugguauguu gcccguuugu ccaut                              25

<210> SEQ ID NO 182
<211> LENGTH: 19
<212> TYPE: RNA
<213> ORGANISM: artificial sequence
<220> FEATURE:
<223> OTHER INFORMATION: HBV RNAi trigger sense strand

<400> SEQUENCE: 182
gugugcacuu cgcuucaca                                     19

<210> SEQ ID NO 183
<211> LENGTH: 21
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-19,21
<223> OTHER INFORMATION: /mod_base = "2'-hydroxy nucleoside"

<400> SEQUENCE: 183
gguggacuuc ucucaauuut a                                  21

<210> SEQ ID NO 184
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 184
cgcgguccgu gugcacuucg cuucaa                             26

<210> SEQ ID NO 185
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 185
gcgguccgug ugcacuucgc uucaca            26

<210> SEQ ID NO 186
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 186
gcggaugugu cugcggcguu uuauca            26

<210> SEQ ID NO 187
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-24,26
<223> OTHER INFORMATION: /mod_base = "2'-hydroxy nucleoside"

<400> SEQUENCE: 187
gcgugugucu gcggcguuuu aucata            26

<210> SEQ ID NO 188
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-25
<223> OTHER INFORMATION: /mod_base = "2'-hydroxy nucleoside"

<400> SEQUENCE: 188
gcgguccgug ugcacuucgc uucact            26

<210> SEQ ID NO 189
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-24
<223> OTHER INFORMATION: /mod_base = "2'-hydroxy nucleoside"

<400> SEQUENCE: 189
gcgugugucu gcggcguuuu aucatt            26

<210> SEQ ID NO 190
<211> LENGTH: 26
<212> TYPE: RNA
<213> ORGANISM: artificial sequence
<220> FEATURE:

-continued

<223> OTHER INFORMATION: HBV RNAi trigger sense strand

<400> SEQUENCE: 190
gcgcgguccg ugugcacuuc gcuuca         26

<210> SEQ ID NO 191
<211> LENGTH: 26
<212> TYPE: RNA
<213> ORGANISM: artificial sequence
<220> FEATURE:
<223> OTHER INFORMATION: HBV RNAi trigger sense strand

<400> SEQUENCE: 191
gcgaagguau guugcccguu ugucca         26

<210> SEQ ID NO 192
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-24,26
<223> OTHER INFORMATION: /mod_base = "2'-hydroxy nucleoside"

<400> SEQUENCE: 192
gcggaggcug uaggcauaaa uuggta         26

<210> SEQ ID NO 193
<211> LENGTH: 19
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-18
<223> OTHER INFORMATION: /mod_base = "2'-hydroxy nucleoside"

<400> SEQUENCE: 193
uguaggcaua aauugguat         19

<210> SEQ ID NO 194
<211> LENGTH: 19
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-18
<223> OTHER INFORMATION: /mod_base = "2'-hydroxy nucleoside"

<400> SEQUENCE: 194
ccucugccua aucaucuat         19

<210> SEQ ID NO 195
<211> LENGTH: 19
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-18
<223> OTHER INFORMATION: /mod_base = "2'-hydroxy nucleoside"

<400> SEQUENCE: 195
cugcggcguu uuaucauau                                              19

<210> SEQ ID NO 196
<211> LENGTH: 22
<212> TYPE: RNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 22
<223> OTHER INFORMATION: /mod_base = "abasic site"

<400> SEQUENCE: 196
cuguaggcau aaauugguau un                                          22

<210> SEQ ID NO 197
<211> LENGTH: 22
<212> TYPE: RNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 22
<223> OTHER INFORMATION: /mod_base = "abasic site"

<400> SEQUENCE: 197
gccuguaggc auaaauuggu an                                          22

<210> SEQ ID NO 198
<211> LENGTH: 21
<212> TYPE: RNA
<213> ORGANISM: artificial sequence
<220> FEATURE:
<223> OTHER INFORMATION: HBV RNAi trigger sense strand

<400> SEQUENCE: 198
gccuguaggc auaaauuggu a                                           21

<210> SEQ ID NO 199
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-19,21
<223> OTHER INFORMATION: /mod_base = "2'-hydroxy nucleoside"
<220> FEATURE:
<221> NAME/KEY: modified base
<222> LOCATION: 22
<223> OTHER INFORMATION: /mod_base = "abasic site"

<400> SEQUENCE: 199
gccuguaggc auaaauuggt an                                          22

<210> SEQ ID NO 200
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 22
<223> OTHER INFORMATION: /mod_base = "abasic site"

```
<400> SEQUENCE: 200
aacuguaggc auaaauuggu an                                           22

<210> SEQ ID NO 201
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 22
<223> OTHER INFORMATION: /mod_base = "abasic site"

<400> SEQUENCE: 201
ucguggugga cuucucucaa un                                           22

<210> SEQ ID NO 202
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 22
<223> OTHER INFORMATION: /mod_base = "abasic site"

<400> SEQUENCE: 202
aaguggugga cuucucucaa un                                           22

<210> SEQ ID NO 203
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-20
<223> OTHER INFORMATION: /mod_base = "2'-hydroxy nucleoside"
<220> FEATURE:
<221> NAME/KEY: modified base
<222> LOCATION: 22
<223> OTHER INFORMATION: /mod_base = "abasic site"

<400> SEQUENCE: 203
ucguggugga cuucucucaa tn                                           22

<210> SEQ ID NO 204
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 22
<223> OTHER INFORMATION: /mod_base = "abasic site"

<400> SEQUENCE: 204
cgugguggac uucucucaau un                                           22

<210> SEQ ID NO 205
<211> LENGTH: 22
<212> TYPE: DNA
<213> ORGANISM: artificial sequence
<220> FEATURE:
<223> OTHER INFORMATION: HBV RNAi trigger sense strand
```

```
<220> FEATURE:
<221> NAME/KEY: modified base
<222> LOCATION: 22
<223> OTHER INFORMATION: /mod_base = "abasic site"

<400> SEQUENCE: 205
aaugguggac uucucucaau un                                              22

<210> SEQ ID NO 206
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1-19
<223> OTHER INFORMATION: /mod_base = "2'-hydroxy nucleoside"
<220> FEATURE:
<221> NAME/KEY: modified base
<222> LOCATION: 22
<223> OTHER INFORMATION: /mod_base = "abasic site"

<400> SEQUENCE: 206
cgugguggac uucucucaat tn                                              22

<210> SEQ ID NO 207
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 22
<223> OTHER INFORMATION: /mod_base = "abasic site"

<400> SEQUENCE: 207
ggacuucucu caauuuucua an                                              22

<210> SEQ ID NO 208
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 22
<223> OTHER INFORMATION: /mod_base = "abasic site"

<400> SEQUENCE: 208
cgugguggac uucucucaau an                                              22

<210> SEQ ID NO 209
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 22
<223> OTHER INFORMATION: /mod_base = "abasic site"

<400> SEQUENCE: 209
ucguggugga cuucucucaa an                                              22

<210> SEQ ID NO 210
```

```
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 210
taccaauuua ugccuacagt t                                              21

<210> SEQ ID NO 211
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 211
taugauaaaa cgccgcagat t                                              21

<210> SEQ ID NO 212
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 212
tagaugauua ggcagaggut t                                              21

<210> SEQ ID NO 213
<211> LENGTH: 21
<212> TYPE: DNA
<213> ORGANISM: artificial sequence
<220> FEATURE:
```

```
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 213
tacaaauggc acuaguaaat t                                              21

<210> SEQ ID NO 214
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 6
<223> OTHER INFORMATION: /mod_base = "2'-3' seco nucleoside"
<220> FEATURE:
<221> NAME/KEY: modified base
<222> LOCATION: 2,4,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 214
taccaauuua ugccuacagt t                                              21

<210> SEQ ID NO 215
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 7
<223> OTHER INFORMATION: /mod_base = "2'-3' seco nucleoside"
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 215
taccaauuua ugccuacagt t                                              21

<210> SEQ ID NO 216
```

```
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 6
<223> OTHER INFORMATION: /mod_base = "2'-3' seco nucleoside"
<220> FEATURE:
<221> NAME/KEY: modified base
<222> LOCATION: 2,4,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 216
tagaugauua ggcagaggut t                                         21

<210> SEQ ID NO 217
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 7
<223> OTHER INFORMATION: /mod_base = "2'-3' seco nucleoside"
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 217
tagaugauua ggcagaggut t                                         21

<210> SEQ ID NO 218
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"
<220> FEATURE:
<221> NAME/KEY: modified base
<222> LOCATION: 1
```

```
<223> OTHER INFORMATION: /mod_base = "phosphate modified nucleoside"

<400> SEQUENCE: 218
taccaauuua ugccuacagt t                                              21

<210> SEQ ID NO 219
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "phosphate modified nucleoside"

<400> SEQUENCE: 219
tagaugauua ggcagagggut t                                             21

<210> SEQ ID NO 220
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 6
<223> OTHER INFORMATION: /mod_base = "2'-3' seco nucleoside"
<220> FEATURE:
<221> NAME/KEY: modified base
<222> LOCATION: 2,4,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 220
taccaauuua ugccuacagt t                                              21

<210> SEQ ID NO 221
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 6
<223> OTHER INFORMATION: /mod_base = "2'-3' seco nucleoside"
<220> FEATURE:
<221> NAME/KEY: modified base
<222> LOCATION: 2,4,8,10,14,16,18
<223> OTHER INFORMATION: /mod_base = "2'-deoxy-3'-fluoro nucleoside"
```

```
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 221
taccaauuua ugccuacagt t                                              21

<210> SEQ ID NO 222
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 7
<223> OTHER INFORMATION: /mod_base = "2'-3' seco nucleoside"
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 222
tagaugauua ggcagaggut t                                              21

<210> SEQ ID NO 223
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 7
<223> OTHER INFORMATION: /mod_base = "2'-3' seco nucleoside"
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 223
tagaugauua ggcagaggut t                                              21

<210> SEQ ID NO 224
<211> LENGTH: 21
<212> TYPE: DNA
<213> ORGANISM: artificial sequence
<220> FEATURE:
<223> OTHER INFORMATION: HBV RNAi trigger antisense strand
```

```
<220> FEATURE:
<221> NAME/KEY: modified base
<222> LOCATION: 6
<223> OTHER INFORMATION: /mod_base = "2'-3' seco nucleoside"
<220> FEATURE:
<221> NAME/KEY: modified base
<222> LOCATION: 2,4,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 224
tacaaauggc acuaguaaat t                                              21

<210> SEQ ID NO 225
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 7
<223> OTHER INFORMATION: /mod_base = "2'-3' seco nucleoside"
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 225
tacaaauggc acuaguaaat t                                              21

<210> SEQ ID NO 226
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 6
<223> OTHER INFORMATION: /mod_base = "2'-3' seco nucleoside"
<220> FEATURE:
<221> NAME/KEY: modified base
<222> LOCATION: 2,4,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 226
tacaaauggc acuaguaaat t                                              21
```

```
<210> SEQ ID NO 227
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 6
<223> OTHER INFORMATION: /mod_base = "2'-3' seco nucleoside"
<220> FEATURE:
<221> NAME/KEY: modified base
<222> LOCATION: 2,4,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 227
tacaaauggc acuaguaaat t                                              21

<210> SEQ ID NO 228
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 7
<223> OTHER INFORMATION: /mod_base = "2'-3' seco nucleoside"
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 228
tacaaauggc acuaguaaat t                                              21

<210> SEQ ID NO 229
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 7
<223> OTHER INFORMATION: /mod_base = "2'-3' seco nucleoside"
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,9,11,12,13,15,17,19
<223> OTHER INFORMATION: /mod_base = "2'-O-Methyl nucleoside"
<220> FEATURE:
```

```
<221> NAME/KEY: modified base
<222> LOCATION: 2,3,20,21
<223> OTHER INFORMATION: /mod_base = "phosphorothioate linked
      nucleoside"

<400> SEQUENCE: 229
tacaaauggc acuaguaaat t                                              21

<210> SEQ ID NO 230
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 6
<223> OTHER INFORMATION: /mod_base = "2'-3' seco nucleoside"
<220> FEATURE:
<221> NAME/KEY: modified base
<222> LOCATION: 2,4,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 230
taugauaaaa cgccgcagat t                                              21

<210> SEQ ID NO 231
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 7
<223> OTHER INFORMATION: /mod_base = "2'-3' seco nucleoside"
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 231
taugauaaaa cgccgcagat t                                              21

<210> SEQ ID NO 232
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 6
<223> OTHER INFORMATION: /mod_base = "2'-3' seco nucleoside"
<220> FEATURE:
```

```
<221> NAME/KEY: modified base
<222> LOCATION: 2,4,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 232
taugauaaaa cgccgcagat t                                              21

<210> SEQ ID NO 233
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 6
<223> OTHER INFORMATION: /mod_base = "2'-3' seco nucleoside"
<220> FEATURE:
<221> NAME/KEY: modified base
<222> LOCATION: 2,4,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 233
taugauaaaa cgccgcagat t                                              21

<210> SEQ ID NO 234
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 7
<223> OTHER INFORMATION: /mod_base = "2'-3' seco nucleoside"
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 234
taugauaaaa cgccgcagat t                                              21

<210> SEQ ID NO 235
<211> LENGTH: 21
<212> TYPE: DNA
```

```
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 7
<223> OTHER INFORMATION: /mod_base = "2'-3' seco nucleoside"
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 235
taugauaaaa cgccgcagat t                                              21

<210> SEQ ID NO 236
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 236
taccaauuua ugccuacagt t                                              21

<210> SEQ ID NO 237
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 237
taccaauuua ugccuacagt t                                              21

<210> SEQ ID NO 238
<211> LENGTH: 21
<212> TYPE: DNA
```

```
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 238
tagaugauua ggcagaggut t                                           21

<210> SEQ ID NO 239
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 239
tagaugauua ggcagaggut t                                           21

<210> SEQ ID NO 240
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 240 tacaauggc acuaguaaat t                                            21

<210> SEQ ID NO 241
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
```

```
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 241
tacaaauggc acuaguaaat t                                              21

<210> SEQ ID NO 242
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 242
taugauaaaa cgccgcagat t                                              21

<210> SEQ ID NO 243
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 243
taugauaaaa cgccgcagat t                                              21

<210> SEQ ID NO 244
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
```

-continued

<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 244
taccaauuua ugccuacagt t                                              21

<210> SEQ ID NO 245
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 245
tagaugauua ggcagaggut t                                              21

<210> SEQ ID NO 246
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 246
tacaaauggc acuaguaaat t                                              21

<210> SEQ ID NO 247
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:

```
<221> NAME/KEY: modified base
<222> LOCATION: 21
<223> OTHER INFORMATION: /mod_base = "phosphorothioate linked
      nucleoside"

<400> SEQUENCE: 247
taugauaaaa cgccgcagat t                                          21

<210> SEQ ID NO 248
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,23,24
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,15,17,19,21,22,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 248
taccaauuua ugccuacagg ccuuau                                     26

<210> SEQ ID NO 249
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,23,24
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,15,17,19,21,22,26
<223> OTHER INFORMATION: /mod_base = "2'-O-Methyl nucleoside"
<220> FEATURE:
<221> NAME/KEY: modified base
<222> LOCATION: 2,24
<223> OTHER INFORMATION: /mod_base = "phosphorothioate linked
      nucleoside"

<400> SEQUENCE: 249
taccaauuua ugccuacagg ccuuau                                     26

<210> SEQ ID NO 250
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
```

<221> NAME/KEY: modified base
<222> LOCATION: 2,4,6,8,10,13,16,18,20,23,24
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,14,15,17,19,21,22,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"

<400> SEQUENCE: 250
taccaauuua ugccuacagg ccuuau                                              26

<210> SEQ ID NO 251
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,16,18,20,23,24
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,14,15,17,19,21,22,26
<223> OTHER INFORMATION: /mod_base = "2'-O-Methyl nucleoside"
<220> FEATURE:
<221> NAME/KEY: modified base
<222> LOCATION: 2,24
<223> OTHER INFORMATION: /mod_base = "phosphorothioate linked nucleoside"

<400> SEQUENCE: 251
taccaauuua ugccuacagg ccuuau                                              26

<210> SEQ ID NO 252
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,23,24
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,15,17,19,21,22,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"

<400> SEQUENCE: 252
taugauaaaa cgccgcagac acauau                                              26

<210> SEQ ID NO 253
<211> LENGTH: 26
<212> TYPE: DNA

```
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,23,24
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,15,17,19,21,22,26
<223> OTHER INFORMATION: /mod_base = "2'-O-Methyl nucleoside"
<220> FEATURE:
<221> NAME/KEY: modified base
<222> LOCATION: 2,24
<223> OTHER INFORMATION: /mod_base = "phosphorothioate linked
      nucleoside"

<400> SEQUENCE: 253
taugauaaaa cgccgcagac acauau                                             26

<210> SEQ ID NO 254
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,16,18,20,23,24
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,14,15,17,19,21,22,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 254
taugauaaaa cgccgcagac acauau                                             26

<210> SEQ ID NO 255
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,16,18,20,23,24
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,14,15,17,19,21,22,26
<223> OTHER INFORMATION: /mod_base = "2'-O-Methyl nucleoside"
<220> FEATURE:
<221> NAME/KEY: modified base
<222> LOCATION: 2,24
<223> OTHER INFORMATION: /mod_base = "phosphorothioate linked
      nucleoside"
```

<400> SEQUENCE: 255
taugauaaaa cgccgcagac acauau                                              26

<210> SEQ ID NO 256
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,23,24
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,15,17,19,21,22,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 256
tagaugauua ggcagagguu gaauau                                              26

<210> SEQ ID NO 257
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,23,24
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,15,17,19,21,22,26
<223> OTHER INFORMATION: /mod_base = "2'-O-Methyl nucleoside"
<220> FEATURE:
<221> NAME/KEY: modified base
<222> LOCATION: 2,24
<223> OTHER INFORMATION: /mod_base = "phosphorothioate linked
      nucleoside"

<400> SEQUENCE: 257
tagaugauua ggcagagguu gaauau                                              26

<210> SEQ ID NO 258
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,16,18,20,23,24
<223> OTHER INFORMATION: /mod_base = "2'-deoxy-3'-fluoro nucleoside"
<220> FEATURE:
<221> NAME/KEY: modified base

```
<222> LOCATION: 3,5,7,9,11,12,14,15,17,19,21,22,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 258
tagaugauua ggcagagguu gaauau                                       26

<210> SEQ ID NO 259
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,16,18,20,23,24
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,14,15,17,19,21,22,26
<223> OTHER INFORMATION: /mod_base = "2'-O-Methyl nucleoside"
<220> FEATURE:
<221> NAME/KEY: modified base
<222> LOCATION: 2,24
<223> OTHER INFORMATION: /mod_base = "phosphorothioate linked
      nucleoside"

<400> SEQUENCE: 259
tagaugauua ggcagagguu gaauau                                       26

<210> SEQ ID NO 260
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,21
<223> OTHER INFORMATION: /mod_base = "phosphorothioate linked
      nucleoside"

<400> SEQUENCE: 260
taccaauuua ugccuacagt t                                            21

<210> SEQ ID NO 261
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
```

<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,21
<223> OTHER INFORMATION: /mod_base = "phosphorothioate linked nucleoside"

<400> SEQUENCE: 261
taugauaaaa cgccgcagat t                                              21

<210> SEQ ID NO 262
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 2,3,21
<223> OTHER INFORMATION: /mod_base = "phosphorothioate linked nucleoside"

<400> SEQUENCE: 262
tagaugauua ggcagaggut t                                              21

<210> SEQ ID NO 263
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked nucleoside"
<220> FEATURE:
<221> NAME/KEY: modified base
<222> LOCATION: 1
<223> OTHER INFORMATION: /mod_base = "phosphate modified nucleoside"

<400> SEQUENCE: 263
taugauaaaa cgccgcagat t                                              21

<210> SEQ ID NO 264
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base

```
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "phosphate modified nucleoside"

<400> SEQUENCE: 264
taugauaaaa cgccgcagat t                                               21

<210> SEQ ID NO 265
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "phosphate modified nucleoside"

<400> SEQUENCE: 265
taccaauuua ugccuacagt t                                               21

<210> SEQ ID NO 266
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,12,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "phosphate modified nucleoside"

<400> SEQUENCE: 266
tagaugauua ggcagaggut t                                               21

<210> SEQ ID NO 267
<211> LENGTH: 26
<212> TYPE: DNA
<213> ORGANISM: artificial sequence
```

```
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 267
ugauaaaacg ccgcagacac aucuau                                            26

<210> SEQ ID NO 268
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 268
ugaacaaaug gcacuaguaa acuuau                                            26

<210> SEQ ID NO 269
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 269
```
ugcgucagca aacacuuggc acauau                                          26

<210> SEQ ID NO 270
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 270
ugaaccacug aacaaauggc acuuau                                          26

<210> SEQ ID NO 271
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 271
uaacgggcaa cauaccuuga uaauau                                          26

<210> SEQ ID NO 272
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26

```
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 272
uacuaguaaa cugagccagg agauau                                            26

<210> SEQ ID NO 273
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 273
uggacaaacg ggcaacauac cuuuau                                            26

<210> SEQ ID NO 274
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 274
uacgggcaac auaccuugau aauuau                                            26

<210> SEQ ID NO 275
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
```

```
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 275
ugaagcgaag ugcacacgga ccguau                                        26

<210> SEQ ID NO 276
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 276
ugauaaaacg ccgcagacac aucuau                                        26

<210> SEQ ID NO 277
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 277
ugaacaaaug gcacuaguaa acuuau                                        26

<210> SEQ ID NO 278
```

```
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 278
ugcgucagca aacacuuggc acauau                                          26

<210> SEQ ID NO 279
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 279
ugaaccacug aacaaauggc acuuau                                          26

<210> SEQ ID NO 280
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
``` nucleoside"

<400> SEQUENCE: 280
uaacgggcaa cauaccuuga uaauau                                           26

<210> SEQ ID NO 281
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
    nucleoside"

<400> SEQUENCE: 281
uacuaguaaa cugagccagg agauau                                           26

<210> SEQ ID NO 282
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
    nucleoside"

<400> SEQUENCE: 282
uggacaaacg ggcaacauac cuuuau                                           26

<210> SEQ ID NO 283
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"

-continued

```
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 283
uacgggcaac auaccuugau aauuau                                              26

<210> SEQ ID NO 284
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 284
ugaagcgaag ugcacacgga ccguau                                              26

<210> SEQ ID NO 285
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 285
uaccaauuua ugccuacagg ccuuau                                              26

<210> SEQ ID NO 286
<211> LENGTH: 26
<212> TYPE: DNA
<213> ORGANISM: artificial sequence
<220> FEATURE:
<223> OTHER INFORMATION: HBV RNAi trigger antisense strand
```

```
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 286
uaccaauuua ugccuacagg ccuuau                                          26

<210> SEQ ID NO 287
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 287
uaugauaaaa cgccgcagac acauau                                          26

<210> SEQ ID NO 288
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked
      nucleoside"

<400> SEQUENCE: 288
uaugauaaaa cgccgcagac acauau                                          26
```

<210> SEQ ID NO 289
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,13,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,12,15,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked nucleoside"

<400> SEQUENCE: 289
uagaugauua ggcagagguu gaauau                          26

<210> SEQ ID NO 290
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,15,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,16,17,19,21,23,24,26
<223> OTHER INFORMATION: /mod_base = "2'-O-Methyl nucleoside"
<220> FEATURE:
<221> NAME/KEY: modified base
<222> LOCATION: 2
<223> OTHER INFORMATION: /mod_base = "phosphorothioate linked nucleoside"

<400> SEQUENCE: 290
uagaugauua ggcagagguu gaauau                          26

<210> SEQ ID NO 291
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked nucleoside"

<400> SEQUENCE: 291
tgauaaaacg ccgcagacat t        21

<210> SEQ ID NO 292
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked nucleoside"

<400> SEQUENCE: 292
tgaacaaaug gcacuaguat t        21

<210> SEQ ID NO 293
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked nucleoside"

<400> SEQUENCE: 293
tgcgucagca aacacuuggt t        21

<210> SEQ ID NO 294
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked nucleoside"

<400> SEQUENCE: 294
tgaaccacug aacaaauggt t        21

<210> SEQ ID NO 295
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked nucleoside"

<400> SEQUENCE: 295
taacgggcaa cauaccuugt t                                          21

<210> SEQ ID NO 296
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked nucleoside"

<400> SEQUENCE: 296
tacuaguaaa cugagccagt t                                          21

<210> SEQ ID NO 297
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked nucleoside"

<400> SEQUENCE: 297
tggacaaacg ggcaacauat t                                          21

<210> SEQ ID NO 298
<211> LENGTH: 21

```
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 298
tacgggcaac auaccuugat t                                             21

<210> SEQ ID NO 299
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 299
tgaagcgaag ugcacacggt t                                             21

<210> SEQ ID NO 300
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"

<400> SEQUENCE: 300
tuccgcggga uucagcgcct t                                             21

<210> SEQ ID NO 301
<211> LENGTH: 26
<212> TYPE: DNA
<213> ORGANISM: artificial sequence
<220> FEATURE:
<223> OTHER INFORMATION: HBV RNAi trigger antisense strand
```

```
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 301
ugaacaaaug gcacuaguaa acuuau                                           26

<210> SEQ ID NO 302
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,26
<223> OTHER INFORMATION: /mod_base = "2'-O-Methyl nucleoside"
<220> FEATURE:
<221> NAME/KEY: modified base
<222> LOCATION: 2,23,24
<223> OTHER INFORMATION: /mod_base = "phosphorothioate linked
      nucleoside"

<400> SEQUENCE: 302
uggacaaacg ggcaacauac cuuuau                                           26

<210> SEQ ID NO 303
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 303
ugaagcgaag ugcacacgga ccguau                                           26
```

```
<210> SEQ ID NO 304
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 304
uaccaauuua ugccuacagg ccuuau                                          26

<210> SEQ ID NO 305
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 305
uagaugauua ggcagagguu gaauau                                          26

<210> SEQ ID NO 306
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,8,10,14
<223> OTHER INFORMATION: /mod_base = "2'-deoxy-3'-fluoro nucleoside"
<220> FEATURE:
<221> NAME/KEY: modified base
<222> LOCATION: 1,3,4,5,6,7,9,11,12,13,15,16,17,18,19,20,21,22,23,24,26
<223> OTHER INFORMATION: /mod_base = "2'-O-Methyl nucleoside"
<220> FEATURE:
```

<221> NAME/KEY: modified base
<222> LOCATION: 2,3,23,24
<223> OTHER INFORMATION: /mod_base = "phosphorothioate linked
      nucleoside"

<400> SEQUENCE: 306
ugaacaaaug gcacuaguaa acuuau                                              26

<210> SEQ ID NO 307
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,8,10,14
<223> OTHER INFORMATION: /mod_base = "2'-deoxy-3'-fluoro nucleoside"
<220> FEATURE:
<221> NAME/KEY: modified base
<222> LOCATION: 1,3,4,5,6,7,9,11,12,13,15,16,17,18,19,20,21,22,23,24,26
<223> OTHER INFORMATION: /mod_base = "2'-O-Methyl nucleoside"
<220> FEATURE:
<221> NAME/KEY: modified base
<222> LOCATION: 2,23,24
<223> OTHER INFORMATION: /mod_base = "phosphorothioate linked
      nucleoside"

<400> SEQUENCE: 307
uggacaaacg ggcaacauac cuuuau                                              26

<210> SEQ ID NO 308
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,8,10,14
<223> OTHER INFORMATION: /mod_base = "2'-deoxy-3'-fluoro nucleoside"
<220> FEATURE:
<221> NAME/KEY: modified base
<222> LOCATION: 1,3,4,5,6,7,9,11,12,13,15,16,17,18,19,20,21,22,23,24,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 308
ugaagcgaag ugcacacgga ccguau                                              26

<210> SEQ ID NO 309
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:

```
<221> NAME/KEY: modified base
<222> LOCATION: 2,8,10,14
<223> OTHER INFORMATION: /mod_base = "2'-deoxy-3'-fluoro nucleoside"
<220> FEATURE:
<221> NAME/KEY: modified base
<222> LOCATION: 1,3,4,5,6,7,9,11,12,13,15,16,17,18,19,20,21,22,23,24,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 309
uaccaauuua ugccuacagg ccuuau                                          26

<210> SEQ ID NO 310
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,8,10,14
<223> OTHER INFORMATION: /mod_base = "2'-deoxy-3'-fluoro nucleoside"
<220> FEATURE:
<221> NAME/KEY: modified base
<222> LOCATION: 1,3,4,5,6,7,9,11,12,13,15,16,17,18,19,20,21,22,23,24,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 310
uagaugauua ggcagagguu gaauau                                          26

<210> SEQ ID NO 311
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 311
uggacaaacg ggcaacauac cuuuau                                          26

<210> SEQ ID NO 312
<211> LENGTH: 26
<212> TYPE: DNA
```

```
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,8,10,14
<223> OTHER INFORMATION: /mod_base = "2'-deoxy-3'-fluoro nucleoside"
<220> FEATURE:
<221> NAME/KEY: modified base
<222> LOCATION: 1,3,4,5,6,7,9,11,12,13,15,16,17,18,19,20,21,22,23,24,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 312
uggacaaacg ggcaacauac cuuuau                                              26

<210> SEQ ID NO 313
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"

<400> SEQUENCE: 313
uaugauaaaa cgccgcagac acauau                                              26

<210> SEQ ID NO 314
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,8,10,14
<223> OTHER INFORMATION: /mod_base = "2'-deoxy-3'-fluoro nucleoside"
<220> FEATURE:
<221> NAME/KEY: modified base
<222> LOCATION: 1,3,4,5,6,7,9,11,12,13,15,16,17,18,19,20,21,22,23,24,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"
```

<400> SEQUENCE: 314
uaugauaaaa cgccgcagac acauau 26

<210> SEQ ID NO 315
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked nucleoside"

<400> SEQUENCE: 315
ugauaaaacg ccgcagacac aucuau 26

<210> SEQ ID NO 316
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,8,10,14
<223> OTHER INFORMATION: /mod_base = "2'-deoxy-3'-fluoro nucleoside"
<220> FEATURE:
<221> NAME/KEY: modified base
<222> LOCATION: 1,3,4,5,6,7,9,11,12,13,15,16,17,18,19,20,21,22,23,24,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked nucleoside"

<400> SEQUENCE: 316
ugauaaaacg ccgcagacac aucuau 26

<210> SEQ ID NO 317
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base

```
<222> LOCATION: 1,3,5,7,9,11,13,15,17,19,21,22,23,24,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "vinyl phophonate modified
      nucleoside"

<400> SEQUENCE: 317
uggacaaacg ggcaacauac cuuuau                                            26

<210> SEQ ID NO 318
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 25
<223> OTHER INFORMATION: /mod_base = "2'-hydroxy nucleoside"
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "vinyl phophonate modified
      nucleoside"

<400> SEQUENCE: 318
uaccaauuua ugccuacagg ccuuau                                            26

<210> SEQ ID NO 319
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 3,5,7,9,11,13,15,17,19
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "phosphorothioate linked
      nucleoside"
<220> FEATURE:
<221> NAME/KEY: modified base
<222> LOCATION: 21
<223> OTHER INFORMATION: /mod_base = "phosphate modified nucleoside"

<400> SEQUENCE: 319
taccaauuua ugccuacagt t                                                 21
```

<210> SEQ ID NO 320
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"

<400> SEQUENCE: 320
aguccgcggg auucagcgcc gacuau                                          26

<210> SEQ ID NO 321
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"

<400> SEQUENCE: 321
uuaaagagag gugcgcccgg ugguau                                          26

<210> SEQ ID NO 322
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"

<400> SEQUENCE: 322
uaagcgaagu gcacacgguc cgguau                                          26

<210> SEQ ID NO 323
<211> LENGTH: 26

```
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 323
uugaagcgaa gugcacacgg accuau                                            26

<210> SEQ ID NO 324
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 324
agugaagcga agugcacacg gacuau                                            26

<210> SEQ ID NO 325
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 325
uagaggugaa gcgaagugca cacuau                                            26

<210> SEQ ID NO 326
<211> LENGTH: 26
<212> TYPE: DNA
<213> ORGANISM: artificial sequence
<220> FEATURE:
<223> OTHER INFORMATION: HBV RNAi trigger antisense strand
```

```
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 326
ucagagguga agcgaagugc acauau                                            26

<210> SEQ ID NO 327
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 327
ugcagaggug aagcgaagug cacuau                                            26

<210> SEQ ID NO 328
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 328
ucggucguug acauugcugg gaguau                                            26

<210> SEQ ID NO 329
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
```

```
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 329
ucaaggucgg ucguugacau ugcuau                                          26

<210> SEQ ID NO 330
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 330
ugaccuuuaa ccuaaucucc uccuau                                          26

<210> SEQ ID NO 331
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 331
auuuaugccu acagccuccu aauuau                                          26

<210> SEQ ID NO 332
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
```

-continued

```
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 332
aauuuaugcc uacagccucc uaauau                                              26

<210> SEQ ID NO 333
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 333
uaauuuaugc uacagccuc cuauau                                               26

<210> SEQ ID NO 334
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 334
ucaauuuaug ccuacagccu ccuuau                                              26

<210> SEQ ID NO 335
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"
```

<400> SEQUENCE: 335
uccaauuuau gccuacagcc uccuau                                      26

<210> SEQ ID NO 336
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 336
uacgccgcag acacauccag cgauau                                      26

<210> SEQ ID NO 337
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 337
uaaaacgccg cagacacauc caguau                                      26

<210> SEQ ID NO 338
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 338
uuaaaacgcc gcagacacau ccauau                                      26

<210> SEQ ID NO 339
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"

<400> SEQUENCE: 339
uugauaaaac gccgcagaca cauuau                                          26

<210> SEQ ID NO 340
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"

<400> SEQUENCE: 340
uacgggcaac auaccuugau aauuau                                          26

<210> SEQ ID NO 341
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"

<400> SEQUENCE: 341
uaacgggcaa cauaccuuga uaauau                                          26

<210> SEQ ID NO 342
<211> LENGTH: 26

```
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 342
uaaacgggca acauaccuug auauau                                          26

<210> SEQ ID NO 343
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 343
ucaaacgggc aacauaccuu gauuau                                          26

<210> SEQ ID NO 344
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 344
uacaaacggg caacauaccu ugauau                                          26

<210> SEQ ID NO 345
<211> LENGTH: 26
<212> TYPE: DNA
<213> ORGANISM: artificial sequence
<220> FEATURE:
<223> OTHER INFORMATION: HBV RNAi trigger antisense strand
```

```
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 345
uaggacaaac gggcaacaua ccuuau                                           26

<210> SEQ ID NO 346
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 346
uacuaguaaa cugagccagg agauau                                           26

<210> SEQ ID NO 347
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 347
uggcacuagu aaacugagcc aaguau                                           26

<210> SEQ ID NO 348
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
```

```
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 348
uuggcacuag uaaacugagc caauau                                              26

<210> SEQ ID NO 349
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 349
uaauggcacu aguaaacuga gccuau                                              26

<210> SEQ ID NO 350
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 350
uaaauggcac uaguaaacug agcuau                                              26

<210> SEQ ID NO 351
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
```

```
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 351
ucaaauggca cuaguaaacu gaguau                                          26

<210> SEQ ID NO 352
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 352
uacaaauggc acuaguaaac ugauau                                          26

<210> SEQ ID NO 353
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 353
uugaacaaau ggcacuagua aacuau                                          26

<210> SEQ ID NO 354
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
``` nucleoside"

<400> SEQUENCE: 354
acugaacaaa uggcacuagu aaauau                                               26

<210> SEQ ID NO 355
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
        nucleoside"

<400> SEQUENCE: 355
uaaccacuga acaaauggca cuauau                                               26

<210> SEQ ID NO 356
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
        nucleoside"

<400> SEQUENCE: 356
ugaaccacug aacaaauggc acuuau                                               26

<210> SEQ ID NO 357
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
        nucleoside"

<400> SEQUENCE: 357
ucgaaccacu gaacaaaugg cacuau                                              26

<210> SEQ ID NO 358
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 358
ucagagguga aaaguugca ugguau                                               26

<210> SEQ ID NO 359
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 359
ugcagaggug aaaaguugc auguau                                               26

<210> SEQ ID NO 360
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 360
ugaugauuag gcagagguga aaauau                                              26

<210> SEQ ID NO 361

```
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 361
ugagaugauu aggcagaggu gaauau                                            26

<210> SEQ ID NO 362
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 362
ucacgagucu agacucugug guauau                                            26

<210> SEQ ID NO 363
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 363
auugagagaa guccaccacg aguuau                                            26

<210> SEQ ID NO 364
<211> LENGTH: 26
<212> TYPE: DNA
<213> ORGANISM: artificial sequence
<220> FEATURE:
```

<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"

<400> SEQUENCE: 364
aauugagaga aguccaccac gaguau                                              26

<210> SEQ ID NO 365
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"

<400> SEQUENCE: 365
uuagaaaauu gagagaaguc cacuau                                              26

<210> SEQ ID NO 366
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked nucleoside"

<400> SEQUENCE: 366
ugcgucagca aacacuuggc acauau                                              26

<210> SEQ ID NO 367
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22

```
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 367
uuauggaucg gcagaggagc cacuau                                          26

<210> SEQ ID NO 368
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 368
ucaguaugga ucggcagagg agcuau                                          26

<210> SEQ ID NO 369
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,24,25,26
<223> OTHER INFORMATION: /mod_base = "2'-O-Methyl nucleoside"
<220> FEATURE:
<221> NAME/KEY: modified base
<222> LOCATION: 2,3,23,24
<223> OTHER INFORMATION: /mod_base = "phosphorothioate linked
      nucleoside"

<400> SEQUENCE: 369
uggaguuccg caguauggau cgguau                                          26

<210> SEQ ID NO 370
<211> LENGTH: 23
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23
```

-continued

<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"

<400> SEQUENCE: 370
uaccaauuua ugccuacagg ccu                                              23

<210> SEQ ID NO 371
<211> LENGTH: 23
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23
<223> OTHER INFORMATION: /mod_base = "2'-O-Methyl nucleoside"
<220> FEATURE:
<221> NAME/KEY: modified base
<222> LOCATION: 2,3,4,23
<223> OTHER INFORMATION: /mod_base = "phosphorothioate linked
      nucleoside"

<400> SEQUENCE: 371
uaccaauuua ugccuacagg ccu                                              23

<210> SEQ ID NO 372
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"

<400> SEQUENCE: 372
uaccaauuua ugccuacagg c                                                21

<210> SEQ ID NO 373
<211> LENGTH: 23
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23
<223> OTHER INFORMATION: /mod_base = "2'-O-Methyl nucleoside"
<220> FEATURE:
<221> NAME/KEY: modified base
<222> LOCATION: 2,3,22,23

<223> OTHER INFORMATION: /mod_base = "phosphorothioate linked
      nucleoside"

<400> SEQUENCE: 373
ugaagcgaag ugcacacgga ccg                                        23

<210> SEQ ID NO 374
<211> LENGTH: 23
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23
<223> OTHER INFORMATION: /mod_base = "2'-O-Methyl nucleoside"
<220> FEATURE:
<221> NAME/KEY: modified base
<222> LOCATION: 2,3,4,23
<223> OTHER INFORMATION: /mod_base = "phosphorothioate linked
      nucleoside"

<400> SEQUENCE: 374
ugaagcgaag ugcacacgga ccg                                        23

<210> SEQ ID NO 375
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"

<400> SEQUENCE: 375
ugaagcgaag ugcacacgga c                                          21

<210> SEQ ID NO 376
<211> LENGTH: 23
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"

<400> SEQUENCE: 376

```
uggacaaacg ggcaacauac cuu                                              23
```

<210> SEQ ID NO 377
<211> LENGTH: 23
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23
<223> OTHER INFORMATION: /mod_base = "2'-O-Methyl nucleoside"
<220> FEATURE:
<221> NAME/KEY: modified base
<222> LOCATION: 2,3,4,23
<223> OTHER INFORMATION: /mod_base = "phosphorothioate linked
      nucleoside"

<400> SEQUENCE: 377

```
uggacaaacg ggcaacauac cuu                                              23
```

<210> SEQ ID NO 378
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"

<400> SEQUENCE: 378

```
uggacaaacg ggcaacauac c                                                21
```

<210> SEQ ID NO 379
<211> LENGTH: 17
<212> TYPE: DNA
<213> ORGANISM: artificial sequence
<220> FEATURE:
<223> OTHER INFORMATION: HBV RNAi trigger antisense strand
      2,4,6,10,12,14, 1,3,5,7,8,9,11,13,15
<220> FEATURE:
<221> NAME/KEY: modified base
<222> LOCATION: 17
<223> OTHER INFORMATION: /mod_base = "phosphorothioate linked
      nucleoside"

<400> SEQUENCE: 379

```
auaaaacgcc gcagatt                                                     17
```

<210> SEQ ID NO 380
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:

```
<221> NAME/KEY: modified base
<222> LOCATION: 2,6,8,9,14,16
<223> OTHER INFORMATION: /mod_base = "2'-deoxy-3'-fluoro nucleoside"
<220> FEATURE:
<221> NAME/KEY: modified base
<222> LOCATION: 1,3,4,5,7,10,11,12,13,15,17,18,19,20,21
<223> OTHER INFORMATION: /mod_base = "2'-O-Methyl nucleoside"
<220> FEATURE:
<221> NAME/KEY: modified base
<222> LOCATION: 2,3,20,21
<223> OTHER INFORMATION: /mod_base = "phosphorothioate linked
      nucleoside"

<400> SEQUENCE: 380
ugugaagcga agugcacacu u                                           21

<210> SEQ ID NO 381
<211> LENGTH: 23
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,6,8,9,14,16
<223> OTHER INFORMATION: /mod_base = "2'-deoxy-3'-fluoro nucleoside"
<220> FEATURE:
<221> NAME/KEY: modified base
<222> LOCATION: 1,3,4,5,7,10,11,12,13,15,17,18,19,20,21,22,23
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"

<400> SEQUENCE: 381
uaaaauugag agaguccac cac                                          23

<210> SEQ ID NO 382
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"

<400> SEQUENCE: 382
uugaagcgaa gugcacacgg accgcg                                      26

<210> SEQ ID NO 383
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
```

<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
    nucleoside"
<220> FEATURE:
<221> NAME/KEY: modified base
<222> LOCATION: 1
<223> OTHER INFORMATION: /mod_base = "vinyl phophonate modified
    nucleoside"

<400> SEQUENCE: 383
uugaagcgaa gugcacacgg accgcg                                         26

<210> SEQ ID NO 384
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
    nucleoside"

<400> SEQUENCE: 384
ugugaagcga agugcacacg gaccgc                                         26

<210> SEQ ID NO 385
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
    nucleoside"
<220> FEATURE:
<221> NAME/KEY: modified base
<222> LOCATION: 1
<223> OTHER INFORMATION: /mod_base = "vinyl phophonate modified
    nucleoside"

<400> SEQUENCE: 385
ugugaagcga agugcacacg gaccgc                                         26

<210> SEQ ID NO 386
<211> LENGTH: 26
<212> TYPE: DNA
<213> ORGANISM: artificial sequence
<220> FEATURE:

```
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"

<400> SEQUENCE: 386
ugauaaaacg ccgcagacac auccgc                                          26

<210> SEQ ID NO 387
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "vinyl phophonate modified
      nucleoside"

<400> SEQUENCE: 387
ugauaaaacg ccgcagacac auccgc                                          26

<210> SEQ ID NO 388
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"

<400> SEQUENCE: 388
uaugauaaaa cgccgcagac acacgc                                          26

<210> SEQ ID NO 389
<211> LENGTH: 26
<212> TYPE: DNA
<213> ORGANISM: artificial sequence
```

```
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "vinyl phophonate modified
      nucleoside"

<400> SEQUENCE: 389
uaugauaaaa cgccgcagac acacgc                                        26

<210> SEQ ID NO 390
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"

<400> SEQUENCE: 390
agugaagcga agugcacacg gaccgc                                        26

<210> SEQ ID NO 391
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"

<400> SEQUENCE: 391
aaugauaaaa cgccgcagac acacgc                                        26

<210> SEQ ID NO 392
<211> LENGTH: 26
<212> TYPE: DNA
```

<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked nucleoside"

<400> SEQUENCE: 392
ugaagcgaag ugcacacgga ccgcgc                                      26

<210> SEQ ID NO 393
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked nucleoside"
<220> FEATURE:
<221> NAME/KEY: modified base
<222> LOCATION: 1
<223> OTHER INFORMATION: /mod_base = "vinyl phophonate modified nucleoside"

<400> SEQUENCE: 393
ugaagcgaag ugcacacgga ccgcgc                                      26

<210> SEQ ID NO 394
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked nucleoside"

<400> SEQUENCE: 394
uggacaaacg ggcaacauac cuucgc                                      26

<210> SEQ ID NO 395
<211> LENGTH: 26

```
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "vinyl phophonate modified
      nucleoside"

<400> SEQUENCE: 395
uggacaaacg ggcaacauac cuucgc                                        26

<210> SEQ ID NO 396
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"

<400> SEQUENCE: 396
uaccaauuua ugccuacagc cuccgc                                        26

<210> SEQ ID NO 397
<211> LENGTH: 26
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,22,23,24,25,26
<223> OTHER INFORMATION: /mod_base = "2'-O-Methyl nucleoside"
<220> FEATURE:
<221> NAME/KEY: modified base
<222> LOCATION: 2,3,22,23
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "vinyl phophonate modified
      nucleoside"

<400> SEQUENCE: 397
```
uaccaauuua ugccuacagc cuccgc    26

<210> SEQ ID NO 398
<211> LENGTH: 17
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15
<223> OTHER INFORMATION: /mod_base = "2'-O-Methyl nucleoside"
<220> FEATURE:
<221> NAME/KEY: modified base
<222> LOCATION: 17
<223> OTHER INFORMATION: /mod_base = "phosphorothioate linked nucleoside"

<400> SEQUENCE: 398
aauuuaugcc uacagtt    17

<210> SEQ ID NO 399
<211> LENGTH: 17
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15
<223> OTHER INFORMATION: /mod_base = "2'-O-Methyl nucleoside"
<220> FEATURE:
<221> NAME/KEY: modified base
<222> LOCATION: 17
<223> OTHER INFORMATION: /mod_base = "phosphorothioate linked nucleoside"

<400> SEQUENCE: 399
ugauuaggca gaggutt    17

<210> SEQ ID NO 400
<211> LENGTH: 17
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,10,12,14
<223> OTHER INFORMATION: /mod_base = "2'-deoxy-3'-fluoro nucleoside"
<220> FEATURE:
<221> NAME/KEY: modified base
<222> LOCATION: 1,3,5,7,8,9,11,13,15
<223> OTHER INFORMATION: /mod_base = "2'-O-Methyl nucleoside"
<220> FEATURE:
<221> NAME/KEY: modified base
<222> LOCATION: 17
<223> OTHER INFORMATION: /mod_base = "phosphorothioate linked nucleoside"

<400> SEQUENCE: 400
aauuuaugcc uacagtt    17

```
<210> SEQ ID NO 401
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,20,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"

<400> SEQUENCE: 401
uaccaauuua ugccuacagu u                                             21

<210> SEQ ID NO 402
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,20,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"

<400> SEQUENCE: 402
uaccaauuua ugccuacagg c                                             21

<210> SEQ ID NO 403
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "vinyl phophonate modified
      nucleoside"

<400> SEQUENCE: 403
uaccaauuua ugccuacagg c                                             21
```

```
<210> SEQ ID NO 404
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,20,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "vinyl phophonate modified
      nucleoside"

<400> SEQUENCE: 404
uaccaauuua ugccuacagu u                                             21

<210> SEQ ID NO 405
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"

<400> SEQUENCE: 405
auugagagaa guccaccacg a                                             21

<210> SEQ ID NO 406
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,20,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"

<400> SEQUENCE: 406
auugagagaa guccaccacg a                                             21
```

<210> SEQ ID NO 407
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,20,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked nucleoside"

<400> SEQUENCE: 407
auugagagaa guccaccacu u                                              21

<210> SEQ ID NO 408
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked nucleoside"
<220> FEATURE:
<221> NAME/KEY: modified base
<222> LOCATION: 1
<223> OTHER INFORMATION: /mod_base = "vinyl phophonate modified nucleoside"

<400> SEQUENCE: 408
uuugagagaa guccaccacg a                                              21

<210> SEQ ID NO 409
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked nucleoside"

<400> SEQUENCE: 409
aauugagaga aguccaccac g                                        21

<210> SEQ ID NO 410
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,20,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"

<400> SEQUENCE: 410
aauugagaga aguccaccac g                                        21

<210> SEQ ID NO 411
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,20,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"

<400> SEQUENCE: 411
aauugagaga aguccaccau u                                        21

<210> SEQ ID NO 412
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "vinyl phophonate modified
      nucleoside"

<400> SEQUENCE: 412

-continued uauugagaga aguccaccac g                                    21

<210> SEQ ID NO 413
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
    nucleoside"

<400> SEQUENCE: 413
uuagaaaauu gagagaaguc c                                    21

<210> SEQ ID NO 414
<211> LENGTH: 21
<212> TYPE: DNA
<213> ORGANISM: artificial sequence
<220> FEATURE:
<223> OTHER INFORMATION: HBV RNAi trigger antisense strand
<220> FEATURE:
<221> NAME/KEY: modified base
<222> LOCATION: 2,4,6,8,10,12,14,16,18,20
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 2,3,4,21
<223> OTHER INFORMATION: /mod_base = "phosphorothioate linked
    nucleoside"
<220> FEATURE:
<221> NAME/KEY: modified base
<222> LOCATION: 1
<223> OTHER INFORMATION: /mod_base = "vinyl phophonate modified
    nucleoside"

<400> SEQUENCE: 414
uuagaaaauu gagagaaguc c                                    21

<210> SEQ ID NO 415
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base

```
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-ALNY modifed nucleoside"

<400> SEQUENCE: 415
uaucuguagg cauaaauugg uat                                               23

<210> SEQ ID NO 416
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-ALNY modifed nucleoside"

<400> SEQUENCE: 416
uauucugcgg cguuuuauca uat                                               23

<210> SEQ ID NO 417
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-ALNY modifed nucleoside"

<400> SEQUENCE: 417
uauaccucug ccuaaucauc uat                                               23

<210> SEQ ID NO 418
<211> LENGTH: 23
<212> TYPE: DNA
```

```
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Toc modifed nucleoside"

<400> SEQUENCE: 418
uauaccucug ccuaaucauc uat                                              23

<210> SEQ ID NO 419
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 419
uauaccucug ccuaaucauc uat                                              23

<210> SEQ ID NO 420
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
```

-continued

```
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = " Chol-C6 modified nucleoside"

<400> SEQUENCE: 420
uaucuguagg cauaaauugg uat                                              23

<210> SEQ ID NO 421
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = " Chol-C6 modified nucleoside"

<400> SEQUENCE: 421
uauaccucug ccuaaucauc uat                                              23

<210> SEQ ID NO 422
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 422
guguaggcau aaauugguat                                                  20

<210> SEQ ID NO 423
<211> LENGTH: 20
<212> TYPE: DNA
<213> ORGANISM: artificial sequence
<220> FEATURE:
```

```
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 423
cccucugccu aaucaucuat                                                    20

<210> SEQ ID NO 424
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 424
uuuacuagug ccauuuguat                                                    20

<210> SEQ ID NO 425
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,8,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 425
```
uaucuguagg cauaaauugg uat                          23

<210> SEQ ID NO 426
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,8,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 426
uauaccucug ccuaaucauc uat                          23

<210> SEQ ID NO 427
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 427
uaucuguagg cauaaauugg uat                          23

<210> SEQ ID NO 428
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:

```
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 428
uauaccucug ccuaaucauc uat                                      23

<210> SEQ ID NO 429
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,5,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 429
guguaggcau aaauugguat                                          20

<210> SEQ ID NO 430
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,5,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 430
cccucugccu aaucaucuat                                          20

<210> SEQ ID NO 431
<211> LENGTH: 20
```

```
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,7,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 431
cccucugccu aaucaucuat                                               20

<210> SEQ ID NO 432
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,9,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 432
cccucugccu aaucaucuat                                               20

<210> SEQ ID NO 433
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,11,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 433
```
cccucugccu aaucaucuat                                                    20

<210> SEQ ID NO 434
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,13,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 434
cccucugccu aaucaucuat                                                    20

<210> SEQ ID NO 435
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,6,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 435
cccucugccu aaucaucuat                                                    20

<210> SEQ ID NO 436
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 436
cccucugccu aaucaucuat                                                    20

<210> SEQ ID NO 437
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,10,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 437
cccucugccu aaucaucuat                                                    20

<210> SEQ ID NO 438
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,12,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 438
cccucugccu aaucaucuat                                                    20

<210> SEQ ID NO 439
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,14,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,16,18
<223> OTHER INFORMATION: /mod_base = "2'-O-Methyl nucleoside"
<220> FEATURE:

```
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 439
cccucugccu aaucaucuat                                                    20

<210> SEQ ID NO 440
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1
<223> OTHER INFORMATION: /mod_base = "2'-3' seco nucleoside"
<220> FEATURE:
<221> NAME/KEY: modified base
<222> LOCATION: 3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 440
cuguaggcau aaauugguat                                                    20

<210> SEQ ID NO 441
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-3' seco nucleoside"
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 441
guguaggcau aaauugguat                                                    20

<210> SEQ ID NO 442
<211> LENGTH: 20
```

-continued

```
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1
<223> OTHER INFORMATION: /mod_base = "2'-3' seco nucleoside"
<220> FEATURE:
<221> NAME/KEY: modified base
<222> LOCATION: 3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 442
accucugccu aaucaucuat                                          20

<210> SEQ ID NO 443
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-3' seco nucleoside"
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 443
cccucugccu aaucaucuat                                          20

<210> SEQ ID NO 444
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
```

```
<223> OTHER INFORMATION: /mod_base = "inverted nucleotide"

<400> SEQUENCE: 444
cuguaggcau aaauugguat                                                    20

<210> SEQ ID NO 445
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"

<400> SEQUENCE: 445
accucugccu aaucaucuat                                                    20

<210> SEQ ID NO 446
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 23
<223> OTHER INFORMATION: /mod_base = "TEG-Biotin modified nucleoside"
<220> FEATURE:
<221> NAME/KEY: modified base
<222> LOCATION: 1
<223> OTHER INFORMATION: /mod_base = " Chol-C6 modified nucleoside"

<400> SEQUENCE: 446
uaucuguagg cauaaauugg uat                                                23

<210> SEQ ID NO 447
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
```

-continued

```
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 23
<223> OTHER INFORMATION: /mod_base = "TEG-Biotin modified nucleoside"
<220> FEATURE:
<221> NAME/KEY: modified base
<222> LOCATION: 1
<223> OTHER INFORMATION: /mod_base = " Chol-C6 modified nucleoside"

<400> SEQUENCE: 447
uauaccucug ccuaaucauc uat                                       23

<210> SEQ ID NO 448
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 448
guguaggcau aaauugguat                                           20

<210> SEQ ID NO 449
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 18,19
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NH2-C6 modified nucleoside"
```

-continued

<400> SEQUENCE: 449
guguaggcau aaauugguau                                         20

<210> SEQ ID NO 450
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 18,19
<223> OTHER INFORMATION: /mod_base = "phosphorothioate linked
    nucleoside"
<220> FEATURE:
<221> NAME/KEY: modified base
<222> LOCATION: 1
<223> OTHER INFORMATION: /mod_base = "NH2-C6 modified nucleoside"

<400> SEQUENCE: 450
cccucugccu aaucaucuau                                         20

<210> SEQ ID NO 451
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 451
uuuacuagug ccauuuguau                                         20

<210> SEQ ID NO 452
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 18,19
<223> OTHER INFORMATION: /mod_base = "phosphorothioate linked nucleoside"
<220> FEATURE:
<221> NAME/KEY: modified base
<222> LOCATION: 1
<223> OTHER INFORMATION: /mod_base = "NH2-C6 modified nucleoside"

<400> SEQUENCE: 452
uuuacuagug ccauuuguat        20

<210> SEQ ID NO 453
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 453
cuguaggcau aaauugguat        20

<210> SEQ ID NO 454
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 454
accucugccu aaucaucuat        20

<210> SEQ ID NO 455
<211> LENGTH: 20

```
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 455
uuuacuagug ccauuuguat                                             20

<210> SEQ ID NO 456
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 456
ucugcggcgu uuuaucauat                                             20

<210> SEQ ID NO 457
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 457
```
ucugcggcgu uuuaucauat                                          20

<210> SEQ ID NO 458
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "NH2-C6 modified nucleoside"

<400> SEQUENCE: 458
ucugcggcgu uuuaucauat                                          20

<210> SEQ ID NO 459
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 18,19
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NH2-C6 modified nucleoside"

<400> SEQUENCE: 459
ucugcggcgu uuuaucauat                                          20

<210> SEQ ID NO 460
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:

```
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 460
accucugccu aaucaucuat                                                    20

<210> SEQ ID NO 461
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 18,19
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 461
accucugccu aaucaucuat                                                    20

<210> SEQ ID NO 462
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 462
cuguaggcau aaauugguat                                                    20

<210> SEQ ID NO 463
<211> LENGTH: 20
<212> TYPE: DNA
<213> ORGANISM: artificial sequence
<220> FEATURE:
```

```
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 18,19
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 463 cguguaggcau aaauugguat                                              20

<210> SEQ ID NO 464
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 18,19
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 464
uuuacuagug ccauuuguat                                               20

<210> SEQ ID NO 465
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
```

```
<220> FEATURE:
<221> NAME/KEY: modified base
<222> LOCATION: 18,19
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 465
ucugcggcgu uuuaucauat                                              20

<210> SEQ ID NO 466
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 18,19
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 466
cuguaggcau aaauugguat                                              20

<210> SEQ ID NO 467
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 18,19
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 467
accucugccu aaucaucuat                                              20
```

<210> SEQ ID NO 468
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 18,19
<223> OTHER INFORMATION: /mod_base = "phosphorothioate linked nucleoside"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 468
uuuacuagug ccauuuguat                                              20

<210> SEQ ID NO 469
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"
<220> FEATURE:
<221> NAME/KEY: modified base
<222> LOCATION: 18,19
<223> OTHER INFORMATION: /mod_base = "phosphorothioate linked nucleoside"
<220> FEATURE:
<221> NAME/KEY: modified base
<222> LOCATION: 1
<223> OTHER INFORMATION: /mod_base = "Alk-SS-C6 modified nucleoside"

<400> SEQUENCE: 469
ucugcggcgu uuuaucauat                                              20

<210> SEQ ID NO 470
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:

```
<221> NAME/KEY: modified base
<222> LOCATION: 4,6,8,10,11,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 470
uaucuguagg cauaaauugg uat                                              23

<210> SEQ ID NO 471
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,11,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 471
uauaccucug ccuaaucauc uat                                              23

<210> SEQ ID NO 472
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,11,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"
```

-continued

<400> SEQUENCE: 472
uauuuuacua gugccauuug uat                                                    23

<210> SEQ ID NO 473
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,11,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 473
uauucugcgg cguuuuauca uat                                                    23

<210> SEQ ID NO 474
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,11,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = " Chol-C6 modified nucleoside"

<400> SEQUENCE: 474
uaucuguagg cauaaauugg uat                                                    23

<210> SEQ ID NO 475
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2

```
<223> OTHER INFORMATION: /mod_base = "2'-hydroxy nucleoside"
<220> FEATURE:
<221> NAME/KEY: modified base
<222> LOCATION: 4,6,8,10,11,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = " Chol-C6 modified nucleoside"

<400> SEQUENCE: 475
uauaccucug ccuaaucauc uat                                         23

<210> SEQ ID NO 476
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,11,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = " Chol-C6 modified nucleoside"

<400> SEQUENCE: 476
uauuuuacua gugccauuug uat                                         23

<210> SEQ ID NO 477
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,11,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
```

<222> LOCATION: 1
<223> OTHER INFORMATION: /mod_base = " Chol-C6 modified nucleoside"

<400> SEQUENCE: 477
uauucugcgg cguuuuauca uat                                           23

<210> SEQ ID NO 478
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6,7,25,26
<223> OTHER INFORMATION: /mod_base = "phosphorothioate linked
    nucleoside"
<220> FEATURE:
<221> NAME/KEY: modified base
<222> LOCATION: 1
<223> OTHER INFORMATION: /mod_base = "Chol-TEG modifed nucleoside"

<400> SEQUENCE: 478
uauaugccug uaggcauaaa uuggua                                        26

<210> SEQ ID NO 479
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 479
uauaugccug uaggcauaaa uuggua                                        26

<210> SEQ ID NO 480
<211> LENGTH: 26
<212> TYPE: DNA
<213> ORGANISM: artificial sequence
<220> FEATURE:
<223> OTHER INFORMATION: HBV RNAi trigger sense strand

```
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,13,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,14,17,19,21,23,25
<223> OTHER INFORMATION: /mod_base = "2'-O-Methyl nucleoside"
<220> FEATURE:
<221> NAME/KEY: modified base
<222> LOCATION: 6,7,25,26
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "Chol-TEG modifed nucleoside"

<400> SEQUENCE: 480
uauaugccug uaggcauaaa uuggua                                    26

<210> SEQ ID NO 481
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,13,15,16,18,20,22,24
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,14,17,19,21,23,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 481
uauaugccug uaggcauaaa uuggua                                    26

<210> SEQ ID NO 482
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
```

```
<222> LOCATION: 6,7,25,26
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "Chol-TEG modifed nucleoside"

<400> SEQUENCE: 482
uauauugucu gcggcguuuu aucaua                                           26

<210> SEQ ID NO 483
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 483
uauauugucu gcggcguuuu aucaua                                           26

<210> SEQ ID NO 484
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,13,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,14,17,19,21,23,25
<223> OTHER INFORMATION: /mod_base = "2'-O-Methyl nucleoside"
<220> FEATURE:
<221> NAME/KEY: modified base
<222> LOCATION: 6,7,25,26
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "Chol-TEG modifed nucleoside"

<400> SEQUENCE: 484
uauauugucu gcggcguuuu aucaua                                           26

<210> SEQ ID NO 485
```

-continued

```
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,13,15,16,18,20,22,24
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,14,17,19,21,23,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 485
uauauugucu gcggcguuuu aucaua                                          26

<210> SEQ ID NO 486
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6,7,25,26
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "Chol-TEG modifed nucleoside"

<400> SEQUENCE: 486
uauaucaacc ucugccuaau caucua                                          26

<210> SEQ ID NO 487
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24
<223> OTHER INFORMATION: /mod_base = "2'-deoxy-3'-fluoro nucleoside"
<220> FEATURE:
```

```
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 487
uauaucaacc ucugccuaau caucua                                              26

<210> SEQ ID NO 488
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,13,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,14,17,19,21,23,25
<223> OTHER INFORMATION: /mod_base = "2'-O-Methyl nucleoside"
<220> FEATURE:
<221> NAME/KEY: modified base
<222> LOCATION: 6,7,25,26
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "Chol-TEG modifed nucleoside"

<400> SEQUENCE: 488
uauaucaacc ucugccuaau caucua                                              26

<210> SEQ ID NO 489
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,13,15,16,18,20,22,24
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,14,17,19,21,23,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 489
```
uauaucaacc ucugccuaau caucua                                              26

<210> SEQ ID NO 490
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"

<400> SEQUENCE: 490
ucugcggcgu uuuaucauat                                                     20

<210> SEQ ID NO 491
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,8,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"

<400> SEQUENCE: 491
ucugcggcgu uuuaucauat                                                     20

<210> SEQ ID NO 492
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = " Chol-C6 modified nucleoside"

<400> SEQUENCE: 492
uauucugcgg cguuuuauca uat                                              23

<210> SEQ ID NO 493
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"

<400> SEQUENCE: 493 cguaggcau aaauugguat                                                   20

<210> SEQ ID NO 494
<211> LENGTH: 20
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 1,3,5,7,8,9,11,13,15,17,19
<223> OTHER INFORMATION: /mod_base = "2'-deoxy-3'-fluoro nucleoside"
<220> FEATURE:
<221> NAME/KEY: modified base
<222> LOCATION: 2,4,6,10,12,14,16,18
<223> OTHER INFORMATION: /mod_base = "2'-O-Methyl nucleoside"
<220> FEATURE:
<221> NAME/KEY: modified base
<222> LOCATION: 20
<223> OTHER INFORMATION: /mod_base = "inverted nucleotide"

<400> SEQUENCE: 494
accucugccu aaucaucuat                                                  20

<210> SEQ ID NO 495
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 495
uauauugugu cugcggcguu uuauca                                          26

<210> SEQ ID NO 496
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
    nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 496
uauauuuuac uagugccauu uguuca                                          26

<210> SEQ ID NO 497
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
    nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 497
uauauugcca aguguuugcu gacgca                                          26

<210> SEQ ID NO 498
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:

```
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 498
uauauugcca uuuguucagu gguuca                                          26

<210> SEQ ID NO 499
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 499
uauauaucaa gguauguugc ccguua                                          26

<210> SEQ ID NO 500
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
```

```
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 500
uauauuccug gcucaguuua cuagua                                          26

<210> SEQ ID NO 501
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 501
uauaugguau guugcccguu ugucca                                          26

<210> SEQ ID NO 502
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 502
uauauuauca agguauguug cccgua                                          26
```

-continued

```
<210> SEQ ID NO 503
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 503
uauauguccg ugugcacuuc gcuuca                                            26

<210> SEQ ID NO 504
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 504
uauauugugu cugcggcguu uuauca                                            26

<210> SEQ ID NO 505
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
```

<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 505
uauauuuuac uagugccauu uguuca                                              26

<210> SEQ ID NO 506
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 506
uauauugcca aguguuugcu gacgca                                              26

<210> SEQ ID NO 507
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26

<223> OTHER INFORMATION: /mod_base = "C6-SS-Alk-Me modified nucleoside"

<400> SEQUENCE: 507
uauauugcca uuuguucagu gguuca                                              26

<210> SEQ ID NO 508
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 508
uauauaucaa gguauguugc ccguua                                              26

<210> SEQ ID NO 509
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 509
uauauuccug gcucaguuua cuagua                                              26

<210> SEQ ID NO 510
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 510 uauauggau guugcccguu ugucca          26

<210> SEQ ID NO 511
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 511
uauauuauca agguauguug cccgua          26

<210> SEQ ID NO 512
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:

```
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 512
uauauguccg ugugcacuuc gcuuca                                          26

<210> SEQ ID NO 513
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 513
uauaugccug uaggcauaaa uuggua                                          26

<210> SEQ ID NO 514
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C11-PEG3-NAG3 modified nucleoside"

<400> SEQUENCE: 514
uauaugccug uaggcauaaa uuggua                                          26
```

<210> SEQ ID NO 515
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 515
uauaugccug uaggcauaaa uuggua                                          26

<210> SEQ ID NO 516
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 516
uauauugucu gcggcguuuu aucaua                                          26

<210> SEQ ID NO 517
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base

```
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C11-PEG3-NAG3 modified nucleoside"

<400> SEQUENCE: 517
uauauugucu gcggcguuuu aucaua                                         26

<210> SEQ ID NO 518
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 518
uauauugucu gcggcguuuu aucaua                                         26

<210> SEQ ID NO 519
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
      nucleoside"
<220> FEATURE:
<221> NAME/KEY: modified base
```

```
<222> LOCATION: 26
<223> OTHER INFORMATION: /mod_base = "C6-SS-Alk-Me modified nucleoside"

<400> SEQUENCE: 519
uauaucaacc ucugccuaau caucua                                        26

<210> SEQ ID NO 520
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,15,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,14,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "C11-PEG3-NAG3 modified nucleoside"

<400> SEQUENCE: 520
uauaucaacc ucugccuaau caucua                                        26

<210> SEQ ID NO 521
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,11,14,16,18,20,22,24,26
<223> OTHER INFORMATION: /mod_base = "2'-deoxy-3'-fluoro nucleoside"
<220> FEATURE:
<221> NAME/KEY: modified base
<222> LOCATION: 1,3,5,7,9,12,13,15,17,19,21,23,25
<223> OTHER INFORMATION: /mod_base = "2'-O-Methyl nucleoside"
<220> FEATURE:
<221> NAME/KEY: modified base
<222> LOCATION: 6
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "C6-SS-Alk-Me modified nucleoside"

<400> SEQUENCE: 521
uauaucaacc ucugccuaau caucua                                        26

<210> SEQ ID NO 522
<211> LENGTH: 23
<212> TYPE: DNA
<213> ORGANISM: artificial sequence
<220> FEATURE:
```

```
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 522
uauugucugc ggcguuuuau cat                                          23

<210> SEQ ID NO 523
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 523
uauuacuagu gccauuuguu cat                                          23

<210> SEQ ID NO 524
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
```

```
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 524
uauccaagug uuugcugacg cat                                              23

<210> SEQ ID NO 525
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 525
uauccauuug uucagugguu cat                                              23

<210> SEQ ID NO 526
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 526
uaucaaggua uguugcccgu uat                                              23

<210> SEQ ID NO 527
<211> LENGTH: 23
<212> TYPE: DNA
```

```
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 527
uaucuggcuc aguuuacuag uat                                          23

<210> SEQ ID NO 528
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 528
uauuauguug cccguuuguc cat                                          23

<210> SEQ ID NO 529
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
```

```
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 529
uauucaaggu auguugcccg uat                                          23

<210> SEQ ID NO 530
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 530
uauccgugug cacuucgcuu cat                                          23

<210> SEQ ID NO 531
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 1
<223> OTHER INFORMATION: /mod_base = "Chol-TEG modifed nucleoside"

<400> SEQUENCE: 531
uauggcgcug aaucccgcgg aat                                          23

<210> SEQ ID NO 532
```

```
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,14,16,18,20,22,24
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 532
uauauuuuac uagugccauu uguuca                                        26

<210> SEQ ID NO 533
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,15,17,18,19,20,21,22,23,24,
      25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 533
uauauuuuac uagugccauu uguuca                                        26

<210> SEQ ID NO 534
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 10,14,16
```

```
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,11,12,13,15,17,18,19,20,21,22,23,24,25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 534
uauauuuuac uagugccauu uguuca                                           26

<210> SEQ ID NO 535
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,14,16,18,20,22,24
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 535
uauaugguau guugcccguu ugucca                                           26

<210> SEQ ID NO 536
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,16,24
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,15,17,18,19,20,21,22,23,25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
```

<223> OTHER INFORMATION: /mod_base = "NAG13 modified nucleoside"

<400> SEQUENCE: 536 uauauggguau guugcccguu ugucca                                    26

<210> SEQ ID NO 537
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,15,17,18,19,20,21,22,23,24,
      25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 537 uauauggguau guugcccguu ugucca                                    26

<210> SEQ ID NO 538
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,14,16,18,20,22,24
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 538
uauauguccg ugugcacuuc gcuuca                                     26

<210> SEQ ID NO 539
<211> LENGTH: 26
<212> TYPE: DNA
<213> ORGANISM: artificial sequence
<220> FEATURE:

```
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 8,14,16,20,22
<223> OTHER INFORMATION: /mod_base = "2'-deoxy-3'-fluoro nucleoside"
<220> FEATURE:
<221> NAME/KEY: modified base
<222> LOCATION: 1,3,5,6,7,9,10,11,12,13,15,17,18,19,21,23,24,25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 539
uauauguccg ugugcacuuc gcuuca                                          26

<210> SEQ ID NO 540
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,15,17,18,19,20,21,22,23,24,
      25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 540
uauauguccg ugugcacuuc gcuuca                                          26

<210> SEQ ID NO 541
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,14,16,18,20,22,24
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,25,26
```

```
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 541
uauaugccug uaggcauaaa uuggua                                        26

<210> SEQ ID NO 542
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 8,14,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,9,10,11,12,13,15,17,18,19,20,21,22,23,24,
      25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 542
uauaugccug uaggcauaaa uuggua                                        26

<210> SEQ ID NO 543
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,15,17,18,19,20,21,22,23,24,
      25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"
```

<400> SEQUENCE: 543
uauaugccug uaggcauaaa uuggua          26

<210> SEQ ID NO 544
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,8,10,12,14,16,18,20,22,24
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17,19,21,23,25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
       nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 544
uauaucaacc ucugccuaau caucua          26

<210> SEQ ID NO 545
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 6,10,12,14,16,24
<223> OTHER INFORMATION: /mod_base = "2'-deoxy-3'-fluoro nucleoside"
<220> FEATURE:
<221> NAME/KEY: modified base
<222> LOCATION: 1,3,5,7,8,9,11,13,15,17,18,19,20,21,22,23,25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
       nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 545
uauaucaacc ucugccuaau caucua          26

<210> SEQ ID NO 546
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base

```
<222> LOCATION: 2,4
<223> OTHER INFORMATION: /mod_base = "2'-hydroxy nucleoside"
<220> FEATURE:
<221> NAME/KEY: modified base
<222> LOCATION: 14,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,15,17,18,19,20,21,22,23,24,
      25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 546
uauaucaacc ucugccuaau caucua                                      26

<210> SEQ ID NO 547
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,17,18,19,20,21,22,23,24,
      25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 547
uauauuuuac uagugccauu uguuca                                      26

<210> SEQ ID NO 548
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,17,18,19,20,21,22,23,24,
      25,26
<223> OTHER INFORMATION: /mod_base = "2'-O-Methyl nucleoside"
```

```
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 548 uauauggguau guugcccguu ugucca                                               26

<210> SEQ ID NO 549
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,17,18,19,20,21,22,23,24,
      25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 549
uauauguccg ugugcacuuc gcuuca                                                26

<210> SEQ ID NO 550
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,17,18,19,20,21,22,23,24,25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 550
```
uauaugccug uaggcauaaa uuggua                                          26

<210> SEQ ID NO 551
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,17,18,19,20,21,22,23,24,25,26
<223> OTHER INFORMATION: /mod_base = "2'-O-Methyl nucleoside"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 551
uauaucaacc ucugccuaau caucua                                          26

<210> SEQ ID NO 552
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,17,18,19,20,21,22,23,24,25,26
<223> OTHER INFORMATION: /mod_base = "2'-O-Methyl nucleoside"
<220> FEATURE:
<221> NAME/KEY: modified base
<222> LOCATION: 7,8
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 552
uauauugucu gcggcguuuu aucaua                                          26

<210> SEQ ID NO 553
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"

```
<220> FEATURE:
<221> NAME/KEY: modified base
<222> LOCATION: 14,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,15,17,18,19,20,21,22,23,24,
      25,26
<223> OTHER INFORMATION: /mod_base = "2'-O-Methyl nucleoside"
<220> FEATURE:
<221> NAME/KEY: modified base
<222> LOCATION: 7,8
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 553
uauauugucu gcggcguuuu aucaua                                          26

<210> SEQ ID NO 554
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,17,18,19,20,21,22,23,24,25,26
<223> OTHER INFORMATION: /mod_base = "2'-O-Methyl nucleoside"
<220> FEATURE:
<221> NAME/KEY: modified base
<222> LOCATION: 7,8
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 554
uauauugugu cugcggcguu uuauca                                          26

<210> SEQ ID NO 555
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4
<223> OTHER INFORMATION: /mod_base = "2'-hydroxy nucleoside"
<220> FEATURE:
<221> NAME/KEY: modified base
<222> LOCATION: 14,16
<223> OTHER INFORMATION: /mod_base = "2'-deoxy-3'-fluoro nucleoside"
<220> FEATURE:
<221> NAME/KEY: modified base
<222> LOCATION: 1,3,5,6,7,8,9,10,11,12,13,15,17,18,19,20,21,22,23,24,
      25,26
<223> OTHER INFORMATION: /mod_base = "2'-O-Methyl nucleoside"
<220> FEATURE:
<221> NAME/KEY: modified base
<222> LOCATION: 7,8
```

```
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 555
uauauugugu cugcggcguu uuauca                                          26

<210> SEQ ID NO 556
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,11,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 23
<223> OTHER INFORMATION: /mod_base = "TEG-Biotin modified nucleoside"
<220> FEATURE:
<221> NAME/KEY: modified base
<222> LOCATION: 1
<223> OTHER INFORMATION: /mod_base = "Chol-TEG modifed nucleoside"

<400> SEQUENCE: 556
uauucugcgg cguuuuauca uat                                             23

<210> SEQ ID NO 557
<211> LENGTH: 23
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2
<223> OTHER INFORMATION: /mod_base = "2'-hydroxy nucleoside"
<220> FEATURE:
<221> NAME/KEY: modified base
<222> LOCATION: 4,6,8,10,11,12,14,16,18,20,22
<223> OTHER INFORMATION: /mod_base = "2'-deoxy-3'-fluoro nucleoside"
<220> FEATURE:
<221> NAME/KEY: modified base
<222> LOCATION: 1,3,5,7,9,13,15,17,19,21
<223> OTHER INFORMATION: /mod_base = "2'-O-Methyl nucleoside"
<220> FEATURE:
<221> NAME/KEY: modified base
<222> LOCATION: 23
<223> OTHER INFORMATION: /mod_base = "inverted nucleotide"
<220> FEATURE:
<221> NAME/KEY: modified base
<222> LOCATION: 23
<223> OTHER INFORMATION: /mod_base = "TEG-Biotin modified nucleoside"
<220> FEATURE:
<221> NAME/KEY: modified base
<222> LOCATION: 1
<223> OTHER INFORMATION: /mod_base = " Chol-C6 modified nucleoside"
```

```
<400> SEQUENCE: 557
uaucuguagg cauaaauugg uat                                          23

<210> SEQ ID NO 558
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 558
uauaucggcg cugaaucccg cggact                                       26

<210> SEQ ID NO 559
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 559
uauauaccgg gcgcaccucu cuuuaa                                       26

<210> SEQ ID NO 560
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
```

```
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 560
uauauggacc gugugcacuu cgcuua                                          26

<210> SEQ ID NO 561
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 561
uauauuccgu gugcacuucg cuucaa                                          26

<210> SEQ ID NO 562
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
```

```
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 562
uauauccgug ugcacuucgc uucact                                       26

<210> SEQ ID NO 563
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 563
uauaugugca cuucgcuuca ccucua                                       26

<210> SEQ ID NO 564
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 564
uauauugcac uucgcuucac cucuga                                       26

<210> SEQ ID NO 565
```

```
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 565
uauaugcacu ucgcuucacc ucugca                                        26

<210> SEQ ID NO 566
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,
     24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 566
uauaucccag caaugucaac gaccga                                        26

<210> SEQ ID NO 567
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
```

-continued

```
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 567
uauauaaugu caacgaccga ccuuga                                            26

<210> SEQ ID NO 568
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 568
uauauaggag auuagguuaa agguca                                            26

<210> SEQ ID NO 569
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
```

<223> OTHER INFORMATION: /mod_base = "NAG13 modified nucleoside"

<400> SEQUENCE: 569
uauauuagga ggcuguaggc auaaat                                          26

<210> SEQ ID NO 570
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 570
uauauaggag gcuguaggca uaaaut                                          26

<210> SEQ ID NO 571
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 571
uauauggagg cuguaggcau aaauua                                          26

<210> SEQ ID NO 572
<211> LENGTH: 26
<212> TYPE: DNA
<213> ORGANISM: artificial sequence
<220> FEATURE:
<223> OTHER INFORMATION: HBV RNAi trigger sense strand

```
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 572
uauaugaggc uguaggcaua aauuga                                          26

<210> SEQ ID NO 573
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 573
uauauaggcu guaggcauaa auugga                                          26

<210> SEQ ID NO 574
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
```

```
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 574
uauaugcugg augugucugc ggcgua                                              26

<210> SEQ ID NO 575
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 575
uauauggaug ugucugcggc guuuua                                              26

<210> SEQ ID NO 576
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 576
uauaugaugu gucugcggcg uuuuaa                                              26
```

<210> SEQ ID NO 577
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 577
uauauguguc ugcggcguuu uaucaa                                    26

<210> SEQ ID NO 578
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 578
uauauuauca agguauguug cccgua                                    26

<210> SEQ ID NO 579
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base

```
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 579
uauauaucaa gguauguugc ccguua                                      26

<210> SEQ ID NO 580
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 580
uauauucaag guauguugcc cguuua                                      26

<210> SEQ ID NO 581
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
```

<222> LOCATION: 26
<223> OTHER INFORMATION: /mod_base = "NAG13 modified nucleoside"

<400> SEQUENCE: 581
uauaucaagg uauguugccc guuuga                                        26

<210> SEQ ID NO 582
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
    nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 582
uauauaaggu auguugcccg uuugua                                        26

<210> SEQ ID NO 583
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
    nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 583
uauauguaug uugcccguuu guccua                                        26

<210> SEQ ID NO 584
<211> LENGTH: 26
<212> TYPE: DNA
<213> ORGANISM: artificial sequence
<220> FEATURE:

```
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 584
uauauuccug gcucaguuua cuagua                                          26

<210> SEQ ID NO 585
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 585
uauauuggcu caguuuacua gugcca                                          26

<210> SEQ ID NO 586
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
```

```
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 586
uauauggcuc aguuuacuag ugccaa                                              26

<210> SEQ ID NO 587
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 587
uauaucucag uuuacuagug ccauua                                              26

<210> SEQ ID NO 588
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 588
uauauucagu uuacuagugc cauuua                                              26
```

<210> SEQ ID NO 589
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 589
uauaucaguu uacuagugcc auuuga                                      26

<210> SEQ ID NO 590
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 590
uauauaguuu acuagugcca uuugua                                      26

<210> SEQ ID NO 591
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:

<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 591
uauauuuacu agugccauuu guucaa        26

<210> SEQ ID NO 592
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 592
uauauuacua gugccauuug uucagt        26

<210> SEQ ID NO 593
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked nucleoside"
<220> FEATURE:

```
<221> NAME/KEY: modified base
<222> LOCATION: 26
<223> OTHER INFORMATION: /mod_base = "NAG13 modified nucleoside"

<400> SEQUENCE: 593
uauaugugcc auuuguucag ugguua                                             26

<210> SEQ ID NO 594
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 594
uauauugcca uuuguucagu gguuca                                             26

<210> SEQ ID NO 595
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
     nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 595
uauaugccau uuguucagug guucga                                             26

<210> SEQ ID NO 596
<211> LENGTH: 26
<212> TYPE: DNA
<213> ORGANISM: artificial sequence
```

```
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 596
uauauaugca acuuuucac cucuga                                         26

<210> SEQ ID NO 597
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 597
uauauugcaa cuuuucacc ucugca                                         26

<210> SEQ ID NO 598
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
```

-continued

```
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 598
uauauuucac cucugccuaa ucauca                                       26

<210> SEQ ID NO 599
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 599
uauaucaccu cugccuaauc aucuca                                       26

<210> SEQ ID NO 600
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 600
```
uauauccaca gagucuagac ucguga                                           26

<210> SEQ ID NO 601
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 601
uauauucgug guggacuucu cucaat                                           26

<210> SEQ ID NO 602
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 602
uauaucgugg uggacuucuc ucaaut                                           26

<210> SEQ ID NO 603
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"

-continued

```
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 603
uauauggacu ucucucaauu uucuaa                                        26

<210> SEQ ID NO 604
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 604
uauauugcca aguguuugcu gacgca                                        26

<210> SEQ ID NO 605
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
```

```
<220> FEATURE:
<221> NAME/KEY: modified base
<222> LOCATION: 26
<223> OTHER INFORMATION: /mod_base = "NAG13 modified nucleoside"

<400> SEQUENCE: 605
uauauggcuc cucugccgau ccauaa                                              26

<210> SEQ ID NO 606
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 606
uauauuccuc ugccgaucca uacuga                                              26

<210> SEQ ID NO 607
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
      nucleoside"
<220> FEATURE:
<221> NAME/KEY: modified base
<222> LOCATION: 26
<223> OTHER INFORMATION: /mod_base = "NAG13 modified nucleoside"

<400> SEQUENCE: 607
uauaugaucc auacugcgga acucca                                              26

<210> SEQ ID NO 608
<211> LENGTH: 25
<212> TYPE: DNA
```

<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 11,12,13
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,14,15,16,17,18,19,20,21,22,23,24
<223> OTHER INFORMATION: /mod_base = "2'-O-Methyl nucleoside"
<220> FEATURE:
<221> NAME/KEY: modified base
<222> LOCATION: 25
<223> OTHER INFORMATION: /mod_base = "inverted nucleotide"
<220> FEATURE:
<221> NAME/KEY: modified base
<222> LOCATION: 3,4,25
<223> OTHER INFORMATION: /mod_base = "phosphorothioate linked
    nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 608
uugccuguag gcauaaauug guaut                                   25

<210> SEQ ID NO 609
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24,25
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 6,7
<223> OTHER INFORMATION: /mod_base = "phosphorothioate linked
    nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 609
uauaugccug uaggcauaaa uuggua                                  26

<210> SEQ ID NO 610
<211> LENGTH: 25
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 11,12,13
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,14,15,16,17,18,19,20,21,22,23,24
<223> OTHER INFORMATION: /mod_base = "2'-O-Methyl nucleoside"
<220> FEATURE:
<221> NAME/KEY: modified base

```
<222> LOCATION: 25
<223> OTHER INFORMATION: /mod_base = "inverted nucleotide"
<220> FEATURE:
<221> NAME/KEY: modified base
<222> LOCATION: 3,4,25
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 610
uuguccgugu gcacuucgcu ucaut                                           25

<210> SEQ ID NO 611
<211> LENGTH: 25
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 11,12,13
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,14,15,16,17,18,19,20,21,22,23,24
<223> OTHER INFORMATION: /mod_base = "2'-O-Methyl nucleoside"
<220> FEATURE:
<221> NAME/KEY: modified base
<222> LOCATION: 25
<223> OTHER INFORMATION: /mod_base = "inverted nucleotide"
<220> FEATURE:
<221> NAME/KEY: modified base
<222> LOCATION: 3,4,25
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 611
uugguauguu gcccguuugu ccaut                                           25

<210> SEQ ID NO 612
<211> LENGTH: 19
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 5,7,8,9
<223> OTHER INFORMATION: /mod_base = "2'-deoxy-3'-fluoro nucleoside"
<220> FEATURE:
<221> NAME/KEY: modified base
<222> LOCATION: 1,2,3,4,6,10,11,12,13,14,15,16,17,18,19
<223> OTHER INFORMATION: /mod_base = "2'-O-Methyl nucleoside"
<220> FEATURE:
<221> NAME/KEY: modified base
<222> LOCATION: 2,3
<223> OTHER INFORMATION: /mod_base = "phosphorothioate linked
      nucleoside"
<220> FEATURE:
<221> NAME/KEY: modified base
<222> LOCATION: 19
<223> OTHER INFORMATION: /mod_base = "NAG13 modified nucleoside"

<400> SEQUENCE: 612
gugugcacuu cgcuucaca                                                  19
```

```
<210> SEQ ID NO 613
<211> LENGTH: 21
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 7,9,10,11,16,17
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,8,12,13,14,15,18,19,20,21
<223> OTHER INFORMATION: /mod_base = "2'-O-Methyl nucleoside"
<220> FEATURE:
<221> NAME/KEY: modified base
<222> LOCATION: 2,3
<223> OTHER INFORMATION: /mod_base = "phosphorothioate linked
      nucleoside"
<220> FEATURE:
<221> NAME/KEY: modified base
<222> LOCATION: 21
<223> OTHER INFORMATION: /mod_base = "NAG13 modified nucleoside"

<400> SEQUENCE: 613
gguggacuuc ucucaauuuu a                                            21

<210> SEQ ID NO 614
<211> LENGTH: 19
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 5,7,8,9
<223> OTHER INFORMATION: /mod_base = "2'-deoxy-3'-fluoro nucleoside"
<220> FEATURE:
<221> NAME/KEY: modified base
<222> LOCATION: 1,2,3,4,6,10,11,12,13,14,15,16,17
<223> OTHER INFORMATION: /mod_base = "2'-O-Methyl nucleoside"
<220> FEATURE:
<221> NAME/KEY: modified base
<222> LOCATION: 19
<223> OTHER INFORMATION: /mod_base = "inverted nucleotide"
<220> FEATURE:
<221> NAME/KEY: modified base
<222> LOCATION: 18
<223> OTHER INFORMATION: /mod_base = "2'-MOE nucleotide"
<220> FEATURE:
<221> NAME/KEY: modified base
<222> LOCATION: 2,3
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 614
gugugcacuu cgcuucaca                                               19

<210> SEQ ID NO 615
<211> LENGTH: 21
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 7,9,10,11,16,17
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,8,12,13,14,15,18,19
```

```
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "inverted nucleotide"
<220> FEATURE:
<221> NAME/KEY: modified base
<222> LOCATION: 20
<223> OTHER INFORMATION: /mod_base = "2'-MOE nucleotide"
<220> FEATURE:
<221> NAME/KEY: modified base
<222> LOCATION: 2,3
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 615
gguggacuuc ucucaauuut a                                             21

<210> SEQ ID NO 616
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 25
<223> OTHER INFORMATION: /mod_base = "2'-MOE nucleotide"
<220> FEATURE:
<221> NAME/KEY: modified base
<222> LOCATION: 7
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 616
cgcgguccgu gugcacuucg cuucaa                                        26

<210> SEQ ID NO 617
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
```

```
<220> FEATURE:
<221> NAME/KEY: modified base
<222> LOCATION: 25
<223> OTHER INFORMATION: /mod_base = "2'-MOE nucleotide"
<220> FEATURE:
<221> NAME/KEY: modified base
<222> LOCATION: 7
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 617
gcgguccgug ugcacuucgc uucaca                                          26

<210> SEQ ID NO 618
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 25
<223> OTHER INFORMATION: /mod_base = "2'-MOE nucleotide"
<220> FEATURE:
<221> NAME/KEY: modified base
<222> LOCATION: 7
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 618
gcggaugugu cugcggcguu uuauca                                          26

<210> SEQ ID NO 619
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 25
<223> OTHER INFORMATION: /mod_base = "2'-MOE nucleotide"
<220> FEATURE:
```

```
<221> NAME/KEY: modified base
<222> LOCATION: 7
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 619 gcguguqucu gcggcguuuu aucata                                      26

<210> SEQ ID NO 620
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 25
<223> OTHER INFORMATION: /mod_base = "2'-MOE nucleotide"
<220> FEATURE:
<221> NAME/KEY: modified base
<222> LOCATION: 7
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 620
gcgguccgug ugcacuucgc uucact                                      26

<210> SEQ ID NO 621
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 25
<223> OTHER INFORMATION: /mod_base = "2'-MOE nucleotide"
<220> FEATURE:
<221> NAME/KEY: modified base
<222> LOCATION: 7
<223> OTHER INFORMATION: /mod_base = "phosphorothioate linked
      nucleoside"
<220> FEATURE:
```

<221> NAME/KEY: modified base
<222> LOCATION: 1
<223> OTHER INFORMATION: /mod_base = "NAG25 modified nucleoside"

<400> SEQUENCE: 621
gcgugugucu gcggcguuuu aucatt                                              26

<210> SEQ ID NO 622
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 25
<223> OTHER INFORMATION: /mod_base = "2'-MOE nucleotide"
<220> FEATURE:
<221> NAME/KEY: modified base
<222> LOCATION: 7
<223> OTHER INFORMATION: /mod_base = "phosphorothioate linked
     nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 622
gcgcgguccg ugugcacuuc gcuuca                                              26

<210> SEQ ID NO 623
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 25
<223> OTHER INFORMATION: /mod_base = "2'-MOE nucleotide"
<220> FEATURE:
<221> NAME/KEY: modified base
<222> LOCATION: 7
<223> OTHER INFORMATION: /mod_base = "phosphorothioate linked
     nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 623 gcgaaggua u guugcccguu ugucca                                26

<210> SEQ ID NO 624
<211> LENGTH: 26
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 14,15,16
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,9,10,11,12,13,17,18,19,20,21,22,23,24
<223> OTHER INFORMATION: /mod_base = "2'-O-Methyl nucleoside"
<220> FEATURE:
<221> NAME/KEY: modified base
<222> LOCATION: 26
<223> OTHER INFORMATION: /mod_base = "inverted nucleotide"
<220> FEATURE:
<221> NAME/KEY: modified base
<222> LOCATION: 25
<223> OTHER INFORMATION: /mod_base = "2'-MOE nucleotide"
<220> FEATURE:
<221> NAME/KEY: modified base
<222> LOCATION: 7
<223> OTHER INFORMATION: /mod_base = "phosphorothioate linked
    nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 624
gcggaggcug uaggcauaaa uuggta                                 26

<210> SEQ ID NO 625
<211> LENGTH: 19
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17
<223> OTHER INFORMATION: /mod_base = "2'-O-Methyl nucleoside"
<220> FEATURE:
<221> NAME/KEY: modified base
<222> LOCATION: 19
<223> OTHER INFORMATION: /mod_base = "inverted nucleotide"

<400> SEQUENCE: 625
uguaggcaua aauugguat                                         19

<210> SEQ ID NO 626
<211> LENGTH: 19
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4,6,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 1,3,5,7,9,11,13,15,17
<223> OTHER INFORMATION: /mod_base = "2'-O-Methyl nucleoside"

-continued

```
<220> FEATURE:
<221> NAME/KEY: modified base
<222> LOCATION: 19
<223> OTHER INFORMATION: /mod_base = "inverted nucleotide"

<400> SEQUENCE: 626
ccucugccua aucaucuat                                                    19

<210> SEQ ID NO 627
<211> LENGTH: 19
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4,6,7,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 1,3,5,9,11,13,15,17
<223> OTHER INFORMATION: /mod_base = "2'-O-Methyl nucleoside"
<220> FEATURE:
<221> NAME/KEY: modified base
<222> LOCATION: 19
<223> OTHER INFORMATION: /mod_base = "inverted nucleotide"

<400> SEQUENCE: 627
cugcggcguu uuaucauat                                                    19

<210> SEQ ID NO 628
<211> LENGTH: 19
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 2,4,6,7,8,10,12,14,16,18
<223> OTHER INFORMATION: /mod_base = "2'-deoxy-3'-fluoro nucleoside"
<220> FEATURE:
<221> NAME/KEY: modified base
<222> LOCATION: 1,3,5,9,11,13,15,17
<223> OTHER INFORMATION: /mod_base = "2'-O-Methyl nucleoside"
<220> FEATURE:
<221> NAME/KEY: modified base
<222> LOCATION: 19
<223> OTHER INFORMATION: /mod_base = "inverted nucleotide"

<400> SEQUENCE: 628
uguaggcaua aauugguat                                                    19

<210> SEQ ID NO 629
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 7,8,9
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,10,11,12,13,14,15,16,17,18,19,20,21
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 1,2,22
```

```
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 629
cuguaggcau aaauugguau un                                            22

<210> SEQ ID NO 630
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19,20,21
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 630
gccuguaggc auaaauuggu an                                            22

<210> SEQ ID NO 631
<211> LENGTH: 21
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19,20
<223> OTHER INFORMATION: /mod_base = "2'-O-Methyl nucleoside"
<220> FEATURE:
<221> NAME/KEY: modified base
<222> LOCATION: 21
<223> OTHER INFORMATION: /mod_base = "inverted nucleotide"
<220> FEATURE:
<221> NAME/KEY: modified base
<222> LOCATION: 1,2,21
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 631
gccuguaggc auaaauuggu a                                             21

<210> SEQ ID NO 632
```

```
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19,20
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 21
<223> OTHER INFORMATION: /mod_base = "2'-MOE nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 632
gccuguaggc auaaauuggu an                                              22

<210> SEQ ID NO 633
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 20,21
<223> OTHER INFORMATION: /mod_base = "2'-MOE nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 633
gccuguaggc auaaauuggt an                                              22

<210> SEQ ID NO 634
<211> LENGTH: 22
<212> TYPE: DNA
<213> ORGANISM: artificial sequence
<220> FEATURE:
<223> OTHER INFORMATION: HBV RNAi trigger sense strand
```

```
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19,20,21
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 634
aacuguaggc auaaauuggu an                                              22

<210> SEQ ID NO 635
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19,20,21
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 635
ucguggugga cuucucucaa un                                              22

<210> SEQ ID NO 636
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19,20,21
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
```

```
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 636
aaguggugga cuucucucaa un                                              22

<210> SEQ ID NO 637
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 20,21
<223> OTHER INFORMATION: /mod_base = "2'-MOE nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 637
ucguggugga cuucucucaa tn                                              22

<210> SEQ ID NO 638
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19,20,21
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"
```

-continued

```
<400> SEQUENCE: 638
cgugguggac uucucucaau un                                              22

<210> SEQ ID NO 639
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19,20,21
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 639
aaugguggac uucucucaau un                                              22

<210> SEQ ID NO 640
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 20,21
<223> OTHER INFORMATION: /mod_base = "2'-MOE nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 640
cgugguggac uucucucaat tn                                              22

<210> SEQ ID NO 641
<211> LENGTH: 22
<212> TYPE: DNA
<213> ORGANISM: artificial sequence
```

-continued

```
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19,20,21
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 641
ggacuucucu caauuuucua an                                            22

<210> SEQ ID NO 642
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19,20,21
<223> OTHER INFORMATION: /mod_base = "2'-O-Methyl nucleoside"
<220> FEATURE:
<221> NAME/KEY: modified base
<222> LOCATION: 22
<223> OTHER INFORMATION: /mod_base = "inverted abasic nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 642
cgugguggac uucucucaau an                                            22

<210> SEQ ID NO 643
<211> LENGTH: 22
<212> TYPE: DNA
<213> ORGANISM: artificial sequence
<220> FEATURE:
<223> OTHER INFORMATION: HBV RNAi trigger sense strand
<220> FEATURE:
<221> NAME/KEY: modified base
<222> LOCATION: 9,10,11
<223> OTHER INFORMATION: /mod_base = "2'-deoxy-3'-fluoro nucleoside"
<220> FEATURE:
<221> NAME/KEY: modified base
<222> LOCATION: 1,2,3,4,5,6,7,8,12,13,14,15,16,17,18,19,20,21
<223> OTHER INFORMATION: /mod_base = "2'-O-Methyl nucleoside"
<220> FEATURE:
<221> NAME/KEY: modified base
<222> LOCATION: 22
```

```
<223> OTHER INFORMATION: /mod_base = "inverted abasic nucleotide"
<220> FEATURE:
<221> NAME/KEY: modified base
<222> LOCATION: 1,2,22
<223> OTHER INFORMATION: /mod_base = "phosphorothioate linked
      nucleoside"
<220> FEATURE:
<221> NAME/KEY: modified base
<222> LOCATION: 1
<223> OTHER INFORMATION: /mod_base = "NAG25 modified nucleoside"

<400> SEQUENCE: 643
ucguggugga cuucucucaa an                                          22

<210> SEQ ID NO 644
<211> LENGTH: 26
<212> TYPE: PRT
<213> ORGANISM: Apis florea

<400> SEQUENCE: 644

Gly Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 645
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 645

Ala Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 646
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 646

Cys Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 647
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 647

Phe Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 648
```

```
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 648

His Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 649
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 649

Ile Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 650
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 650

Leu Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 651
<211> LENGTH: 26
<212> TYPE: PRT
<213> ORGANISM: Artificial Sequence
<220> FEATURE:
<223> OTHER INFORMATION: Melittin-like peptide
<220> FEATURE:
<221> NAME/KEY: misc_feature
<222> LOCATION: (1)..(1)
<223> OTHER INFORMATION: Xaa is Nle

<400> SEQUENCE: 651

Xaa Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 652
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 652

Val Ile Gly Ala Ile Leu Lys Val Leu Ala Thr Gly Leu Pro Thr Leu
1               5                   10                  15
```

```
Ile Ser Trp Ile Lys Asn Lys Arg Lys Gln
            20                  25

<210> SEQ ID NO 653
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 653

Trp Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 654
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 654

Tyr Ile Gly Ala Ile Leu Lys Val Leu Ala Thr Gly Leu Pro Thr Leu
1               5                   10                  15

Ile Ser Trp Ile Lys Asn Lys Arg Lys Gln
            20                  25

<210> SEQ ID NO 655
<211> LENGTH: 26
<212> TYPE: PRT
<213> ORGANISM: Artificial Sequence
<220> FEATURE:
<223> OTHER INFORMATION: D-form Apis florea melittin sequence

<400> SEQUENCE: 655

Gly Ile Gly Ala Ile Leu Lys Val Leu Ala Cys Gly Leu Pro Thr Leu
1               5                   10                  15

Ile Ser Trp Ile Lys Asn Lys Arg Lys Gln
            20                  25

<210> SEQ ID NO 656
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 656

Gly Ile Gly Ala Ile Leu Lys Val Leu Ala Thr Leu Leu Pro Thr Leu
1               5                   10                  15

Ile Ser Trp Ile Lys Asn Lys Arg Lys Gln
            20                  25

<210> SEQ ID NO 657
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 657

Gly Ile Gly Ala Ile Leu Lys Val Leu Ala Thr Trp Leu Pro Thr Leu
1               5                   10                  15
```

```
Ile Ser Trp Ile Lys Asn Lys Arg Lys Gln
            20                  25

<210> SEQ ID NO 658
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 658

Gly Ile Gly Ala Ile Leu Lys Val Leu Ala Thr Gly Leu Pro Thr Leu
1               5                   10                  15

Ile Ser Trp Ile Lys Thr Lys Arg Lys Gln
            20                  25

<210> SEQ ID NO 659
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 659

Tyr Ile Gly Ala Ile Leu Asn Val Leu Ala Thr Gly Leu Pro Thr Leu
1               5                   10                  15

Ile Ser Trp Ile Lys Asn Lys Arg Lys Gln
            20                  25

<210> SEQ ID NO 660
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 660

Tyr Ile Gly Ala Ile Leu Ala Val Leu Ala Thr Gly Leu Pro Thr Leu
1               5                   10                  15

Ile Ser Trp Ile Lys Asn Lys Arg Lys Gln
            20                  25

<210> SEQ ID NO 661
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 661

Leu Ile Gly Ala Ile Leu Ser Val Leu Ala Thr Gly Leu Pro Thr Leu
1               5                   10                  15

Ile Ser Trp Ile Lys Asn Lys Arg Lys Gln
            20                  25

<210> SEQ ID NO 662
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 662

Leu Ile Gly Ala Ile Leu Arg Val Leu Ala Thr Gly Leu Pro Thr Leu
```

Ile Ser Trp Ile Lys Asn Lys Arg Lys Gln
            20                  25

<210> SEQ ID NO 663
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 663

Leu Ile Gly Ala Ile Leu His Val Leu Ala Thr Gly Leu Pro Thr Leu
1               5                   10                  15

Ile Ser Trp Ile Lys Asn Lys Arg Lys Gln
            20                  25

<210> SEQ ID NO 664
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 664

Leu Ile Gly Ala Ile Leu Lys Val Leu Ala Cys Gly Leu Pro Thr Leu
1               5                   10                  15

Ile Ser Trp Ile Lys Asn Lys Arg Lys Gln
            20                  25

<210> SEQ ID NO 665
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 665

Leu Ile Gly Ala Ile Leu Lys Val Leu Ala Thr Leu Leu Pro Thr Leu
1               5                   10                  15

Ile Ser Trp Ile Lys Asn Lys Arg Lys Gln
            20                  25

<210> SEQ ID NO 666
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 666

Tyr Ile Gly Ala Ile Leu Lys Val Leu Ala Thr Gly Leu Leu Thr Leu
1               5                   10                  15

Ile Ser Trp Ile Lys Asn Lys Arg Lys Gln
            20                  25

<210> SEQ ID NO 667
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 667

Leu Ile Gly Ala Ile Leu Lys Val Leu Ala Thr Gly Leu Pro Cys Leu
1               5                   10                  15

Ile Ser Trp Ile Lys Asn Lys Arg Lys Gln
            20                  25

<210> SEQ ID NO 668
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 668

Leu Ile Gly Ala Ile Leu Lys Val Leu Ala Thr Gly Leu Pro Thr Leu
1               5                   10                  15

Ile Cys Trp Ile Lys Asn Lys Arg Lys Gln
            20                  25

<210> SEQ ID NO 669
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 669

Tyr Ile Gly Ala Ile Leu Lys Val Leu Ala Thr Gly Leu Pro Thr Leu
1               5                   10                  15

Ile Ser Ala Ile Lys Asn Lys Arg Lys Gln
            20                  25

<210> SEQ ID NO 670
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 670

Gly Ile Gly Ala Ile Leu Lys Val Leu Ala Cys Gly Leu Pro Thr Leu
1               5                   10                  15

Ile Ser Trp Leu Lys Asn Lys Arg Lys Gln
            20                  25

<210> SEQ ID NO 671
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 671

Tyr Ile Gly Ala Ile Leu Lys Val Leu Ala Thr Gly Leu Pro Thr Leu
1               5                   10                  15

Ile Ser Trp Ile Ala Asn Lys Arg Lys Gln
            20                  25

<210> SEQ ID NO 672
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 672

```
Tyr Ile Gly Ala Ile Leu Lys Val Leu Ala Thr Gly Leu Pro Thr Leu
1               5                   10                  15

Ile Ser Trp Ile Lys Asn Ala Arg Lys Gln
            20                  25

<210> SEQ ID NO 673
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 673

Leu Ile Gly Ala Ile Leu Lys Val Leu Ala Thr Gly Leu Pro Thr Leu
1               5                   10                  15

Ile Ser Trp Ile Lys Asn Lys Ala Lys Gln
            20                  25

<210> SEQ ID NO 674
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 674

Tyr Ile Gly Ala Ile Leu Lys Val Leu Ala Thr Gly Leu Pro Thr Leu
1               5                   10                  15

Ile Ser Trp Ile Lys Asn Lys Arg Ala Gln
            20                  25

<210> SEQ ID NO 675
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 675

Tyr Ile Gly Ala Ile Leu Lys Val Leu Ala Thr Gly Leu Pro Thr Leu
1               5                   10                  15

Ile Ser Trp Ile Lys Asn Lys Arg Lys Cys
            20                  25

<210> SEQ ID NO 676
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 676

Leu Leu Gly Ala Ile Leu Lys Val Leu Ala Cys Gly Leu Pro Thr Leu
1               5                   10                  15

Ile Ser Trp Ile Lys Asn Lys Arg Lys Gln
            20                  25

<210> SEQ ID NO 677
<211> LENGTH: 26
<212> TYPE: PRT
<213> ORGANISM: Artificial Sequence
<220> FEATURE:
<223> OTHER INFORMATION: Melittin-like peptide
```

-continued

<400> SEQUENCE: 677

Leu Ile Gly Ala Leu Leu Lys Val Leu Ala Cys Gly Leu Pro Thr Leu
1               5                   10                  15

Ile Ser Trp Ile Lys Asn Lys Arg Lys Gln
            20                  25

<210> SEQ ID NO 678
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 678

Tyr Ile Gly Ala Ile Leu Ala Val Leu Ala Thr Gly Leu Pro Thr Leu
1               5                   10                  15

Ile Ser Trp Ile Ala Asn Lys Arg Lys Gln
            20                  25

<210> SEQ ID NO 679
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 679

Tyr Ile Gly Ala Ile Leu Ala Val Leu Ala Thr Gly Leu Pro Thr Leu
1               5                   10                  15

Ile Ser Trp Ile Lys Asn Ala Arg Lys Gln
            20                  25

<210> SEQ ID NO 680
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 680

Leu Ile Gly Ala Ile Leu Lys Val Leu Ala Cys Gly Leu Pro Thr Leu
1               5                   10                  15

Leu Ser Trp Ile Lys Asn Lys Arg Lys Gln
            20                  25

<210> SEQ ID NO 681
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 681

Leu Ile Gly Ala Ile Leu Lys Val Leu Ala Cys Gly Leu Pro Thr Leu
1               5                   10                  15

Ile Cys Trp Ile Lys Asn Lys Arg Lys Gln
            20                  25

<210> SEQ ID NO 682
<211> LENGTH: 26
<212> TYPE: PRT
<213> ORGANISM: Artificial Sequence
<220> FEATURE:
<223> OTHER INFORMATION: Melittin-like peptide

```
<400> SEQUENCE: 682

Gly Ile Gly Ala Ile Leu Lys Val Leu Ala Cys Gly Leu Pro Gly Leu
1               5                   10                  15

Ile Gly Trp Ile Lys Asn Lys Arg Lys Gln
            20                  25

<210> SEQ ID NO 683
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 683

Gly Ile Gly Ala Ile Leu Lys Val Leu Ala Cys Gly Leu Pro Ala Leu
1               5                   10                  15

Ile Ala Trp Ile Lys Asn Lys Arg Lys Gln
            20                  25

<210> SEQ ID NO 684
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 684

Tyr Ile Gly Ala Ile Leu Ala Val Leu Ala Thr Gly Leu Pro Thr Leu
1               5                   10                  15

Ile Ser Trp Ile Ala Asn Ala Arg Lys Gln
            20                  25

<210> SEQ ID NO 685
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 685

Tyr Ile Ala Ala Ile Leu Lys Val Leu Ala Ala Ala Leu Ala Thr Leu
1               5                   10                  15

Ile Ser Trp Ile Lys Asn Lys Arg Lys Gln
            20                  25

<210> SEQ ID NO 686
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 686

Leu Leu Gly Ala Leu Leu Lys Val Leu Ala Thr Gly Leu Pro Thr Leu
1               5                   10                  15

Leu Ser Trp Leu Lys Asn Lys Arg Lys Gln
            20                  25

<210> SEQ ID NO 687
<211> LENGTH: 26
<212> TYPE: PRT
<213> ORGANISM: Artificial Sequence
<220> FEATURE:
```

```
<223> OTHER INFORMATION: Melittin-like peptide
<220> FEATURE:
<221> NAME/KEY: misc_feature
<222> LOCATION: 2, 5, 17, 20
<223> OTHER INFORMATION: Xaa is Nle

<400> SEQUENCE: 687

Leu Xaa Gly Ala Xaa Leu Lys Val Leu Ala Thr Gly Leu Pro Thr Leu
1               5                   10                  15

Xaa Ser Trp Xaa Lys Asn Lys Arg Lys Gln
            20                  25

<210> SEQ ID NO 688
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 688

Leu Val Gly Ala Val Leu Lys Val Leu Ala Thr Gly Leu Pro Thr Leu
1               5                   10                  15

Val Ser Trp Val Lys Asn Lys Arg Lys Gln
            20                  25

<210> SEQ ID NO 689
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 689

Gly Leu Gly Ala Leu Leu Lys Val Leu Ala Cys Gly Leu Pro Thr Leu
1               5                   10                  15

Leu Ser Trp Leu Lys Asn Lys Arg Lys Gln
            20                  25

<210> SEQ ID NO 690
<211> LENGTH: 26
<212> TYPE: PRT
<213> ORGANISM: Artificial Sequence
<220> FEATURE:
<223> OTHER INFORMATION: Melittin-like peptide
<220> FEATURE:
<221> NAME/KEY: misc_feature
<222> LOCATION: 2, 5, 17, 20
<223> OTHER INFORMATION: Xaa is Nle

<400> SEQUENCE: 690

Gly Xaa Gly Ala Xaa Leu Lys Val Leu Ala Cys Gly Leu Pro Thr Leu
1               5                   10                  15

Xaa Ser Trp Xaa Lys Asn Lys Arg Lys Gln
            20                  25

<210> SEQ ID NO 691
<211> LENGTH: 31
<212> TYPE: PRT
<213> ORGANISM: Artificial Sequence
<220> FEATURE:
<223> OTHER INFORMATION: Melittin-like peptide

<400> SEQUENCE: 691

Cys Glu Asp Asp Leu Leu Leu Gly Ala Ile Leu Lys Val Leu Ala Thr
1               5                   10                  15
```

-continued

Gly Leu Pro Thr Leu Ile Ser Trp Ile Lys Asn Lys Arg Lys Gln
            20                  25                  30

<210> SEQ ID NO 692
<211> LENGTH: 31
<212> TYPE: PRT
<213> ORGANISM: Artificial Sequence
<220> FEATURE:
<223> OTHER INFORMATION: Melittin-like peptide

<400> SEQUENCE: 692

Cys Leu Val Val Leu Ile Val Val Ala Ile Leu Lys Val Leu Ala Thr
1               5                   10                  15

Gly Leu Pro Thr Leu Ile Ser Trp Ile Lys Asn Lys Arg Lys Gln
            20                  25                  30

<210> SEQ ID NO 693
<211> LENGTH: 26
<212> TYPE: PRT
<213> ORGANISM: Apis mellifera

<400> SEQUENCE: 693

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 694
<211> LENGTH: 27
<212> TYPE: PRT
<213> ORGANISM: Artificial Sequence
<220> FEATURE:
<223> OTHER INFORMATION: Melittin-like peptide

<400> SEQUENCE: 694

Cys Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 695
<211> LENGTH: 27
<212> TYPE: PRT
<213> ORGANISM: Artificial Sequence
<220> FEATURE:
<223> OTHER INFORMATION: Melittin-like peptide
<220> FEATURE:
<221> NAME/KEY: misc_feature
<222> LOCATION: (2)..(2)
<223> OTHER INFORMATION: Xaa is Nle

<400> SEQUENCE: 695

Cys Xaa Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 696
<211> LENGTH: 27
<212> TYPE: PRT
<213> ORGANISM: Artificial Sequence
<220> FEATURE:
<223> OTHER INFORMATION: Melittin-like peptide

<400> SEQUENCE: 696

-continued

Gly Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 697
<211> LENGTH: 27
<212> TYPE: PRT
<213> ORGANISM: Artificial Sequence
<220> FEATURE:
<223> OTHER INFORMATION: Melittin-like peptide

<400> SEQUENCE: 697

Leu Leu Ile Gly Ala Ile Leu Lys Val Leu Ala Thr Gly Leu Pro Thr
1               5                   10                  15

Leu Ile Ser Trp Ile Lys Asn Lys Arg Lys Gln
            20                  25

<210> SEQ ID NO 698
<211> LENGTH: 29
<212> TYPE: PRT
<213> ORGANISM: Artificial Sequence
<220> FEATURE:
<223> OTHER INFORMATION: Melittin-like peptide

<400> SEQUENCE: 698

Lys Leu Lys Leu Ile Gly Ala Ile Leu Lys Val Leu Ala Thr Gly Leu
1               5                   10                  15

Pro Thr Leu Ile Ser Trp Ile Lys Asn Lys Arg Lys Gln
            20                  25

<210> SEQ ID NO 699
<211> LENGTH: 29
<212> TYPE: PRT
<213> ORGANISM: Artificial Sequence
<220> FEATURE:
<223> OTHER INFORMATION: Melittin-like peptide

<400> SEQUENCE: 699

Lys Leu Lys Tyr Ile Gly Ala Ile Leu Lys Val Leu Ala Thr Gly Leu
1               5                   10                  15

Pro Thr Leu Ile Ser Trp Ile Lys Asn Lys Arg Lys Gln
            20                  25

<210> SEQ ID NO 700
<211> LENGTH: 30
<212> TYPE: PRT
<213> ORGANISM: Artificial Sequence
<220> FEATURE:
<223> OTHER INFORMATION: Melittin-like peptide

<400> SEQUENCE: 700

Cys Lys Leu Lys Leu Ile Gly Ala Ile Leu Lys Val Leu Ala Thr Gly
1               5                   10                  15

Leu Pro Thr Leu Ile Ser Trp Ile Lys Asn Lys Arg Lys Gln
            20                  25                  30

<210> SEQ ID NO 701
<211> LENGTH: 30
<212> TYPE: PRT
<213> ORGANISM: Artificial Sequence
<220> FEATURE:
<223> OTHER INFORMATION: Melittin-like peptide
<220> FEATURE:
<221> NAME/KEY: misc_feature
<222> LOCATION: (5)..(5)
<223> OTHER INFORMATION: Xaa is Nle

<400> SEQUENCE: 701

Cys Lys Leu Lys Xaa Ile Gly Ala Ile Leu Lys Val Leu Ala Thr Gly
1               5                   10                  15

Leu Pro Thr Leu Ile Ser Trp Ile Lys Asn Lys Arg Lys Gln
            20                  25                  30

<210> SEQ ID NO 702
<211> LENGTH: 30
<212> TYPE: PRT
<213> ORGANISM: Artificial Sequence
<220> FEATURE:
<223> OTHER INFORMATION: Melittin-like peptide

<400> SEQUENCE: 702

Gly Lys Leu Lys Leu Ile Gly Ala Ile Leu Lys Val Leu Ala Thr Gly
1               5                   10                  15

Leu Pro Thr Leu Ile Ser Trp Ile Lys Asn Lys Arg Lys Gln
            20                  25                  30

<210> SEQ ID NO 703
<211> LENGTH: 30
<212> TYPE: PRT
<213> ORGANISM: Artificial Sequence
<220> FEATURE:
<223> OTHER INFORMATION: D-form Melittin-like peptide

<400> SEQUENCE: 703

Cys Pro Ala Asn Leu Ile Gly Ala Ile Leu Lys Val Leu Ala Thr Gly
1               5                   10                  15

Leu Pro Thr Leu Ile Ser Trp Ile Lys Asn Lys Arg Lys Gln
            20                  25                  30

<210> SEQ ID NO 704
<211> LENGTH: 31
<212> TYPE: PRT
<213> ORGANISM: Artificial Sequence
<220> FEATURE:
<223> OTHER INFORMATION: Melittin-like peptide

<400> SEQUENCE: 704

Asp Glu Pro Leu Arg Ala Ile Gly Ala Ile Leu Lys Val Leu Ala Thr
1               5                   10                  15

Gly Leu Pro Thr Leu Ile Ser Trp Ile Lys Asn Lys Arg Lys Gln
            20                  25                  30

<210> SEQ ID NO 705
<211> LENGTH: 27
<212> TYPE: PRT
<213> ORGANISM: Artificial Sequence
<220> FEATURE:
<223> OTHER INFORMATION: Melittin-like peptide

<400> SEQUENCE: 705

Gly Ile Gly Ala Ile Leu Lys Val Leu Ala Thr Gly Leu Pro Thr Leu
1               5                   10                  15

Ile Ser Trp Ile Lys Asn Lys Arg Lys Gln Cys
            20                  25

<210> SEQ ID NO 706
<211> LENGTH: 27
<212> TYPE: PRT

<213> ORGANISM: Artificial Sequence
<220> FEATURE:
<223> OTHER INFORMATION: Melittin-like peptide

<400> SEQUENCE: 706

Leu Ile Gly Ala Ile Leu Lys Val Leu Ala Thr Gly Leu Pro Thr Leu
1               5                   10                  15

Ile Ser Trp Ile Lys Asn Lys Arg Lys Gln Cys
            20                  25

<210> SEQ ID NO 707
<211> LENGTH: 27
<212> TYPE: PRT
<213> ORGANISM: Artificial Sequence
<220> FEATURE:
<223> OTHER INFORMATION: Melittin-like peptide
<220> FEATURE:
<221> NAME/KEY: misc_feature
<222> LOCATION: (1)..(1)
<223> OTHER INFORMATION: Xaa is Nle

<400> SEQUENCE: 707

Xaa Ile Gly Ala Ile Leu Lys Val Leu Ala Thr Gly Leu Pro Thr Leu
1               5                   10                  15

Ile Ser Trp Ile Lys Asn Lys Arg Lys Gln Cys
            20                  25

<210> SEQ ID NO 708
<211> LENGTH: 30
<212> TYPE: PRT
<213> ORGANISM: Artificial Sequence
<220> FEATURE:
<223> OTHER INFORMATION: Melittin-like peptide

<400> SEQUENCE: 708

Leu Ile Gly Ala Ile Leu Lys Val Leu Ala Thr Gly Leu Pro Thr Leu
1               5                   10                  15

Ile Ser Trp Ile Lys Asn Lys Arg Lys Gln Lys Leu Lys Cys
            20                  25                  30

<210> SEQ ID NO 709
<211> LENGTH: 34
<212> TYPE: PRT
<213> ORGANISM: Artificial Sequence
<220> FEATURE:
<223> OTHER INFORMATION: Melittin-like peptide

<400> SEQUENCE: 709

Tyr Ile Gly Ala Ile Leu Lys Val Leu Ala Thr Gly Leu Pro Thr Leu
1               5                   10                  15

Ile Ser Trp Ile Lys Asn Lys Arg Lys Gln Pro Leu Gly Ile Ala Gly
            20                  25                  30

Gln Cys

<210> SEQ ID NO 710
<211> LENGTH: 31
<212> TYPE: PRT
<213> ORGANISM: Artificial Sequence
<220> FEATURE:
<223> OTHER INFORMATION: Melittin-like peptide

<400> SEQUENCE: 710

Leu Ile Gly Ala Ile Leu Lys Val Leu Ala Thr Gly Leu Pro Thr Leu
1               5                   10                  15

Ile Ser Trp Ile Lys Asn Lys Arg Lys Gln Lys Lys Lys Lys
            20                  25                  30

<210> SEQ ID NO 711
<211> LENGTH: 31
<212> TYPE: PRT
<213> ORGANISM: Artificial Sequence
<220> FEATURE:
<223> OTHER INFORMATION: Melittin-like peptide

<400> SEQUENCE: 711

Tyr Ile Gly Ala Ile Leu Lys Val Leu Ala Thr Gly Leu Pro Thr Leu
1               5                   10                  15

Ile Ser Trp Ile Lys Asn Lys Arg Lys Gln Gly Phe Lys Gly Cys
            20                  25                  30

<210> SEQ ID NO 712
<211> LENGTH: 30
<212> TYPE: PRT
<213> ORGANISM: Artificial Sequence
<220> FEATURE:
<223> OTHER INFORMATION: Melittin-like peptide

<400> SEQUENCE: 712

Cys Phe Lys Leu Ile Gly Ala Ile Leu Lys Val Leu Ala Thr Gly Leu
1               5                   10                  15

Pro Thr Leu Ile Ser Trp Ile Lys Asn Lys Arg Lys Gln Cys
            20                  25                  30

<210> SEQ ID NO 713
<211> LENGTH: 25
<212> TYPE: PRT
<213> ORGANISM: Artificial Sequence
<220> FEATURE:
<223> OTHER INFORMATION: Melittin-like peptide

<400> SEQUENCE: 713

Phe Gly Ala Ile Leu Lys Val Leu Ala Thr Gly Leu Pro Thr Leu Ile
1               5                   10                  15

Ser Trp Ile Lys Asn Lys Arg Lys Gln
            20                  25

<210> SEQ ID NO 714
<211> LENGTH: 23
<212> TYPE: PRT
<213> ORGANISM: Artificial Sequence
<220> FEATURE:
<223> OTHER INFORMATION: Melittin-like peptide

<400> SEQUENCE: 714

Leu Ile Gly Ala Ile Leu Lys Val Leu Ala Thr Gly Leu Pro Thr Leu
1               5                   10                  15

Ile Ser Trp Ile Lys Asn Lys
            20

<210> SEQ ID NO 715
<211> LENGTH: 21
<212> TYPE: PRT
<213> ORGANISM: Artificial Sequence
<220> FEATURE:
<223> OTHER INFORMATION: Melittin-like peptide

<400> SEQUENCE: 715

Leu Ile Gly Ala Val Leu Lys Val Leu Thr Thr Gly Leu Pro Ala Leu
1               5                   10                  15

Ile Ser Trp Ile Lys
            20

<210> SEQ ID NO 716
<211> LENGTH: 23
<212> TYPE: PRT
<213> ORGANISM: Artificial Sequence
<220> FEATURE:
<223> OTHER INFORMATION: Melittin-like peptide

<400> SEQUENCE: 716

Leu Ile Gly Ala Val Leu Lys Val Leu Thr Thr Gly Leu Pro Ala Leu
1               5                   10                  15

Ile Ser Trp Ile Lys Gly Glu
            20

<210> SEQ ID NO 717
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 717

Gln Lys Arg Lys Asn Lys Ile Trp Ser Ile Leu Thr Pro Leu Gly Thr
1               5                   10                  15

Ala Leu Val Lys Leu Ile Ala Gly Ile Leu
            20                  25

<210> SEQ ID NO 718
<211> LENGTH: 29
<212> TYPE: PRT
<213> ORGANISM: Artificial Sequence
<220> FEATURE:
<223> OTHER INFORMATION: Melittin-like peptide

<400> SEQUENCE: 718

Lys Leu Lys Gln Lys Arg Lys Asn Lys Ile Trp Ser Ile Leu Thr Pro
1               5                   10                  15

Leu Gly Thr Ala Leu Val Lys Leu Ile Ala Gly Ile Leu
            20                  25

<210> SEQ ID NO 719
<211> LENGTH: 27
<212> TYPE: PRT
<213> ORGANISM: Artificial Sequence
<220> FEATURE:
<223> OTHER INFORMATION: Melittin-like peptide

<400> SEQUENCE: 719

Gly Ile Gly Ala Val Leu Lys Val Leu Thr Thr Gly Leu Pro Ala Leu
1               5                   10                  15

Ile Ser Trp Ile Ser Arg Lys Lys Arg Gln Gln
            20                  25

<210> SEQ ID NO 720
<211> LENGTH: 25
<212> TYPE: PRT
<213> ORGANISM: Artificial Sequence
<220> FEATURE:
<223> OTHER INFORMATION: Melittin-like peptide

<400> SEQUENCE: 720

Gly Ile Gly Ala Arg Leu Lys Val Leu Thr Thr Gly Leu Pro Arg Ile

```
                1               5                  10                  15
Ser Trp Ile Lys Arg Lys Arg Gln Gln
            20                  25

<210> SEQ ID NO 721
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 721

Gly Ile Gly Ala Ile Leu Lys Val Leu Ser Thr Gly Leu Pro Ala Leu
1               5                  10                  15

Ile Ser Trp Ile Lys Arg Lys Arg Gln Glu
            20                  25

<210> SEQ ID NO 722
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 722

Gly Ile Gly Ala Val Leu Lys Val Leu Thr Thr Gly Leu Pro Ala Leu
1               5                  10                  15

Ile Gly Trp Ile Lys Arg Lys Arg Gln Gln
            20                  25

<210> SEQ ID NO 723
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 723

Gly Ile Gly Ala Val Leu Lys Val Leu Ala Thr Gly Leu Pro Ala Leu
1               5                  10                  15

Ile Ser Trp Ile Lys Arg Lys Arg Gln Gln
            20                  25

<210> SEQ ID NO 724
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 724

Gly Ile Gly Ala Val Leu Lys Val Leu Ser Thr Gly Leu Pro Ala Leu
1               5                  10                  15

Ile Ser Trp Ile Lys Arg Lys Arg Gln Gln
            20                  25

<210> SEQ ID NO 725
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 725
```

```
Gly Ile Gly Ala Ile Leu Arg Val Leu Ala Thr Gly Leu Pro Thr Leu
1               5                   10                  15

Ile Ser Trp Ile Lys Asn Lys Arg Lys Gln
            20                  25
```

<210> SEQ ID NO 726
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 726

```
Gly Ile Gly Ala Ile Leu Lys Val Leu Ala Thr Gly Leu Pro Thr Leu
1               5                   10                  15

Ile Ser Trp Ile Lys Arg Lys Arg Lys Gln
            20                  25
```

<210> SEQ ID NO 727
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 727

```
Gly Ile Gly Ala Ile Leu Lys Val Leu Ala Thr Gly Leu Pro Thr Leu
1               5                   10                  15

Ile Ser Trp Ile Lys Lys Lys Lys Gln Gln
            20                  25
```

<210> SEQ ID NO 728
<211> LENGTH: 32
<212> TYPE: PRT
<213> ORGANISM: Artificial Sequence
<220> FEATURE:
<223> OTHER INFORMATION: Melittin-like peptide

<400> SEQUENCE: 728

```
Gly Ile Gly Ala Ile Leu Lys Val Leu Ala Thr Gly Leu Pro Thr Leu
1               5                   10                  15

Ile Ser Trp Ile Lys Asn Lys Arg Lys Gln Gly Ser Lys Lys Lys Lys
            20                  25                  30
```

<210> SEQ ID NO 729
<211> LENGTH: 28
<212> TYPE: PRT
<213> ORGANISM: Artificial Sequence
<220> FEATURE:
<223> OTHER INFORMATION: Melittin-like peptide

<400> SEQUENCE: 729

```
Lys Lys Gly Ile Gly Ala Ile Leu Lys Val Leu Ala Thr Gly Leu Pro
1               5                   10                  15

Thr Leu Ile Ser Trp Ile Lys Asn Lys Arg Lys Gln
            20                  25
```

<210> SEQ ID NO 730
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 730

Gly Ile Gly Ala Ile Leu Glu Val Leu Ala Thr Gly Leu Pro Thr Leu
1               5                   10                  15

Ile Ser Trp Ile Lys Asn Lys Arg Lys Gln
            20                  25

<210> SEQ ID NO 731
<211> LENGTH: 24
<212> TYPE: PRT
<213> ORGANISM: Artificial Sequence
<220> FEATURE:
<223> OTHER INFORMATION: Melittin-like peptide

<400> SEQUENCE: 731

Gly Ile Gly Ala Val Leu Lys Val Leu Thr Thr Gly Leu Pro Ala Leu
1               5                   10                  15

Ile Ser Trp Ile Lys Arg Lys Arg
            20

<210> SEQ ID NO 732
<211> LENGTH: 22
<212> TYPE: PRT
<213> ORGANISM: Artificial Sequence
<220> FEATURE:
<223> OTHER INFORMATION: Melittin-like peptide

<400> SEQUENCE: 732

Gly Ile Gly Ala Val Leu Lys Val Leu Thr Thr Gly Leu Pro Ala Leu
1               5                   10                  15

Ile Ser Trp Ile Lys Arg
            20

<210> SEQ ID NO 733
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 733

Cys Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 734
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 734

Gln Gln Arg Lys Arg Lys Ile Trp Ser Ile Leu Ala Pro Leu Gly Thr
1               5                   10                  15

Thr Leu Val Lys Leu Val Ala Gly Ile Gly
            20                  25

<210> SEQ ID NO 735
<211> LENGTH: 26
<212> TYPE: PRT
<213> ORGANISM: Artificial Sequence
<220> FEATURE:
<223> OTHER INFORMATION: Melittin-like peptide -continued

```
<400> SEQUENCE: 735

Gln Gln Arg Lys Arg Lys Ile Trp Ser Ile Leu Ala Pro Leu Gly Thr
1               5                   10                  15

Thr Leu Val Lys Leu Val Ala Gly Ile Cys
            20                  25

<210> SEQ ID NO 736
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 736

Gln Gln Lys Lys Lys Lys Ile Trp Ser Ile Leu Ala Pro Leu Gly Thr
1               5                   10                  15

Thr Leu Val Lys Leu Val Ala Gly Ile Cys
            20                  25

<210> SEQ ID NO 737
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 737

Gln Lys Arg Lys Asn Lys Ile Trp Ser Ile Leu Thr Pro Leu Gly Thr
1               5                   10                  15

Ala Leu Val Lys Leu Ile Ala Gly Ile Gly
            20                  25

<210> SEQ ID NO 738
<211> LENGTH: 26
<212> TYPE: PRT
<213> ORGANISM: Artificial Sequence
<220> FEATURE:
<223> OTHER INFORMATION: Melittin-like peptide

<400> SEQUENCE: 738

Gln Gln Arg Lys Arg Lys Ile Trp Ser Ile Leu Ala Ala Leu Gly Thr
1               5                   10                  15

Thr Leu Val Lys Leu Val Ala Gly Ile Cys
            20                  25

<210> SEQ ID NO 739
<211> LENGTH: 26
<212> TYPE: PRT
<213> ORGANISM: Artificial Sequence
<220> FEATURE:
<223> OTHER INFORMATION: D-form Melittin-like peptide

<400> SEQUENCE: 739

Gln Lys Arg Lys Asn Lys Ile Trp Ser Ile Leu Thr Pro Leu Gly Thr
1               5                   10                  15

Ala Leu Val Lys Leu Ile Ala Gly Ile Gly
            20                  25

<210> SEQ ID NO 740
<211> LENGTH: 18
<212> TYPE: DNA
<213> ORGANISM: artificial sequence
<220> FEATURE:
<223> OTHER INFORMATION: Hepatitis B virus PCR primer
```

```
<400> SEQUENCE: 740
gccggacctg catgacta                                                    18

<210> SEQ ID NO 741
<211> LENGTH: 25
<212> TYPE: DNA
<213> ORGANISM: artificial sequence
<220> FEATURE:
<223> OTHER INFORMATION: Hepatitis B virus PCR primer

<400> SEQUENCE: 741
ggtacagcaa caggagggat acata                                            25

<210> SEQ ID NO 742
<211> LENGTH: 16
<212> TYPE: DNA
<213> ORGANISM: artificial sequence
<220> FEATURE:
<223> OTHER INFORMATION: Hepatitis B virus probe

<400> SEQUENCE: 742
ctgctcaagg aacctc                                                      16

<210> SEQ ID NO 743
<211> LENGTH: 23
<212> TYPE: DNA
<213> ORGANISM: artificial sequence
<220> FEATURE:
<223> OTHER INFORMATION: HCR gene PCR primer

<400> SEQUENCE: 743
catgccacct ccaacatcca ctc                                              23

<210> SEQ ID NO 744
<211> LENGTH: 24
<212> TYPE: DNA
<213> ORGANISM: artificial sequence
<220> FEATURE:
<223> OTHER INFORMATION: HCR gene PCR primer

<400> SEQUENCE: 744
ggcatagcca cttactgacg actc                                             24

<210> SEQ ID NO 745
<211> LENGTH: 28
<212> TYPE: DNA
<213> ORGANISM: artificial sequence
<220> FEATURE:
<223> OTHER INFORMATION: HCR gene probe

<400> SEQUENCE: 745
ttgtcctggc gtggtttagg tagtgtga                                         28

<210> SEQ ID NO 746
<211> LENGTH: 18
<212> TYPE: DNA
<213> ORGANISM: artificial sequence
<220> FEATURE:
<223> OTHER INFORMATION: Hepatitis B virus PCR primer

<400> SEQUENCE: 746
gccggacctg catgacta                                                    18

<210> SEQ ID NO 747
```

```
<211> LENGTH: 25
<212> TYPE: DNA
<213> ORGANISM: artificial sequence
<220> FEATURE:
<223> OTHER INFORMATION: Hepatitis B virus PCR primer

<400> SEQUENCE: 747
ggtacagcaa caggagggat acata                                        25

<210> SEQ ID NO 748
<211> LENGTH: 16
<212> TYPE: DNA
<213> ORGANISM: artificial sequence
<220> FEATURE:
<223> OTHER INFORMATION: Hepatitis B virus probe

<400> SEQUENCE: 748
ctgctcaagg aacctc                                                  16

<210> SEQ ID NO 749
<211> LENGTH: 20
<212> TYPE: DNA
<213> ORGANISM: artificial sequence
<220> FEATURE:
<223> OTHER INFORMATION: Hepatitis B virus PNA standard
<220> FEATURE:
<221> NAME/KEY: modified base
<222> LOCATION: 1-19
<223> OTHER INFORMATION: /mod_base = "2'-hydroxy corresponding
      nucleoside"

<400> SEQUENCE: 749
cuguaggcau aaauugguat                                              20

<210> SEQ ID NO 750
<211> LENGTH: 21
<212> TYPE: DNA
<213> ORGANISM: artificial sequence
<220> FEATURE:
<223> OTHER INFORMATION: Hepatitis B virus PNA standard
<220> FEATURE:
<221> NAME/KEY: modified base
<222> LOCATION: 2-19
<223> OTHER INFORMATION: /mod_base = "2'-hydroxy corresponding
      nucleoside"

<400> SEQUENCE: 750
taccaauuua ugccuacagt t                                            21

<210> SEQ ID NO 751
<211> LENGTH: 20
<212> TYPE: DNA
<213> ORGANISM: artificial sequence
<220> FEATURE:
<223> OTHER INFORMATION: Hepatitis B virus PNA standard
<220> FEATURE:
<221> NAME/KEY: modified base
<222> LOCATION: 1-19
<223> OTHER INFORMATION: /mod_base = "2'-hydroxy corresponding
      nucleoside"

<400> SEQUENCE: 751
accucugccu aaucaucuat                                              20

<210> SEQ ID NO 752
<211> LENGTH: 21
<212> TYPE: DNA
<213> ORGANISM: artificial sequence
<220> FEATURE:
```

<223> OTHER INFORMATION: Hepatitis B virus PNA standard
<220> FEATURE:
<221> NAME/KEY: modified base
<222> LOCATION: 2-19
<223> OTHER INFORMATION: /mod_base = "2'-hydroxy corresponding nucleoside"

<400> SEQUENCE: 752
tagaugauua ggcagaggut t    21

<210> SEQ ID NO 753
<211> LENGTH: 15
<212> TYPE: DNA
<213> ORGANISM: artificial sequence
<220> FEATURE:
<223> OTHER INFORMATION: Peptide nucleic acid probe

<400> SEQUENCE: 753
ctgtaggcat aaatt    15

<210> SEQ ID NO 754
<211> LENGTH: 15
<212> TYPE: DNA
<213> ORGANISM: artificial sequence
<220> FEATURE:
<223> OTHER INFORMATION: Peptide nucleic acid probe

<400> SEQUENCE: 754
acctctgcct aatca    15

<210> SEQ ID NO 755
<211> LENGTH: 20
<212> TYPE: DNA
<213> ORGANISM: artificial sequence
<220> FEATURE:
<223> OTHER INFORMATION: Hepatitis B virus PCR primer

<400> SEQUENCE: 755
cgaggcaggt cccctagaag    20

<210> SEQ ID NO 756
<211> LENGTH: 16
<212> TYPE: DNA
<213> ORGANISM: artificial sequence
<220> FEATURE:
<223> OTHER INFORMATION: Hepatitis B virus PCR primer

<400> SEQUENCE: 756
tgcgacgcgg ygattg    16

<210> SEQ ID NO 757
<211> LENGTH: 23
<212> TYPE: DNA
<213> ORGANISM: artificial sequence
<220> FEATURE:
<223> OTHER INFORMATION: Hepatitis B virus probe

<400> SEQUENCE: 757
agaactccct cgcctcgcag acg    23

<210> SEQ ID NO 758
<211> LENGTH: 21
<212> TYPE: DNA
<213> ORGANISM: artificial sequence
<220> FEATURE:
<223> OTHER INFORMATION: Hepatitis B virus PCR primer

<400> SEQUENCE: 758
ccgtctgtgc cttctcatct g                                      21

<210> SEQ ID NO 759
<211> LENGTH: 29
<212> TYPE: DNA
<213> ORGANISM: artificial sequence
<220> FEATURE:
<223> OTHER INFORMATION: Hepatitis B virus PCR primer

<400> SEQUENCE: 759
agtccaagag tyctcttatg yaagacctt                              29

<210> SEQ ID NO 760
<211> LENGTH: 26
<212> TYPE: DNA
<213> ORGANISM: artificial sequence
<220> FEATURE:
<223> OTHER INFORMATION: Hepatitis B virus probe

<400> SEQUENCE: 760
ccgtgtgcac ttcgcttcac ctctgc                                 26

<210> SEQ ID NO 761
<211> LENGTH: 23
<212> TYPE: DNA
<213> ORGANISM: artificial sequence
<220> FEATURE:
<223> OTHER INFORMATION: Firefly luciferase siRNA strand
<220> FEATURE:
<221> NAME/KEY: modified base
<222> LOCATION: 1-22
<223> OTHER INFORMATION: /mod_base = "2'-hydroxy corresponding
      nucleoside"

<400> SEQUENCE: 761
uaucuuacgc ugaguacuuc gat                                    23

<210> SEQ ID NO 762
<211> LENGTH: 21
<212> TYPE: DNA
<213> ORGANISM: artificial sequence
<220> FEATURE:
<223> OTHER INFORMATION: Firefly luciferase siRNA strand
<220> FEATURE:
<221> NAME/KEY: modified base
<222> LOCATION: 1-19
<223> OTHER INFORMATION: /mod_base = "2'-hydroxy corresponding
      nucleoside"

<400> SEQUENCE: 762
ucgaaguacu cagcguaagt t                                      21

<210> SEQ ID NO 763
<211> LENGTH: 25
<212> TYPE: DNA
<213> ORGANISM: artificial sequence
<220> FEATURE:
<223> OTHER INFORMATION: mouse GADPH PCR primer

<400> SEQUENCE: 763 gccctatcc tatcaacact tccgg                                   25

<210> SEQ ID NO 764
<211> LENGTH: 20
<212> TYPE: DNA
<213> ORGANISM: artificial sequence

```
<220> FEATURE:
<223> OTHER INFORMATION: mouse GADPH PCR primer

<400> SEQUENCE: 764
ttcgtctgcg aggcgaggga                                               20

<210> SEQ ID NO 765
<211> LENGTH: 19
<212> TYPE: DNA
<213> ORGANISM: artificial sequence
<220> FEATURE:
<223> OTHER INFORMATION: mouse GADPH PCR primer

<400> SEQUENCE: 765
tctggaaagc tgtggcgtg                                                19

<210> SEQ ID NO 766
<211> LENGTH: 20
<212> TYPE: DNA
<213> ORGANISM: artificial sequence
<220> FEATURE:
<223> OTHER INFORMATION: mouse GADPH PCR primer

<400> SEQUENCE: 766
ccagtgagct tcccgttcag                                               20
```